US011332741B1

(12) United States Patent
Li

(10) Patent No.: US 11,332,741 B1
(45) Date of Patent: May 17, 2022

(54) COMPOSITIONS AND METHODS FOR TREATING LEBER'S HEREDITARY OPTIC NEUROPATHY

(71) Applicant: Wuhan Neurophth Biotechnology Limited Company, Hubei (CN)

(72) Inventor: Bin Li, Hubei (CN)

(73) Assignee: Wuhan Neurophth Biotechnology Limited Company, Hubei (CN)

( * ) Notice: Subject to any disclaimer, the term of this patent is extended or adjusted under 35 U.S.C. 154(b) by 0 days.

(21) Appl. No.: 17/320,388

(22) Filed: May 14, 2021

Related U.S. Application Data

(60) Division of application No. 16/836,644, filed on Mar. 31, 2020, now Pat. No. 11,034,954, which is a continuation of application No. PCT/CN2019/094136, filed on Jul. 1, 2019.

(30) Foreign Application Priority Data

| | | |
|---|---|---|
| Jun. 29, 2018 | (CN) | CN201810702492.7 |
| Jun. 29, 2018 | (CN) | CN201810703168.7 |
| Jul. 9, 2018 | (WO) | PCT/CN2018/095023 |
| Aug. 20, 2018 | (CN) | CN201810948193.1 |
| Sep. 4, 2018 | (WO) | PCT/CN2018/103937 |
| Oct. 19, 2018 | (CN) | CN201811221305.X |
| Oct. 22, 2018 | (CN) | CN201811230856.2 |
| Nov. 2, 2018 | (WO) | PCT/CN2018/113799 |
| Nov. 30, 2018 | (WO) | PCT/CN2018/118662 |
| Jan. 4, 2019 | (WO) | PCT/CN2019/070461 |

(51) Int. Cl.

| | |
|---|---|
| ***C12N 15/11*** | (2006.01) |
| ***C12N 9/02*** | (2006.01) |
| ***C12N 15/86*** | (2006.01) |
| ***C12N 7/00*** | (2006.01) |
| ***A61K 31/573*** | (2006.01) |
| ***A61K 31/664*** | (2006.01) |
| ***A61K 9/00*** | (2006.01) |
| ***A61K 35/76*** | (2015.01) |

(52) U.S. Cl.
CPC ............ *C12N 15/11* (2013.01); *A61K 9/0019* (2013.01); *A61K 9/0048* (2013.01); *A61K 31/573* (2013.01); *A61K 31/664* (2013.01); *A61K 35/76* (2013.01); *C12N 7/00* (2013.01); *C12N 9/0004* (2013.01); *C12N 15/86* (2013.01); *C12Y 106/99003* (2013.01); *C12N 2750/14143* (2013.01)

(58) Field of Classification Search
CPC .......... C12N 15/11; C12N 15/86; C12N 7/00; C12N 9/0004; C12N 2750/14143; A61K 9/0048; A61K 9/0019; A61K 35/76; A61K 31/664; A61K 31/573; C12Y 106/99003
See application file for complete search history.

(56) References Cited

U.S. PATENT DOCUMENTS

| | | | |
|---|---|---|---|
| 3,625,214 | A | 12/1971 | Higuchi |
| 4,789,734 | A | 12/1988 | Pierschbacher |
| 4,897,268 | A | 1/1990 | Tice et al. |
| 4,906,474 | A | 3/1990 | Langer et al. |
| 4,925,673 | A | 5/1990 | Steiner et al. |
| 5,075,109 | A | 12/1991 | Tice et al. |
| 5,811,128 | A | 9/1998 | Tice et al. |
| 5,814,344 | A | 9/1998 | Tice et al. |
| 5,820,883 | A | 10/1998 | Tice et al. |
| 5,853,763 | A | 12/1998 | Tice et al. |
| 5,928,647 | A | 7/1999 | Rock |
| 5,942,252 | A | 8/1999 | Tice et al. |
| 6,207,392 | B1 | 3/2001 | Weiss et al. |
| 7,704,721 | B2 | 4/2010 | Wright et al. |
| 8,637,257 | B2 | 1/2014 | Brys et al. |
| 9,701,961 | B2 | 7/2017 | Feinstein et al. |
| 10,308,987 | B2 | 6/2019 | Parr et al. |
| 10,906,931 | B2 | 2/2021 | Moghadam |
| 11,034,954 | B2 | 6/2021 | Li |
| 2008/0166724 | A1 | 7/2008 | Gerber et al. |
| 2009/0306188 | A1 | 12/2009 | Corral-Debrinski et al. |
| 2010/0272688 | A1 | 10/2010 | Acland et al. |
| 2015/0250869 | A1 | 9/2015 | Sene et al. |
| 2016/0206706 | A1 | 7/2016 | Wright et al. |
| 2016/0289674 | A1 | 10/2016 | Bancel et al. |
| 2018/0207293 | A1 | 7/2018 | Shimizu et al. |

(Continued)

FOREIGN PATENT DOCUMENTS

| | | | |
|---|---|---|---|
| CN | 102517304 | A | 6/2012 |
| CN | 102634527 | A | 8/2012 |

(Continued)

OTHER PUBLICATIONS

Hudry et al. "Therapeutic AAV Gene Transfer to the Nervous System: A Clinical Reality."Neuron. Mar. 6, 2019;101 (5):839-862. (Year: 2019).*

(Continued)

*Primary Examiner* — Titilayo Moloye
(74) *Attorney, Agent, or Firm* — Cooley LLP

(57) ABSTRACT

Disclosed herein is a recombinant nucleic acid, comprising: a mitochondrial targeting sequence; a mitochondrial protein coding sequence, wherein said mitochondrial protein coding sequence encodes a polypeptide comprising a mitochondrial protein; and a 3'UTR nucleic acid sequence. Also disclosed is a pharmaceutical composition comprising the recombinant nucleic acid and a method of treating Leber's hereditary optic neuropathy (LHON) using the pharmaceutical composition.

21 Claims, 18 Drawing Sheets

Specification includes a Sequence Listing.

(56) References Cited

U.S. PATENT DOCUMENTS

| | | | |
|---|---|---|---|
| 2020/0263172 | A1 | 8/2020 | Li |
| 2021/0163898 | A1 | 6/2021 | Towheed et al. |
| 2021/0189429 | A1 | 6/2021 | Li |
| 2021/0353774 | A1 | 11/2021 | Li |

FOREIGN PATENT DOCUMENTS

| | | | |
|---|---|---|---|
| CN | 102634527 | B | 8/2012 |
| CN | 104450747 | B | 3/2015 |
| EP | 2913403 | A1 | 9/2015 |
| WO | WO-9739776 | A1 | 10/1997 |
| WO | WO 2006/117250 | A2 | 11/2006 |
| WO | WO 2008/063802 | A2 | 5/2008 |
| WO | WO 2016/044023 | A1 | 3/2016 |
| WO | WO 2017/011519 | A1 | 1/2017 |
| WO | WO-2019033119 | A1 | 2/2019 |
| WO | WO-2019241206 | A1 | 12/2019 |
| WO | WO 2020/010491 | A1 | 1/2020 |
| WO | WO 2020/037938 | A1 | 2/2020 |
| WO | WO 2020/038352 | A1 | 2/2020 |
| WO | WO 2020/077756 | A1 | 4/2020 |
| WO | WO 2020/082417 | A1 | 4/2020 |

OTHER PUBLICATIONS

Greenwood et al. "Current research into brain barriers and the delivery of therapeutics for neurological diseases: a report on CNS barrier congress London, UK, 2017." Fluids and Barriers of the CNS vol. 14, Article No. 31 (2017) (Year: 2017).*

Manfredsson et al. "AAV9: a potential blood-brain barrier buster." Mol Ther. Mar. 2009; 17(3): 403-405.. (Year: 2009).*

Ribera et al. "Biochemical, histological and functional correction of mucopolysaccharidosis type IIIB by intra-cerebrospinal fluid gene therapy."Hum Mol Genet .Apr. 1, 2015;24(7):2078-95. (Year: 2015).*

Hocquemiller et al. "Adeno-Associated Virus-Based Gene Therapy for CNS Diseases."Hum Gene Ther. Jul. 2016;27(7):478-96. (Year: 2016).*

Kotterman et al. "Antibody neutralization poses a barrier to intravitreal adeno-associated viral vector gene delivery to non-human primates." Gene Ther.Feb. 2015;22(2):116-26. (Year: 2015).*

GenBank LX309664, dated Oct. 28, 2017, 2 pages.

GenBank LX309667, dated Oct. 28, 2017, 2 pages.

GenBank LX309670, dated Oct. 28, 2017,2 pages.

Allocca et al., "Novel Adeno-Associated Virus Serotypes Efficiently Transduce Murine Photoreceptors," J Viol 81(20):11372-11380 (2007).

Bainbridge et al., "Effect of gene therapy on visual function in Leber's congenital amaurosis," N Engl J Med. 358(21):2231-2239 (2008).

Bonnet, Crystel et al. The optimized allotopic expression of ND1 or ND4 genes restores respiratory chain complex I activity in fibroblasts harboring mutations in these genes Biochimica et Biophysica Acta 31 No. 10(1783):1707-1717 (2008).

Choi et al., "AAV hybrid serotypes: improved vectors for gene delivery," Curr Gene Ther. 5(3):299-310 (2005).

Coura, et al. "The state of the art of adeno-associated virus-based vectors in gene therapy." Virol J. Oct. 16, 2007;4:99, pp. 1-7. doi: 10.1186/1743-422X-4-99.

Cronin, et al., "Functional Genomics Study of the RdCVF-/- Mouse Model", Investigative Ophthalmology & Visual Science, vol. 49, No. 3058, 2008, D1048, 2 pages.

Cwerman-Thibault. et al. "Nuclear Expression of Mitochondrial Nd4 Leads to the Protein Assembling in Complex I and Prevents Optic Atrophy and Visual Loss," Molecular Therapy-Methods & Clinical Development. 2(15003):1-15 (2015).

Devereux et al., "A comprehensive set of sequence analysis programs for the VAX," Nucleic Acids Research 12, 387-395 (1984).

Gao et al., "Comparison of Immunosuppressive Effects and ND4 Expression among Different Immunosuppressive Strategies following AAV2-ND4 Gene Treatment for Leber Hereditary Optic Neuropathy," Acta Medicinae Universitatis Scientiae et Technologiae Huazhong 42(2):187-191 (2013).

Greenwood et al. "Current research into brain barriers and the delivery of therapeutics for neurological diseases: a report on CNS barrier congress London, UK, 2017." Fluids Barriers CNS. 2017; 14: 31 (2017).

Gregoriadis. "Liposomes." Drug Carriers in Biology and Medicine. Chapter 14: pp. 2.sup. 287-341 (Academic Press, 1979).

Guy, et al. "Gene Therapy for Leber Hereditary Optic Neuropathy: Low- and Medium-Dose Visual Results." Ophthalmology. Nov. 2017;124(11):1621-1634. doi: 10.1016/j.ophtha.2017.05.016.

Hocquemiller et al. "Adena-Associated Virus-Based Gene Therapy for CNS Diseases." Hum Gene Ther. Jul. 1, 2016; 27(7): 478-496 (2016).

International Search Report and Written Opinion issued by the International Searching Authority for Application No. PCT/CN2018/095023, dated Apr. 9, 2019, 14 pages including English translation of ISR.

International Search Report and Written Opinion issued by the International Searching Authority for Application No. PCT/CN2018/103937, dated Apr. 3, 2019, 19 pages including English translation of Search Report.

International Search Report and Written Opinion issued by the International Searching Authority for Application No. PCT/CN2018/113799, dated Aug. 5, 2019, 15 pages including English translation of Search Report.

International Search Report and Written Opinion issued by the International Searching Authority for Application No. PCT/CN2018/118662, dated Jul. 18, 2019, 18 pages including English translation of ISR.

International Search Report and Written Opinion issued by the International Searching Authority for Application No. PCT/CN2019/070461, dated May 22, 2019, 13 pages including translation of ISR.

International Search Report and Written Opinion issued by the International Searching Authority for Application No. PCT/CN2019/094136, dated Oct. 10, 2019, 10 pages.

International Search Report and Written Opinion issued by the International Searching Authority for Application No. PCT/CN2019/101538, dated Nov. 29, 2019, 14 pages.

Karlin, S. and Altschul, S., "Applications and statistics for multiple high-scoring segments in molecular sequences," Proc. Natl. Acad. Sci. USA, 90-5873-5877 (1993).

Kim, et al. "Preparation of multilamellar vesicles of defined size-distribution by solvent-spherule evaporation." Biochim Biophys Acta. Feb. 14, 1985;812(3):793-801. doi: 10.1016/0005-2736(85)90274-3.

Koilkonda, R. D. et al. "Safety and Effects of the Vector for the Leber Hereditary Optic Neuropathy Gene Therapy Clinical Trial." JAMA Ophthalmol. 132(4):409-420 (2014).

Kotterman et al. "Antibody Neutralization Poses a Barrier to Intravitreal Adena-Associated Viral Vector Gene Delivery to Non-Human Primates." Gene Ther. Feb. 2015; 22(2): 116-126. (Year: 2015).

Kushnareva et al., "Mitochondrial Dysfunction in an Op1 $^{Q285TOP}$ Mouse Model of Dominant Optic Atrophy Results from Opal1 Haploinsufficiency," Cell Death and Disease Jul. 7, 2016(7):e-2309, 13 pages.

Laughlin et al., "Spliced adenovirus-associated virus RNA.," PNAS, 76:5567-5571 (1979).

Mancuso et al., "Gene therapy for red-green colour blindness in adult primates," Nature 461:784-787 (2009).

NCBI Gene ID: 4535. MT-ND1 mitochondrially encoded NADH dehydrogenase 1 [ *Homo sapiens* (human) ]. Updated on Apr. 20, 2021, 8 pages.

NCBI Gene ID: 4538. "MT-ND4 mitochondrially encoded NADH dehydrogenase 4 [ *Homo sapiens* (human) ]." Updated on Apr. 20, 2021, 8 pages.

NCBI Gene ID: 4541. "MT-ND6 mitochondrially encoded NADH dehydrogenase 6 [ *Homo sapiens* (human) ]," Updated on Apr. 20, 2021, 7 pages.

NCBI Reference Sequence: NC_001829.1, dated Aug. 13, 2018, 3 pages.

(56) References Cited

OTHER PUBLICATIONS

NCBI Reference Sequence: NC_002077.1, dated Aug. 13, 2018, 3 pages.
NCBI Reference Sequence: NC_001729.1, dated Aug. 13, 2018, 3 pages.
NCBI Reference Sequence: NC_004828.1 Aug. 13, 2018, 3 pages.
NCBI Reference Sequence: NC_005889.1 Aug. 13, 2018, 3 pages.
NCBI. "Genbank Accession No. KP240659.1" GenBank, Dec. 4, 2016 (Dec. 4, 2016), 8 pages.
NCBI. "Genbank Accession No. LX309664.1" GenBank, Oct. 28, 2017 (Oct. 28, 2017).
NCBI. "Genbank Accession No. LX309670.1" GenBank, Oct. 28, 2017 (Oct. 28, 2017), 2 pages.
NCBI. "Genbank Accession No. MF522909.1" GenBank, Oct. 21, 2017 (Oct. 21, 2017), 8 pages.
NCBI. "Genbank Accession No. YP_003024026.1" GenBank, Oct. 31, 2014 (Oct. 31, 2014), 2 pages.
Ribera et al. "Biochemical, histological and functional correction of mucopolysaccharidosis type 1118 by intra-cerebrospinal fluid gen therapy" Hum Mol Genet Apr. 1, 2015;24(7):2078-95. (Year: 2015).
Sun et al., "Detection of Neutralizing Antibody to Human Adenovirus Type 5 in Marmosets," J. South Med. Univ., 36(4):582-587 (2016).
Szoka et al., "Procedure for preparation of liposomes with large internal aqueous space and high capture by reverse-phase evaporation," Proc. Natl Acad. Sci. USA 75: 4194-4198 (1978).
Vignal, et al. "Safety of rAAV2/2-ND4 Gene Therapy for Leber Hereditary Optic Neuropathy." Ophthalmology. Jun. 2018;125(6):945-947. doi: 10.1016/j.ophtha.2017.12.036.
Wan et al., "Efficacy and Safety of rAAV2-ND4 Treatment for Leber's Hereditary Optic Neuropathy," Scientific Reports, vol. 6, Article 21587, pp. 1-10 (2016).
Wu et al., "Adeno-associated virus serotypes: vector toolkit for human gene therapy," Molecular Therapy. 14(3):316-327 (2006).
Yang et al., "Long-Term Outcomes of Gene Therapy for the Treatment of Leber's Hereditary Optic Neuropathy," EBIOMEDICINE 10:258-268 (2016).
Yang et al., "Study on transfection of adeno associated virus 2-ND4 gene into mitochondria," Chinese Journal of Experimental Ophthalmology 8(32):693-695 (2014).
Yang, S. et al. "Chemical and material communication between the optic nerves in rats," Clinical and Experimental Ophthalmology 43:742-748 (2015).
Yang, Y, Codon and Anticodon, Foreign Medical Molecular Biology Fascicule 7(4): 156-163 (1985). (English translation included).
Yu et al. "Mutant NADH dehydrogenase subunit 4 gene delivery to mitochondria by targeting sequence-modified adeno-associated virus induces visual loss and optic atrophy in mice," Molecular Vision 18:1668-1683 (2012).
Yu et al., "Gene delivery to mitochondria by targeting modified adenoassociated virus suppresses Leber's hereditary optic neuropathy in a mouse model," PNAS, pp. EI238-EI247 (2012).
Cross et al., "Characterization of Adsorption of Adeno-Associated Virus to Commonly Used Catheter Materials: AAV2 vs. AAV1/2", Molecular Therapy, No. 512 (2006).
Croyle et al., "Development of formulations that enhance physical stability of viral vectors for gene therapy," Gene Therapy 8: 1281-1290 (2001).
Daya S, Berns KI. Gene therapy using adeno-associated virus vectors. Clinical microbiology reviews. Oct. 2008;21(4):583-93. (Year: 2008).
Entezari et al., "High-dose intravenous methylprednisolone in recent traumatic optic neuropathy; a randomized double-masked placebo-controlled clinical trial." Graefe's Archive for Clinical and Experimental Ophthalmology vol. 245, pp. 1267-1271 (2007) (Year: 2007).
Fumoto, S. et al., "Targeted Gene Delivery: Importance of Administration Routes," Intech, Chapter 1:3-31 (2013).
Glerum DM, Tzagoloff A. Isolation of a human cDNA for heme A: farnesyltransferase by functional complementation of a yeast cox10 mutant. Proceedings of the National Academy of Sciences. Aug. 30, 1994;91(18):8452-6. (Year: 1994).
Guidance on nonclinical safety studies for the conduct of human clinical trials and marketing authorization for pharmaceuticals. ICH/M3 (R2), 26 pages (2009).
Guy J, Qi X, Koilkonda RD, Arguello T, Chou TH, Ruggeri M, Porciatti V, Lewin AS, Hauswirth WW. Efficiency and safety of AAV-mediated gene delivery of the human ND4 complex I subunit in the mouse visual system. Investigative ophthalmology & visual science. Sep. 1, 2009;50(9):4205-14. (Year: 2009).
Kattenhorn et al., Adeno-Associated Virus Gene Therapy for Liver Disease, 2016, Human Gene Therapy, vol. 27 No. 12, pp. 947-961 (Year: 2016).
Mingozzi et al. "Immune responses to AAV vectors: overcoming barriers to successful gene therapy" Blood, 122 (1):23-36 (2013).
Newman NJ. Treatment of hereditary optic neuropathies. Nature Reviews Neurology. Oct. 2012;8(10):545-56. (Year: 2012).
Patel et al., "Poloxamers: A pharmaceutical excipients with therapeutic behaviors," International Journal of PharmTech Research 1(2):299-303 (2009).
Perrin S. Preclinical research: Make mouse studies work. Nature News. Mar. 27, 2014;507(7493):423. (Year: 2014).
Sequence alignment SEQ ID No. 10 of 17181849 and SEQ ID No. 19870 of 15174219; US20160289674A1 Publ: Oct. 6, 2016. Alignment Aug. 2021 (Year: 2016), 4 pages.
Sequence alignment SEQ ID No. 12 of 17181849 and SEQ ID No. 19864 of 15174219; US20160289674A1 Publ: Oct. 6, 2016. Alignment Aug. 2021 (Year: 2016), 5 pages.
Yuan et al., "Preliminary clinical observation of creatine phosphate sodium treatment for Leber hereditary optic neuropathy." Mar. 2017 Ophthalmology in China 26(2):126-130 (Year: 2017).

* cited by examiner rAAV2-ND4 rAAV2-opt_ND4 rAAV2-ND4 rAAV2-opt_ND4*

A B C

COMPOSITIONS AND METHODS FOR TREATING LEBER'S HEREDITARY OPTIC NEUROPATHY

CROSS-REFERENCE

This application is a divisional application of U.S. patent application Ser. No. 16/836,644, filed Mar. 31, 2020, which is a continuation application of PCT Application No. PCT/CN2019/094136, filed Jul. 1, 2019, which claims the benefit of PCT Application No. PCT/CN2018/095023, filed on Jul. 9, 2018; PCT Application No. PCT/CN2018/103937, filed on Sep. 4, 2018; Chinese Application Nos. CN201810703168.7 and CN201810702492.7, both filed on Jun. 29, 2018; PCT Application No. PCT/CN2018/113799, filed on Nov. 2, 2018; Chinese Application No. CN201811230856.2, filed on Oct. 22, 2018; PCT Application No. PCT/CN2018/118662, filed on Nov. 30, 2018; Chinese Application No. CN201811221305.X, filed on Oct. 19, 2018; PCT Application No. PCT/CN2019/070461, filed on Jan. 4, 2019; Chinese Application No. CN201810948193.1, filed on Aug. 20, 2018; all of which are incorporated herein by reference in their entirety.

REFERENCE TO A SEQUENCE LISTING

The instant application contains a Sequence Listing which has been submitted in ASCII format via EFS-Web and is hereby incorporated by reference in its entirety. Said ASCII copy, created on May 13, 2021, is named WNBT_002_04US_SeqList_ST25.txt and is about 297 kilobytes in size.

BACKGROUND OF THE INVENTION

Leber's hereditary optic neuropathy (LHON) is a mitochondrially inherited (transmitted from mother to offspring) degeneration of retinal ganglion cells (RGCs) and their axons that leads to an acute or subacute loss of central vision; this affects predominantly young adult males. LHON is only transmitted through the mother, as it is primarily due to mutations in the mitochondrial (not nuclear) genome, and only the egg contributes mitochondria to the embryo. LHON is usually due to one of three pathogenic mitochondrial DNA (mtDNA) point mutations. These mutations are at nucleotide positions 11778 G to A (G11778A), 3460 G to A (G3460A) and 14484 T to C (T14484C), respectively in the NADH dehydrogenase subunit-4 protein (ND4), NADH dehydrogenase subunit-1 protein (ND1) and NADH dehydrogenase subunit-6 protein (ND6) subunit genes of complex I of the oxidative phosphorylation chain in mitochondria. Each mutation is believed to have significant risk of permanent loss of vision. It typically progresses within several weeks to several months without pain, until the binocular vision deteriorate to below 0.1, which seriously affects the quality of life of the patient. Two LHON mutants, G3460A and T14484C, results in the reduction of the patient's platelets isolated mitochondrial NADH dehydrogenase activity by 80%. Ninety percent of the Chinese LHON patients carry the G11778A mutation. The G11778A mutation changes an arginine into histidine in the ND4 protein, resulting the dysfunction and optic nerve damage in LHON patients. There is a need for developing compositions and methods for treating LHON with higher transfection efficiency and treatment efficacy.

SUMMARY OF THE INVENTION

Disclosed here recombinant nucleic acids, pharmaceutical compositions, and methods for treating LHON. In one aspect, disclosed herein is a recombinant nucleic acid, comprising: a mitochondrial targeting sequence; a mitochondrial protein coding sequence comprising a sequence that is at least 99% identical to a sequence selected from the group consisting of SEQ ID NO: 7, 8, 10, and 12; and a 3'UTR nucleic acid sequence.

In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising: a mitochondrial targeting sequence comprising a sequence that is at least 90% identical to a sequence selected from the group consisting of SEQ ID NO: 2, 3, 4, and 5; a mitochondrial protein coding sequence, wherein the mitochondrial protein coding sequence encodes a polypeptide comprising a mitochondrial protein; and a 3'UTR nucleic acid sequence.

In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein is selected from a group consisting of NADH dehydrogenase 4 (ND4), NADH dehydrogenase 6 (ND6), NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90%, at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-84.

In another aspect, disclosed herein is a recombinant nucleic acid, comprising: a mitochondrial targeting sequence; a mitochondrial protein coding sequence comprising a sequence that is at least 90%, at least 95%, at least 97%, at least 99%, or 100% identical to a sequence selected from the group consisting of SEQ ID NO: 7, 8, 10, and 12; and a 3'UTR nucleic acid sequence.

In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATP5G3, crATP6_hsADCK3, ncATP9_ncATP9, zmLOC100282174, ncATP9_zmLOC-100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100-282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2 or 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising a mitochondrial targeting sequence that is at least 90%, at least 95%, at least 97%, at least 99%, or 100% identical to a sequence selected from the group consisting of SEQ ID NO: 2, 3, and 4. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4.

In some cases, the recombinant nucleic acid further comprises a mitochondrial protein coding sequence, wherein the mitochondrial protein coding sequence encodes a polypeptide comprising a mitochondrial protein. In some cases, the mitochondrial protein is selected from a group consisting of NADH dehydrogenase 4 (ND4), NADH dehydrogenase 6 (ND6), NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90%, at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the recombinant nucleic acid further comprises a 3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-70.

In another aspect, disclosed herein is a recombinant nucleic acid, comprising a mitochondrial protein coding sequence, wherein the mitochondrial protein coding sequence encodes a polypeptide comprising a mitochondrial protein, wherein the mitochondrial protein coding sequence comprises a sequence that is at least 90%, at least 95%, at least 97%, at least 99%, or 100% identical to a sequence selected from the group consisting of SEQ ID NO: 7, 8, 10, and 12.

In some cases, the recombinant nucleic acid further comprises a mitochondrial targeting sequence. In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the recombinant nucleic acid further comprises a 3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a viral vector comprising the recombinant nucleic acid disclosed herein. In some cases, the viral vector is an adeno-associated virus (AAV) vector. In some cases, the AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors. In some cases, the AAV vector is a recombinant AAV (rAAV) vector. In some cases, the rAAV vector is rAAV2 vector.

In another aspect, disclosed herein is a pharmaceutical composition, comprising an adeno-associated virus (AAV) comprising any recombinant nucleic acid disclosed herein. In some cases, the pharmaceutical composition further comprises a pharmaceutically acceptable excipient thereof. Also disclosed is a pharmaceutical composition, comprising the viral vector disclosed herein, and a pharmaceutically acceptable excipient thereof, wherein the viral vector comprises any recombinant nucleic acid disclosed herein. Also disclosed is a pharmaceutical composition, comprising: an adeno-associated virus (AAV) comprising any recombinant nucleic acid disclosed herein, wherein the recombinant nucleic acid comprises a sequence that is at least 90%, at least 95%, at least 97%, at least 99%, or 100% identical to a sequence as set forth in SEQ ID NO: 15; and a pharmaceutically acceptable excipient.

In some cases, the pharmaceutically acceptable excipient comprises phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof. In some cases, the pharmaceutically acceptable excipient is selected from phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, and any combination thereof. In some cases, the pharmaceutically acceptable excipient comprises poloxamer 188. In some cases, the pharmaceutically acceptable excipient comprises 0.0001%-0.01% poloxamer 188. In some cases, the pharmaceutically acceptable excipient comprises 0.001% poloxamer 188. In some cases, the pharmaceutically acceptable excipient further comprises one or more salts. In some cases, the one or more salts comprises NaCl, $NaH_2PO_4$, $Na_2HPO_4$, and $KH_2PO_4$. In some cases, the one or more salts comprises 80 mM NaCl, 5 mM $NaH_2PO_4$, 40 mM $Na_2HPO_4$, and 5 mM $KH_2PO_4$. In some cases, the pharmaceutical composition has a pH of 6-8. In some cases, the pharmaceutical composition has a pH of 7.2-7.4. In some cases, the pharmaceutical composition has a pH of 7.3. In some cases, the pharmaceutical composition has a viral titer of at least $1.0\times10^{10}$ vg/mL. In some cases, the pharmaceutical composition has a viral titer of at least $5.0\times10^{10}$ vg/mL.

In some cases, the pharmaceutical composition is subject to five freeze/thaw cycles, the pharmaceutical composition retains at least 60%, 70%, 80%, or 90% of a viral titer as compared to the viral titer prior to the five freeze/thaw cycles. In some cases, the pharmaceutical composition, when administered to a patient with Leber's hereditary optic neuropathy, generates a higher average recovery of vision than a comparable pharmaceutical composition without the recombinant nucleic acid. In some cases, the pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

In another aspect, disclosed herein is a method of treating an eye disorder, comprising administering any pharmaceutical composition disclosed herein to a patient in need thereof. In some cases, the eye disorder is Leber's hereditary optic neuropathy (LHON). In some cases, the method comprises administering the pharmaceutical composition to one or both eyes of the patient. In some cases, the pharmaceutical composition is administered via intraocular or intravitreal injection. In some cases, the pharmaceutical composition is administered via intravitreal injection. In some cases, about 0.01-0.1 mL of the pharmaceutical composition is administered via intravitreal injection. In some cases, about 0.05 mL of the pharmaceutical composition is administered via intravitreal injection.

In some cases, the method further comprises administering methylprednisolone to the patient. In some cases, the methylprednisolone is administered prior to the intravitreal injection of the pharmaceutical composition. In some cases, the methylprednisolone is administered orally In some cases, the methylprednisolone is administered daily for at least 1, 2, 3, 4, 5, 6, or 7 days prior to the intravitreal injection of the pharmaceutical composition. In some cases, the methylprednisolone is administered daily. In some cases, the a daily dosage of about 32 mg/60 kg methylprednisolone is administered. In some cases, the methylprednisolone is administered after the intravitreal injection of the pharmaceutical composition. In some cases, the method further comprises administering creatine phosphate sodium to the patient. In some cases, the creatine phosphate sodium is administered intravenously. In some cases, the methylprednisolone is administered intravenously or orally. In some cases, the method comprises administering methylprednisolone intravenously for at least one day, which is followed by administering methylprednisolone orally for at least a week. In some cases, the method comprises administering methylprednisolone intravenously for about 3 days, which is followed by administering methylprednisolone orally for at least about 6 weeks. In some cases, the methylprednisolone is administered intravenously at a daily dose of about 80 mg/60 kg. In some cases, the administering the pharmaceutical composition generates a higher average recovery of vision than a comparable pharmaceutical composition without the recombinant nucleic acid. In some cases, the administering the pharmaceutical composition generates a higher average recovery of vision than a comparable pharmaceutical composition comprising a recombinant nucleic acid as set forth in SEQ ID NO: 15.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
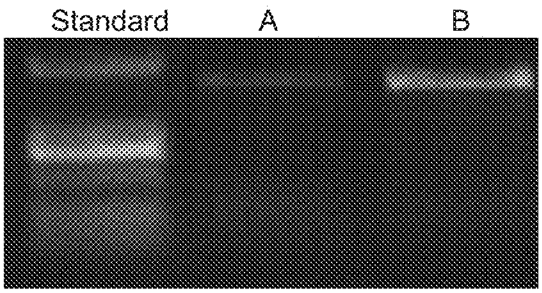
FIG. 1 shows the PCR nucleic acid electrophoresis verification of ND4 (lane A) and optimized ND4 (lane B) gene cloning results.

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth.

As used herein, unless otherwise indicated, the term "or" can be conjunctive or disjunctive. As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "subject" refers to a mammal that has been or will be the object of treatment, observation or experiment. The term "mammal" is intended to have its standard meaning, and encompasses humans, dogs, cats, sheep, and cows, for example. The methods described herein can be useful in both human therapy and veterinary applications. In some embodiments, the subject is a human.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

The term “therapeutically effective amount” of a chemical entity described herein refers to an amount effective, when administered to a human or non-human subject, to provide a therapeutic benefit such as amelioration of symptoms, slowing of disease progression, or prevention of disease.

As used herein, unless otherwise indicated, the terms “nucleic acid” and “polynucleotide” can be used interchangeably.

Nucleic Acid and Polypeptide Sequences

Table 1 discloses all the nucleic acid and polypeptide sequences disclosed herein. The first column shows the SEQ ID NO of each sequence. The second column describes the nucleic acid or polypeptide construct. For example, the construct COX10-ND6-3'UTR is a nucleic acid combining the nucleic acid sequences of COX10 (SEQ ID NO: 1), ND6 (SEQ ID NO: 9), and 3'UTR (SEQ ID NO: 13) (from 5' to 3' without linker between the nucleic acid sequences.

TABLE 1 nucleic acid and polypeptide sequences and SEQ ID NOs

| SEQ | description | sequence |
|---|---|---|
| 1 | COX10 | ATGGCCGCATCTCCGCACACTCTCTCCTCACGCCTCCTGACAGGTTGCGTAGGAGGCTCTGTCTGGT<br>ATCTTGAAAGAAGAACT |
| 2 | opt_COX10 | ATGGCCGCCTCTCCACACACACTGAGTAGCAGACTGCTGACCGGCTGTGTTGGCGGCTCTGTGTGGT<br>ATCTGGAACGGCGGACA |
| 3 | opt_COX10* | ATGGCCGCCAGCCCCCACACCCTGAGCAGCCGCCTGCTGACCGGCTGCGTGGGCGGCAGCGTGTG<br>GTACCTGGAGCGCCGCACC |
| 4 | COX3 | ATGTCCGTCCTGACGCGCCTGCTGCTGCGGGGCTTGACACGGCTCGGCTCGGCGGCTCCAGTGCGG<br>CGCGCCAGAATCCATTCGTTG |
| 5 | OPA1 | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTG |
| 6 | ND4 | ATGCTAAAACTAATCGTCCCAACAATTATGTTACTACCACTGACATGGCTTTCCAAAAAACACATGATTT<br>GGATCAACACAACCACCCACAGCCTAATTATTAGCATCATCCCTCTACTATTTTTTAACCAAATCAACAA<br>CAACCTATTTAGCTGTTCCCCAACCTTTTCCTCCGACCCCCTAACAACCCCCCTCCTAATGCTAACTAC<br>CTGGCTCCTACCCCTCACAATCATGGCAAGCCAACGCCACTTATCCAGTGAACCACTATCACGAAAAA<br>AACTCTACCTCTCTATGCTAATCTCCCTACAAATCTCCTTAATTATGACATTCACAGCCACAGAACTAAT<br>CATGTTTTATATCTTCTTCGAAACCACACTTATCCCCACCTTGGCTATCATCACCCGATGGGGCAACCA<br>GCCAGAACGCCTGAACGCAGGCACATACTTCCTATTCTACACCCTAGTAGGCTCCCTTCCCCTACTCA<br>TCGCACTAATTTACACTCACAACACCCTAGGCTCACTAAACATTCTACTACTCACTCTCACTGCCCAAG<br>AACTATCAAACTCCTGGGCCAACAACTTAATGTGGCTAGCTTACACAATGGCTTTTATGGTAAAGATGC<br>CTCTTTACGGACTCCACTTATGGCTCCCTAAAGCCCATGTCGAAGCCCCCATCGCTGGGTCAATGGTA<br>CTTGCCGCAGTACTCTTAAAACTAGGCGGCTATGGTATGATGCGCCTCACACTCATTCTCAACCCCCT<br>GACAAAACACATGGCCTACCCCTTCCTTGTACTATCCCTATGGGGCATGATTATGACAAGCTCCATCTG<br>CCTACGACAAACAGACCTAAAATCGCTCATTGCATACTCTTCAATCAGCCACATGGCCCTCGTAGTAAC<br>AGCCATTCTCATCCAAACCCCCTGGAGCTTCACCGGCGCAGTCATTCTCATGATCGCCCACGGGCTTA<br>CATCCTCATTACTATTCTGCCTAGCAAACTCAAACTACGAACGCACTCACAGTCGCATCATGATCCTCT<br>CTCAAGGACTTCAAACTCTACTCCCACTAATGGCTTTTTGGTGGCTTCTAGCAAGCCTCGCTAACCTCG<br>CCTTACCCCCCACTATTAACCTACTGGGAGAACTCTCTGTGCTAGTAACCACGTTCTCCTGGTCAAATA<br>TCACTCTCCTACTTACAGGACTCAACATGCTAGTCACAGCCCTATACTCCCTCTACATGTTTACCACAA<br>CACAATGGGGCTCACTCACCCACCACATTAACAACATGAAACCCTCATTCACACGAGAAAACACCCTC<br>ATGTTCATGCACCTATCCCCCATTCTCCTCCTATCCCTCAACCCCGACATCATTACCGGGTTTTCCTCT<br>TAA |
| 7 | opt_ND4 | ATGCTGAAGCTGATCGTGCCCACCATCATGCTGCTGCCTCTGACCTGGCTGAGCAAGAAACACATGAT<br>CTGGATCAACACCACCACGCACAGCCTGATCATCAGCATCATCCCTCTGCTGTTCTTCAACCAGATCA<br>ACAACAACCTGTTCAGCTGCAGCCCCACCTTCAGCAGCGACCCTCTGACAACACCTCTGCTGATGCTG<br>ACCACCTGGCTGCTGCCCCTCACAATCATGGCCTCTCAGAGACACCTGAGCAGCGAGCCCCTGAGCC<br>GGAAGAAACTGTACCTGAGCATGCTGATCTCCCTGCAGATCTCTCTGATCATGACCTTCACCGCCACC<br>GAGCTGATCATGTTCTACATCTTTTTCGAGACAACGCTGATCCCCACACTGGCCATCATCACCAGATG<br>GGGCAACCAGCCTGAGAGACTGAACGCCGGCACCTACTTTCTGTTCTACACCCTCGTGGGCAGCCTG<br>CCACTGCTGATTGCCCTGATCTACACCCACAACACCCTGGGCTCCCTGAACATCCTGCTGCTGACACT<br>GACAGCCCAAGAGCTGAGCAACAGCTGGGCCAACAATCTGATGTGGCTGGCCTACACAATGGCCTTC<br>ATGGTCAAGATGCCCCTGTACGGCCTGCACCTGTGGCTGCCTAAAGCTCATGTGGAAGCCCCTATCG<br>CCGGCTCTATGGTGCTGGCTGCAGTGCTGCTGAAACTCGGCGGCTACGGCATGATGCGGCTGACCCT<br>GATTCTGAATCCCCTGACCAAGCACATGGCCTATCCATTTCTGGTGCTGAGCCTGTGGGGCATGATTA<br>TGACCAGCAGCATCTGCCTGCGGCAGACCGATCTGAAGTCCCTGATCGCCTACAGCTCCATCAGCCA<br>CATGGCCCTGGTGGTCACCGCCATCCTGATTCAGACCCCTTGGAGCTTTACAGGCGCCGTGATCCTG<br>ATGATTGCCCACGGCCTGACAAGCAGCCTGCTGTTTTGTCTGGCCAACAGCAACTACGAGCGGACCC<br>ACAGCAGAATCATGATCCTGTCTCAGGGCCTGCAGACCCTCCTGCCTCTTATGGCTTTTTGGTGGCTG<br>CTGGCCTCTCTGGCCAATCTGGCACTGCCTCCTACCATCAATCTGCTGGGCGAGCTGAGCGTGCTGG<br>TCACCACATTCAGCTGGTCCAATATCACCCTGCTGCTCACCGGCCTGAACATGCTGGTTACAGCCCTG<br>TACTCCCTGTACATGTTCACCACCACACAGTGGGGAAGCCTGACACACCACATCAACAATATGAAGCC<br>CAGCTTCACCCGCGAGAACACCCTGATGTTCATGCATCTGAGCCCCATTCTGCTGCTGTCCCTGAATC<br>CTGATATCATCACCGGCTTCTCCAGCTGA |
| 8 | opt_ND4* | ATGCTGAAGCTGATCGTGCCCACCATCATGCTGCTGCCCCTGACCTGGCTGAGCAAGAAGCACATGA<br>TCTGGATCAACACCACCACCCACAGCCTGATCATCAGCATCATCCCCCTGCTGTTCTTCAACCAGATC<br>AACAACAACCTGTTCAGCTGCAGCCCCACCTTCAGCAGCGACCCCCTGACCACCCCCCTGCTGATGC<br>TGACCACCTGGCTGCTGCCCCTGACCATCATGGCCAGCCAGCGCCACCTGAGCAGCGAGCCCCTGA<br>GCCGCAAGAAGCTGTACCTGAGCATGCTGATCAGCCTGCAGATCAGCCTGATCATGACCTTCACCGC<br>CACCGAGCTGATCATGTTCTACATCTTCTTCGAGACCACCCTGATCCCCACCCTGGCCATCATCACCC<br>GCTGGGGCAACCAGCCCGAGCGCCTGAACGCCGGCACCTACTTCCTGTTCTACACCCTGGTGGGCA<br>GCCTGCCCCTGCTGATCGCCCTGATCTACACCCACAACACCCTGGGCAGCCTGAACATCCTGCTGCT |

TABLE 1-continued nucleic acid and polypeptide sequences and SEQ ID NOs

| SEQ | description | sequence |
|---|---|---|
| | | GACCCTGACCGCCCAGGAGCTGAGCAACAGCTGGGCCAACAACCTGATGTGGCTGGCCTACACCAT<br>GGCCTTCATGGTGAAGATGCCCCTGTACGGCCTGCACCTGTGGCTGCCCAAGGCCCACGTGGAGGC<br>CCCCATCGCCGGCAGCATGGTGCTGGCCGCCGTGCTGCTGAAGCTGGGCGGCTACGGCATGATGCG<br>CCTGACCCTGATCCTGAACCCCCTGACCAAGCACATGGCCTACCCCTTCCTGGTGCTGAGCCTGTGG<br>GGCATGATCATGACCAGCAGCATCTGCCTGCGCCAGACCGACCTGAAGAGCCTGATCGCCTACAGCA<br>GCATCAGCCACATGGCCCTGGTGGTGACCGCCATCCTGATCCAGACCCCCTGGAGCTTCACCGGCG<br>CCGTGATCCTGATGATCGCCCACGGCCTGACCAGCAGCCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA<br>TCAACAACATGAAGCCCAGCTTCACCCGCGAGAACACCCTGATGTTCATGCACCTGAGCCCCATCCTG<br>CTGCTGAGCCTGAACCCCGACATCATCACCGGCTTCAGCAGCTAA |
| 9 | ND6 | ATGATGTATGCTTTGTTTCTGTTGAGTGTGGGTTTAGTAATGGGGTTTGTGGGGTTTTCTTCTAAGCCT<br>TCTCCTATTTATGGGGGTTTAGTATTGATTGTTAGCGGTGTGGTCGGGTGTGTTATTATTCTGAATTTTG<br>GGGGAGGTTATATGGGTTTAATGGTTTTTTTAATTTATTTAGGGGGAATGATGGTTGTCTTTGGATATAC<br>TACAGCGATGGCTATTGAGGAGTATCCTGAGGCATGGGGGTCAGGGGTTGAGGTCTTGGTGAGTGTT<br>TTAGTGGGGTTAGCGATGGAGGTAGGATTGGTGCTGTGGGTGAAAGAGTATGATGGGGTGGTGGTTG<br>TGGTAAACTTTAATAGTGTAGGAAGCTGGATGATTTATGAAGGAGAGGGGTCAGGGTTGATTCGGGAG<br>GATCCTATTGGTGCGGGGGCTTTGTATGATTATGGGCGTTGGTTAGTAGTAGTTACTGGTTGGACATT<br>GTTTGTTGGTGTATATATTGTAATTGAGATTGCTCGGGGGAATTAG |
| 10 | opt_ND6 | ATGATGTACGCCCTGTTCCTGCTGAGCGTGGGCCTGGTGATGGGCTTCGTGGGCTTCAGCAGCAAGC<br>CCAGCCCCATCTACGGCGGCCTGGTGCTGATCGTGAGCGGCGTGGTGGGCTGCGTGATCATCCTGA<br>ACTTCGGCGGCGGCTACATGGGCCTGATGGTGTTCCTGATCTACCTGGGCGGCATGATGGTGGTGTT<br>CGGCTACACCACCGCCATGGCCATCGAGGAGTACCCCGAGGCCTGGGGCAGCGGCGTGGAGGTGC<br>TGGTGAGCGTGCTGGTGGGCCTGGCCATGGAGGTGGGCCTGGTGCTGTGGGTGAAGGAGTACGACG<br>GCGTGGTGGTGGTGGTGAACTTCAACAGCGTGGGCAGCTGGATGATCTACGAGGGCGAGGGCAGCG<br>GCCTGATCCGCGAGGACCCCATCGGCGCCGGCGCCCTGTACGACTACGGCCGCTGGCTGGTGGTG<br>GTGACCGGCTGGACCCTGTTCGTGGGCGTGTACATCGTGATCGAGATCGCCCGCGGCAACTAA |
| 11 | ND1 | ATGGCCAACCTCCTACTCCTCATTGTACCCATTCTAATCGCAATGGCATTCCTAATGCTTACCGAACGA<br>AAAATTCTAGGCTATATGCAACTACGCAAAGGCCCCAACGTTGTAGGCCCCTACGGGCTACTACAACC<br>CTTCGCTGACGCCATAAAACTCTTCACCAAAGAGCCCCTAAAACCCGCCACATCTACCATCACCCTCT<br>ACATCACCGCCCCGACCTTAGCTCTCACCATCGCTCTTCTACTATGGACCCCCCTCCCCATGCCCAAC<br>CCCCTGGTCAACCTCAACCTAGGCCTCCTATTTATTCTAGCCACCTCTAGCCTAGCCGTTTACTCAATC<br>CTCTGGTCAGGGTGGGCATCAAACTCAAACTACGCCCTGATCGGCGCACTGCGAGCAGTAGCCCAAA<br>CAATCTCATATGAAGTCACCCTAGCCATCATTCTACTATCAACATTACTAATGAGTGGCTCCTTWACCT<br>CTCCACCCTTATCACAACACAAGAACACCTCTGGTTACTCCTGCCATCATGGCCCTTGGCCATGATGT<br>GGTTTATCTCCACACTAGCAGAGACCAACCGAACCCCCTTCGACCTTGCCGAAGGGGAGTCCGAACT<br>AGTCTCAGGCTTCAACATCGAATACGCCGCAGGCCCCTTCGCCCTATTCTTCATGGCCGAATACACAA<br>ACATTATTATGATGAACACCCTCACCACTACAATCTTCCTAGGAACAACATATGACGCACTCTCCCCTG<br>AACTCTACACAACATATTTTGTCACCAAGACCCTACTTCTAACCTCCCTGTTCTTATGGATTCGAACAGC<br>ATACCCCCGATTCCGCTACGACCAACTCATGCACCTCCTATGGAAAAACTTCCTACCACTCACCCTAG<br>CATTACTTATGTGGTATGTCTCCATGCCCATTACAATCTCCAGCATTCCCCCTCAAACCTAA |
| 12 | opt_ND1 | ATGGCCAACCTGCTGCTGCTGATCGTGCCCATCCTGATCGCCATGGCCTTCCTGATGCTGACCGAGC<br>GCAAGATCCTGGGCTACATGCAGCTGCGCAAGGGCCCCAACGTGGTGGGCCCCTACGGCCTGCTGC<br>AGCCCTTCGCCGACGCCATCAAGCTGTTCACCAAGGAGCCCCTGAAGCCCGCCACCAGCACCATCAC<br>CCTGTACATCACCGCCCCCACCCTGGCCCTGACCATCGCCCTGCTGCTGTGGACCCCCCTGCCCATG<br>CCCAACCCCCTGGTGAACCTGAACCTGGGCCTGCTGTTCATCCTGGCCACCAGCAGCCTGGCCGTGT<br>ACAGCATCCTGTGGAGCGGCTGGGCCAGCAACAGCAACTACGCCCTGATCGGCGCCCTGCGCGCCG<br>TGGCCCAGACCATCAGCTACGAGGTGACCCTGGCCATCATCCTGCTGAGCACCCTGCTGATGAGCGG<br>CAGCTTCAACCTGAGCACCCTGATCACCACCCAGGAGCACCTGTGGCTGCTGCTGCCCAGCTGGCCC<br>CTGGCCATGATGTGGTTCATCAGCACCCTGGCCGAGACCAACCGCACCCCCTTCGACCTGGCCGAGG<br>GCGAGAGCGAGCTGGTGAGCGGCTTCAACATCGAGTACGCCGCCGGCCCCTTCGCCCTGTTCTTCAT<br>GGCCGAGTACACCAACATCATCATGATGAACACCCTGACCACCACCATCTTCCTGGGCACCACCTACG<br>ACGCCCTGAGCCCCGAGCTGTACACCACCTACTTCGTGACCAAGACCCTGCTGCTGACCAGCCTGTT<br>CCTGTGGATCCGCACCGCCTACCCCCGCTTCCGCTACGACCAGCTGATGCACCTGCTGTGGAAGAAC<br>TTCCTGCCCCTGACCCTGGCCCTGCTGATGTGGTACGTGAGCATGCCCATCACCATCAGCAGCATCC<br>CCCCCCAGACCTAA |
| 13 | 3'UTR* | GAGCACTGGGACGCCCACCGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGGTGCTCAGTGATCACTTGAC<br>AGTTTTTTTTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCTCTATTCT<br>GTTTCTTCCTCCTCACATGGGGGTACACATACACAGCTTCCTCTTTTGGTTCCATCCTTACCACCACAC<br>CACACGCACACTCCACATGCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACCCCCTTCCTTGTGACTGAG<br>CCAGGGCCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCAAGCT<br>GGACTGCCAGCCCCTGTCCTCCCTTCACCCCCATTGCGTATGAGCATTTCAGAACTCCAAGGAGTCAC<br>AGGCATCTTTATAGTTCACGTTAACATATAGACACTGTTGGAAGCAGTTCCTTCTAAAAGGGTAGCCCT<br>GGACTTAATACCAGCCGGATACCTCTGGCCCCCACCCCATTACTGTACCTCTGGAGTCACTACTGTGG<br>GTCGCCACTCCTCTGCTACACAGCACGGCTTTTTCAAGGCTGTATTGAGAAGGGAAGTTAGGAAGAAG<br>GGTGTGCTGGGCTAACCAGCCCACAGAGCTCACATTCCTGTCCCTTGGGTGAAAAATACATGTCCATC<br>CTGATATCTCCTGAATTCAGAAATTAGCCTCCACATGTGCAATGGCTTTAAGAGCCAGAAGCAGGGTT<br>CTGGGAATTTTGCAAGTTACCTGTGGCCAGGTGTGGTCTCGGTTACCAAATACGGTTACCTGCAGCTT<br>TTTAGTCCTTTGTGCTCCCACGGGTCTAGAGAGTCCCATCTGCCCAAAGGTCTTGAAGCTTGACAGGA<br>TGTTTTCGATTACTCAGTCTCCCAGGGCACTACTGGTCCGTAGGATTCGATTGGTCGGGGTAGGAGAG |

TABLE 1-continued nucleic acid and polypeptide sequences and SEQ ID NOs

| SEQ | description | sequence |
|---|---|---|
| | | TTAAACAACATTTAAACAGAGTTCTCTCAAAAATGTCTAAAGGGATTGTAGGTAGATAACATCCAATCAC<br>TGTTTGCACTTATCTGAAATCTTCCCTCTTGGCTGCCCCCAGGTATTTACTGTGGAGAACATTGCATAG<br>GAATGTCTGGAAAAAGCTTCTACAACTTGTTACAGCCTTCACATTTGTAGAAGCTTT |
| 14 | 3'UTR* | GAGCACTGGGACGCCCACCGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGGTGCTCAGTGATCACTTGAC<br>AGTTTTTTTTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCTCTATTCT<br>GTTTCTTCCTCCTCACATGGGGGTACACATACACAGCTTCCTCTTTTGGTTCCATCCTTACCACCACAC<br>CACACGCACACTCCACATGCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACCCCCTTCCTTGTGACTGAG<br>CCAGGGCCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCAAGCT<br>GGACTGCCA |
| 15 | COX10-ND4-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGCTAAAACTAATCGTCCCAACAATTATGTTACTACCACTGACATGGCTTTC<br>CAAAAAACACATGATTTGGATCAACACAACCACCCACAGCCTAATTATTAGCATCATCCCTCTACTATTT<br>TTTAACCAAATCAACAACAACCTATTTAGCTGTTCCCCAACCTTTTCCTCCGACCCCCTAACAACCCCC<br>CTCCTAATGCTAACTACCTGGCTCCTACCCCTCACAATCATGGCAAGCCAACGCCACTTATCCAGTGA<br>ACCACTATCACGAAAAAAACTCTACCTCTCTATGCTAATCTCCCTACAAATCTCCTTAATTATGACATTC<br>ACAGCCACAGAACTAATCATGTTTTATATCTTCTTCGAAACCACACTTATCCCCACCTTGGCTATCATCA<br>CCCGATGGGGCAACCAGCCAGAACGCCTGAACGCAGGCACATACTTCCTATTCTACACCCTAGTAGG<br>CTCCCTTCCCCTACTCATCGCACTAATTTACACTCACAACACCCTAGGCTCACTAAACATTCTACTACT<br>CACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAAATCGCTCATTGCATACTCTTCAATCAGCCAC<br>ATGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCAGCCCCTGTCCTCCCTTCACCCCCATTGCGTATGAGCATT<br>TCAGAACTCCAAGGAGTCACAGGCATCTTTATAGTTCACGTTAACATATAGACACTGTTGGAAGCAGTT<br>CCTTCTAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGTATTGA<br>GAAGGGAAGTTAGGAAGAAGGGTGTGCTGGGCTAACCAGCCCACAGAGCTCACATTCCTGTCCCTTG<br>GGTGAAAAATACATGTCCATCCTGATATCTCCTGAATTCAGAAATTAGCCTCCACATGTGCAATGGCTT<br>TAAGAGCCAGAAGCAGGGTTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTACAGAGTCCCATCTGCCCAAA<br>GGTCTTGAAGCTTGACAGGATGTTTTCGATTACTCAGTCTCCCAGGGCACTACTGGTCCGTAGGATTC<br>GATTGGTCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCCAGGTATTT<br>ACTGTGGAGAACATTGCATAGGAATGTCTGGAAAAAGCTTCTACAACTTGTTACAGCCTTCACATTTGT<br>AGAAGCTTT |
| 16 | COX10-ND4-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGCTAAAACTAATCGTCCCAACAATTATGTTACTACCACTGACATGGCTTTC<br>CAAAAAACACATGATTTGGATCAACACAACCACCCACAGCCTAATTATTAGCATCATCCCTCTACTATTT<br>TTTAACCAAATCAACAACAACCTATTTAGCTGTTCCCCAACCTTTTCCTCCGACCCCCTAACAACCCCC<br>CTCCTAATGCTAACTACCTGGCTCCTACCCCTCACAATCATGGCAAGCCAACGCCACTTATCCAGTGA<br>ACCACTATCACGAAAAAAACTCTACCTCTCTATGCTAATCTCCCTACAAATCTCCTTAATTATGACATTC<br>ACAGCCACAGAACTAATCATGTTTTATATCTTCTTCGAAACCACACTTATCCCCACCTTGGCTATCATCA<br>CCCGATGGGGCAACCAGCCAGAACGCCTGAACGCAGGCACATACTTCCTATTCTACACCCTAGTAGG<br>CTCCCTTCCCCTACTCATCGCACTAATTTACACTCACAACACCCTAGGCTCACTAAACATTCTACTACT<br>CACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAAATCGCTCATTGCATACTCTTCAATCAGCCAC<br>ATGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC |

TABLE 1-continued nucleic acid and polypeptide sequences and SEQ ID NOs

| SEQ | description | sequence |
| --- | --- | --- |
| | | ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCA |
| 17 | COX10-opt_ND4-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCTCTGACCTGGCTG<br>AGCAAGAAACACATGATCTGGATCAACACCACCACGCACAGCCTGATCATCAGCATCATCCCTCTGCT<br>GTTCTTCAACCAGATCAACAACAACCTGTTCAGCTGCAGCCCCACCTTCAGCAGCGACCCTCTGACAA<br>CACCTCTGCTGATGCTGACCACCTGGCTGCTGCCCCTCACAATCATGGCCTCTCAGAGACACCTGAG<br>CAGCGAGCCCCTGAGCCGGAAGAAACTGTACCTGAGCATGCTGATCTCCCTGCAGATCTCTCTGATC<br>ATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGGCATGATTATGACCAGCAGCATCTGCCTGCGGCAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACAGCAGAATCATGATCCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCCTGAA<br>CATGCTGGTTACAGCCCTGTACTCCCTGTACATGTTCACCACCACACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTTTTAAATAT<br>TACCCAAAATGCTCCCCAAATAAGAAATGCATCAGCTCAGTCAGTGAATACAAAAAAGGAATTATTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCAGCCCCTGTCC<br>TCCCTTCACCCCCATTGCGTATGAGCATTTCAGAACTCCAAGGAGTCACAGGCATCTTTATAGTTCACG<br>TTAACATATAGACACTGTTGGAAGCAGTTCCTTCTAAAAGGGTAGCCCTGGACTTAATACCAGCCGGAT<br>ACCTCTGGCCCCCACCCCATTACTGTACCTCTGGAGTCACTACTGTGGGTCGCCACTCCTCTGCTACA<br>CAGCACGGCTTTTTCAAGGCTGTATTGAGAAGGGAAGTTAGGAAGAAGGGTGTGCTGGGCTAACCAG<br>CCCACAGAGCTCACATTCCTGTCCCTTGGGTGAAAAATACATGTCCATCCTGATATCTCCTGAATTCAG<br>AAATTAGCCTCCACATGTGCAATGGCTTTAAGAGCCAGAAGCAGGGTTCTGGGAATTTTGCAAGTTAC<br>CTGTGGCCAGGTGTGGTCTCGGTTACCAAATACGGTTACCTGCAGCTTTTTAGTCCTTTGTGCTCCCA<br>CGGGTCTACAGAGTCCCATCTGCCCAAAGGTCTTGAAGCTTGACAGGATGTTTTCGATTACTCAGTCT<br>CCCAGGGCACTACTGGTCCGTAGGATTCGATTGGTCGGGGTAGGAGAGTTAAACAACATTTAAACAGA<br>GTTCTCTCAAAAATGTCTAAAGGGATTGTAGGTAGATAACATCCAATCACTGTTTGCACTTATCTGAAAT<br>CTTCCCTCTTGGCTGCCCCCAGGTATTTACTGTGGAGAACATTGCATAGGAATGTCTGGAAAAAGCTT<br>CTACAACTTGTTACAGCCTTCACATTTGTAGAAGCTTT |
| 18 | COX10-opt_ND4-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCTCTGACCTGGCTG<br>AGCAAGAAACACATGATCTGGATCAACACCACCACGCACAGCCTGATCATCAGCATCATCCCTCTGCT<br>GTTCTTCAACCAGATCAACAACAACCTGTTCAGCTGCAGCCCCACCTTCAGCAGCGACCCTCTGACAA<br>CACCTCTGCTGATGCTGACCACCTGGCTGCTGCCCCTCACAATCATGGCCTCTCAGAGACACCTGAG<br>CAGCGAGCCCCTGAGCCGGAAGAAACTGTACCTGAGCATGCTGATCTCCCTGCAGATCTCTCTGATC<br>ATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGGCATGATTATGACCAGCAGCATCTGCCTGCGGCAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACAGCAGATGATCCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCCTGAA<br>CATGCTGGTTACAGCCCTGTACTCCCTGTACATGTTCACCACCACACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC |

TABLE 1-continued

| nucleic acid and polypeptide sequences and SEQ ID NOs | | |
|---|---|---|
| SEQ | description | sequence |
| | | GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTTTAAATAT<br>TACCCAAAATGCTCCCCAAATAAGAAATGCATCAGCTCAGTCAGTGAATACAAAAAAGGAATTATTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCA |
| 19 | COX10-opt_ND4*-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCCCTGACCTGGCTG<br>AGCAAGAAGCACATGATCTGGATCAACACCACCACCCACAGCCTGATCATCAGCATCATCCCCCTGCT<br>GTTCTTCAACCAGATCAACAACAACCTGTTCAGCTGCAGCCCCACCTTCAGCAGCGACCCCCTGACCA<br>CCCCCCTGCTGATGCTGACCACCTGGCTGCTGCCCCTGACCATCATGGCCAGCCAGCGCCACCTGAG<br>CAGCGAGCCCCTGAGCCGCAAGAAGCTGTACCTGAGCATGCTGATCAGCCTGCAGATCAGCCTGATC<br>ATGACCTTCACCGCCACCGAGCTGATCATGTTCTACATCTTCTTCGAGACCACCCTGATCCCCACCCT<br>GGCCATCATCACCCGCTGGGGCAACCAGCCCGAGCGCCTGAACGCCGGCACCTACTTCCTGTTCTAC<br>ACCCTGGTGGGCAGCCTGCCCCTGCTGATCGCCCTGATCTACACCCACAACACCCTGGGCAGCCTGA<br>ACATCCTGCTGCTGACCCTGACCGCCCAGGAGCTGAGCAACAGCTGGGCCAACAACCTGATGTGGCT<br>GGCCTACACCATGGCCTTCATGGTGAAGATGCCCCTGTACGGCCTGCACCTGTGGCTGCCCAAGGCC<br>CACGTGGAGGCCCCCATCGCCGGCAGCATGGTGCTGGCCGCCGTGCTGCTGAAGCTGGGCGGCTAC<br>GGCATGATGCGCCTGACCCTGATCCTGAACCCCCTGACCAAGCACATGGCCTACCCCTTCCTGGTGC<br>TGAGCCTGTGGGGCATGATCATGACCAGCAGCATCTGCCTGCGCCAGACCGACCTGAAGAGCCTGAT<br>CGCCTACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTGGCCA<br>ACAGCAACTACGAGCGCACCCACAGCCGCATCATGATCCTGAGCCAGGGCCTGCAGACCCTGCTGCC<br>CCTGATGGCCTTCTGGTGGCTGCTGGCCAGCCTGGCCAACCTGGCCCTGCCCCCCACCATCAACCTG<br>CTGGGCGAGCTGAGCGTGCTGGTGACCACCTTCAGCTGGAGCAACATCACCCTGCTGCTGACCGGC<br>CTGAACATGCTGGTGACCGCCCTGTACAGCCTGTACATGTTCACCACCACCCAGTGGGGCAGCCTGA<br>CCCACCACATCAACAACATGAAGCCCAGCTTCACCCGCGAGAACACCCTGATGTTCATGCACCTGAGC<br>CCCATCCTGCTGCTGAGCCTGAACCCCGACATCATCACCGGCTTCAGCAGCTAAGAGCACTGGGACG<br>CCCACCGCCCCTTTCCCTCCGCTGCCAGGCGAGCATGTTGTGGTAATTCTGGAACACAAGAAGAGAA<br>ATTGCTGGGTTTAGAACAAGATTATAAACGAATTCGGTGCTCAGTGATCACTTGACAGTTTTTTTTTTTT<br>TTAAATATTACCCAAAATGCTCCCCAAATAAGAAATGCATCAGCTCAGTCAGTGAATACAAAAAAGGAA<br>TTATTTTTCCCTTTGAGGGTCTTTTATACATCTCTCCTCCAACCCCACCCTCTATTCTGTTTCTTCCTCCT<br>CACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTGCACTGGGACTGGGGATTCCACATGTTTGCCTTGGGAGTCTCAAGCTGGACTGCCAGCC<br>CCTGTCCTCCCTTCACCCCCATTGCGTATGAGCATTTCAGAACTCCAAGGAGTCACAGGCATCTTTATA<br>GTTCACGTTAACATATAGACACTGTTGGAAGCAGTTCCTTCTAAAAGGGTAGCCCTGGACTTAATACCA<br>GCCGGATACCTCTGGCCCCCACCCCATTACTGTACCTCTGGAGTCACTACTGTGGGTCGCCACTCCT<br>CTGCTACACAGCACGGCTTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACATGTCCATCCTGATATCTCCT<br>GAATTCAGAAATTAGCCTCCACATGTGCAATGGCTTTAAGAGCCAGAAGCAGGGTTCTGGGAATTTTG<br>CAAGTTACCTGTGGCCAGGTGTGGTCTCGGTTACCAAATACGGTTACCTGCAGCTTTTTAGTCCTTTGT<br>GCTCCCACGGGTCTACAGAGTCCCATCTGCCCAAAGGTCTTGAAGCTTGACAGGATGTTTTCGATTAC<br>TCAGTCTCCCAGGGCACTACTGGTCCGTAGGATTCGATTGGTCGGGGTAGGAGAGTTAAAACAACATTT<br>AAACAGAGTTCTCTCAAAAATGTCTAAAGGGATTGTAGGTAGATAACATCCAATCACTGTTTGCACTTAT<br>CTGAAATCTTCCCTCTTGGCTGCCCCCAGGTATTTACTGTGGAGAACATTGCATAGGAATGTCTGGAA<br>AAAGCTTCTACAACTTGTTACAGCCTTCACATTTGTAGAAGCTTT |
| 20 | COX10-opt_ND4*-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCCCTGACCTGGCTG<br>AGCAAGAAGCACATGATCTGGATCAACACCACCACCCACAGCCTGATCATCAGCATCATCCCCCTGCT<br>GTTCTTCAACCAGATCAACAACAACCTGTTCAGCTGCAGCCCCACCTTCAGCAGCGACCCCCTGACCA<br>CCCCCCTGCTGATGCTGACCACCTGGCTGCTGCCCCTGACCATCATGGCCAGCCAGCGCCACCTGAG<br>CAGCGAGCCCCTGAGCCGCAAGAAGCTGTACCTGAGCATGCTGATCAGCCTGCAGATCAGCCTGATC<br>ATGACCTTCACCGCCACCGAGCTGATCATGTTCTACATCTTCTTCGAGACCACCCTGATCCCCACCCT<br>GGCCATCATCACCCGCTGGGGCAACCAGCCCGAGCGCCTGAACGCCGGCACCTACTTCCTGTTCTAC<br>ACCCTGGTGGGCAGCCTGCCCCTGCTGATCGCCCTGATCTACACCCACAACACCCTGGGCAGCCTGA<br>ACATCCTGCTGCTGACCCTGACCGCCCAGGAGCTGAGCAACAGCTGGGCCAACAACCTGATGTGGCT<br>GGCCTACACCATGGCCTTCATGGTGAAGATGCCCCTGTACGGCCTGCACCTGTGGCTGCCCAAGGCC<br>CACGTGGAGGCCCCCATCGCCGGCAGCATGGTGCTGGCCGCCGTGCTGCTGAAGCTGGGCGGCTAC<br>GGCATGATGCGCCTGACCCTGATCCTGAACCCCCTGACCAAGCACATGGCCTACCCCTTCCTGGTGC<br>TGAGCCTGTGGGGCATGATCATGACCAGCAGCATCTGCCTGCGCCAGACCGACCTGAAGAGCCTGAT<br>CGCCTACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTGGCCA<br>ACAGCAACTACGAGCGCACCCACAGCCGCATCATGATCCTGAGCCAGGGCCTGCAGACCCTGCTGCC<br>CCTGATGGCCTTCTGGTGGCTGCTGGCCAGCCTGGCCAACCTGGCCCTGCCCCCCACCATCAACCTG<br>CTGGGCGAGCTGAGCGTGCTGGTGACCACCTTCAGCTGGAGCAACATCACCCTGCTGCTGACCGGC<br>CTGAACATGCTGGTGACCGCCCTGTACAGCCTGTACATGTTCACCACCACCCAGTGGGGCAGCCTGA<br>CCCACCACATCAACAACATGAAGCCCAGCTTCACCCGCGAGAACACCCTGATGTTCATGCACCTGAGC<br>CCCATCCTGCTGCTGAGCCTGAACCCCGACATCATCACCGGCTTCAGCAGCTAAGAGCACTGGGACG<br>CCCACCGCCCCTTTCCCTCCGCTGCCAGGCGAGCATGTTGTGGTAATTCTGGAACACAAGAAGAGAA<br>ATTGCTGGGTTTAGAACAAGATTATAAACGAATTCGGTGCTCAGTGATCACTTGACAGTTTTTTTTTTTT |

TABLE 1-continued

| nucleic acid and polypeptide sequences and SEQ ID NOs | | |
|---|---|---|
| SEQ | description | sequence |
| | | TTAAATATTACCCAAAATGCTCCCCAAATAAGAAATGCATCAGCTCAGTCAGTGAATACAAAAAAGGAA<br>TTATTTTTCCCTTTGAGGGTCTTTTATACATCTCTCCTCCAACCCCACCCTCTATTCTGTTTCTTCCTCCT<br>CACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTGCACTGGGACTGGGGATTCCACATGTTTGCCTTGGGAGTCTCAAGCTGGACTGCCA |
| 21 | COX10-ND6-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGATGTATGCTTTGTTTCTGTTGAGTGTGGGTTTAGTAATGGGGTTTGTGG<br>GGTTTTCTTCTAAGCCTTCTCCTATTTATGGGGGTTTAGTATTGATTGTTAGCGGTGTGGTCGGGTGTG<br>TTATTATTCTGAATTTTGGGGGAGGTTATATGGGTTTAATGGTTTTTTTAATTTATTTAGGGGGAATGAT<br>GGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGPAGCTGGATGATTTATGAAGGAGAGGGG<br>TCAGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCAGCCCCTGTCCTCCCTTCACCCCCATTGCGTATGAGCATTTCAGAACTCCAAGGAGTCACAGGC<br>ATCTTTATAGTTCACGTTAACATATAGACACTGTTGGAAGCAGTTCCTTCTAAAAGGGTAGCCCTGGAC<br>TTAATACCAGCCGGATACCTCTGGCCCCCACCCCATTACTGTACCTCTGGAGTCACTACTGTGGGTCG<br>CCACTCCTCTGCTACACAGCACGGCTTTTTCAAGGCTGTATTGAGAAGGGAAGTTAGGAAGAAGGGTG<br>TGCTGGGCTAACCAGCCCACAGAGCTCACATTCCTGTCCCTTGGGTGAAAAATACATGTCCATCCTGA<br>TATCTCCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCTTTTTAG<br>TCCTTTGTGCTCCCACGGGTCTACAGAGTCCCATCTGCCCAAAGGTCTTGAAGCTTGACAGGATGTTT<br>TCGATTACTCAGTCTCCCAGGGCACTACTGGTCCGTAGGATTCGATTGGTCGGGGTAGGAGAGTTAAA<br>CAACATTTAAACAGAGTTCTCTCAAAAATGTCTAAAGGGATTGTAGGTAGATAACATCCAATCACTGTTT<br>GCACTTATCTGAAATCTTCCCTCTTGGCTGCCCCCAGGTATTTACTGTGGAGAACATTGCATAGGAATG<br>TCTGGAAAAAGCTTCTACAACTTGTTACAGCCTTCACATTTGTAGAAGCTTT |
| 22 | COX10-ND6-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGATGTATGCTTTGTTTCTGTTGAGTGTGGGTTTAGTAATGGGGTTTGTGG<br>GGTTTTCTTCTAAGGCCTTCTCCTATTTATGGGGGTTTAGTATTGATTGTTAGCGGTGTGGTCGGGTGTG<br>TTATTATTCTGAATTTTGGGGGAGGTTATATGGGTTTAATGGTTTTTTTAATTTATTTAGGGGGAATGAT<br>GGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGAAGCTGGATGATTTATGAAGGAGAGGGG<br>TCAGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCA |
| 23 | COX10-opt_ND6-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGATGTACGCCCTGTTCCTGCTGAGCGTGGGCCTGGTGATGGGCTTCGTG<br>GGCTTCAGCAGCAAGCCCAGCCCCATCTACGGCGGCCTGGTGCTGATCGTGAGCGGCGTGGTGGGC<br>TGCGTGATCATCCTGAACTTCGGCGGCGGCTACATGGGCCTGATGGTGTTCCTGATCTACCTGGGCG<br>GCATGATGGTGGTGTTCGGCTACACCACCGCCATGGCCATCGAGGAGTACCCCGAGGCCTGGGGCA<br>GCGGCGTGGAGGTGCTGGTGAGCGTGCTGGTGGGCCTGGCCATGGAGGTGGGCCTGGTGCTGTGG<br>GTGAAGGAGTACGACGGCGTGGTGGTGGTGGTGAACTTCAACAGCGTGGGCAGCTGGATGATCTAC<br>GAGGGCGAGGGCAGCGGCCTGATCCGCGAGGACCCCATCGGCGCCGGCGCCCTGTACGACTACGG<br>CCGCTGGCTGGTGGTGGTGACCGGCTGGACCCTGTTCGTGGGCGTGTACATCGTGATCGAGATCGC<br>CCGCGGCAACTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCAGCCCCTGTCCTCCCTTCACCCCCATTGCGTATGAGCATTTCAGAACT<br>CCAAGGAGTCACAGGCATCTTTATAGTTCACGTTAACATATAGACACTGTTGGAAGCAGTTCCTTCTAA |

TABLE 1-continued

| nucleic acid and polypeptide sequences and SEQ ID NOs | | |
|---|---|---|
| SEQ | description | sequence |
| | | AAGGGTAGCCCTGGACTTAATACCAGCCGGATACCTCTGGCCCCCACCCCATTACTGTACCTCTGGA<br>GTCACTACTGTGGGTCGCCACTCCTCTGCTACACAGCACGGCTTTTTCAAGGCTGTATTGAGAAGGGA<br>AGTTAGGAAGAAGGGTGTGCTGGGCTAACCAGCCCACAGAGCTCACATTCCTGTCCCTTGGGTGAAA<br>AATACATGTCCATCCTGATATCTCCTGAATTCAGAAATTAGCCTCCACATGTGCAATGGCTTTAAGAGC<br>CAGAAGCAGGGTTCTGGGAATTTTGCAAGTTACCTGTGGCCAGGTGTGGTCTCGGTTACCAAATACGG<br>TTACCTGCAGCTTTTTAGTCCTTTGTGCTCCCACGGGTCTACAGAGTCCCATCTGCCCAAAGGTCTTGA<br>AGCTTGACAGGATGTTTTCGATTACTCAGTCTCCCAGGGCACTACTGGTCCGTAGGATTCGATTGGTC<br>GGGGTAGGAGAGTTAAACAACATTTAAACAGAGTTCTCTCAAAAATGTCTAAAGGGATTGTAGGTAGAT<br>AACATCCAATCACTGTTTGCACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCTTCACATTTGTAGAAGCTT<br>T |
| 24 | COX10-opt_ND6-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGATGTACGCCCTGTTCCTGCTGAGCGTGGGCCTGGTGATGGGCTTCGTG<br>GGCTTCAGCAGCAAGCCCAGCCCCATCTACGGCGGCCTGGTGCTGATCGTGAGCGGCGTGGTGGGC<br>TGCGTGATCATCCTGAACTTCGGCGGCGGCTACATGGGCCTGATGGTGTTCCTGATCTACCTGGGCG<br>GCATGATGGTGGTGTTCGGCTACACCACCGCCATGGCCATCGAGGAGTACCCCGAGGCCTGGGGCA<br>GCGGCGTGGAGGTGCTGGTGAGCGTGCTGGTGGGCCTGGCCATGGAGGTGGGCCTGGTGCTGTGG<br>GTGAAGGAGTACGACGGCGTGGTGGTGGTGGTGAACTTCAACAGCGTGGGCAGCTGGATGATCTAC<br>GAGGGCGAGGGCAGCGGCCTGATCCGCGAGGACCCCATCGGCGCCGGCGCCCTGTACGACTACGG<br>CCGCTGGCTGGTGGTGGTGACCGGCTGGACCCTGTTCGTGGGCGTGTACATCGTGATCGAGATCGC<br>CCGCGGCAACTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCA |
| 25 | COX10-ND1-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTCCTACTCCTCATTGTACCCATTCTAATCGCAATGGCATTCC<br>TAATGCTTACCGAACGAAAAATTCTAGGCTATATGCAACTACGCAAAGGCCCCAACGTTGTAGGCCCC<br>TACGGGCTACTACAACCCTTCGCTGACGCCATAAAACTCTTCACCAAAGAGCCCCTAAAACCCGCCAC<br>ATCTACCATCACCCTCTACATCACCGCCCCGACCTTAGCTCTCACCATCGCTCTTCTACTATGGACCCC<br>CCTCCCCATGCCCAACCCCCTGGTCAACCTCAACCTAGGCCTCCTATTTATTCTAGCCACCTCTAGCC<br>TAGCCGTTTACTCAATCCTCTGGTCAGGGTGGGCATCAAACTCAAACTACGCCCTGATCGGCGCACTG<br>CGAGCAGTAGCCCAAACAATCTCATATGAAGTCACCCTAGCCATCATTCTACTATCAACATTACTAATG<br>AGTGGCTCCTTTAACCTCTCCACCCTTATCACAACACCACAAGAACACCTCTGGTTACTCCTGCCATCATGG<br>CCCTTGGCCATGATGTGGTTTATCTCCACACTAGCAGAGACCAACCGAACCCCCTTCGACCTTGCCGA<br>AGGGGAGTCCGAACTAGTCTCAGGCTTCAACATCGAATACGCCGCAGGCCCCTTCGCCCTATTCTTCA<br>TGGCCGAATACACAAACATTATTATGATGAACACCCTCACCACTACAATCTTCCTAGGAACAACATATG<br>ACGCACTCTCCCCTGAACTCTACACAACATATTTTGTCACCAAGACCCTACTTCTAACCTCCCTGTTCT<br>TATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCAGCCCCTGTCCTCCCTTCACCCCCATTGCGTATGAGCATTTCAGAACTCCAAG<br>GAGTCACAGGCATCTTTATAGTTCACGTTAACATATAGACACTGTTGGAAGCAGTTCCTTCTAAAAGGG<br>TAGCCCTGGACTTAATACCAGCCGGATACCTCTGGCCCCCACCCCATTACTGTACCTCTGGAGTCACT<br>ACTGTGGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAATACAT<br>GTCCATCCTGATATCTCCTGAATTCAGAAATTAGCCTCCACATGTGCAATGGCTTTAAGAGCCAGAAGC<br>AGGGTTCTGGGAATTTTGCAAGTTACCTGTGGCCAGGTGTGGTCTCGGTTACCAAATACGGTTACCTG<br>CAGCTTTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCGGGGTA<br>GGAGAGTTAAACAACATTTAAACAGAGTTCTCTCAAAAATGTCTAAAGGGATTGTAGGTAGATAACATC<br>CAATCACTGTTTGCACTTATCTGAAATCTTCCCTCTTGGCTGCCCCCAGGTATTTACTGTGGAGAACAT<br>TGCATAGGAATGTCTGGAAAAAGCTTCTACAACTTGTTACAGCCTTCACATTTGTAGAAGCTTT |
| 26 | COX10-ND1-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTCCTACTCCTCATTGTACCCATTCTAATCGCAATGGCATTCC<br>TAATGCTTACCGAACGAAAAATTCTAGGCTATATGCAACTACGCAAAGGCCCCAACGTTGTAGGCCCC<br>TACGGGCTACTACAACCCTTCGCTGACGCCATAAAACTCTTCACCAAAGAGCCCCTAAAACCCGCCAC<br>ATCTACCATCACCCTCTACATCACCGCCCCGACCTTAGCTCTCACCATCGCTCTTCTACTATGGACCCC<br>CCTCCCCATGCCCAACCCCCTGGTCAACCTCAACCTAGGCCTCCTATTTATTCTAGCCACCTCTAGCC<br>TAGCCGTTTACTCAATCCTCTGGTCAGGGTGGGCATCAAACTCAAACTACGCCCTGATCGGCGCACTG<br>CGAGCAGTAGCCCAAACAATCTCATATGAAGTCACCCTAGCCATCATTCTACTATCAACATTACTAATG<br>AGTGGCTCCTTTAACCTCTCCACCCTTATCACAACACAAGAACACCTCTGGTTACTCCTGCCATCATGG<br>CCCTTGGCCATGATGTGGTTTATCTCCACACTAGCAGAGACCAACCGAACCCCCTTCGACCTTGCCGA |

TABLE 1-continued nucleic acid and polypeptide sequences and SEQ ID NOs

| SEQ | description | sequence |
|---|---|---|
| | | AGGGGAGTCCGAACTAGTCTCAGGCTTCAACATCGAATACGCCGCAGGCCCCTTCGCCCTATTCTTCA<br>TGGCCGAATACACAAACATTATTATGATGAACACCCTCACCACTACAATCTTCCTAGGAACAACATATG<br>ACGCACTCTCCCCTGAACTCTACACAACATATTTTGTCACCAAGACCCTACTTCTAACCTCCCTGTTCT<br>TATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCA |
| 27 | COX10-opt_ND1-3'UTR | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTGCTGCTGCTGATCGTGCCCATCCTGATCGCCATGGCCTTC<br>CTGATGCTGACCGAGCGCAAGATCCTGGGCTACATGCAGCTGCGCAAGGGCCCCAACGTGGTGGGC<br>CCCTACGGCCTGCTGCAGCCCTTCGCCGACGCCATCAAGCTGTTCACCAAGGAGCCCCTGAAGCCCG<br>CCACCAGCACCATCACCCTGTACATCACCGCCCCCACCCTGGCCCTGACCATCGCCCTGCTGCTGTG<br>GACCCCCCTGCCCATGCCCAACCCCCTGGTGAACCTGAACCTGGGCCTGCTGTTCATCCTGGCCACC<br>AGCAGCCTGGCCGTGTACAGCATCCTGTGGAGCGGCTGGGCCAGCAACAGCAACTACGCCCTGATC<br>GGCGCCCTGCGCGCCGTGGCCCAGACCATCAGCTACGAGGTGACCCTGGCCATCATCCTGCTGAGC<br>ACCCTGCTGATGAGCGGCAGCTTCAACCTGAGCACCCTGATCACCACCCAGGAGCACCTGTGGCTGC<br>TGCTGCCCAGCTGGCCCCTGGCCATGATGTGGTTCATCAGCACCCTGGCCGAGACCAACCGCACCCC<br>CTTCGACCTGGCCGAGGGCGAGAGCGAGCTGGTGAGCGGCTTCAACATCGAGTACGCCGCCGGCCC<br>CTTCGCCCTGTTCTTCATGGCCGAGTACACCAACATCATCATGATGAACACCCTGACCACCACCATCTT<br>CCTCGGCACCACCTACGACGCCCTGAGCCCCGAGCTGTACACCACCTACTTCGTGACCAAGACCCTG<br>CTGCTGACCAGCCTGTTCCTGTGGATCCGCACCGCCTACCCCCGCTTCCGCTACGACCAGCTGATGC<br>ACCTGCTGTGGAAGAACTTCCTGCCCCTGACCCTGGCCCTGCTGATGTGGTACGTGAGCATGCCCAT<br>CACCATCAGCAGCATCCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAAGATTA<br>TAAACGAATTCGGTGCTCAGTGATCACTTGACAGTTTTTTTTTTTTTTAAATATTACCCAAAATGCTCCC<br>CAAATAAGAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACATACACAG<br>CTTCCTCTTTTGGTTCCATCCTTACCACCACACCACACGCACACTCCACATGCCCAGCAGAGTGGCAC<br>TTGGTGGCCAGAAAGTGTGAGCCTCATGATCTGCTGTCTGTAGTTCTGTGAGCTCAGGTCCCTCAAAG<br>GCCTCGGAGCACCCCCTTCCTTGTGACTGAGCCAGGGCCTGCATTTTTGGTTTTCCCCACCCCACACA<br>TTCTCAACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCAGCCCCTGTCCTCCCTTCACCCCCATTGC<br>GTATGAGCATTTCAGAACTCCAAGGAGTCACAGGCATCTTTATAGTTCACGTTAACATATAGACACTGT<br>TGGAAGCAGTTCCTTCTAAAAGGGTAGCCCTGGACTTAATACCAGCCGGATACCTCTGGCCCCCACCC<br>CATTACTGTACCTCTGGAGTCACTACTGTGGGTCGCCACTCCTCTGCTACACAGCACGGCTTTTTCAA<br>GGCTGTATTGAGAAGGGAAGTTAGGAAGAAGGGTGTGCTGGGCTAACCAGCCCACAGAGCTCACATT<br>CCTGTCCCTTGGGTGAAAAATACATGTCCATCCTGATATCTCCTGAATTCAGAAATTAGCCTCCACATG<br>TGCAATGGCTTTAAGAGCCAGAAGCAGGGTTCTGGGAATTTTGCAAGTTACCTGTGGCCAGGTGTGGT<br>CTCGGTTACCAAATACGGTTACCTGCAGCTTTTTAGTCCTTTGTGCTCCCACGGGTCTACAGAGTCCC<br>ATCTGCCCAAAGGTCTTGAAGCTTGACAGGATGTTTTCGATTACTCAGTCTCCCAGGGCACTACTGGT<br>CCGTAGGATTCGATTGGTCGGGGTAGGAGAGTTAAACAACATTTAAACAGAGTTCTCTCAAAAATGTCT<br>AAAGGGATTGTAGGTAGATAACATCCAATCACTGTTTGCACTTATCTGAAATCTTCCCTCTTGGCTGCC<br>CCCAGGTATTTACTGTGGAGAACATTGCATAGGAATGTCTGGAAAAAGCTTCTACAACTTGTTACAGCC<br>TTCACATTTGTAGAAGCTTT |
| 28 | COX10-opt_ND1-3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTGCTGCTGCTGATCGTGCCCATCCTGATCGCCATGGCCTTC<br>CTGATGCTGACCGAGCGCAAGATCCTGGGCTACATGCAGCTGCGCAAGGGCCCCAACGTGGTGGGC<br>CCCTACGGCCTGCTGCAGCCCTTCGCCGACGCCATCAAGCTGTTCACCAAGGAGCCCCTGAAGCCCG<br>CCACCAGCACCATCACCCTGTACATCACCGCCCCCACCCTGGCCCTGACCATCGCCCTGCTGCTGTG<br>GACCCCCCTGCCCATGCCCAACCCCCTGGTGAACCTGAACCTGGGCCTGCTGTTCATCCTGGCCACC<br>AGCAGCCTGGCCGTGTACAGCATCCTGTGGAGCGGCTGGGCCAGCAACAGCAACTACGCCCTGATC<br>GGCGCCCTGCGCGCCGTGGCCCAGACCATCAGCTACGAGGTGACCCTGGCCATCATCCTGCTGAGC<br>ACCCTGCTGATGAGCGGCAGCTTCAACCTGAGCACCCTGATCACCACCCAGGAGCACCTGTGGCTGC<br>TGCTGCCCAGCTGGCCCCTGGCCATGATGTGGTTCATCAGCACCCTGGCCGAGACCAACCGCACCCC<br>CTTCGACCTGGCCGAGGGCGAGAGCGAGCTGGTGAGCGGCTTCAACATCGAGTACGCCGCCGGCCC<br>CTTCGCCCTGTTCTTCATGGCCGAGTACACCAACATCATCATGATGAACACCCTGACCACCACCATCTT<br>CCTGGGCACCACCTACGACGCCCTGAGCCCCGAGCTGTACACCACCTACTTCGTGACCAAGACCCTG<br>CTGCTGACCAGCCTGTTCCTGTGGATCCGCACCGCCTACCCCCGCTTCCGCTACGACCAGCTGATGC<br>ACCTGCTGTGGAAGAACTTCCTGCCCCTGACCCTGGCCCTGCTGATGTGGTACGTGAGCATGCCCAT<br>CACCATCAGCAGCATCCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAAGATTA<br>TAAACGAATTCGGTGCTCAGTGATCACTTGACAGTTTTTTTTTTTTTTAAATATTACCCAAAATGCTCCC<br>CAAATAAGAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACATACACAG<br>CTTCCTCTTTTGGTTCCATCCTTACCACCACACCACACGCACACTCCACATGCCCAGCAGAGTGGCAC<br>TTGGTGGCCAGAAAGTGTGAGCCTCATGATCTGCTGTCTGTAGTTCTGTGAGCTCAGGTCCCTCAAAG<br>GCCTCGGAGCACCCCCTTCCTTGTGACTGAGCCAGGGCCTGCATTTTTGGTTTTCCCCACCCCACACA |

TABLE 1-continued nucleic acid and polypeptide sequences and SEQ ID NOs

| SEQ | description | sequence |
|---|---|---|
| | | TTCTCAACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCA |
| 29 | opt_COX10-ND4-3'UTR | ATGGCCGCCTCTCCACACACACTGAGTAGCAGACTGCTGACCGGCTGTGTTGGCGGCTCTGTGTGGT<br>ATCTGGAACGGCGGACAATGCTAAAACTAATCGTCCCAACAATTATGTTACTACCACTGACATGGCTTT<br>CCAAAAAACACATGATTTGGATCAACACAACCACCCACAGCCTAATTATTAGCATCATCCCTCTACTATT<br>TTTTAACCAAATCAACAACAACCTATTTAGCTGTTCCCCAACCTTTTCCTCCGACCCCCTAACAACCCC<br>CCTCCTAATGCTAACTACCTGGCTCCTACCCCTCACAATCATGGCAAGCCAACGCCACTTATCCAGTG<br>AACCACTATCACGAAAAAAACTCTACCTCTCTATGCTAATCTCCCTACAAATCTCCTTAATTATGACATT<br>CACAGCCACAGAACTAATCATGTTTTATATCTTCTTCGAAACCACACTTATCCCCACCTTGGCTATCATC<br>ACCCGATGGGGCAACCAGCCAGAACGCCTGAACGCAGGCACATACTTCCTATTCTACACCCTAGTAG<br>GCTCCCTTCCCCTACTCATCGCACTAATTTACACTCACAACACCCTAGGCTCACTAAACATTCTACTAC<br>TCACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAAATCGCTCATTGCATACTCTTCAATCAGCCAC<br>ATGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCAGCCCCTGTCCTCCCTTCACCCCCATTGCGTATGAGCATT<br>TCAGAACTCCAAGGAGTCACAGGCATCTTTATAGTTCACGTTAACATATAGACACTGTTGGAAGCAGTT<br>CCTTCTAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGTATTGA<br>GAAGGGAAGTTAGGAAGAAGGGTGTGCTGGGCTAACCAGCCCACAGAGCTCACATTCCTGTCCCTTG<br>GGTGAAAAATACATGTCCATCCTGATATCTCCTGAATTCAGAAATTAGCCTCCACATGTGCAATGGCTT<br>TAAGAGCCAGAAGCAGGGTTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTACAGAGTCCCATCTGCCCAAA<br>GGTCTTGAAGCTTGACAGGATGTTTTCGATTACTCAGTCTCCCAGGGCACTACTGGTCCGTAGGATTC<br>GATTGGTCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCCAGGTATTT<br>ACTGTGGAGAACATTGCATAGGAATGTCTGGAAAAAGCTTCTACAACTTGTTACAGCCTTCACATTTGT<br>AGAAGCTTT |
| 30 | opt_COX10-ND4-3'UTR* | ATGGCCGCCTCTCCACACACACTGAGTAGCAGACTGCTGACCGGCTGTGTTGGCGGCTCTGTGTGGT<br>ATCTGGAACGGCGGACAATGCTAAAACTAATCGTCCCAACAATTATGTTACTACCACTGACATGGCTTT<br>CCAAAAAACACATGATTTGGATCAACACAACCACCCACAGCCTAATTATTAGCATCATCCCTCTACTATT<br>TTTTAACCAAATCAACAACAACCTATTTAGCTGTTCCCCAACCTTTTCCTCCGACCCCCTAACAACCCC<br>CCTCCTAATGCTAACTACCTGGCTCCTACCCCTCACAATCATGGCAAGCCAACGCCACTTATCCAGTG<br>AACCACTATCACGAAAAAAACTCTACCTCTCTATGCTAATCTCCCTACAAATCTCCTTAATTATGACATT<br>CACAGCCACAGAACTAATCATGTTTTATATCTTCTTCGAAACCACACTTATCCCCACCTTGGCTATCATC<br>ACCCGATGGGGCAACCAGCCAGAACGCCTGAACGCAGGCACATACTTCCTATTCTACACCCTAGTAG<br>GCTCCCTTCCCCTACTCATCGCACTAATTTACACTCACAACACCCTAGGCTCACTAAACATTCTACTAC<br>TCACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAAATCGCTCATTGCATACTCTTCAATCAGCCAC<br>ATGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCA |

TABLE 1-continued nucleic acid and polypeptide sequences and SEQ ID NOs

| SEQ | description | sequence |
|---|---|---|
| 31 | opt_COX10-opt_ND4-3'UTR | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCTCTGACCTGGCT<br>GAGCAAGAAACACATGATCTGGATCAACACCACCACGCACAGCCTGATCATCAGCATCATCCCTCTGC<br>TGTTCTTCAACCAGATCAACAACAACCTGTTCAGCTGCAGCCCCACCTTCAGCAGCGACCCTCTGACA<br>ACACCTCTGCTGATGCTGACCACCTGGCTGCTGCCCCTCACAATCATGGCCTCTCAGAGACACCTGA<br>GCAGCGAGCCCCTGAGCCGGAAGAAACTGTACCTGAGCATGCTGATCTCCCTGCAGATCTCTCTGAT<br>CATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGGCATGATTATGACCAGCAGCATCTGCCTGCGGCAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACAGCAATCATGATCCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCCTGAA<br>CATGCTGGTTACAGCCCTGTACTCCCTGTACATGTTCACCACCACACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTTTAAATAT<br>TACCCAAAATGCTCCCCAAATAAGAAATGCATCAGCTCAGTCAGTGAATACAAAAAAGGAATTATTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCAGCCCCTGTCC<br>TCCCTTCACCCCCATTGCGTATGAGCATTTCAGAACTCCAAGGAGTCACAGGCATCTTTATAGTTCACG<br>TTAACATATAGACACTGTTGGAAGCAGTTCCTTCTAAAAGGGTAGCCCTGGACTTAATACCAGCCGGAT<br>ACCTCTGGCCCCCACCCCATTACTGTACCTCTGGAGTCACTACTGTGGGTCGCCACTCCTCTGCTACA<br>CAGCACGGCTTTTTCAAGGCTGTATTGAGAAGGGAAGTTAGGAAGAAGGGTGTGCTGGGCTAACCAG<br>CCCACAGAGCTCACATTCCTGTCCCTTGGGTGAAAAATACATGTCCATCCTGATATCTCCTGAATTCAG<br>AAATTAGCCTCCACATGTGCAATGGCTTTAAGAGCCAGAAGCAGGGTTCTGGGAATTTTGCAAGTTAC<br>CTGTGGCCAGGTGTGGTCTCGGTTACCAAATACGGTTACCTGCAGCTTTTTAGTCCTTTGTGCTCCCA<br>CGGGTCTACAGAGTCCCATCTGCCCAAAGGTCTTGAAGCTTGACAGGATGTTTTCGATTACTCAGTCT<br>CCCAGGGCACTACTGGTCCGTAGGATTCGATTGGTCGGGGTAGGAGAGTTAAACAACATTTAAACAGA<br>GTTCTCTCAAAAATGTCTAAAGGGATTGTAGGTAGATAACATCCAATCACTGTTTGCACTTATCTGAAAT<br>CTTCCCTCTTGGCTGCCCCCAGGTATTTACTGTGGAGAACATTGCATAGGAATGTCTGGAAAAAGCTT<br>CTACAACTTGTTACAGCCTTCACATTTGTAGAAGCTTT |
| 32 | opt_COX10-opt_ND4-3'UTR* | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCTCTGACCTGGCT<br>GAGCAAGAAACACATGATCTGGATCAACACCACCACGCACAGCCTGATCATCAGCATCATCCCTCTGC<br>TGTTCTTCAACCAGATCAACAACAACCTGTTCAGCTGCAGCCCCACCTTCAGCAGCGACCCTCTGACA<br>ACACCTCTGCTGATGCTGACCACCTGGCTGCTGCCCCTCACAATCATGGCCTCTCAGAGACACCTGA<br>GCAGCGAGCCCCTGAGCCGGAAGAAACTGTACCTGAGCATGCTGATCTCCCTGCAGATCTCTCTGAT<br>CATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGGCATGATTATGACCAGCAGCATCTGCCTGCGGCAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACAGCAGAATCATGATCCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCC'TGAA<br>CATGCTGGTTACAGCCCTGTACTCCCTGTACATGTTCACCACCACACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTTTAAATAT<br>TACCCAAAATGCTCCCCAAATAAGAAATGCATCAGCTCAGTCAGTGAATACAAAAAAGGAATTATTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCA |

TABLE 1-continued nucleic acid and polypeptide sequences and SEQ ID NOs

| SEQ | description | sequence |
|---|---|---|
| 33 | opt_COX10-opt_ND4*-3'UTR | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCCCTGACCTGGCT<br>GAGCAAGAAGCACATGATCTGGATCAACACCACCACCCACAGCCTGATCATCAGCATCATCCCCCTGC<br>TGTTCTTCAACCAGATCAACAACAACCTGTTCAGCTGCAGCCCCACCTTCAGCAGCGACCCCCTGACC<br>ACCCCCCTGCTGATGCTGACCACCTGGCTGCTGCCCCTGACCATCATGGCCAGCCAGCGCCACCTGA<br>GCAGCGAGCCCCTGAGCCGCAAGAAGCTGTACCTGAGCATGCTGATCAGCCTGCAGATCAGCCTGAT<br>CATGACCTTCACCGCCACCGAGCTGATCATGTTCTACATCTTCTTCGAGACCACCCTGATCCCCACCC<br>TGGCCATCATCACCCGCTGGGGCAACCAGCCCGAGCGCCTGAACGCCGGCACCTACTTCCTGTTCTA<br>CACCCTGGTGGGCAGCCTGCCCCTGCTGATCGCCCTGATCTACACCCACAACACCCTGGGCAGCCTG<br>AACATCCTGCTGCTGACCCTGACCGCCCAGGAGCTGAGCAACAGCTGGGCCAACAACCTGATGTGGC<br>TGGCCTACACCATGGCCTTCATGGTGAAGATGCCCCTGTACGGCCTGCACCTGTGGCTGCCCAAGGC<br>CCACGTGGAGGCCCCCATCGCCGGCAGCATGGTGCTGGCCGCCGTGCTGCTGAAGCTGGGCGGCTA<br>CGGCATGATGCGCCTGACCCTGATCCTGAACCCCCTGACCAAGCACATGGCCTACCCCTTCCTGGTG<br>CTGAGCCTGTGGGGCATGATCATGACCAGCAGCATCTGCCTGCGCCAGACCGACCTGAAGAGCCTGA<br>TCGCCTACAGCAGCATCAGCCACATGGCCCTGGTGGTGACCGCCATCCTGATCCAGACCCCCTGGAG<br>CTTCACCGGCGCCGTGATCCTGATGATCGCCCACGGCCTGACCAGCAGCCTGCTGTTCTGCCTGGCC<br>AACAGCAACTACGAGCGCACCCACAGCCGCATCATGATCCTGAGCCAGGGCCTGCAGACCCTGCTGC<br>CCCTGATGGCCTTCTGGTGGCTGCTGGCCAGCCTGGCCAACCTGGCCCTGCCCCCCACCATCAACCT<br>GCTGGGCGAGCTGAGCGTGCTGGTGACCACCTTCAGCTGGAGCAACATCACCCTGCTGCTGACCGG<br>CCTGAACATGCTGGTGACCGCCCTGTACAGCCTGTACATGTTCACCACCACCCAGTGGGGCAGCCTG<br>ACCCACCACATCAACAACATGAAGCCCAGCTTCACCCGCGAGAACACCCTGATGTTCATGCACCTGAG<br>CCCCATCCTGCTGCTGAGCCTGAACCCCGACATCATCACCGGCTTCAGCAGCTAAGAGCACTGGGAC<br>GCCCACCGCCCCTTTCCCTCCGCTGCCAGGCGAGCATGTTGTGGTAATTCTGGAACACAAGAAGAGA<br>AATTGCTGGGTTTAGAACAAGATTATAAACGAATTCGGTGCTCAGTGATCACTTGACAGTTTTTTTTTTT<br>TTTAAATATTACCCAAAATGCTCCCCAAATAAGAAATGCATCAGCTCAGTCAGTGAATACAAAAAAGGA<br>ATTATTTTTCCCTTTGAGGGTCTTTTATACATCTCTCCTCCAACCCCACCCTCTATTCTGTTTCTTCCTCC<br>TCACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTGCACTGGGACTGGGGATTCCACATGTTTGCCTTGGGAGTCTCAAGCTGGACTGCCAGCC<br>CCTGTCCTCCCTTCACCCCCATTGCGTATGAGCATTTCAGAACTCCAAGGAGTCACAGGCATCTTTATA<br>GTTCACGTTAACATATAGACACTGTTGGAAGCAGTTCCTTCTAAAAGGGTAGCCCTGGACTTAATACCA<br>GCCGGATACCTCTGGCCCCACCCCATTACTGTACCTCTGGAGTCACTACTGTGGGTCGCCACTCCT<br>CTGCTACACAGCACGGCTTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACATGTCCATCCTGATATCTCCT<br>GAATTCAGAAATTAGCCTCCACATGTGCAATGGCTTTAAGAGCCAGAAGCAGGGTTCTGGGAATTTTG<br>CAAGTTACCTGTGGCCAGGTGTGGTCTCGGTTACCAAATACGGTTACCTGCAGCTTTTTAGTCCTTTGT<br>GCTCCCACGGGTCTACAGAGTCCCATCTGCCCAAAGGTCTTGAAGCTTGACAGGATGTTTTCGATTAC<br>TCAGTCTCCCAGGGCACTACTGGTCCGTAGGATTCGATTGGTCGGGGTAGGAGAGTTAAACAACATTT<br>AAACAGAGTTCTCTCAAAAATGTCTAAAGGGATTGTAGGTAGATAACATCCAATCACTGTTTGCACTTAT<br>CTGAAATCTTCCCTCTTGGCTGCCCCCAGGTATTTACTGTGGAGAACATTGCATAGGAATGTCTGGAA<br>AAAGCTTCTACAACTTGTTACAGCCTTCACATTTGTAGAAGCTTT |
| 34 | opt_COX10-opt_ND4*-3'UTR* | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCCCTGACCTGGCT<br>GAGCAAGAAGCACATGATCTGGATCAACACCACCACCCACAGCCTGATCATCAGCATCATCCCCCTGC<br>TGTTCTTCAACCAGATCAACAACAACCTGTTCAGCTGCAGCCCCACCTTCAGCAGCGACCCCCTGACC<br>ACCCCCCTGCTGATGCTGACCACCTGGCTGCTGCCCCTGACCATCATGGCCAGCCAGCGCCACCTGA<br>GCAGCGAGCCCCTGAGCCGCAAGAAGCTGTACCTGAGCATGCTGATCAGCCTGCAGATCAGCCTGAT<br>CATGACCTTCACCGCCACCGAGCTGATCATGTTCTACATCTTCTTCGAGACCACCCTGATCCCCACCC<br>TGGCCATCATCACCCGCTGGGGCAACCAGCCCGAGCGCCTGAACGCCGGCACCTACTTCCTGTTCTA<br>CACCCTGGTGGGCAGCCTGCCCCTGCTGATCGCCCTGATCTACACCCACAACACCCTGGGCAGCCTG<br>AACATCCTGCTGCTGACCCTGACCGCCCAGGAGCTGAGCAACAGCTGGGCCAACAACCTGATGTGGC<br>TGGCCTACACCATGGCCTTCATGGTGAAGATGCCCCTGTACGGCCTGCACCTGTGGCTGCCCAAGGC<br>CCACGTGGAGGCCCCCATCGCCGGCAGCATGGTGCTGGCCGCCGTGCTGCTGAAGCTGGGCGGCTA<br>CGGCATGATGCGCCTGACCCTGATCCTGAACCCCCTGACCAAGCACATGGCCTACCCCTTCCTGGTG<br>CTGAGCCTGTGGGGCATGATCATGACCAGCAGCATCTGCCTGCGCCAGACCGACCTGAAGAGCCTGA<br>TCGCCTACAGCAGCATCAGCCACATGGCCCTGGTGGTGACCGCCATCCTGATCCAGACCCCCTGGAG<br>CTTCACCGGCGCCGTGATCCTGATGATCGCCCACGGCCTGACCAGCAGCCTGCTGTTCTGCCTGGCC<br>AACAGCAACTACGAGCGCACCCACAGCCGCATCATGATCCTGAGCCAGGGCCTGCAGACCCTGCTGC<br>CCCTGATGGCCTTCTGGTGGCTGCTGGCCAGCCTGGCCAACCTGGCCCTGCCCCCCACCATCAACCT<br>GCTGGGCGAGCTGAGCGTGCTGGTGACCACCTTCAGCTGGAGCAACATCACCCTGCTGCTGACCGG<br>CCTGAACATGCTGGTGACCGCCCTGTACAGCCTGTACATGTTCACCACCACCCAGTGGGGCAGCCTG<br>ACCCACCACATCAACAACATGAAGCCCAGCTTCACCCGCGAGAACACCCTGATGTTCATGCACCTGAG<br>CCCCATCCTGCTGCTGAGCCTGAACCCCGACATCATCACCGGCTTCAGCAGCTAAGAGCACTGGGAC<br>GCCCACCGCCCCTTTCCCTCCGCTGCCAGGCGAGCATGTTGTGGTAATTCTGGAACACAAGAAGAGA<br>AATTGCTGGGTTTAGAACAAGATTATAAACGAATTCGGTGCTCAGTGATCACTTGACAGTTTTTTTTTTT<br>TTTAAATATTACCCAAAATGCTCCCCAAATAAGAAATGCATCAGCTCAGTCAGTGAATACAAAAAAGGA<br>ATTATTTTTCCCTTTGAGGGTCTTTTATACATCTCTCCTCCAACCCCACCCTCTATTCTGTTTCTTCCTCC<br>TCACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTCCACTGGGACTGGGGATTCCACATGTTTGCCTTGGGAGTCTCAAGCTGGACTGCCA |

TABLE 1-continued nucleic acid and polypeptide sequences and SEQ ID NOs

| SEQ | description | sequence |
| --- | --- | --- |
| 35 | opt_COX10-ND6-3'UTR | ATGGCCGCCTCTCCACACACACTGAGTAGCAGACTGCTGACCGGCTGTGTTGGCGGCTCTGTGTGGT<br>ATCTGGAACGGCGGACAATGATGTATGCTTTGTTTCTGTTGAGTGTGGGTTTAGTAATGGGGTTTGTG<br>GGGTTTTCTTCTAAGCCTTCTCCTATTTATGGGGGTTTAGTATTGATTGTTAGCGGTGTGGTCGGGTGT<br>GTTATTATTCTGAATTTTGGGGGAGGTTATATGGGTTTAATGGTTTTTTTAATTTATTTAGGGGGAATGA<br>TGGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGAAGCTGGATGATTTATGAAGGAGAGGGG<br>TCAGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCAGCCCCTGTCCTCCCTTCACCCCCATTGCGTATGAGCATTTCAGAACTCCAAGGAGTCACAGGC<br>ATCTTTATAGTTCACGTTAACATATAGACACTGTTGGAAGCAGTTCCTTCTAAAAGGGTAGCCCTGGAC<br>TTAATACCAGCCGGATACCTCTGGCCCCCACCCCATTACTGTACCTCTGGAGTCACTACTGTGGGTCG<br>CCACTCCTCTGCTACACAGCACGGCTTTTTCAAGGCTGTATTGAGAAGGGAAGTTAGGAAGAAGGGTG<br>TGCTGGGCTAACCAGCCCACAGAGCTCACATTCCTGTCCCTTGGGTGAAAAATACATGTCCATCCTGA<br>TATCTCCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCTTTTTAG<br>TCCTTTGTGCTCCCACGGGTCTACAGAGTCCCATCTGCCCAAAGGTCTTGAAGCTTGACAGGATGTTT<br>TCGATTACTCAGTCTCCCAGGGCACTACTGGTCCGTAGGATTCGATTGGTCGGGGTAGGAGAGTTAAA<br>CAACATTTAAACAGAGTTCTCTCAAAAATGTCTAAAGGGATTGTAGGTAGATAACATCCAATCACTGTTT<br>GCACTTATCTGAAATCTTCCCTCTTGGCTGCCCCCAGGTATTTACTGTGGAGAACATTGCATAGGAATG<br>TCTGGAAAAAGCTTCTACAACTTGTTACAGCCTTCACATTTGTAGAAGCTTT |
| 36 | opt_COX10-ND6-3'UTR* | ATGGCCGCCTCTCCACACACACTGAGTAGCAGACTGCTGACCGGCTGTGTTGGCGGCTCTGTGTGGT<br>ATCTGGAACGGCGGACAATGATGTATGCTTTGTTTCTGTTGAGTGTGGGTTTAGTAATGGGGTTTGTG<br>GGGTTTTCTTCTAAGCCTTCTCCTATTTATGGGGGTTTAGTATTGATTGTTAGCGGTGTGGTCGGGTGT<br>GTTATTATTCTGAATTTTGGGGGAGGTTATATGGGTTTAATGGTTTTTTTAATTTATTTAGGGGGAATGA<br>TGGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGAAGCTGGATGATTTATGAAGGAGAGGGG<br>TCAGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCA |
| 37 | opt_COX10-opt_ND6-3'UTR | ATGGCCGCCTCTCCACACACACTGAGTAGCAGACTGCTGACCGGCTGTGTTGGCGGCTCTGTGTGGT<br>ATCTGGAACGGCGGACAATGATGTACGCCCTGTTCCTGCTGAGCGTGGGCCTGGTGATGGGCTTCGT<br>GGGCTTCAGCAGCAAGCCCAGCCCCATCTACGGCGGCCTGGTGCTGATCGTGAGCGGCGTGGTGGG<br>CTGCGTGATCATCCTGAACTTCGGCGGCGGCTACATGGGCCTGATGGTGTTCCTGATCTACCTGGGC<br>GGCATGATGGTGGTGTTCGGCTACACCACCGCCATGGCCATCGAGGAGTACCCCGAGGCCTGGGGC<br>AGCGGCGTGGAGGTGCTGGTGAGCGTGCTGGTGGGCCTGGCCATGGAGGTGGGCCTGGTGCTGTG<br>GGTGAAGGAGTACGACGGCGTGGTGGTGGTGGTGAACTTCAACAGCGTGGGCAGCTGGATGATCTA<br>CGAGGGCGAGGGCAGCGGCCTGATCCGCGAGGACCCCATCGGCGCCGGCGCCCTGTACGACTACG<br>GCCGCTGGCTGGTGGTGGTGACCGGCTGGACCCTGTTCGTGGGCGTGTACATCGTGATCGAGATCG<br>CCCGCGGCAACTAAGAGCACTGGGACGCCCACCGCCCCTTTCCCTCCGCTGCCAGGCGAGCATGTT<br>GTGGTAATTCTGGAACACAAGAAGAGAAATTGCTGGGTTTAGAACAAGATTATAAACGAATTCGGTGCT<br>CAGTGATCACTTGACAGTTTTTTTTTTTTTTAAATATTACCCAAAATGCTCCCCAAATAAGAAATGCATCA<br>GCTCAGTCAGTGAATACAAAAAAGGAATTATTTTTCCCTTTGAGGGTCTTTTATACATCTCTCCTCCAAC<br>CCCACCCTCTATTCTGTTTCTTCCTCCTCACATGGGGGTACACATACACAGCTTCCTCTTTTGGTTCCA<br>TCCTTACCACCACACCACACGCACACTCCACATGCCCAGCAGAGTGGCACTTGGTGGCCAGAAAGTG<br>TGAGCCTCATGATCTGCTGTCTGTAGTTCTGTGAGCTCAGGTCCCTCAAAGGCCTCGGAGCACCCCCT<br>TCCTTGTGACTGAGCCAGGGCCTGCATTTTTGGTTTTCCCCACCCCACACATTCTCAACCATAGTCCTT<br>CTAACAATACCAATAGCTAGGACCCGGCTGCTGTGCACTGGGACTGGGGATTCCACATGTTTGCCTTG<br>GGAGTCTCAAGCTGGACTGCCAGCCCCTGTCCTCCCTTCACCCCCATTGCGTATGAGCATTTCAGAAC<br>TCCAAGGAGTCACAGGCATCTTTATAGTTCACGTTAACATATAGACACTGTTGGAAGCAGTTCCTTCTA<br>AAAGGGTAGCCCTGGACTTAATACCAGCCGGATACCTCTGGCCCCCACCCCATTACTGTACCTCTGGA<br>GTCACTACTGTGGGTCGCCACTCCTCTGCTACACAGCACGGCTTTTTCAAGGCTGTATTGAGAAGGGA<br>AGTTAGGAAGAAGGGTGTGCTGGGCTAACCAGCCCACAGAGCTCACATTCCTGTCCCTTGGGTGAAA<br>AATACATGTCCATCCTGATATCTCCTGAATTCAGAAATTAGCCTCCACATGTGCAATGGCTTTAAGAGC<br>CAGAAGCAGGGTTCTGGGAATTTTGCAAGTTACCTGTGGCCAGGTGTGGTCTCGGTTACCAAATACGG<br>TTACCTGCAGCTTTTTAGTCCTTTGTGCTCCCACGGGTCTACAGAGTCCCATCTGCCCAAAGGTCTTGA<br>AGCTTGACAGGATGTTTTCGATTACTCAGTCTCCCAGGGCACTACTGGTCCGTAGGATTCGATTGGTC |

TABLE 1-continued nucleic acid and polypeptide sequences and SEQ ID NOs

| SEQ | description | sequence |
|---|---|---|
| | | GGGGTAGGAGAGTTAAACAACATTTAAACAGAGTTCTCTCAAAAATGTCTAAAGGGATTGTAGGTAGAT<br>AACATCCAATCACTGTTTGCACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCTTCACATTTGTAGAAGCTT<br>T |
| 38 | opt_COX10-opt_ND6-3'UTR* | ATGGCCGCCTCTCCACACACACTGAGTAGCAGACTGCTGACCGGCTGTGTTGGCGGCTCTGTGTGGT<br>ATCTGGAACGGCGGACAATGATGTACGCCCTGTTCCTGCTGAGCGTGGGCCTGGTGATGGGCTTCGT<br>GGGCTTCAGCAGCAAGCCCAGCCCCATCTACGGCGGCCTGGTGCTGATCGTGAGCGGCGTGGTGGG<br>CTGCGTGATCATCCTGAACTTCGGCGGCGGCTACATGGGCCTGATGGTGTTCCTGATCTACCTGGGC<br>GGCATGATGGTGGTGTTCGGCTACACCACCGCCATGGCCATCGAGGAGTACCCCGAGGCCTGGGGC<br>AGCGGCGTGGAGGTGCTGGTGAGCGTGCTGGTGGGCCTGGCCATGGAGGTGGGCCTGGTGCTGTG<br>GGTGAAGGAGTACGACGGCGTGGTGGTGGTGGTGAACTTCAACAGCGTGGGCAGCTGGATGATCTA<br>CGAGGGCGAGGGCAGCGGCCTGATCCGCGAGGACCCCATCGGCGCCGGCGCCCAATACGACTACG<br>GCCGCTGGCTGGTGGTGGTGACCGGCTGGACCCTGTTCGTGGGCGTGTACATCGTGATCGAGATCG<br>CCCGCGGCAACTAAGAGCACTGGGACGCCCACCGCCCCTTTCCCTCCGCTGCCAGGCGAGCATGTT<br>GTGGTAATTCTGGAACACAAGAAGAGAAATTGCTGGGTTTAGAACAAGATTATAAACGAATTCGGTGCT<br>CAGTGATCACTTGACAGTTTTTTTTTTTTTTTAAATATTACCCAAATGCTCCCCAAATAAGAAATGCATCA<br>GCTCAGTCAGTGAATACAAAAAAGGAATTATTTTTCCCTTTGAGGGTCTTTTATACATCTCTCCTCCAAC<br>CCCACCCTCTATTCTGTTTCTTCCTCCTCACATGGGGGTACACATACACAGCTTCCTCTTTTGGTTCCA<br>TCCTTACCACCACACCACACGCACACTCCACATGCCCAGCAGAGTGGCACTTGGTGGCCAGAAAGTG<br>TGAGCCTCATGATCTGCTGTCTGTAGTTCTGTGAGCTCAGGTCCCTCAAGGCCTCGGAGCACCCCCT<br>TCCTTGTGACTGAGCCAGGGCCTGCATTTTTGGTTTTCCCCACCCCACACATTCTCAACCATAGTCCTT<br>CTAACAATACCAATAGCTAGGACCCGGCTGCTGTGCACTGGGACTGGGGATTCCACATGTTTGCCTTG<br>GGAGTCTCAAGCTGGACTGCCA |
| 39 | opt_COX10-ND1-3'UTR | ATGGCCGCCTCTCCACACACACTGAGTAGCAGACTGCTGACCGGCTGTGTTGGCGGCTCTGTGTGGT<br>ATCTGGAACGGCGGACAATGGCCAACCTCCTACTCCTCATTGTACCCATTCTAATCGCAATGGCATTC<br>CTAATGCTTACCGAACGAAAAATTCTAGGCTATATGCAACTACGCAAAGGCCCCAACGTTGTAGGCCC<br>CTACGGGCTACTACAACCCTTCGCTGACGCCATAAAACTCTTCACCAAAGAGCCCCTAAAACCCGCCA<br>CATCTACCATCACCCTCTACATCACCGCCCCGACCTTAGCTCTCACCATCGCTCTTCTACTATGGACCC<br>CCCTCCCCATGCCCAACCCCCTGGTCAACCTCAACCTAGGCCTCCTATTTATTCTAGCCACCTCTAGC<br>CTAGCCGTTTACTCAATCCTCTGGTCAGGGTGGGCATCAAACTCAAACTACGCCCTGATCGGCGCACT<br>GCGAGCAGTAGCCCAAACAATCTCATATGAAGTCACCCTAGCCATCATTCTACTATCAAATTACTAAT<br>GAGTGGCTCCTTTAACCTCTCCACCCTTATCACAACACAAGAACACCTCTGGTTACTCCTGCCATCATG<br>GCCCTTGGCCATGATGTGGTTTATCTCCACACTAGCAGAGACCAACCGAACCCCCTTCGACCTTGCCG<br>AAGGGGAGTCCGAACTAGTCTCAGGCTTCAACATCGAATACGCCGCAGGCCCCTTCGCCCTATTCTTC<br>ATGGCCGAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCCCTGTTC<br>TTATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCAGCCCCTGTCCTCCCTTCACCCCCATTGCGTATGAGCATTTCAGAACTCCAAG<br>GAGTCACAGGCATCTTTATAGTTCACGTTAACATATAGACACTGTTGGAAGCAGTTCCTTCTAAAAGGG<br>TAGCCCTGGACTTAATACCAGCCGGATACCTCTGGCCCCCACCCCATTACTGTACCTCTGGAGTCACT<br>ACTGTGGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAATACAT<br>GTCCATCCTGATATCTCCTGAATTCAGAAATTAGCCTCCACATGTGCAATGGCTTTAAGAGCCAGAAGC<br>AGGGTTCTGGGAATTTTGCAAGTTACCTGTGGCCAGGTGTGGTCTCGGTTACCAAATACGGTTACCTG<br>CAGCTTTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCGGGGTA<br>GGAGAGTTAAACAACATTTAAACAGAGTTCTCTCAAAAATGTCTAAAGGGATTGTAGGTAGATAACATC<br>CAATCACTGTTTGCACTTATCTGAAATCTTCCCTCTTGGCTGCCCCCAGGTATTTACTGTGGAGAACAT<br>TGCATAGGAATGTCTGGAAAAAGCTTCTACAACTTGTTACAGCCTTCACATTTGTAGAAGCTTT |
| 40 | Opt_COX10-ND1-3'UTR* | ATGGCCGCCTCTCCACACACACTGAGTAGCAGACTGCTGACCGGCTGTGTTGGCGGCTCTGTGTGCT<br>ATCTGGAACGGCGGACAATGGCCAACCTCCTACTCCTCATTGTACCCATTCTAATCGCAATGGCATTC<br>CTAATGCTTACCGAACGAAAAATTCTAGGCTATATGCAACTACGCAAAGGCCCCAACGTTGTAGGCCC<br>CTACGGGCTACTACAACCCTTCGCTGACGCCATAAAACTCTTCACCAAAGAGCCCCTAAAACCCGCCA<br>CATCTACCATCACCCTCTACATCACCGCCCCGACCTTAGCTCTCACCATCGCTCTTCTACTATGGACCC<br>CCCTCCCCATGCCCAACCCCCTGGTCAACCTCAACCTAGGCCTCCTATTTATTCTAGCCACCTCTAGC<br>CTAGCCGTTTACTCAATCCTCTGGTCAGGGTGGGCATCAAACTCAAACTACGCCCTGATCGGCGCACT<br>GCGAGCAGTAGCCCAAACAATCTCATATGAAGTCACCCTAGCCATCATTCTACTATCAACATTACTAAT<br>GAGTGGCTCCTTTAACCTCTCCACCCTTATCACAACACAAGAACACCTCTGGTTACTCCTGCCATCATG<br>GCCCTTGGCCATGATGTGGTTTATCTCCACACTAGCAGAGACCAACCGAACCCCCTTCGACCTTGCCG<br>AAGGGGAGTCCGAACTAGTCTCAGGCTTCAACATCGAATACGCCGCAGGCCCCTTCGCCCTATTCTTC<br>ATGGCCGAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCCCTGTTC<br>TTATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA |

TABLE 1-continued nucleic acid and polypeptide sequences and SEQ ID NOs

| SEQ | description | sequence |
|---|---|---|
| | | TCACTTGACAGTTTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCA |
| 41 | opt_COX10-opt_ND1-3'UTR | ATGGCCGCCTCTCCACACACACTGAGTAGCAGACTGCTGACCGGCTGTGTTGGCGGCTCTGTGTGGT<br>ATCTGGAACGGCGGACAATGGCCAACCTGCTGCTGCTGATCGTGCCCATCCTGATCGCCATGGCCTT<br>CCTGATGCTGACCGAGCGCAAGATCCTGGGCTACATGCAGCTGCGCAAGGGCCCCAACGTGGTGGG<br>CCCCTACGGCCTGCTGCAGCCCTTCGCCGACGCCATCAAGCTGTTCACCAAGGAGCCCCTGAAGCCC<br>GCCACCAGCACCATCACCCTGTACATCACCGCCCCCACCCTGGCCCTGACCATCGCCCTGCTGCTGT<br>GGACCCCCCTGCCCATGCCCAACCCCCTGGTGAACCTGAACCTGGGCCTGCTGTTCATCCTGGCCAC<br>CAGCAGCCTGGCCGTGTACAGCATCCTGTGGAGCGGCTGGGCCAGCAACAGCAACTACGCCCTGAT<br>CGGCGCCCTGCGCGCCGTGGCCCAGACCATCAGCTACGAGGTGACCCTGGCCATCATCCTGCTGAG<br>CACCCTGCTGATGAGCGGCAGCTTCAACCTGAGCACCCTGATCACCACCCAGGAGCACCTGTGGCTG<br>CTGCTGCCCAGCTGGCCCCTGGCCATGATGTGGTTCATCAGCACCCTGGCCGAGACCAACCGCACCC<br>CCTTCGACCTGGCCGAGGGCGAGAGCGAGCTGGTGAGCGGCTTCAACATCGAGTACGCCGCCGGCC<br>CCTTCGCCCTGTTCTTCATGGCCGAGTACACCAACATCATCATGATGAACACCCTGACCACCACCATC<br>TTCCTGGGCACCACCTACGACGCCCTGAGCCCCGAGCTGTACACCACCTACTTCGTGACCAAGACCC<br>TGCTGCTGACCAGCCTGTTCCTGTGGATCCGCACCGCCTACCCCCGCTTCCGCTACGACCAGCTGAT<br>GCACCTGCTGTGGAAGAACTTCCTGCCCCTGACCCTGGCCCTGCTGATGTGGTACGTGAGCATGCCC<br>ATCACCATCAGCAGCATCCCCCCCCAGACCTAAGAGCACTGGGACGCCCACCGCCCCTTTCCCTCCG<br>CTGCCAGGCGAGCATGTTGTGGTAATTCTGGAACACAAGAAGAGAAATTGCTGGGTTTAGAACAAGAT<br>TATAAACGAATTCGGTGCTCAGTGATCACTTGACAGTTTTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTCTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCTAACAATACCAATAGCTAGGACCCGGCTGCTGTGCACTGGGACTGGG<br>GATTCCACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATAGACACT<br>GTTGGAAGCAGTTCCTTCTAAAAGGGTAGCCCTGGACTTAATACCAGCCGGATACCTCTGGCCCCCAC<br>CCCATTACTGTACCTCTGGAGTCACTACTGTGGGTCGCCACTCCTCTGCTACACAGCACGGCTTTTTc<br>AAGGCTGTATTGAGAAGGGAAGTTAGGAAGAAGGGTGTGCTGGGCTAACCAGCCCACAGAGCTCACA<br>TTCCTGTCCCTTGGGTGAAAAATACATGTCCATCCTGATATCTCCTGAATTCAGAAATTAGCCTCCACA<br>TGTGCAATGGCTTTAAGAGCCAGAAGCAGGGTTCTGGGAATTTTGCAAGTTACCTGTGGCCAGGTGTG<br>GTCTCGGTTACCAAATACGGTTACCTGCAGCTTTTTAGTCCTTTGTGCTCCCACGGGTCTACAGAGTC<br>CCATCTGCCCAAAGGTCTTGAAGCTTGACAGGATGTTTTCGATTACTCAGTCTCCCAGGGCACTACTG<br>GTCCGTAGGATTCGATTGGTCGGGGTAGGAGAGTTAAACAACATTTAAACAGAGTTCTCTCAAAAATGT<br>CTAAAGGGATTGTAGGTAGATAACATCCAATCACTGTTTGCACTTATCTGAAATCTTCCCTCTTGGCTG<br>CCCCCAGGTATTTACTGTGGAGAACATTGCATAGGAATGTCTGGAAAAAGCTTCTACAACTTGTTACAG<br>CCTTCACATTTGTAGAAGCTTT |
| 42 | opt_COX10-opt_ND1-3'UTR* | ATGGCCGCCTCTCCACACACACTGAGTAGCAGACTGCTGACCGGCTGTGTTGGCGGCTCTGTGTGGT<br>ATCTGGAACGGCGGACAATGGCCAACCTGCTGCTGCTGATCGTGCCCATCCTGATCGCCATGGCCTT<br>CCTGATGCTGACCGAGCGCAAGATCCTGGGCTACATGCAGCTGCGCAAGGGCCCCAACGTGGTGGG<br>CCCCTACGGCCTGCTGCAGCCCTTCGCCGACGCCATCAAGCTGTTCACCAAGGAGCCCCTGAAGCCC<br>GCCACCAGCACCATCACCCTGTACATCACCGCCCCCACCCTGGCCCTGACCATCGCCCTGCTGCTGT<br>GGACCCCCCTGCCCATGCCCAACCCCCTGGTGAACCTGAACCTGGGCCTGCTGTTCATCCTGGCCAC<br>CAGCAGCCTGGCCGTGTACAGCATCCTGTGGAGCGGCTGGGCCAGCAACAGCAACTACGCCCTGAT<br>CGGCGCCCTGCGCGCCGTGGCCCAGACCATCAGCTACGAGGTGACCCTGGCCATCATCCTGCTGAG<br>CACCCTGCTGATGAGCGGCAGCTTCAACCTGAGCACCCTGATCACCACCCAGGAGCACCTGTGGCTG<br>CTGCTGCCCAGCTGGCCCCTGGCCATGATGTGGTTCATCAGCACCCTGGCCGAGACCAACCGCACCC<br>CCTTCGACCTGGCCGAGGGCGAGAGCGAGCTGGTGAGCGGCTTCAACATCGAGTACGCCGCCGGCC<br>CCTTCGCCCTGTTCTTCATGGCCGAGTACACCAACATCATCATGATGAACACCCTGACCACCACCATC<br>TTCCTGGGCACCACCTACGACGCCCTGAGCCCCGAGCTGTACACCACCTACTTCGTGACCAAGACCC<br>TGCTGCTGACCAGCCTGTTCCTGTGGATCCGCACCGCCTACCCCCGCTTCCGCTACGACCAGCTGAT<br>GCACCTGCTGTGGAAGAACTTCCTGCCCCTGACCCTGGCCCTGCTGATGTGGTACGTGAGCATGCCC<br>ATCACCATCAGCAGCATCCCCCCCCAGACCTAAGAGCACTGGGACGCCCACCGCCCCTTTCCCTCCG<br>CTGCCAGGCGAGCATGTTGTGGTAATTCTGGAACACAAGAAGAGAAATTGCTGGGTTTAGAACAAGAT<br>TATAAACGAATTCGGTGCTCAGTGATCACTTGACAGTTTTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCTAACAATACCAATAGCTAGGACCCGGCTGCTGTGCACTGGGACTGGG<br>GATTCCACATGTTTGCCTTGGGAGTCTCAAGCTGGACTGCCA |
| 43 | opt_COX10*-ND4-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGCTAAAACTAATCGTCCCAACAATTATGTTACTACCACTGACATGGC<br>TTTCCAAAAAACACATGATTTGGATCAACACAACCACCCACAGCCTAATTATTAGCATCATCCCTCTACT<br>ATTTTTTAACCAAATCAACAACAACCTATTTAGCTGTTCCCCAACCTTTTCCTCCGACCCCCTAACAACC<br>CCCCTCCTAATGCTAACTACCTGGCTCCTACCCCTCACAATCATGGCAAGCCAACGCCACTTATCCAG<br>TGAACCACTATCACGAAAAAAACTCTACCTCTCTATGCTAATCTCCCTACAAATCTCCTTAATTATGACA |

TABLE 1-continued

| nucleic acid and polypeptide sequences and SEQ ID NOs | | |
|---|---|---|
| SEQ | description | sequence |
| | | TTCACAGCCACAGAACTAATCATGTTTTATATCTTCTTCGAAACCACACTTATCCCCACCTTGGCTATCA TCACCCGATGGGGCAACCAGCCAGAACGCCTGAACGCAGGCACATACTTCCTATTCTACACCCTAGTA GGCTCCCTTCCCCTACTCATCGCACTAATTTACACTCACAACACCCTAGGCTCACTAAACATTCTACTA CTCACTCTCACTGCCCAAGAACTATCAAACTCCTGGGCCAACAACTTAATGTGGCTAGCTTACACAATG GCTTTTATGGTAAAGATGCCTCTTTACGGACTCCACTTATGGCTCCCTAAAGCCCATGTCGAAGCCCC CATCGCTGGGTCAATGGTACTTGCCGCAGTACTCTTAAAACTAGGCGGCTATGGTATGATGCGCCTCA CACTCATTCTCAACCCCCTGACAAAACACATGGCCTACCCCTTCCTTGTACTATCCCTATGGGGCATGA TTATGACAAGCTCCATCTGCCTACGACAAACAGACCTAAAATCGCTCATTGCATACTCTTCAATCAGCC ACATGGCCCTCGTAGTAACAGCCATTCTCATCCAAACCCCCTGGAGCTTCACCGGCGCAGTCATTCTC ATGATCGCCCACGGGCTTACATCCTCATTACTATTCTGCCTAGCAAACTCAAACTACGAACGCACTCAC AGTCGCATCATGATCCTCTCTCAAGGACTTCAAACTCTACTCCCACTAATGGCTTTTTGGTGGCTTCTA GCAAGCCTCGCTAACCTCGCCTTACCCCCCACTATTAACCTACTGGGAGAACTCTCTGTGCTAGTAAC CACGTTCTCCTGGTCAAATATCACTCTCCTACTTACAGGACTCAACATGCTAGTCACAGCCCTATACTC CCTCTACATGTTTACCACAACACAATGGGGCTCACTCACCCACCACATTAACAACATGAAACCCTCATT CACACGAGAAAACACCCTCATGTTCATGCACCTATCCCCCATTCTCCTCCTATCCCTCAACCCCGACAT CATTACCGGGTTTTCCTCTTAAGAGCACTGGGACGCCCACCGCCCCTTTCCCTCCGCTGCCAGGCGA GCATGTTGTGGTAATTCTGGAACACAAGAAGAGAAATTGCTGGGTTTAGAACAAGATTATAAACGAATT CGGTGCTCAGTGATCACTTGACAGTTTTTTTTTTTTTTAAATATTACCCAAAATGCTCCCCAAATAAGAA ATGCATCAGCTCAGTCAGTGAATACAAAAAAGGAATTATTTTTCCCTTTGAGGGTCTTTTATACATCTCT CCTCCAACCCCACCCTCTATTCTGTTTCTTCCTCCTCACATGGGGGTACACATACACAGCTTCCTCTTT TGGTTCCATCCTTACCACCACACCACACGCACACTCCACATGCCCAGCAGAGTGGCACTTGGTGGCC AGAAAGTGTGAGCCTCATGATCTGCTGTCTGTAGTTCTGTGAGCTCAGGTCCCTCAAAGGCCTCGGAG CACCCCCTTCCTTGTGACTGAGCCAGGGCCTGCATTTTTGGTTTTCCCCACCCCACACATTCTCAACC ATAGTCCTTCTAACAATACCAATAGCTAGGACCCGGCTGCTGTGCACTGGGACTGGGGATTCCACATG TTTGCCTTGGGAGTCTCAAGCTGGACTGCCAGCCCCTGTCCTCCCTTCACCCCCATTGCGTATGAGCA TTTCAGAACTCCAAGGAGTCACAGGCATCTTTATAGTTCACGTTAACATATAGACACTGTTGGAAGCAG TTCCTTCTAAAAGGGTAGCCCTGGACTTAATACCAGCCGGATACCTCTGGCCCCCACCCCATTACTGT ACCTCTGGAGTCACTACTGTGGGTCGCCACTCCTCTGCTACACAGCACGGCTTTTTCAAGGCTGTATT GAGAAGGGAAGTTAGGAAGAAGGGTGTGCTGGGCTAACCAGCCCACAGAGCTCACATTCCTGTCCCT TGGGTGAAAAATACATGTCCATCCTGATATCTCCTGAATTCAGAAATTAGCCTCCACATGTGCAATGGC TTTAAGAGCCAGAAGCAGGGTTCTGGGAATTTTGCAAGTTACCTGTGGCCAGGTGTGGTCTCGGTTAC CAAATACGGTTACCTGCAGCTTTTTAGTCCTTTGTGCTCCCACGGGTCTACAGAGTCCCATCTGCCCA AAGGTCTTGAAGCTTGACAGGATGTTTTCGATTACTCAGTCTCCCAGGGCACTACTGGTCCGTAGGAT TCGATTGGTCGGGGTAGGAGAGTTAAACAACATTTAAACAGAGTTCTCTCAAWATGTCTAAAGGGATT GTAGGTAGATAACATCCAATCACTGTTTGCACTTATCTGAAATCTTCCCTCTTGGCTGCCCCCAGGTAT TTACTGTGGAGAACATTGCATAGGAATGTCTGGAAAAAGCTTCTACAACTTGTTACAGCCTTCACATTT GTAGAAGCTTT |
| 44 | opt_COX10*-ND4-3'UTR* | ATGGCCGCCAGCCCCCACACCCTGAGCAGCCGCCTGCTGACCGGCTGCGTGGGCGGCAGCGTGTG GTACCTGGAGCGCCGCACCATGCTAAAACTAATCGTCCCAACAATTATGTTACTACCACTGACATGGC TTTCCAAAAAACACATGATTTGGATCAACACAACCACCCACAGCCTAATTATTAGCATCATCCCTCTACT ATTTTTTAACCAAATCAACAACAACCTATTTAGCTGTTCCCCAACCTTTTCCTCCGACCCCCTAACAACC CCCCTCCTAATGCTAACTACCTGGCTCCTACCCCTCACAATCATGGCAAGCCAACGCCACTTATCCAG TGAACCACTATCACGAAAAAAACTCTACCTCTCTATGCTAATCTCCCTACAAATCTCCTTAATTATGACA TTCACAGCCACAGAACTAATCATGTTTTATATCTTCTTCGAAACCACACTTATCCCCACCTTGGCTATCA TCACCCGATGGGGCAACCAGCCAGAACGCCTGAACGCAGGCACATACTTCCTATTCTACACCCTAGTA GGCTCCCTTCCCCTACTCATCGCACTAATTTACACTCACAACACCCTAGGCTCACTAAACATTCTACTA CTCACTCTCACTGCCCAAGAACTATCAAACTCCTGGGCCAACAACTTAATGTGGCTAGCTTACACAATG GCTTTTATGGTAAAGATGCCTCTTTACGGACTCCACTTATGGCTCCCTAAAGCCCATGTCGAAGCCCC CATCGCTGGGTCAATGGTACTTGCCGCAGTACTCTTAAAACTAGGCGGCTATGGTATGATGCGCCTCA CACTCATTCTCAACCCCCTGACAAAACACATGGCCTACCCCTTCCTTGTACTATCCCTATGGGGCATGA TTATGACAAGCTCCATCTGCCTACGACAAACAGACCTAAAATCGCTCATTGCATACTCTTCAATCAGCC ACATGGCCCTCGTAGTAACAGCCATTCTCATCCAAACCCCCTGGAGCTTCACCGGCGCAGTCATTCTC ATGATCGCCCACGGGCTTACATCCTCATTACTATTCTGCCTAGCAAACTCAAACTACGAACGCACTCAC AGTCGCATCATGATCCTCTCTCAAGGACTTCAAACTCTACTCCCACTAATGGCTTTTTGGTGGCTTCTA GCAAGCCTCGCTAACCTCGCCTTACCCCCCACTATTAACCTACTGGGAGAACTCTCTGTGCTAGTAAC CACGTTCTCCTGGTCAAATATCACTCTCCTACTTACAGGACTCAACATGCTAGTCACAGCCCTATACTC CCTCTACATGTTTACCACAACACAATGGGGCTCACTCACCCACCACATTAACAACATGAAACCCTCATT CACACGAGAAAACACCCTCATGTTCATGCACCTATCCCCCATTCTCCTCCTATCCCTCAACCCCGACAT CATTACCGGGTTTTCCTCTTAAGAGCACTGGGACGCCCACCGCCCCTTTCCCTCCGCTGCCAGGCGA GCATGTTGTGGTAATTCTGGAACACAAGAAGAGAAATTGCTGGGTTTAGAACAAGATTATAAACGAATT CGGTGCTCAGTGATCACTTGACAGTTTTTTTTTTTTTTAAATATTACCCAAAATGCTCCCCAAATAAGAA ATGCATCAGCTCAGTCAGTGAATACAAAAAAGGAATTATTTTTCCCTTTGAGGGTCTTTTATACATCTCT CCTCCAACCCCACCCTCTATTCTGTTTCTTCCTCCTCACATGGGGGTACACATACACAGCTTCCTCTTT TGGTTCCATCCTTACCACCACACCACACGCACACTCCACATGCCCAGCAGAGTGGCACTTGGTGGCC AGAAAGTGTGAGCCTCATGATCTGCTGTCTGTAGTTCTGTGAGCTCAGGTCCCTCAAAGGCCTCGGAG CACCCCCTTCCTTGTGACTGAGCCAGGGCCTGCATTTTTGGTTTTCCCCACCCCACACATTCTCAACC ATAGTCCTTCTAACAATACCAATAGCTAGGACCCGGCTGCTGTGCACTGGGACTGGGGATTCCACATG TTTGCCTTGGGAGTCTCAAGCTGGACTGCCA |
| 45 | opt_COX10*-opt_ND4-3'UTR | ATGGCCGCCAGCCCCCACACCCTGAGCAGCCGCCTGCTGACCGGCTGCGTGGGCGGCAGCGTGTG GTACCTGGAGCGCCGCACCATGCTGAAGCTGATCGTGCCCACCATCATGCTGCTGCCTCTGACCTGG CTGAGCAAGAAACACATGATCTGGATCAACACCACCACGCACAGCCTGATCATCAGCATCATCCCTCT GCTGTTCTTCAACCAGATCAACAACAACCTGTTCAGCTGCAGCCCCACCTTCAGCAGCGACCCTCTGA CAACACCTCTGCTGATGCTGACCACCTGGCTGCTGCCCCTCACAATCATGGCCTCTCAGAGACACCTG AGCAGCGAGCCCCTGAGCCGGAAGAAACTGTACCTGAGCATGCTGATCTCCCTGCAGATCTCTCTGA TCATGACCTTCACCGCCACCGAGCTGATCATGTTCTACATCTTTTTCGAGACAACGCTGATCCCCACAC TGGCCATCATCACCAGATGGGGCAACCAGCCTGAGAGACTGAACGCCGGCACCTACTTTCTGTTCTA |

TABLE 1-continued nucleic acid and polypeptide sequences and SEQ ID NOs

| SEQ | description | sequence |
|---|---|---|
| | | CACCCTCGTGGGCAGCCTGCCACTGCTGATTGCCCTGATCTACACCCACAACACCCTGGGCTCCCTG<br>AACATCCTGCTGCTGACACTGACAGCCCAAGAGCTGAGCAACAGCTGGGCCAACAATCTGATGTGGC<br>TGGCCTACACAATGGCCTTCATGGTCAAGATGCCCCTGTACGGCCTGCACCTGTGGCTGCCTAAAGC<br>TCATGTGGAAGCCCCTATCGCCGGCTCTATGGTGCTGGCTGCAGTGCTGCTGAAACTCGGCGGCTAC<br>GGCATGATGCGGCTGACCCTGATTCTGAATCCCCTGACCAAGCACATGGCCTATCCATTTCTGGTGCT<br>GAGCCTGTGGGGCATGATTATGACCAGCAGCATCTGCCTGCGGCAGACCGATCTGAAGTCCCTGATC<br>GCCTACAGCTCCATCAGCCACATGGCCCTGGTGGTCACCGCCATCCTGATTCAGACCCCTTGGAGCT<br>TTACAGGCGCCGTGATCCTGATGATTGCCCACGGCCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAATACATGTCCATCCTGATATCTCCTGAATTC<br>AGAAATTAGCCTCCACATGTGCAATGGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC<br>CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA<br>AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 46 | opt_COX10*-<br>opt_ND4-<br>3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCTCTGACCTGG<br>CTGAGCAAGAAACACATGATCTGGATCAACACCACCACGCACAGCCTGATCATCAGCATCATCCCTCT<br>GCTGTTCTTCAACCAGATCAACAACAACCTGTTCAGCTGCAGCCCCACCTTCAGCAGCGACCCTCTGA<br>CAACACCTCTGCTGATGCTGACCACCTGGCTGCTGCCCCTCACAATCATGGCCTCTCAGAGACACCTG<br>AGCAGCGAGCCCCTGAGCCGGAAGAAACTGTACCTGAGCATGCTGATCTCCCTGCAGATCTCTCTGA<br>TCATGACCTTCACCGCCACCGAGCTGATCATGTTCTACATCTTTTTCGAGACAACGCTGATCCCCACAC<br>TGGCCATCATCACCAGATGGGGCAACCAGCCTGAGAGACTGAACGCCGGCACCTACTTTCTGTTCTA<br>CACCCTCGTGGGCAGCCTGCCACTGCTGATTGCCCTGATCTACACCCACAACACCCTGGGCTCCCTG<br>AACATCCTGCTGCTGACACTGACAGCCCAAGAGCTGAGCAACAGCTGGGCCAACAATCTGATGTGGC<br>TGGCCTACACAATGGCCTTCATGGTCAAGATGCCCCTGTACGGCCTGCACCTGTGGCTGCCTAAAGC<br>TCATGTGGAAGCCCCTATCGCCGGCTCTATGGTGCTGGCTGCAGTGCTGCTGAAACTCGGCGGCTAC<br>GGCATGATGCGGCTGACCCTGATTCTGAATCCCCTGACCAAGCACATGGCCTATCCATTTCTGGTGCT<br>GAGCCTGTGGGGCATGATTATGACCAGCAGCATCTGCCTGCGGCAGACCGATCTGAAGTCCCTGATC<br>GCCTACAGCTCCATCAGCCACATGGCCCTGGTGGTCACCGCCATCCTGATTCAGACCCCTTGGAGCT<br>TTACAGGCGCCGTGATCCTGATGATTGCCCACGGCCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 47 | opt_COX10*-<br>opt_ND4*-<br>3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCCCTGACCTGG<br>CTGAGCAAGAAGCACATGATCTGGATCAACACCACCACCCACAGCCTGATCATCAGCATCATCCCCCT<br>GCTGTTCTTCAACCAGATCAACAACAACCTGTTCAGCTGCAGCCCCACCTTCAGCAGCGACCCCCTGA<br>CCACCCCCCTGCTGATGCTGACCACCTGGCTGCTGCCCCTGACCATCATGGCCAGCCAGCGCCACCT<br>GAGCAGCGAGCCCCTGAGCCGCAAGAAGCTGTACCTGAGCATGCTGATCAGCCTGCAGATCAGCCTG<br>ATCATGACCTTCACCGCCACCGAGCTGATCATGTTCTACATCTTCTTCGAGACCACCCTGATCCCCAC<br>CCTGGCCATCATCACCCGCTGGGGCAACCAGCCCGAGCGCCTGAACGCCGGCACCTACTTCCTGTTC<br>TACACCCTGGTGGGCAGCCTGCCCCTGCTGATCGCCCTGATCTACACCCACAACACCCTGGGCAGCC<br>TGAACATCCTGCTGCTGACCCTGACCGCCCAGGAGCTGAGCAACAGCTGGGCCAACAACCTGATGTG |

TABLE 1-continued nucleic acid and polypeptide sequences and SEQ ID NOs

| SEQ | description | sequence |
|---|---|---|
| | | GCTGGCCTACACCATGGCCTTCATGGTGAAGATGCCCCTGTACGGCCTGCACCTGTGGCTGCCCAAG GCCCACGTGGAGGCCCCCATCGCCGGCAGCATGGTGCTGGCCGCCGTGCTGCTGAAGCTGGGCGG CTACGGCATGATGCGCCTGACCCTGATCCTGAACCCCCTGACCAAGCACATGGCCTACCCCTTCCTG GTGCTGAGCCTGTGGGGCATGATCATGACCAGCAGCATCTGCCTGCGCCAGACCGACCTGAAGAGC CTGATCGCCTACAGCAGCATCAGCCACATGGCCCTGGTGGTGACCGCCATCCTGATCCAGACCCCCT GGAGCTTCACCGGCGCCGTGATCCTGATGATCGCCCACGGCCTGACCAGCAGCCTGCTGTTCTGCCT GGCCAACAGCAACTACGAGCGCACCCACAGCCGCATCATGATCCTGAGCCAGGGCCTGCAGACCCT GCTGCCCCTGATGGCCTTCTGGTGGCTGCTGGCCAGCCTGGCCAACCTGGCCCTGCCCCCCACCAT CAACCTGCTGGGCGAGCTGAGCGTGCTGGTGACCACCTTCAGCTGGAGCAACATCACCCTGCTGCTG ACCGGCCTGAACATGCTGGTGACCGCCCTGTACAGCCTGTACATGTTCACCACCACCCAGTGGGGCA GCCTGACCCACCACATCAACAACATGAAGCCCAGCTTCACCCGCGAGAACACCCTGATGTTCATGCAC CTGAGCCCCATCCTGCTGCTGAGCCTGAACCCCGACATCATCACCGGCTTCAGCAGCTAAGAGCACT GGGACGCCCACCGCCCCTTTCCCTCCGCTGCCAGGCGAGCATGTTGTGGTAATTCTGGAACACAAGA AGAGAAATTGCTGGGTTTAGAACAAGATTATAAACGAATTCGGTGCTCAGTGATCACTTGACAGTTTTT TTTTTTTTTAAATATTACCCAAAATGCTCCCCAAATAAGAAATGCATCAGCTCAGTCAGTGAATACAAAA AAGGAATTATTTTTCCCTTTGAGGGTCTTTTATACATCTCTCCTCCAACCCCACCCTCTATTCTGTTTCT TCCTCCTCACATGGGGGTACACATACACAGCTTCCTCTTTTGGTTCCATCCTTACCACCACACCACACG CACACTCCACATGCCCAGCAGAGTGGCACTTGGTGGCCAGAAAGTGTGAGCCTCATGATCTGCTGTC TGTAGTTCTGTGAGCTCAGGTCCCTCAAAGGCCTCGGAGCACCCCCTTCCTTGTGACTGAGCCAGGG CCTGCATTTTTGGTTTTCCCCACCCCACACATTCTCAACCATAGTCCTTCTAACAATACCAATAGCTAG GACCCGGCTGCTGTGCACTGGGACTGGGGATTCCACATGTTTGCCTTGGGAGTCTCAAGCTGGACTG CCAGCCCCTGTCCTCCCTTCACCCCCATTGCGTATGAGCATTTCAGAACTCCAAGGAGTCACAGGCAT CTTTATAGTTCACGTTAACATATAGACACTGTTGGAAGCAGTTCCTTCTAAAAGGGTAGCCCTGGACTT AATACCAGCCGGATACCTCTGGCCCCCACCCCATTACTGTACCTCTGGAGTCACTACTGTGGGTCGCC ACTCCTCTGCTACACAGCACGGCTTTTTCAAGGCTGTATTGAGAAGGGAAGTTAGGAAGAAGGGTGTG CTGGGCTAACCAGCCCACAGAGCTCACATTCCTGTCCCTTGGGTGAAAAATACATGTCCATCCTGATA TCTCCTGAATTCAGAAATTAGCCTCCACATGTGCAATGGCTTTAAGAGCCAGAAGCAGGGTTCTGGGA ATTTTGCAAGTTACCTGTGGCCAGGTGTGGTCTCGGTTACCAAATACGGTTACCTGCAGCTTTTTAGTC CTTTGTGCTCCCACGGGTCTACAGAGTCCCATCTGCCCAAAGGTCTTGAAGCTTGACAGGATGTTTTC GATTACTCAGTCTCCCAGGGCACTACTGGTCCGTAGGATTCGATTGGTCGGGGTAGGAGAGTTAAACA ACATTTAAACAGAGTTCTCTCAAAAATGTCTAAAGGGATTGTAGGTAGATAACATCCAATCACTGTTTGC ACTTATCTGAAATCTTCCCTCTTGGCTGCCCCCAGGTATTTACTGTGGAGAACATTGCATAGGAATGTC TGGAAAAAGCTTCTACAACTTGTTACAGCCTTCACATTTGTAGAAGCTTT |
| 48 | opt_COX10*-opt_ND4*-3'UTR* | ATGGCCGCCAGCCCCCACACCCTGAGCAGCCGCCTGCTGACCGGCTGCGTGGGCGGCAGCGTGTG GTACCTGGAGCGCCGCACCATGCTGAAGCTGATCGTGCCCACCATCATGCTGCTGCCCCTGACCTGG CTGAGCAAGAAGCACATGATCTGGATCAACACCACCACCCACAGCCTGATCATCAGCATCATCCCCCT GCTGTTCTTCAACCAGATCAACAACAACCTGTTCAGCTGCAGCCCCACCTTCAGCAGCGACCCCCTGA CCACCCCCCTGCTGATGCTGACCACCTGGCTGCTGCCCCTGACCATCATGGCCAGCCAGCGCCACCT GAGCAGCGAGCCCCTGAGCCGCAAGAAGCTGTACCTGAGCATGCTGATCAGCCTGCAGATCAGCCTG ATCATGACCTTCACCGCCACCGAGCTGATCATGTTCTACATCTTCTTCGAGACCACCCTGATCCCCAC CCTGGCCATCATCACCCGCTGGGGCAACCAGCCCGAGCGCCTGAACGCCGGCACCTACTTCCTGTTC TACACCCTGGTGGGCAGCCTGCCCCTGCTGATCGCCCTGATCTACACCCACAACACCCTGGGCAGCC TGAACATCCTGCTGCTGACCCTGACCGCCCAGGAGCTGAGCAACAGCTGGGCCAACAACCTGATGTG GCTGGCCTACACCATGGCCTTCATGGTGAAGATGCCCCTGTACGGCCTGCACCTGTGGCTGCCCAAG GCCCACGTGGAGGCCCCCATCGCCGGCAGCATGGTGCTGGCCGCCGTGCTGCTGAAGCTGGGCGG CTACGGCATGATGCGCCTGACCCTGATCCTGAACCCCCTGACCAAGCACATGGCCTACCCCTTCCTG GTGCTGAGCCTGTGGGGCATGATCATGACCAGCAGCATCTGCCTGCGCCAGACCGACCTGAAGAGC CTGATCGCCTACAGCAGCATCAGCCACATGGCCCTGGTGGTGACCGCCATCCTGATCCAGACCCCCT GGAGCTTCACCGGCGCCGTGATCCTGATGATCGCCCACGGCCTGACCAGCAGCCTGCTGTTCTGCCT GGCCAACAGCAACTACGAGCGCACCCACAGCCGCATCATGATCCTGAGCCAGGGCCTGCAGACCCT GCTGCCCCTGATGGCCTTCTGGTGGCTGCTGGCCAGCCTGGCCAACCTGGCCCTGCCCCCCACCAT CAACCTGCTGGGCGAGCTGAGCGTGCTGGTGACCACCTTCAGCTGGAGCAACATCACCCTGCTGCTG ACCGGCCTGAACATGCTGGTGACCGCCCTGTACAGCCTGTACATGTTCACCACCACCCAGTGGGGCA GCCTGACCCACCACATCAACAACATGAAGCCCAGCTTCACCCGCGAGAACACCCTGATGTTCATGCAC CTGAGCCCCATCCTGCTGCTGAGCCTGAACCCCGACATCATCACCGGCTTCAGCAGCTAAGAGCACT GGGACGCCCACCGCCCCTTTCCCTCCGCTGCCAGGCGAGCATGTTGTGGTAATTCTGGAACACAAGA AGAGAAATTGCTGGGTTTAGAACAAGATTATAAACGAATTCGGTGCTCAGTGATCACTTGACAGTTTTT TTTTTTTTTAAATATTACCCAAAATGCTCCCCAAATAAAGAAATGCATCAGCTCAGTCAGTGAATACAAAA AAGGAATTATTTTTCCCTTTGAGGGTCTTTTATACATCTCTCCTCCAACCCCACCCTCTATTCTGTTTCT TCCTCCTCACATGGGGGTACACATACACAGCTTCCTCTTTTGGTTCCATCCTTACCACCACACCACACG CACACTCCACATGCCCAGCAGAGTGGCACTTGGTGGCCAGAAAGTGTGAGCCTCATGATCTGCTGTC TGTAGTTCTGTGAGCTCAGGTCCCTCAAAGGCCTCGGAGCACCCCCTTCCTTGTGACTGAGCCAGGG CCTGCATTTTTGGTTTTCCCCACCCCACACATTCTCAACCATAGTCCTTCTAACAATACCAATAGCTAG GACCCGGCTGCTGTGCACTGGGACTGGGGATTCCACATGTTTGCCTTGGGAGTCTCAAGCTGGACTG CCA |
| 49 | opt_COX10*-ND6-3'UTR | ATGGCCGCCAGCCCCCACACCCTGAGCAGCCGCCTGCTGACCGGCTGCGTGGGCGGCAGCGTGTG GTACCTGGAGCGCCGCACCATGATGTATGCTTTGTTTCTGTTGAGTGTGGGTTTAGTAATGGGGTTTG TGGGGTTTTCTTCTAAGCCTTCTCCTATTTATGGGGGTTTAGTATTGATTGTTAGCGGTGTGGTCGGGT GTGTTATTATTCTGAATTTTGGGGGAGGTTATATGGGTTTAATGGTTTTTTTAATTTATTTAGGGGGAAT GATGGTTGTCTTTGGATATACTACAGCGATGGCTATTGAGGAGTATCCTGAGGCATGGGGGTCAGGG GTTGAGGTCTTGGTGAGTGTTTTAGTGGGGTTAGCGATGGAGGTAGGATTGGTGCTGTGGGTGAAAG AGTATGATGGGGTGGTGGTTGTGGTAAACTTTAATAGTGTAGGAAGCTGGATGATTTATGAAGGAGAG GGGTCAGGGTTGATTCGGGAGGATCCTATTGGTGCGGGGGCTTTGTATGATTATGGGCGTTGGTTAG TAGTAGTTACTGGTTGGACATTGTTTGTTGGTGTATATATTGTAATTGAGATTGCTCGGGGGAATTAGG AGCACTGGGACGCCCACCGCCCCTTTCCCTCCGCTGCCAGGCGAGCATGTTGTGGTAATTCTGGAAC ACAAGAAGAGAAATTGCTGGGTTTAGAACAAGATTATAAACGAATTCGGTGCTCAGTGATCACTTGACA |

TABLE 1-continued

| nucleic acid and polypeptide sequences and SEQ ID NOs | | |
|---|---|---|
| SEQ | description | sequence |
| | | GTTTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCAGCCCCTGTCCTCCCTTCACCCCCATTGCGTATGAGCATTTCAGAACTCCAAGGAGTCACAG<br>GCATCTTTATAGTTCACGTTAACATATAGACACTGTTGGAAGCAGTTCCTTCTAAAAGGGTAGCCCTGG<br>ACTTAATACCAGCCGGATACCTCTGGCCCCCACCCCATTACTGTACCTCTGGAGTCACTACTGTGGGT<br>CGCCACTCCTCTGCTACACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGTGAAAAATACATGTCCATCC<br>TGATATCTCCTGAATTCAGAAAATTAGCCTCCACATGTGCAATGGCTTTAAGAGCCAGAAGCAGGGTTCT<br>GGGAATTTTGCAAGTTACCTGTGGCCAGGTGTGGTCTCGGTTACCAAATACGGTTACCTGCAGCTTTT<br>TAGTCCTTTGTGCTCCCACGGGTCTACAGAGTCCCATCTGCCCAAAGGTCTTGAAGCTTGACAGGATG<br>TTTTCGATTACTCAGTCTCCCAGGGCACTACTGGTCCGTAGGATTCGATTGGTCGGGGTAGGAGAGTT<br>AAACAACATTTAAACAGAGTTCTCTCAAAAATGTCTAAAGGGATTGTAGGTAGATAACATCCAATCACT<br>GTTTGCACTTATCTGAAATCTTCCCTCTTGGCTGCCCCCAGGTATTTACTGTGGAGAACATTGCATAGG<br>AATGTCTGGAAAAAGCTTCTACAACTTGTTACAGCCTTCACATTTGTAGAAGCTTT |
| 50 | opt_COX10*-ND6-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGATGTATGCTTTGTTTCTGTTGAGTGTGGGTTTAGTAATGGGGTTTG<br>TGGGGTTTTCTTCTAAGCCTTCTCCTATTTATGGGGGTTTAGTATTGATTGTTAGCGGTGTGGTCGGGT<br>GTGTTATTATTCTGAATTTTGGGGGAGGTTATATGGGTTTAATGGTTTTTTTAATTTATTTAGGGGGAAT<br>GATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACTTTAATAGTGTAGGAAGCTGGATGATTTATGAAGGAGAG<br>GGGTCAGGGTTGATTCGGGAGGATCCTATTGGTGCGGGGGCTTTGTATGATTATGGGCGTTGGTTAG<br>TAGTAGTTACTGGTTGGACATTGTTTGTTGGTGTATATATTGTAATTGAGATTGCTCGGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCA |
| 51 | opt_COX10*-opt_ND6-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGATGTACGCCCTGTTCCTGCTGAGCGTGGGCCTGGTGATGGGCTTC<br>GTGGGCTTCAGCAGCAAGCCCAGCCCCATCTACGGCGGCCTGGTGCTGATCGTGAGCGGCGTGGTG<br>GGCTGCGTGATCATCCTGAACTTCGGCGGCGGCTACATGGGCCTGATGGTGTTCCTGATCTACCTGG<br>GCGGCATGATGGTGGTGTTCGGCTACACCACCGCCATGGCCATCGAGGAGTACCCCGAGGCCTGGG<br>GCAGCGGCGTGGAGGTGCTGGTGAGCGTGCTGGTGGGCCTGGCCATGGAGGTGGGCCTGGTGCTG<br>TGGGTGAAGGAGTACGACGGCGTGGTGGTGGTGGTGAACTTCAACAGCGTGGGCAGCTGGATGATC<br>TACGAGGGCGAGGGCAGCGGCCTGATCCGCGAGGACCCCATCGGCGCCGGCGCCCTGTACGACTA<br>CGGCCGCTGGCTGGTGGTGGTGACCGGCTGGACCCTGTTCGTGGGCGTGTACATCGTGATCGAGAT<br>CGCCCGCGGCAACTAAGAGCACTGGGACGCCCACCGCCCCTTTCCCTCCGCTGCCAGGCGAGCATG<br>TTGTGGTAATTCTGGAACACAAGAAGAGAAATTGCTGGGTTTAGAACAAGATTATAAACGAATTCGGTG<br>CTCAGTGATCACTTGACAGTTTTTTTTTTTTTTTAAATATTACCCAAAATGCTCCCCAAAAAAAGAAATGCAT<br>CAGCTCAGTCAGTGAATACAAAAAAGGAATTATTTTTCCCTTTGAGGGTCTTTTATACATCTCTCCTCCA<br>ACCCCACCCTCTATTCTGTTTCTTCCTCCTCACATGGGGGTACACATACACAGCTTCCTCTTTTGGTTC<br>CATCCTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGCACCCC<br>CTTCCTTGTGACTGAGCCAGGGCCTGCATTTTTGGTTTTCCCCACCCCACACATTCTCAACCATAGTCC<br>TTCTAACAATACCAATAGCTAGGACCCGGCTGCTGTGCACTGGGACTGGGGATTCCACATGTTTGCCT<br>TGGGAGTCTCAAGCTGGACTGCCAGCCCCTGTCCTCCCTTCACCCCCATTGCGTATGAGCATTTCAGA<br>ACTCCAAGGAGTCACAGGCATCTTTATAGTTCACGTTAACATATAGACACTGTTGGAAGCAGTTCCTTC<br>TAAAAGGGTAGCCCTGGACTTAATACCAGCCGGATACCTCTGGCCCCCACCCCATTACTGTACCTCTG<br>GAGTCACTACTGTGGGTCGCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACATTCCTGTCCCTTGGGTGA<br>AAAATACATGTCCATCCTGATATCTCCTGAATTCAGAAATTAGCCTCCACATGTGCAATGGCTTTAAGA<br>GCCAGAAGCAGGGTTCTGGGAATTTTGCAAGTTACCTGTGGCCAGGTGTGGTCTCGGTTACCAAATAC<br>GGTTACCTGCAGCTTTTTAGTCCTTTGTGCTCCCACGGGTCTACAGAGTCCCATCTGCCCAAAGGTCT<br>TGAAGCTTGACAGGATGTTTTCGATTACTCAGTCTCCCAGGGCACTACTGGTCCGTAGGATTCGATTG<br>GTCGGGGTAGGAGAGTTAAAACAACATTTAAACAGAGTTCTCTCAAAAATGTCTAAAGGGATTGTAGGTA<br>GATAACATCCAATCACTGTTTGCACTTATCTGAAATCTTCCCTCTTGGCTGCCCCCAGGTATTTACTGT<br>GGAGAACATTGCATAGGAATGTCTGGAAAAAGCTTCTACAACTTGTTACAGCCTTCACATTTGTAGAAG<br>CTTT |
| 52 | opt_COX10*-opt_ND6-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGATGTACGCCCTGTTCCTGCTGAGCGTGGGCCTGGTGATGGGCTTC<br>GTGGGCTTCAGCAGCAAGCCCAGCCCCATCTACGGCGGCCTGGTGCTGATCGTGAGCGGCGTGGTG<br>GGCTGCGTGATCATCCTGAACTTCGGCGGCGGCTACATGGGCCTGATGGTGTTCCTGATCTACCTGG<br>GCGGCATGATGGTGGTGTTCGGCTACACCACCGCCATGGCCATCGAGGAGTACCCCGAGGCCTGGG<br>GCAGCGGCGTGGAGGTGCTGGTGAGCGTGCTGGTGGGCCTGGCCATGGAGGTGGGCCTGGTGCTG<br>TGGGTGAAGGAGTACGACGGCGTGGTGGTGGTGGTGAACTTCAACAGCGTGGGCAGCTGGATGATC |

TABLE 1-continued

| nucleic acid and polypeptide sequences and SEQ ID NOs | | |
|---|---|---|
| SEQ | description | sequence |
| | | TACGAGGGCGAGGGCAGCGGCCTGATCCGCGAGGACCCCATCGGCGCCGGCGCCCTGTACGACTA<br>CGGCCGCTGGCTGGTGGTGGTGACCGGCTGGACCCTGTTCGTGGGCGTGTACATCGTGATCGAGAT<br>CGCCCGCGGCAACTAAGAGCACTGGGACGCCCACCGCCCCTTTCCCTCCGCTGCCAGGCGAGCATG<br>TTGTGGTAATTCTGGAACACAAGAAGAGAAATTGCTGGGTTTAGAACAAGATTATAAACGAATTCGGTG<br>CTCAGTGATCACTTGACAGTTTTTTTTTTTTTTAAATATTACCCAAAATGCTCCCCAAATAAGAAATGCAT<br>CAGCTCAGTCAGTGAATACAAAAAATTATTTTTCCCTTTGAGGGTCTTTTATACATCTCTCCTCCA<br>ACCCCACCCTCTATTCTGTTTCTTCCTCCTCACATGGGGGTACACATACACAGCTTCCTCTTTTGGTTC<br>CATCCTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGCACCCC<br>CTTCCTTGTGACTGAGCCAGGGCCTGCATTTTTGGTTTTCCCCACCCCACACATTCTCAACCATAGTCC<br>TTCTAACAATACCAATAGCTAGGACCCGGCTGCTGTGCACTGGGACTGGGGATTCCACATGTTTGCCT<br>TGGGAGTCTCAAGCTGGACTGCCA |
| 53 | opt_COX10*-<br>ND1-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTGTAGGC<br>CCCTACGGGCTACTACAACCCTTCGCTGACGCCATAAAACTCTTCACCAAAGAGCCCCTAAAACCCGC<br>CACATCTACCATCACCCTCTACATCACCGCCCCGACCTTAGCTCTCACCATCGCTCTTCTACTATGGAC<br>CCCCCTCCCCATGCCCAACCCCCTGGTCAACCTCAACCTAGGCCTCCTATTTATTCTAGCCACCTCTA<br>GCCTAGCCGTTTACTCAATCCTCTGGTCAGGGTGGGCATCAAACTCAAACTACGCCCTGATCGGCGCA<br>CTGCGAGCAGTAGCCCAAACAATCTCATATGAAGTCACCCTAGCCATCATTCTACTATCAACATTACTA<br>ATGAGTGGCTCCTTTAACCTCTCCACCCTTATCACAACACAAGAACACCTCTGGTTACTCCTGCCATCA<br>TGGCCCTTGGCCATGATGTGGTTTATCTCCACACTAGCAGAGACCAACCGAACCCCCTTCGACCTTGC<br>CGAAGGGGAGTCCGAACTAGTCTCAGGCTTCAACATCGAATACGCCGCAGGCCCCTTCGCCCTATTC<br>TTCATGGCCGAATACACAAACATTATTATGATGAACACCCTCACCACTACAATCTTCCTAGGAACAACA<br>TATGACGCACTCTCCCCTGAACTCTACACAACATATTTGTCACcAAGACCCTACTTCTAACCTCCCTG<br>TTCTTATGGATTCGAACAGCATACCCCCGATTCCGCTACGACCAACTCATGCACCTCCTATGGAAAAAC<br>TTCCTACCACTCACCCTAGCATTACTTATGTGGTATGTCTCCATGCCCATTACAATCTCCAGCATTCCC<br>CCTCAAACCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGTGCTCAG<br>TGATCACTTGACAGTTTTTTTTTTTTTTAAATATTACCCAAAATGCTCCCCAAATAAGAAATGCATCAGCT<br>CAGTCAGTGAATACAAAAAGGAATTATTTTTCCCTTTGAGGGTCTTTTATACATCTCTCCTCCAACCCC<br>ACCCTCTATTCTGTTTCTTCCTCCTCACATGGGGGTACACATACACAGCTTCCTCTTTTGGTTCCATCC<br>TTACCACCACACCACACGCACACTCCACATGCCCAGCAGAGTGGCACTTGGTGGCCAGAAAGTGTGA<br>GCCTCATGATCTGCTGTCTGTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATTCTCAACCATAGTCCTTCTA<br>ACAATACCAATAGCTAGGACCCGGCTGCTGTGCACTGGGACTGGGGATTCCACATGTTTGCCTTGGG<br>AGTCTCAAGCTGGACTGCCAGCCCCTGTCCTCCCTTCACCCCCATTGCGTATGAGCATTTCAGAACTC<br>CAAGGAGTCACAGGCATCTTTATAGTTCACGTTAACATATAGACACTGTTGGAAGCAGTTCCTTCTAAA<br>AGGGTAGCCCTGGACTTAATACCAGCCGGATACCTCTGGCCCCCACCCCATTACTGTACCTCTGGAGT<br>CACTACTGTGGGTCGCCACTCCTCTGCTACACAGCACGGCTTTTTCAAGGCTGTATTGAGAAGGGAAG<br>TTAGGAAGAAGGGTGTGCTGGGCTAACCAGCCCACAGAGCTCACATTCCTGTCCCTTGGGTGAAAAAT<br>ACATGTCCATCCTGATATCTCCTGAATTCAGAAATTAGCCTCCACATGTGCAATGGCTTTAAGAGCCAG<br>AAGCAGGGTTCTGGGAATTTTGCAAGTTACCTGTGGCCAGGTGTGGTCTCGGTTACCAAATACGGTTA<br>CCTGCAGCTTTTTAGTCCTTTGTGCTCCCACGGGTCTACAGAGTCCCATCTGCCCAAAGGTCTTGAAG<br>CTTGACAGGATGTTTTCGATTACTCAGTCTCCCAGGGCACTACTGGTCCGTAGGATTCGATTGGTCGG<br>GGTAGGAGAGTTAAAACAACATTTAAACAGAGTTCTCTCAAAAATGTCTAAAGGGATTGTAGGTAGATAA<br>CATCCAATCACTGTTTGCACTTATCTGAAATCTTCCCTCTTGGCTGCCCCCAGGTATTTACTGTGGAGA<br>ACATTGCATAGGAATGTCTGGAAAAAGCTTCTACAACTTGTTACAGCCTTCACATTTGTAGAAGCTTT |
| 54 | opt_COX10*-<br>ND1-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTGTAGGC<br>CCCTACGGGCTACTACAACCCTTCGCTGACGCCATAAAACTCTTCACCAAAGAGCCCCTAAAACCCGC<br>CACATCTACCATCACCCTCTACATCACCGCCCCGACCTTAGCTCTCACCATCGCTCTTCTACTATGGAC<br>CCCCCTCCCCATGCCCAACCCCCTGGTCAACCTCAACCTAGGCCTCCTATTTATTCTAGCCACCTCTA<br>GCCTAGCCGTTTACTCAATCCTCTGGTCAGGGTGGGCATCAAACTCAAACTACGCCCTGATCGGCGCA<br>CTGCGAGCAGTAGCCCAAACAATCTCATATGAAGTCACCCTAGCCATCATTCTACTATCAACATTACTA<br>ATGAGTGGCTCCTTTAACCTCTCCACCCTTATCACAACACAAGAACACCTCTGGTTACTCCTGCCATCA<br>TGGCCCTTGGCCATGATGTGGTTTATCTCCACACTAGCAGAGACCAACCGAACCCCCTTCGACCTTGC<br>CGAAGGGGAGTCCGAACTAGTCTCAGGCTTCAACATCGAATACGCCGCAGGCCCCTTCGCCCTATTC<br>TTCATGGCCGAATACACAAACATTATTATGATGAACACCCTCACCACTACAATCTTCCTAGGAACAACA<br>TATGACGCACTCTCCCCTGAACTCTACACAACATATTTGTCACCAAGACCCTACTTTCTAACCTCCCTG<br>TTCTTATGGATTCGAACAGCATACCCCCGATTCCGCTACGACCAACTCATGCACCTCCTATGGAAAAAC<br>TTCCTACCACTCACCCTAGCATTACTTATGTGGTATGTCTCCATGCCCATTACAATCTCCAGCATTCCC<br>CCTCAAACCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGTGCTCAG<br>TGATCACTTGACAGTTTTTTTTTTTTTTAAATATTACCCAAAATGCTCCCCAAATAAGAAATGCATCAGCT<br>CAGTCAGTGAATACAAAAAAGGAATTATTTTTCCCTTTGAGGGTCTTTTATACATCTCTCCTCCAACCCC<br>ACCCTCTATTCTGTTTCTTCCTCCTCACATGGGGGTACACATACACAGCTTCCTCTTTTGGTTCCATCC<br>TTACCACCACACCACACGCACACTCCACATGCCCAGCAGAGTGGCACTTGGTGGCCAGAAAGTGTGA<br>GCCTCATGATCTGCTGTCTGTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATTCTCAACCATAGTCCTTCTA<br>ACAATACCAATAGCTAGGACCCGGCTGCTGTGCACTGGGACTGGGGATTCCACATGTTTGCCTTGGG<br>AGTCTCAAGCTGGACTGCCA |

TABLE 1-continued

| nucleic acid and polypeptide sequences and SEQ ID NOs | | |
|---|---|---|
| SEQ | description | sequence |
| 55 | opt_COX10*-opt_ND1-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTGCTGCTGCTGATCGTGCCCATCCTGATCGCCATGGCC<br>TTCCTGATGCTGACCGAGCGCAAGATCCTGGGCTACATGCAGCTGCGCAAGGGCCCCAACGTGGTG<br>GGCCCCTACGGCCTGCTGCAGCCCTTCGCCGACGCCATCAAGCTGTTCACCAAGGAGCCCCTGAAG<br>CCCGCCACCAGCACCATCACCCTGTACATCACCGCCCCCACCCTGGCCCTGACCATCGCCCTGCTGC<br>TGTGGACCCCCCTGCCCATGCCCAACCCCCTGGTGAACCTGAACCTGGGCCTGCTGTTCATCCTGGC<br>CACCAGCAGCCTGGCCGTGTACAGCATCCTGTGGAGCGGCTGGGCCAGCAACAGCAACTACGCCCT<br>GATCGGCGCCCTGCGCGCCGTGGCCCAGACCATCAGCTACGAGGTGACCCTGGCCATCATCCTGCT<br>GAGCACCCTGCTGATGAGCGGCAGCTTCAACCTGAGCACCCTGATCACCACCCAGGAGCACCTGTGG<br>CTGCTGCTGCCCAGCTGGCCCCTGGCCATGATGTGGTTCATCAGCACCCTGGCCGAGACCAACCGCA<br>CCCCCTTCGACCTGGCCGAGGGCGAGAGCGAGCTGGTGAGCGGCTTCAACATCGAGTACGCCGCCG<br>GCCCCTTCGCCCTGTTCTTCATGGCCGAGTACACCAACATCATCATGATGAACACCCTGACCACCACC<br>ATCTTCCTGGGCACCACCTACGACGCCCTGAGCCCCGAGCTGTACACCACCTACTTCGTGACCAAGA<br>CCCTGCTGCTGACCAGCCTGTTCCTGTGGATCCGCACCGCCTACCCCCGCTTCCGCTACGACCAGCT<br>GATGCACCTGCTGTGGAAGAACTTCCTGCCCCTGACCCTGGCCCTGCTGATGTGGTACGTGAGCATG<br>CCCATCACCATCAGCAGCATCCCCCCCCAGACCTAAGAGCACTGGGACGCCCACCGCCCCTTTCCCT<br>CCGCTGCCAGGCGAGCATGTTGTGGTAATTCTGGAACACAAGTAAGAGAAATTGCTGGGTTTAGAACAA<br>GATTATAAACGAATTCGGTGCTCAGTGATCACTTGACAGTTTTTTTTTTTTTTAAATATTACCCAAAATGC<br>TCCCCAAATAAGAAATGCATCAGCTCAGTCAGTGAATACAWAAGGAATTATTTTTCCCTTTGAGGGT<br>CTTTTATACATCTCTCCTCCAACCCCACCCTCTATTCTGTTTCTTCCTCCTCACATGGGGGTACACATAC<br>ACAGCTTCCTCTTTTGGTTCCATCCTTACCACCACACCACACGCACACTCCACATGCCCAGCAGAGTG<br>GCACTTGGTGGCCAGAAAGTGTGAGCCTCATGATCTGCTGTCTGTAGTTCTGTGAGCTCAGGTCCCTC<br>AAAGGCCTCGGAGCACCCCCTTCCTTGTGACTGAGCCAGGGCCTGCATTTTTGGTTTTCCCCACCCCA<br>CACATTCTCAACCATAGTCCTTCTAACAATACCAATAGCTAGGACCCGGCTGCTGTGCACTGGGACTG<br>GGGATTCCACATGTTTGCCTTGGGAGTCTCAAGCTGGACTGCCAGCCCCTGTCCTCCCTTCACCCCCA<br>TTGCGTATGAGCATTTCAGAACTCCAAGGAGTCACAGGCATCTTTATAGTTCACGTTAACATATAGACA<br>CTGTTGGAAGCAGTTCCTTCTAAAAGGGTAGCCCTGGACTTAATACCAGCCGGATACCTCTGGCCCCC<br>ACCCCATTACTGTACCTCTGGAGTCACTACTGTGGGTCGCCACTCCTCTGCTACACAGCACGGCTTTT<br>TCAAGGCTGTATTGAGAAGGGAAGTTAGGAAGAAGGGTGTGCTGGGCTAACCAGCCCACAGAGCTCA<br>CATTCCTGTCCCTTGGGTGAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAAGTTACCTGTGGCCAGGTG<br>TGGTCTCGGTTACCAAATACGGTTACCTGCAGCTTTTTAGTCCTTTGTGCTCCCACGGGTCTACAGAGT<br>CCCATCTGCCCAAAGGTCTTGAAGCTTGACAGGATGTTTTCGATTACTCAGTCTCCCAGGGCACTACT<br>GGTCCGTAGGATTCGATTGGTCGGGGTAGGAGAGTTAAACAACATTTAAACAGAGTTCTCTCAAAAAT<br>GTCTAAAGGGATTGTAGGTAGATAACATCCAATCACTGTTTGCACTTATCTGAAATCTTCCCTCTTGGC<br>TGCCCCCAGGTATTTACTGTGGAGAACATTGCATAGGAATGTCTGGAAAAAGCTTCTACAACTTGTTAC<br>AGCCTTCACATTTGTAGAAGCTTT |
| 56 | opt_COX10*-opt_ND1-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTGCTGCTGCTGATCGTGCCCATCCTGATCGCCATGGCC<br>TTCCTGATGCTGACCGAGCGCAAGATCCTGGGCTACATGCAGCTGCGCAAGGGCCCCAACGTGGTG<br>GGCCCCTACGGCCTGCTGCAGCCCTTCGCCGACGCCATCAAGCTGTTCACCAAGGAGCCCCTGAAG<br>CCCGCCACCAGCACCATCACCCTGTACATCACCGCCCCCACCCTGGCCCTGACCATCGCCCTGCTGC<br>TGTGGACCCCCCTGCCCATGCCCAACCCCCTGGTGAACCTGAACCTGGGCCTGCTGTTCATCCTGGC<br>CACCAGCAGCCTGGCCGTGTACAGCATCCTGTGGAGCGGCTGGGCCAGCAACAGCAACTACGCCCT<br>GATCGGCGCCCTGCGCGCCGTGGCCCAGACCATCAGCTACGAGGTGACCCTGGCCATCATCCTGCT<br>GAGCACCCTGCTGATGAGCGGCAGCTTCAACCTGAGCACCCTGATCACCACCCAGGAGCACCTGTGG<br>CTGCTGCTGCCCAGCTGGCCCCTGGCCATGATGTGGTTCATCAGCACCCTGGCCGAGACCAACCGCA<br>CCCCCTTCGACCTGGCCGAGGGCGAGAGCGAGCTGGTGAGCGGCTTCAACATCGAGTACGCCGCCG<br>GCCCCTTCGCCCTGTTCTTCATGGCCGAGTACACCAACATCATCATGATGAACACCCTGACCACCACC<br>ATCTTCCTGGGCACCACCTACGACGCCCTGAGCCCCGAGCTGTACACCACCTACTTCGTGACCAAGA<br>CCCTGCTGCTGACCAGCCTGTTCCTGTGGATCCGCACCGCCTACCCCCGCTTCCGCTACGACCAGCT<br>GATGCACCTGCTGTGGAAGAACTTCCTGCCCCTGACCCTGGCCCTGCTGATGTGGTACGTGAGCATG<br>CCCATCACCATCAGCAGCATCCCCCCCCAGACCTAAGAGCACTGGGACGCCCACCGCCCCTTTCCCT<br>CCGCTGCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTTAAATATTACCCAAAATGC<br>TCCCCAAATAAGAAATGCATCAGCTCAGTCAGTGAATACAAAAAAGGAATTATTTTTCCCTTTGAGGGT<br>CTTTTATACATCTCTCCTCCAACCCCACCCTCTATTCTGTTTCTTCCTCCTCACATGGGGGTACACATAC<br>ACAGCTTCCTCTTTTGGTTCCATCCTTACCACCACACCACACGCACACTCCACATGCCCAGCAGAGTG<br>GCACTTGGTGGCCAGAAAGTGTGAGCCTCATGATCTGCTGTCTGTAGTTCTGTGAGCTCAGGTCCCTC<br>AAAGGCCTCGGAGCACCCCCTTCCTTGTGACTGAGCCAGGGCCTGCATTTTTGGTTTTCCCCACCCCA<br>CACATTCTCAACCATAGTCCTTCTAACAATACCAATAGCTAGGACCCGGCTGCTGTGCACTGGGACTG<br>GGGATTCCACATGTTTGCCTTGGGAGTCTCAAGCTGGACTGCCA |
| 57 | COX8-ND4-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTAAAACTAATCGTCCCAACAATTATGTTACTACCACTGACATGG<br>CTTTCCAAAAAACACATGATTTGGATCAACACAACCACCCACAGCCTAATTATTAGCATCATCCCTCTA<br>CTATTTTTTAACCAAATCAACAACAACCTATTTAGCTGTTCCCCAACCTTTTCCTCCGACCCCCTAACAA<br>CCCCCCTCCTAATGCTAACTACCTGGCTCCTACCCCTCACAATCATGGCAAGCCAACGCCACTTATCC<br>AGTGAACCACTATCACGAAAAAAACTCTACCTCTCTATGCTAATCTCCCTACAAATCTCCTTAATTATGA<br>CATTCACAGCCACAGAACTAATCATGTTTTATATCTTCTTCGAAACCACACTTATCCCCACCTTGGCTAT<br>CATCACCCGATGGGGCAACCAGCCAGAACGCCTGAACGCAGGCACATACTTCCTATTCTACACCCTA<br>GTAGGCTCCCTTCCCCTACTCATCGCACTAATTTACACTCACAACACCCTAGGCTCACTAACATTCTA<br>CTACTCACTCTCACTGCCCAAGAACTATCAAACTCCTGGGCCAACAACTTAATGTGGCTAGCTTACACA<br>ATGGCTTTTATGGTAAAGATGCCTCTTTACGGACTCCACTTATGGCTCCCTAAAGCCCATGTCGAAGCC<br>CCCATCGCTGGGTCAATGGTACTTGCCGCAGTACTCTTAAAACTAGGCGGCTATGGTATGATGCGCCT<br>CACACTCATTCTCAACCCCCTGACAAAACACATGGCCTACCCCTTCCTTGTACTATCCCTATGGGGCAT<br>GATTATGACAAGCTCCATCTGCCTACGACAAACAGACCTAAAATCGCTCATTGCATACTCTTCAATCAG |

TABLE 1-continued nucleic acid and polypeptide sequences and SEQ ID NOs

| SEQ | description | sequence |
|---|---|---|
| | | CCACATGGCCCTCGTAGTAACAGCCATTCTCATCCAAACCCCCTGGAGCTTCACCGGCGCAGTCATTC<br>TCATGATCGCCCACGGGCTTACATCCTCATTACTATTCTGCCTAGCAAACTCAAACTACGAACGCACTC<br>ACAGTCGCATCATGATCCTCTCTCAAGGACTTCAAACTCTACTCCCACTAATGGCTTTTTGGTGGCTTC<br>TAGCAAGCCTCGCTAACCTCGCCTTACCCCCCACTATTAACCTACTGGGAGAACTCTCTGTGCTAGTA<br>ACCACGTTCTCCTGGTCAAATATCACTCTCCTACTTACAGGACTCAACATGCTAGTCACAGCCCTATAC<br>TCCCTCTACATGTTTACCACAACACAATGGGGCTCACTCACCCACCACATTAACAACATGAAACCCTCA<br>TTCACACGAGAAAACACCCTCATGTTCATGCACCTATCCCCCATTCTCCTCCTATCCCTCAACCCCGAC<br>ATCATTACCGGGTTTTCCTCTTAAGAGCACTGGGACGCCCACCGCCCCTTTCCCTCCGCTGCCAGGC<br>GAGCATGTTGTGGTAATTCTGGAACACAAGAAGAGAAATTGCTGGGTTTAGAACAAGATTATAAACGAA<br>TTCGGTGCTCAGTGATCACTTGACAGTTTTTTTTTTTTTTTAAATATTACCCAAAATGCTCCCCAAATAAG<br>AAATGCATCAGCTCAGTCAGTGAATACAAAAAAGGAATTATTTTTCCCTTTGAGGGTCTTTTATACATCT<br>CTCCTCCAACCCCACCCTCTATTCTGTTTCTTCCTCCTCACATGGGGGTACACATACACAGCTTCCTCT<br>TTTGGTTCCATCCTTACCACCACACCACACGCACACTCCACATGCCCAGCAGAGTGGCACTTGGTGGC<br>CAGAAAGTGTGAGCCTCATGATCTGCTGTCTGTAGTTCTGTGAGCTCAGGTCCCTCAAAGGCCTCGGA<br>GCACCCCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTCCACAT<br>GTTTGCCTTGGGAGTCTCAAGCTGGACTGCCAGCCCCTGTCCTCCCTTCACCCCCATTGCGTATGAGC<br>ATTTCAGAACTCCAAGGAGTCACAGGCATCTTTATAGTTCACGTTAACATATAGACACTGTTGGAAGCA<br>GTTCCTTCTAAAAAGGGTAGCCCTGGACTTAATACCAGCCGGATACCTCTGGCCCCCACCCCATTACTG<br>TACCTCTGGAGTCACTACTGTGGGTCGCCACTCCTCTGCTACACAGCACGGCTTTTTCAAGGCTGTAT<br>TGAGAAGGGAAGTTAGGAAGAAGGGTGTGCTGGGCTAACCAGCCCACAGAGCTCACATTCCTGTCCC<br>TTGGGTGAAAAATACATGTCCATCCTGATATCTCCTGAATTCAGAAATTAGCCTCCACATGTGCAATGG<br>CTTTAAGAGCCAGAAGCAGGGTTCTGGGAATTTTGCAAGTTACCTGTGGCCAGGTGTGGTCTCGGTTA<br>CCAAATACGGTTACCTGCAGCTTTTTAGTCCTTTGTGCTCCCACGGGTCTACAGAGTCCCATCTGCCC<br>AAAGGTCTTGAAGCTTGACAGGATGTTTTCGATTACTCAGTCTCCCAGGGCACTACTGGTCCGTAGGA<br>TTCGATTGGTCGGGGTAGGAGAGTTAAACAACATTTAAACAGAGTTCTCTCAAAAATGTCTAAAGGGAT<br>TGTAGGTAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTTCACATT<br>TGTAGAAGCTTT |
| 58 | COX8-ND4-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTAAAACTAATCGTCCCAACAATTATGTTACTACCACTGACATGG<br>CTTTCCAAAAAACACATGATTTGGATCAACACAACCACCCACAGCCTAATTATTAGCATCATCCCTCTA<br>CTATTTTTTAACCAAATCAACAACAACCTATTTAGCTGTTCCCCAACCTTTTCCTCCGACCCCCTAACAA<br>CCCCCCTCCTAATGCTAACTACCTGGCTCCTACCCCTCACAATCATGGCAAGCCAACGCCACTTATCC<br>AGTGAACCACTATCACGAAAAAAACTCTACCTCTCTATGCTAATCTCCCTACAAATCTCCTTAATTATGA<br>CATTCACAGCCACAGAACTAATCATGTTTTATATCTTCTTCGAAACCACACTTATCCCCACCTTGGCTAT<br>CATCACCCGATGGGGCAACCAGCCAGAACGCCTGAACGCAGGCACATACTTCCTATTCTACACCCTA<br>GTAGGCTCCCTTCCCCTACTCATCGCACTAATTTACACTCACAACACCCTAGGCTCACTAAACATTCTA<br>CTACTCACTCTCACTGCCCAAGAACTATCAAACTCCTGGGCCAACAACTTAATGTGGCTAGCTTACACA<br>ATGGCTTTTATGGTAAAGATGCCTCTTTACGGACTCCACTTATGGCTCCCTAAAGCCCATGTCGAAGCC<br>CCCATCGCTGGGTCAATGGTACTTGCCGCAGTACTCTTAAAACTAGGCGGCTATGGTATGATGCGCCT<br>CACACTCATTCTCAACCCCCTGACNVAACACATGGCCTACCCCTTCCTTGTACTATCCCTATGGGGCAT<br>GATTATGACAAGCTCCATCTGCCTACGACAAACAGACCTAAAATCGCTCATTGCATACTCTTCAATCAG<br>CCACATGGCCCTCGTAGTAACAGCCATTCTCATCCAACCCCCTGGAGCTTCACCGGCGCAGTCATTC<br>TCATGATCGCCCACGGGCTTACATCCTCATTACTATTCTGCCTAGCAAACTCAAACTACGAACGCACTC<br>ACAGTCGCATCATGATCCTCTCTCAAGGACTTCAAACTCTACTCCCACTAATGGCTTTTTGGTGGCTTC<br>TAGCAAGCCTCGCTAACCTCGCCTTACCCCCCACTATTAACCTACTGGGAGAACTCTCTGTGCTAGTA<br>ACCACGTTCTCCTGGTCAAATATCACTCTCCTACTTACAGGACTCAACATGCTAGTCACAGCCCTATAC<br>TCCCTCTACATGTTTACCACAACACAATGGGGCTCACTCACCCACCACATTAACAACATGAAACCCTCA<br>TTCACACGAGAAAACACCCTCATGTTCATGCACCTATCCCCCATTCTCCTCCTATCCCTCAACCCCGAC<br>ATCATTACCGGGTTTTCCTCTTAAGAGCACTGGGACGCCCACCGCCCCTTTCCCTCCGCTGCCAGGC<br>GAGCATGTTGTGGTAATTCTGGAACACAAGAAGAGAAATTGCTGGGTTTAGAACAAGATTATAAACGAA<br>TTCGGTGCTCAGTGATCACTTGACAGTTTTTTTTTTTTTTTAAATATTACCCAAAATGCTCCCCAAATAAG<br>AAATGCATCAGCTCAGTCAGTGAATACAAAAAAGGAATTATTTTTCCCTTTGAGGGTCTTTTATACATCT<br>CTCCTCCAACCCCACCCTCTATTCTGTTTCTTCCTCCTCACATGGGGGTACACATACACAGCTTCCTCT<br>TTTGGTTCCATCCTTACCACCACACCACACGCACACTCCACATGCCCAGCAGAGTGGCACTTGGTGGC<br>CAGAAAGTGTGAGCCTCATGATCTGCTGTCTGTAGTTCTGTGAGCTCAGGTCCCTCAAAGGCCTCGGA<br>GCACCCCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTCCACAT<br>GTTTGCCTTGGGAGTCTCAAGCTGGACTGCCA |
| 59 | COX8-opt_ND4-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCTCTGACCTG<br>GCTGAGCAAGAAACACATGATCTGGATCAACACCACCACGCACAGCCTGATCATCAGCATCATCCCTC<br>TGCTGTTCTTCAACCAGATCAACAACAACCTGTTCAGCTGCAGCCCCACCTTCAGCAGCGACCCTCTG<br>ACAACACCTCTGCTGATGCTGACCACCTGGCTGCTGCCCCTCACAATCATGGCCTCTCAGAGACACCT<br>GAGCAGCGAGCCCCTGAGCCGGAAGAAACTGTACCTGAGCATGCTGATCTCCCTGCAGATCTCTCTG<br>ATCATGACCTTCACCGCCACCGAGCTGATCATGTTCTACATCTTTTTCGAGACAACGCTGATCCCCACA<br>CTGGCCATCATCACCAGATGGGGCAACCAGCCTGAGAGACTGAACGCCGGCACCTACTTTCTGTTCT<br>ACACCCTCGTGGGCAGCCTGCCACTGCTGATTGCCCTGATCTACACCCACAACACCCTGGGCTCCCT<br>GAACATCCTGCTGCTGACACTGACAGCCCAAGAGCTGAGCAACAGCTGGGCCAACAATCTGATGTGG<br>CTGGCCTACACAATGGCCTTCATGGTCAAGATGCCCCTGTACGGCCTGCACCTGTGGCTGCCTAAAG<br>CTCATGTGGAAGCCCCTATCGCCGGCTCTATGGTGCTGGCTGCAGTGCTGCTGAAACTCGGCGGCTA<br>CGGCATGATGCGGCTGACCCTGATTCTGAATCCCCTGACCAAGCACATGGCCTATCCATTTCTGGTGC<br>TGAGCCTGTGGGGCATGATTATGACCAGCAGCATCTGCCTGCGGCAGACCGATCTGAAGTCCCTGAT<br>CGCCTACAGCTCCATCAGCCACATGGCCCTGGTGGTCACCGCCATCCTGATTCAGACCCCTTGGAGC<br>TTTACAGGCGCCGTGATCCTGATGATTGCCCACGGCCTGACAAGCAGCCTGCTGTTTTGTCTGGCCAA |

TABLE 1-continued nucleic acid and polypeptide sequences and SEQ ID NOs

| SEQ | description | sequence |
|---|---|---|
| | | CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAAATACATGTCCATCCTGATATCTCCTGAATTC<br>AGAAATTAGCCTCCACATGTGCAATGGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC<br>CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA<br>AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 60 | COX8-opt_ND4-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCTCTGACCTG<br>GCTGAGCAAGAAACACATGATCTGGATCAACACCACCACGCACAGCCTGATCATCAGCATCATCCCTC<br>TGCTGTTCTTCAACCAGATCAACAACAACCTGTTCAGCTGCAGCCCCACCTTCAGCAGCGACCCTCTG<br>ACAACACCTCTGCTGATGCTGACCACCTGGCTGCTGCCCCTCACAATCATGGCCTCTCAGAGACACCT<br>GAGCAGCGAGCCCCTGAGCCGGAAGAAACTGTACCTGAGCATGCTGATCTCCCTGCAGATCTCTCTG<br>ATCATGACCTTCACCGCCACCGAGCTGATCATGTTCTACATCTTTTTCGAGACAACGCTGATCCCCACA<br>CTGGCCATCATCACCAGATGGGGCAACCAGCCTGAGAGACTGAACGCCGGCACCTACTTTCTGTTCT<br>ACACCCTCGTGGGCAGCCTGCCACTGCTGATTGCCCTGATCTACACCCACAACACCCTGGGCTCCCT<br>GAACATCCTGCTGCTGACACTGACAGCCCAAGAGCTGAGCAACAGCTGGGCCAACAATCTGATGTGG<br>CTGGCCTACACAATGGCCTTCATGGTCAAGATGCCCCTGTACGGCCTGCACCTGTGGCTGCCTAAAG<br>CTCATGTGGAAGCCCCTATCGCCGGCTCTATGGTGCTGGCTGCAGTGCTGCTGAAACTCGGCGGCTA<br>CGGCATGATGCGGCTGACCCTGATTCTGAATCCCCTGACCAAGCACATGGCCTATCCATTTCTGGTGC<br>TGAGCCTGTGGGGCATGATTATGACCAGCAGCATCTGCCTGCGGCAGACCGATCTGAAGTCCCTGAT<br>CGCCTACAGCTCCATCAGCCACATGGCCCTGGTGGTCACCGCCATCCTGATTCAGACCCCTTGGAGC<br>TTTACAGGCGCCGTGATCCTGATGATTGCCCACGGCCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 61 | COX8-opt_ND4*-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCCCTGACCT<br>GGCTGAGCAAGAAGCACATGATCTGGATCAACACCACCACCCACAGCCTGATCATCAGCATCATCCCC<br>CTGCTGTTCTTCAACCAGATCAACAACAACCTGTTCAGCTGCAGCCCCACCTTCAGCAGCGACCCCCT<br>GACCACCCCCCTGCTGATGCTGACCACCTGGCTGCTGCCCCTGACCATCATGGCCAGCCAGCGCCAC<br>CTGAGCAGCGAGCCCCTGAGCCGCAAGAAGCTGTACCTGAGCATGCTGATCAGCCTGCAGATCAGCC<br>TGATCATGACCTTCACCGCCACCGAGCTGATCATGTTCTACATCTTCTTCGAGACCACCCTGATCCCC<br>ACCCTGGCCATCATCACCCGCTGGGGCAACCAGCCCGAGCGCCTGAACGCCGGCACCTACTTCCTGT<br>TCTACACCCTGGTGGGCAGCCTGCCCCTGCTGATCGCCCTGATCTACACCCACAACACCCTGGGCAG<br>CCTGAACATCCTGCTGCTGACCCTGACCGCCCAGGAGCTGAGCAACAGCTGGGCCAACAACCTGATG<br>TGGCTGGCCTACACCATGGCCTTCATGGTGAAGATGCCCCTGTACGGCCTGCACCTGTGGCTGCCCA<br>AGGCCCACGTGGAGGCCCCCATCGCCGGCAGCATGGTGCTGGCCGCCGTGCTGCTGAAGCTGGGC<br>GGCTACGGCATGATGCGCCTGACCCTGATCCTGAACCCCCTGACCAAGCACATGGCCTACCCCTTCC<br>TGGTGCTGAGCCTGTGGGGCATGATCATGACCAGCAGCATCTGCCTGCGCCAGACCGACCTGAAGAG<br>CCTGATCGCCTACAGCAGCATCAGCCACATGGCCCTGGTGGTGACCGCCATCCTGATCCAGACCCCC<br>TGGAGCTTCACCGGCGCCGTGATCCTGATGATCGCCCACGGCCTGACCAGCAGCCTGCTGTTCTGCC<br>TGGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACCTGGCCCTGCCCCCCACCAT |

TABLE 1-continued nucleic acid and polypeptide sequences and SEQ ID NOs

| SEQ | description | sequence |
|---|---|---|
| | | CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCCAGTGGGGCA<br>GCCTGACCCACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTTAAATATTACCCAAAATGCTCCCCAAATAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACTCCAAGGAGTCACAGGCAT<br>CTTTATAGTTCACGTTAACATATAGACACTGTTGGAAGCAGTTCCTTCTAAAAGGGTAGCCCTGGACTT<br>AATACCAGCCGGATACCTCTGGCCCCCACCCCATTACTGTACCTCTGGAGTCACTACTGTGGGTCGCC<br>ACTCCTCTGCTACACAGCACGGCTTTTTCAAGGCTGTATTGAGAAGGGAAGTTAGGAAGAAGGGTGTG<br>CTGGGCTAACCAGCCCACAGAGCTCACATTCCTGTCCCTTGGGTGAAAAATACATGTCCATCCTGATA<br>TCTCCTGAATTCAGAAATTAGCCTCCACATGTGCAATGGCTTTAAGAGCCAGAAGCAGGGTTCTGGGA<br>ATTTGCAAGTTACCTGTGGCCAGGTGTGGTCTCGGTTACCAAATACGGTTACCTGCAGCTTTTTAGTC<br>CTTTGTGCTCCCACGGGTCTACAGAGTCCCATCTGCCCAAAGGTCTTGAAGCTTGACAGGATGTTTTC<br>GATTACTCAGTCTCCCAGGGCACTACTGGTCCGTAGGATTCGATTGGTCGGGGTAGGAGAGTTAAACA<br>ACATTTAAACAGAGTTCTCTCAAAAATGTCTAAAGGGATTGTAGGTAGATAACATCCAATCACTGTTTGC<br>ACTTATCTGAAATCTTCCCTCTTGGCTGCCCCCAGGTATTTACTGTGGAGAACATTGCATAGGAATGTC<br>TGGAAAAAGCTTCTACAACTTGTTACAGCCTTCACATTTGTAGAAGCTTT |
| 62 | COX8-opt_ND4*-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCCCTGACcT<br>GGCTGAGCAAGAAGCACATGATCTGGATCAACACCACCACCCACAGCCTGATCATCAGCATCATCCCC<br>CTGCTGTTCTTCAACCAGATCAACAACAACCTGTTCAGCTGCAGCCCCACCTTCAGCAGCGACCCCCT<br>GACCACCCCCCTGCTGATGCTGACCACCTGGCTGCTGCCCCTGACCATCATGGCCAGCCAGCGCCAC<br>CTGAGCAGCGAGCCCCTGAGCCGCAAGAAGCTGTACCTGAGCATGCTGATCAGCCTGCAGATCAGCC<br>TGATCATGACCTTCACCGCCACCGAGCTGATCATGTTCTACATCTTCTTCGAGACCACCCTGATCCCC<br>ACCCTGGCCATCATCACCCGCTGGGGCAACCAGCCCGAGCGCCTGAACGCCGGCACCTACTTCCTGT<br>TCTACACCCTGGTGGGCAGCCTGCCCCTGCTGATCGCCCTGATCTACACCCACAACACCCTGGGCAG<br>CCTGAACATCCTGCTGCTGACCCTGACCGCCCAGGAGCTGAGCAACAGCTGGGCCAACAACCTGATG<br>TGGCTGGCCTACACCATGGCCTTCATGGTGAAGATGCCCCTGTACGGCCTGCACCTGTGGCTGCCCA<br>AGGCCCACGTGGAGGCCCCCATCGCCGGCAGCATGGTGCTGGCCGCCGTGCTGCTGAAGCTGGGC<br>GGCTACGGCATGATGCGCCTGACCCTGATCCTGAACCCCCTGACCAAGCACATGGCCTACCCCTTCC<br>TGGTGCTGAGCCTGTGGGGCATGATCATGACCAGCAGCATCTGCCTGCGCCAGACCGACCTGAAGAG<br>CCTGATCGCCTACAGCAGCATCAGCCACATGGCCCTGGTGGTGACCGCCATCCTGATCCAGACCCCC<br>TGGAGCTTCACCGGCGCCGTGATCCTGATGATCGCCCACGGCCTGACCAGCAGCCTGCTGTTCTGCC<br>TGGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACCTGGCCCTGCCCCCCACCAT<br>CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCCAGTGGGGCA<br>GCCTGACCCACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTTAAATATTACCCAAAATGCTCCCCAAATAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCA |
| 63 | COX3-ND6-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTATGCTTTGTTTCTGTTGAGTGTGGGTTTAGTAATGGGGTTT<br>GTGGGGTTTTCTTCTAAGCCTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTTTAATTTATTTAGGGGGAA<br>TGATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACTTTAATAGTGTAGGAAGCTGGATGATTTATGAAGGAGAG<br>GGGTCAGGGTTGATTCGGGAGGATCCTATTGGTGCGGGGGCTTTGTATGATTATGGGCGTTGGTTAG<br>TAGTAGTTACTGGTTGGACATTGTTTGTTGGTGTATATATTGTAATTGAGATTGCTCGGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCAGCCCCTGTCCTCCCTTCACCCCCATTGCGTATGAGCATTTCAGAACTCCAAGGAGTCACAG |

TABLE 1-continued

| nucleic acid and polypeptide sequences and SEQ ID NOs | | |
|---|---|---|
| SEQ | description | sequence |
| | | GCATCTTTATAGTTCACGTTAACATATAGACACTGTTGGAAGCAGTTCCTTCTAAAAGGGTAGCCCTGG<br>ACTTAATACCAGCCGGATACCTCTGGCCCCCACCCCATTACTGTACCTCTGGAGTCACTACTGTGGGT<br>CGCCACTCCTCTGCTACACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGTGAAAAATACATGTCCATCC<br>TGATATCTCCTGAATTCAGAAATTAGCCTCCACATGTGCAATGGCTTTAAGAGCCAGAAGCAGGGTTCT<br>GGGAATTTTGCAAGTTACCTGTGGCCAGGTGTGGTCTCGGTTACCAAATACGGTTACCTGCAGCTTTT<br>TAGTCCTTTGTGCTCCCACGGGTCTACAGAGTCCCATCTGCCCAAAGGTCTTGAAGCTTGACAGGATG<br>TTTTCGATTACTCAGTCTCCCAGGGCACTACTGGTCCGTAGGATTCGATTGGTCGGGGTAGGAGAGTT<br>AAACAACATTTAAACAGAGTTCTCTCAAAAATGTCTAAAGGGATTGTAGGTAGATAACATCCAATCACT<br>GTTTGCACTTATCTGAAATCTTCCCTCTTGGCTGCCCCCAGGTATTTACTGTGGAGAACATTGCATAGG<br>AATGTCTGGAAAAAGCTTCTACAACTTGTTACAGCCTTCACATTTGTAGAAGCTTT |
| 64 | COX8-ND6-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTATGCTTTGTTTCTGTTGAGTGTGGGTTTAGTAATGGGGTTT<br>GTGGGGTTTTCTTCTAAGCCTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTTTAATTTATTTAGGGGGAA<br>TGATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACTTTAATAGTGTAGGAAGCTGGATGATTTATGAAGGAGAG<br>GGGTCAGGGTTGATTCGGGAGGATCCTATTGGTGCGGGGGCTTTGTATGATTATGGGCGTTGGTTAG<br>TAGTAGTTACTGGTTGGACATTGTTTGTTGGTGTATATATTGTAATTGAGATTGCTCGGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCA |
| 65 | COX8-opt_ND6-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTACGCCCTGTTCCTGCTGAGCGTGGGCCTGGTGATGGGCT<br>TCGTGGGCTTCAGCAGCAAGCCCAGCCCCATCTACGGCGGCCTGGTGCTGATCGTGAGCGGCGTGG<br>TGGGCTGCGTGATCATCCTGAACTTCGGCGGCGGCTACATGGGCCTGATGGTGTTCCTGATCTACCT<br>GGGCGGCATGATGGTGGTGTTCGGCTACACCACCGCCATGGCCATCGAGGAGTACCCCGAGGCCTG<br>GGGCAGCGGCGTGGAGGTGCTGGTGAGCGTGCTGGTGGGCCTGGCCATGGAGGTGGGCCTGGTGC<br>TGTGGGTGAAGGAGTACGACGGCGTGGTGGTGGTGGTGAACTTCAACAGCGTGGGCAGCTGGATGA<br>TCTACGAGGGCGAGGGCAGCGGCCTGATCCGCGAGGACCCCATCGGCGCCGGCGCCCTGTACGAC<br>TACGGCCGCTGGCTGGTGGTGGTGACCGGCTGGACCCTGTTCGTGGGCGTGTACATCGTGATCGAG<br>ATCGCCCGCGGCAACTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGAATTCGG<br>TGCTCAGTGATCACTTGACAGTTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCAGCCCCTGTCCTCCCTTCACCCCCATTGCGTATGAGCATTTCA<br>GAACTCCAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATTGAGAA<br>GGGAAGTTAGGAAGAAAGGGTGTGCTGGGCTAACCAGCCCACAGAGCTCACATTCCTGTCCCTTGGGT<br>GAAAAATACATGTCCATCCTGATATCTCCTGAATTCAGAAATTAGCCTCCACATGTGCAATGGCTTTAA<br>GAGCCAGAAGCAGGGTTCTGGGAATTTTGCAAGTTACCTGTGGCCAGGTGTGGTCTCGGTTACCAAAT<br>ACGGTTACCTGCAGCTTTTTAGTCCTTTGTGCTCCCACGGGTCTACAGAGTCCCATCTGCCCAAAGGT<br>CTTGAAGCTTGACAGGATGTTTTCGATTACTCAGTCTCCCAGGGCACTACTGGTCCGTAGGATTCGAT<br>TGGTCGGGGTAGGAGAGTTAAACAACATTTAAACAGAGTTCTCTCAAAAATGTCTAAAGGGATTGTAG<br>GTAGATAACATCCAATCACTGTTTGCACTTATCTGAAATCTTCCCTCTTGGCTGCCCCCAGGTATTTAC<br>TGTGGAGAACATTGCATAGGAATGTCTGGAAAAAGCTTCTACAACTTGTTACAGCCTTCACATTTGTAG<br>AAGCTTT |
| 66 | COX8-opt_ND6-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTACGCCCTGTTCCTGCTGAGCGTGGGCCTGGTGATGGGCT<br>TCGTGGGCTTCAGCAGCAAGCCCAGCCCCATCTACGGCGGCCTGGTGCTGATCGTGAGCGGCGTGG<br>TGGGCTGCGTGATCATCCTGAACTTCGGCGGCGGCTACATGGGCCTGATGGTGTTCCTGATCTACCT<br>GGGCGGCATGATGGTGGTGTTCGGCTACACCACCGCCATGGCCATCGAGGAGTACCCCGAGGCCTG<br>GGGCAGCGGCGTGGAGGTGCTGGTGAGCGTGCTGGTGGGCCTGGCCATGGAGGTGGGCCTGGTGC<br>TGTGGGTGAAGGAGTACGACGGCGTGGTGGTGGTGGTGAACTTCAACAGCGTGGGCAGCTGGATGA<br>TCTACGAGGGCGAGGGCAGCGGCCTGATCCGCGAGGACCCCATCGGCGCCGGCGCCCTGTACGAC<br>TACGGCCGCTGGCTGGTGGTGGTGACCGGCTGGACCCTGTTCGTGGGCGTGTACATCGTGATCGAG<br>ATCGCCCGCGGCAACTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGAATTCGG<br>TGCTCAGTGATCACTTGACAGTTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA |

TABLE 1-continued nucleic acid and polypeptide sequences and SEQ ID NOs

| SEQ | description | sequence |
|---|---|---|
| | | AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCA |
| 67 | COX8-ND1-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTCCTACTCCTCATTGTACCCATTCTAATCGCAATGGC<br>ATTCCTAATGCTTACCGAACGAAAAATTCTAGGCTATATGCAACTACGCAAAGGCCCCAACGTTGTAGG<br>CCCCTACGGGCTACTACAACCCTTCGCTGACGCCATAAAACTCTTCACCAAAGAGCCCCTAAAACCCG<br>CCACATCTACCATCACCCTCTACATCACCGCCCCGACCTTAGCTCTCACCATCGCTCTTCTACTATGGA<br>CCCCCCTCCCCATGCCCAACCCCCTGGTCAACCTCAACCTAGGCCTCCTATTTATTCTAGCCACCTCT<br>AGCCTAGCCGTTTACTCAATCCTCTGGTCAGGGTGGGCATCAAACTCAAACTACGCCCTGATCGGCGC<br>ACTGCGAGCAGTAGCCCAAACAATCTCATATGAAGTCACCCTAGCCATCATTCTACTATCAACATTACT<br>AATGAGTGGCTCCTTTAACCTCTCCACCCTTATCACAACACAAGAACACCTCTGGTTACTCCTGCCATC<br>ATGGCCCTTGGCCATGATGTGGTTTATCTCCACACTAGCAGAGACCAACCGAACCCCCTTCGACCTTG<br>CCGAAGGGGAGTCCGAACTAGTCTCAGGCTTCAACATCGAATACGCCGCAGGCCCCTTCGCCCTATT<br>CTTCATGGCCGAATACACAAACATTATTATGATGAACACCCTCACCACTACAATCTTCCTAGGAACAAC<br>ATATGACGCACTCTCCCCTGAACTCTACACAACATATTTTGTCACCAAGACCCTACTTCTAACCTCCCT<br>GTTCTTATGGATTCGAACAGCATACCCCCGATTCCGCTACGACCAACTCATGCACCTCCTATGGAAAA<br>ACTTCCTACCACTCACCCTAGCATTACTTATGTGGTATGTCTCCATGCCCATTACAATCTCCAGCATTC<br>CCCCTCAAACCTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCAGCCCCTGTCCTCCCTTCACCCCCATTGCGTATGAGCATTTCAGAACT<br>CCAAGGAGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTCTGGA<br>GTCACTACTGTGGGTCGCCACTCCTCTGCTACACAGCACGGCTTTTTCAAGGCTGTATTGAGAAGGGA<br>AGTTAGGAAGAAGGGTGTGCTGGGCTAACCAGCCCACAGAGCTCACATTCCTGTCCCTTGGGTGAAA<br>AATACATGTCCATCCTGATATCTCCTGAATTCAGAAATTAGCCTCCACATGTGCAATGGCTTTAAGAGC<br>CAGAAGCAGGGTTCTGGGAATTTTGCAAGTTACCTGTGGCCAGGTGTGGTCTCGGTTACCAAATACGG<br>TTACCTGCAGCTTTTTAGTCCTTTGTGCTCCCACGGGTCTACAGAGTCCCATCTGCCCAAAGGTCTTGA<br>AGCTTGACAGGATGTTTTCGATTACTCAGTCTCCCAGGGCACTACTGGTCCGTAGGATTCGATTGGTC<br>GGGGTAGGAGAGTTAAACAACATTTAAACAGAGTTCTCTCAAAAATGTCTAAAGGGATTGTAGGTAGAT<br>AACATCCAATCACTGTTTGCACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCTTCACATTTGTAGAAGCTT<br>T |
| 68 | COX8-ND1-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTCCTACTCCTCATTGTACCCATTCTAATCGCAATGGC<br>ATTCCTAATGCTTACCGAACGAAAAATTCTAGGCTATATGCAACTACGCAAAGGCCCCAACGTTGTAGG<br>CCCCTACGGGCTACTACAACCCTTCGCTGACGCCATAAAACTCTTCACCAAAGAGCCCCTAAAACCCG<br>CCACATCTACCATCACCCTCTACATCACCGCCCCGACCTTAGCTCTCACCATCGCTCTTCTACTATGGA<br>CCCCCCTCCCCATGCCCAACCCCCTGGTCAACCTCAACCTAGGCCTCCTATTTATTCTAGCCACCTCT<br>AGCCTAGCCGTTTACTCAATCCTCTGGTCAGGGTGGGCATCAAACTCAAACTACGCCCTGATCGGCGC<br>ACTGCGAGCAGTAGCCCAAACAATCTCATATGAAGTCACCCTAGCCATCATTCTACTATCAACATTACT<br>AATGAGTGGCTCCTTTAACCTCTCCACCCTTATCACAACACAAGAACACCTCTGGTTACTCCTGCCATC<br>ATGGCCCTTGGCCATGATGTGGTTTATCTCCACACTAGCAGAGACCAACCGAACCCCCTTCGACCTTG<br>CCGAAGGGGAGTCCGAACTAGTCTCAGGCTTCAACATCGAATACGCCGCAGGCCCCTTCGCCCTATT<br>CTTCATGGCCGAATACACAAACATTATTATGATGAACACCCTCACCACTACAATCTTCCTAGGAACAAC<br>ATATGACGCACTCTCCCCTGAACTCTACACAACATATTTTGTCACCAAGACCCTACTTCTAACCTCCCT<br>GTTCTTATGGATTCGAACAGCATACCCCCGATTCCGCTACGACCAACTCATGCACCTCCTATGGAAAA<br>ACTTCCTACCACTCACCCTAGCATTACTTATGTGGTATGTCTCCATGCCCATTACAATCTCCAGCATTC<br>CCCCTCAAACCTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCA |
| 69 | COX8-opt_ND1-3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTGCTGCTGCTGATCGTGCCCATCCTGATCGCCATGG<br>CCTTCCTGATGCTGACCGAGCGCAAGATCCTGGGCTACATGCAGCTGCGCAAGGGCCCCAACGTGGT<br>GGGCCCCTACGGCCTGCTGCAGCCCTTCGCCGACGCCATCAAGCTGTTCACCAAGGAGCCCCTGAA<br>GCCCGCCACCAGCACCATCACCCTGTACATCACCGCCCCCACCCTGGCCCTGACCATCGCCCTGCTG<br>CTGTGGACCCCCCTGCCCATGCCCAACCCCCTGGTGAACCTGAACCTGGGCCTGCTGTTCATCCTGG<br>CCACCAGCAGCCTGGCCGTGTACAGCATCCTGTGGAGCGGCTGGGCCAGCAACAGCAACTACGCCC<br>TGATCGGCGCCCTGCGCGCCGTGGCCCAGACCATCAGCTACGAGGTGACCCTGGCCATCATCCTGC<br>TGAGCACCCTGCTGATGAGCGGCAGCTTCAACCTGAGCACCCTGATCACCACCCAGGAGCACCTGTG<br>GCTGCTGCTGCCCAGCTGGCCCCTGGCCATGATGTGGTTCATCAGCACCCTGGCCGAGACCAACCG |

TABLE 1-continued nucleic acid and polypeptide sequences and SEQ ID NOs

| SEQ | description | sequence |
| --- | --- | --- |
| | | CACCCCCTTCGACCTGGCCGAGGGCGAGAGCGAGCTGGTGAGCGGCTTCAACATCGAGTACGCCGC<br>CGGCCCCTTCGCCCTGTTCTTCATGGCCGAGTACACCAACATCATCATGATGAACACCCTGACCACCA<br>CCATCTTCCTGGGCACCACCTACGACGCCCTGAGCCCCGAGCTGTACACCACCTACTTCGTGACCAA<br>GACCCTGCTGCTGACCAGCCTGTTCCTGTGGATCCGCACCGCCTACCCCCGCTTCCGCTACGACCAG<br>CTGATGCACCTGCTGTGGAAGAACTTCCTGCCCCTGACCCTGGCCCTGCTGATGTGGTACGTGAGCA<br>TGCCCATCACCATCAGCAGCATCCCCCCCCAGACCTAAGAGCACTGGGACGCCCACCGCCCCTTTCC<br>CTCCGCTGCCAGGCGAGCATGTTGTGGTAATTCTGGAACACAAGAAGAGAAATTGCTGGGTTTAGAAC<br>AAGATTATAAACGAATTCGGTGCTCAGTGATCACTTGACAGTTTTTTTTTTTTTTTAAATATTACCCAAAAT<br>GCTCCCCAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAGCAGAG<br>TGGCACTTGGTGGCCAGAAAGTGTGAGCCTCATGATCTGCTGTCTGTAGTTCTGTGAGCTCAGGTCCC<br>TCAAAGGCCTCGGAGCACCCCCTTCCTTGTGACTGAGCCAGGGCCTGCATTTTTGGTTTTCCCCACCC<br>CACACATTCTCAACCATAGTCCTTCTAACAATACCAATAGCTAGGACCCGGCTGCTGTGCACTGGGAC<br>TGGGGATTCCACATGTTTGCCTTGGGAGTCTCAAGCTGGACTGCCAGCCCCTGTCCTCCCTTCACCCC<br>CATTGCGTATGAGCATTTCAGAACTCCAAGGAGTCACAGGCATCTTTATAGTTCACGTTAACATATAGA<br>CACTGTTGGAAGCAGTTCCTTCTAAAAGGGTAGCCCTGGACTTAATACCAGCCGGATACCTCTGGCCC<br>CCACCCCATTACTGTACCTCTGGAGTCACTACTGTGGGTCGCCACTCCTCTGCTACACAGCACGGCTT<br>TTTCAAGGCTGTATTGAGAAGGGAAGTTAGGAAGAAGGGTGTGCTGGGCTAACCAGCCCACAGAGCT<br>CACATTCCTGTCCCTTGGGTGAAAAATACATGTCCATCCTGATATCTCCTGAATTCAGAAATTAGCCTC<br>CACATGTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTCTACAGA<br>GTCCCATCTGCCCAAAGGTCTTGAAGCTTGACAGGATGTTTTCGATTACTCAGTCTCCCAGGGCACTA<br>CTGGTCCGTAGGATTCGATTGGTCGGGGTAGGAGAGTTAAACAACATTTAAACAGAGTTCTCTCAAAA<br>ATGTCTAAAGGGATTGTAGGTAGATAACATCCAATCACTGTTTGCACTTATCTGAAATCTTCCCTCTTG<br>GCTGCCCCCAGGTATTTACTGTGGAGAACATTGCATAGGAATGTCTGGAAAAAGCTTCTACAACTTGTT<br>ACAGCCTTCACATTTGTAGAAGCTTT |
| 70 | COX8-opt_ND1-3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTGCTGCTGCTGATCGTGCCCATCCTGATCGCCATGG<br>CCTTCCTGATGCTGACCGAGCGCAAGATCCTGGGCTACATGCAGCTGCGCAAGGGCCCCAACGTGGT<br>GGGCCCCTACGGCCTGCTGCAGCCCTTCGCCGACGCCATCAAGCTGTTCACCAAGGAGCCCCTGAA<br>GCCCGCCACCAGCACCATCACCCTGTACATCACCGCCCCCACCCTGGCCCTGACCATCGCCCTGCTG<br>CTGTGGACCCCCCTGCCCATGCCCAACCCCCTGGTGAACCTGAACCTGGGCCTGCTGTTCATCCTGG<br>CCACCAGCAGCCTGGCCGTGTACAGCATCCTGTGGAGCGGCTGGGCCAGCAACAGCAACTACGCCC<br>TGATCGGCGCCCTGCGCGCCGTGGCCCAGACCATCAGCTACGAGGTGACCCTGGCCATCATCCTGC<br>TGAGCACCCTGCTGATGAGCGGCAGCTTCAACCTGAGCACCCTGATCACCACCCAGGAGCACCTGTG<br>GCTGCTGCTGCCCAGCTGGCCCCTGGCCATGATGTGGTTCATCAGCACCCTGGCCGAGACCAACCG<br>CACCCCCTTCGACCTGGCCGAGGGCGAGAGCGAGCTGGTGAGCGGCTTCAACATCGAGTACGCCGC<br>CGGCCCCTTCGCCCTGTTCTTCATGGCCGAGTACACCAACATCATCATGATGAACACCCTGACCACCA<br>CCATCTTCCTGGGCACCACCTACGACGCCCTGAGCCCCGAGCTGTACACCACCTACTTCGTGACCAA<br>GACCCTGCTGCTGACCAGCCTGTTCCTGTGGATCCGCACCGCCTACCCCCGCTTCCGCTACGACCAG<br>CTGATGCACCTGCTGTGGAAGAACTTCCTGCCCCTGACCCTGGCCCTGCTGATGTGGTACGTGAGCA<br>TGCCCATCACCATCAGCAGCATCCCCCCCCAGACCTAAGAGCACTGGGACGCCCACCGCCCCTTTCC<br>CTCCGCTGCCAGGCGAGCATGTTGTGGTAATTCTGGAACACAAGAAGAGAAATTGCTGGGTTTAGAAC<br>AAGATTATAAACGAATTCGGTGCTCAGTGATCACTTGACAGTTTTTTTTTTTTTTTAAATATTACCCAAAAT<br>GCTCCCCAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAGCAGAG<br>TGGCACTTGGTGGCCAGAAAGTGTGAGCCTCATGATCTGCTGTCTGTAGTTCTGTGAGCTCAGGTCCC<br>TCAAAGGCCTCGGAGCACCCCCTTCCTTGTGACTGAGCCAGGGCCTGCATTTTTGGTTTTCCCCACCC<br>CACACATTCTCAACCATAGTCCTTCTAACAATACCAATAGCTAGGACCCGGCTGCTGTGCACTGGGAC<br>TGGGGATTCCACATGTTTGCCTTGGGAGTCTCAAGCTGGACTGCCA |
| 71 | OPA1-ND4-3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTAAAACTAATCGTCCCAACAATTATGTTACTACCACTGACATGGCTTTCCAAAAAACACATG<br>ATTTGGATCAACACAACCACCCACAGCCTAATTATTAGCATCATCCCTCTACTATTTTTAACCAAATCA<br>ACAACAACCTATTTAGCTGTTCCCCAACCTTTTCCTCCGACCCCCTAACAACCCCCCTCCTAATGCTAA<br>CTACCTGGCTCCTACCCCTCACAATCATGGCAAGCCAACGCCACTTATCCAGTGAACCACTATCACGA<br>AAAAAACTCTACCTCTCTATGCTAATCTCCCTACAAATCTCCTTAATTATGACATTCACAGCCACAGAAC<br>TAATCATGTTTTATATCTTCTTCGAAACCACACTTATCCCCACCTTGGCTATCATCACCCGATGGGGCA<br>ACCAGCCAGAACGCCTGAACGCAGGCACATACTTCCTATTCTACACCCTAGTAGGCTCCCTTCCCCTA<br>CTCATCGCACTAATTACACTCACAACACCCTAGGCTCACTAAACATTCTACTACTCACTCTCACTGCC<br>CAAGAACTATCAAACTCCTGGGCCAACAACTTAATGTGGCTAGCTTACACAATGGCTTTTATGGTAAAG<br>ATGCCTCTTTACGGACTCCACTTATGGCTCCCTAAAGCCCATGTCGAAGCCCCCATCGCTGGGTCAAT<br>GGTACTTGCCGCAGTACTCTTAAAACTAGGCGGCTATGGTATGATGCGCCTCACACTCATTCTCAACC<br>CCCTGACAAAACACATGGCCTACCCCTTCCTTGTACTATCCCTATGGGGCATGATTATGACAAGCTCC<br>ATCTGCCTACGACAAACAGACCTAAAATCGCTCATTGCATACTCTTCAATCAGCCACATGGCCCTCGTA<br>GTAACAGCCATTCTCATCCAAACCCCCTGGAGCTTCACCGGCGCAGTCATTCTCATGATCGCCCACGG<br>GCTTACATCCTCATTACTATTCTGCCTAGCAAACTCAAACTACGAACGCACTCACAGTCGCATCATGAT<br>CCTCTCTCAAGGACTTCAAACTCTACTCCCACTAATGGCTTTTTGGTGGCTTCTAGCAAGCCTCGCTAA<br>CCTCGCCTTACCCCCCACTATTAACCTACTGGGAGAACTCTCTGTGCTAGTAACCACGTTCTCCTGGT<br>CAAATATCACTCTCCTACTTACAGGACTCAACATGCTAGTCACAGCCCTATACTCCCTCTACATGTTTA<br>CCACAACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACCGGGTTT |

TABLE 1-continued nucleic acid and polypeptide sequences and SEQ ID NOs

| SEQ | description | sequence |
|---|---|---|
| | | TCCTCTTAAGAGCACTGGGACGCCCACCGCCCCTTTCCCTCCGCTGCCAGGCGAGCATGTTGTGGTA |
| | | ATTCTGGAACACAAGAAGAGAAATTGCTGGGTTTAGAACAAGATTATAAACGAATTCGGTGCTCAGTGA |
| | | TCACTTGACAGTTTTTTTTTTTTTTTAAATATTACCCAAAATGCTCCCCAAATAAGAAATGCATCAGCTCAG |
| | | TCAGTGAATACAAAAAAGGAATTATTTTTCCCTTTGAGGGTCTTTTATACATCTCTCCTCCAACCCCACC |
| | | CTCTATTCTGTTTCTTCCTCCTCACATGGGGGTACACATACACAGCTTCCTCTTTTGGTTCCATCCTTAC |
| | | CACCACACCCACACGCACACTCCACATGCCCAGCAGAGTGGCACTTGGTGGCCAGAAAGTGTGAGCCT |
| | | CATGATCTGCTGTCTGTAGTTCTGTGAGCTCAGGTCCCTCAAAGGCCTCGGAGCACCCCCTTCCTTGT |
| | | GACTGAGCCAGGGCCTGCATTTTTGGTTTTCCCCACCCCACACATTCTCAACCATAGTCCTTCTAACAA |
| | | TACCAATAGCTAGGACCCGGCTGCTGTGCACTGGGACTGGGGATTCCACATGTTTGCCTTGGGAGTC |
| | | TCAAGCTGGACTGCCAGCCCCTGTCCTCCCTTCACCCCCATTGCGTATGAGCATTTCAGAACTCCAAG |
| | | GAGTCACAGGCATCTTTATAGTTCACGTTAACATATAGACACTGTTGGAAGCAGTTCCTTCTAAAAGGG |
| | | TAGCCCTGGACTTAATACCAGCCGGATACCTCTGGCCCCCACCCCATTACTGTACCTCTGGAGTCACT |
| | | ACTGTGGGTCGCCACTCCTCTGCTACACAGCACGGCTTTTTCAAGGCTGTATTGAGAAGGGAAGTTAG |
| | | GAAGAAGGGTGTGCTGGGCTAACCAGCCCACAGAGCTCACATTCCTGTCCCTTGGGTGAAAAATACAT |
| | | GTCCATCCTGATATCTCCTGAATTCAGAAATTAGCCTCCACATGTGCAATGGCTTTAAGAGCCAGAAGC |
| | | AGGGTTCTGGGAATTTTGCAAGTTACCTGTGGCCAGGTGTGGTCTCGGTTACCAAATACGGTTACCTG |
| | | CAGCTTTTTAGTCCTTTGTGCTCCCACGGGTCTACAGAGTCCCATCTGCCCAAAGGTCTTGAAGCTTG |
| | | ACAGGATGTTTTCGATTACTCAGTCTCCCAGGGCACTACTGGTCCGTAGGATTCGATTGGTCGGGGTA |
| | | GGAGAGTTAAACAACATTTAAACAGAGTTCTCTCAAAAATGTCTAAAGGGATTGTAGGTAGATAACATC |
| | | CAATCACTGTTTGCACTTATCTGAAATCTTCCCTCTTGGCTGCCCCCAGGTATTTACTGTGGAGAACAT |
| | | TGCATAGGAATGTCTGGAAAAAGCTTCTACAACTTGTTACAGCCTTCACATTTGTAGAAGCTTT |
| 72 | OPA1-ND4-3'UTR* | GTGCTGCCCGCCTAGAAAGGGTGAAGTGGTTGTTTCCGTGACGGACTGAGTACGGGTGCCTGTCAGG |
| | | CTCTTGCGGAAGTCCATGCGCCATTGGGAGGGCCTCGGCCGCGGCTCTGTGCCCTTGCTGCTGAGG |
| | | GCCACTTCCTGGGTCATTCCTGGACCGGGAGCCGGGCTGGGGCTCACACGGGGGCTCCCGCGTGG |
| | | CCGTCTCGGCGCCTGCGTGACCTCCCCGCCGGCGGGATGTGGCGACTACGTCGGGCCGCTGTGGC |
| | | CTGATGCTAAAACTAATCGTCCCAACAATTATGTTACTACCACTGACATGGCTTTCCAAAAAACACATG |
| | | ATTTGGATCAACACAACCACCCACAGCCTAATTATTAGCATCATCCCTCTACTATTTTTTAACCAAATCA |
| | | ACAACAACCTATTTAGCTGTTCCCCAACCTTTTCCTCCGACCCCCTAACAACCCCCCTCCTAATGCTAA |
| | | CTACCTGGCTCCTACCCCTCACAATCATGGCAAGCCAACGCCACTTATCCAGTGAACCACTATCACGA |
| | | AAAAAACTCTACCTCTCTATGCTAATCTCCCTACAAATCTCCTTAAAATTATGACATTCACAGCCACAGAAC |
| | | TAATCATGTTTTATATCTTCTTCGAAACCACACTTATCCCCACCTTGGCTATCATCACCCGATGGGGCA |
| | | ACCAGCCAGAACGCCTGAACGCAGGCACATACTTCCTATTCTACACCCTAGTAGGCTCCCTTCCCCTA |
| | | CTCATCGCACTAATTTACACTCACAACACCCTAGGCTCACTAAACATTCTACTACTCACTCTCACTGCC |
| | | CAAGAACTATCAAACTCCTGGGCCAACAACTTAATGTGGCTAGCTTACACAATGGCTTTTATGGTAAAG |
| | | ATGCCTCTTTACGGACTCCACTTATGGCTCCCTAAAGCCCATGTCGAAGCCCCCATCGCTGGGTCAAT |
| | | GGTACTTGCCGCAGTACTCTTAAAACTAGGCGGCTATGGTATGATGCGCCTCACACTCATTCTCAACC |
| | | CCCTGACAAAACACATGGCCTACCCCTTCCTTGTACTATCCCTATGGGGCATGATTATGACAAGCTCC |
| | | ATCTGCCTACGACAAACAGACCTAAAATCGCTCATTGCATACTCTTCAATCAGCCACATGGCCCTCGTA |
| | | GTAACAGCCATTCTCATCCAAACCCCCTGGAGCTTCACCGGCGCAGTCATTCTCATGATCGCCCACGG |
| | | GCTTACATCCTCATTACTATTCTGCCTAGCAAACTCAAACTACGAACGCACTCACAGTCGCATCATGAT |
| | | CCTCTCTCAAGGACTTCAAACTCTACTCCCACTAATGGCTTTTTGGTGGCTTCTAGCAAGCCTCGCTAA |
| | | CCTCGCCTTACCCCCCACTATTAACCTACTGGGAGAACTCTCTGTGCTAGTAACCACGTTCTCCTGGT |
| | | CAAATATCACTCTCCTACTTACAGGACTCAACATGCTAGTCACAGCCCTATACTCCCTCTACATGTTTA |
| | | CCACAACACAATGGGGCTCACTCACCCACCACATTAACAACATGAAACCCTCATTCACACGAGAAAAC |
| | | ACCCTCATGTTCATGCACCTATCCCCCATTCTCCTCCTATCCCTCAACCCCGACATCATTACCGGGTTT |
| | | TCCTCTTAAGAGCACTGGGACGCCCACCGCCCCTTTCCCTCCGCTGCCAGGCGAGCATGTTGTGGTA |
| | | ATTCTGGAACACAAGAAGAGAAATTGCTGGGTTTAGAACAAGATTATAAACGAATTCGGTGCTCAGTGA |
| | | TCACTTGACAGTTTTTTTTTTTTTTTAAATATTACCCAAAATGCTCCCCAAATAAGAAATGCATCAGCTCAG |
| | | TCAGTGAATACAAAAAAGGAATTATTTTTCCCTTTGAGGGTCTTTTATACATCTCTCCTCCAACCCCACC |
| | | CTCTATTCTGTTTCTTCCTCCTCACATGGGGGTACACATACACAGCTTCCTCTTTTGGTTCCATCCTTAC |
| | | CACCACACCCACACGCACACTCCACATGCCCAGCAGAGTGGCACTTGGTGGCCAGAAAGTGTGAGCCT |
| | | CATGATCTGCTGTCTGTAGTTCTGTGAGCTCAGGTCCCTCAAAGGCCTCGGAGCACCCCCTTCCTTGT |
| | | GACTGAGCCAGGGCCTGCATTTTTGGTTTTCCCCACCCCACACATTCTCAACCATAGTCCTTCTAACAA |
| | | TACCAATAGCTAGGACCCGGCTGCTGTGCACTGGGACTGGGGATTCCACATGTTTGCCTTGGGAGTC |
| | | TCAAGCTGGACTGCCA |
| 73 | OPA1-opt_ND4-3'UTR | GTGCTGCCCGCCTAGAAAGGGTGAAGTGGTTGTTTcCGTGACGGACTGAGTACGGGTGCCTGTCAGG |
| | | CTCTTGCGGAAGTCCATGCGCCATTGGGAGGGCCTCGGCCGCGGCTCTGTGCCCTTGCTGCTGAGG |
| | | GCCACTTCCTGGGTCATTCCTGGACCGGGAGCCGGGCTGGGGCTCACACGGGGGCTCCCGCGTGG |
| | | CCGTCTCGGCGCCTGCGTGACCTCCCCGCCGGCGGGATGTGGCGACTACGTCGGGCCGCTGTGGC |
| | | CTGATGCTGAAGCTGATCGTGCCCACCATCATGCTGCTGCCTCTGACCTGGCTGAGCAAGAAACACAT |
| | | GATCTGGATCAACACCACCACGCACAGCCTGATCATCAGCATCATCCCTCTGCTGTTCTTCAACCAGA |
| | | TCAACAACAACCTGTTCAGCTGCAGCCCCACCTTCAGCAGCGACCCTCTGACAACACCTCTGCTGATG |
| | | CTGACCACCTGGCTGCTGCCCCTCACAATCATGGCCTCTCAGAGACACCTGAGCAGCGAGCCCCTGA |
| | | GCCGGAAGAAACTGTACCTGAGCATGCTGATCTCCCTGCAGATCTCTCTGATCATGACCTTCACCGCC |
| | | ACCGAGCTGATCATGTTCTACATCTTTTTCGAGACAACGCTGATCCCCACACTGGCCATCATCACCAG |
| | | ATGGGGCAACCAGCCTGAGAGACTGAACGCCGGCACCTACTTTCTGTTCTACACCCTCGTGGGCAGC |
| | | CTGCCACTGCTGATTGCCCTGATCTACACCCACAACACCCTGGGCTCCCTGAACATCCTGCTGCTGAC |
| | | ACTGACAGCCCAAGAGCTGAGCAACAGCTGGGCCAACAATCTGATGTGGCTGGCCTACACAATGGCC |
| | | TTCATGGTCAAGATGCCCCTGTACGGCCTGCACCTGTGGCTGCCTAAAGCTCATGTGGAAGCCCCTAT |
| | | CGCCGGCTCTATGGTGCTGGCTGCAGTGCTGCTGAAACTCGGCGGCTACGGCATGATGCGGCTGAC |
| | | CCTGATTCTGAATCCCCTGACCAAGCACATGGCCTATCCATTTCTGGTGCTGAGCCTGTGGGGCATGA |
| | | TTATGACCAGCAGCATCTGCCTGCGGCAGACCGATCTGAAGTCCCTGATCGCCTACAGCTCCATCAG |
| | | CCACATGGCCCTGGTGGTCACCGCCATCCTGATTCAGACCCCTTGGAGCTTTACAGGCGCCGTGATC |
| | | CTGATGATTGCCCACGGCCTGACAAGCAGCCTGCTGTTTTGTCTGGCCAACAGCAACTACGAGCGGA |
| | | CCCACAGCAGAATCATGATCCTGTCTCAGGGCCTGCAGACCCTCCTGCCTCTTATGGCTTTTTGGTGG |
| | | CTGCTGGCCTCTCTGGCCAATCTGGCACTGCCTCCTACCATCAATCTGCTGGGCGAGCTGAGCGTGC |

TABLE 1-continued

| nucleic acid and polypeptide sequences and SEQ ID NOs | | |
|---|---|---|
| SEQ | description | sequence |
| | | TGGTCACCACATTCAGCTGGTCCAATATCACCCTGCTGCTCACCGGCCTGAACATGCTGGTTACAGCC<br>CTGTACTCCCTGTACATGTTCACCACCACACAGTGGGGAAGCCTGACACACCACATCAACAATATGAA<br>GCCCAGCTTCACCCGCGAGAACACCCTGATGTTCATGCATCTGAGCCCCATTCTGCTGCTGTCCCTGA<br>ATCCTGATATCATCACCGGCTTCTCCAGCTGAGAGCACTGGGACGCCCACCGCCCCTTTCCCTCCGC<br>TGCCAGGCGAGCATGTTGTGGTAATTCTGGAACACAAGAAGAGAAATTGCTGGGTTTAGAACAAGATT<br>ATAAACGAATTCGGTGCTCAGTGATCACTTGACAGTTTTTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCAAAACAATACCAATAGCTAGGACCCGGCTGCTGTGCACTGGGACTGGG<br>GATTCCACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATAGACACT<br>GTTGGAAGCAGTTCCTTCTAAAAGGGTAGCCCTGGACTTAATACCAGCCGGATACCTCTGGCCCCCAC<br>CCCATTACTGTACCTCTGGAGTCACTACTGTGGGTCGCCACTCCTCTGCTACACAGCACGGCTTTTTC<br>AAGGCTGTATTGAGAAGGGAAGTTAGGAAGAAGGGTGTGCTGGGCTAACCAGCCCACAGAGCTCACA<br>TTCCTGTCCCTTGGGTGAAAAATACATGTCCATCCTGATATCTCCTGAATTCAGAAATTAGCCTCCACA<br>TGTGCAATGGCTTTAAGAGCCAGAAGCAGGGTTCTGGGAATTTTGCAAGTTACCTGTGGCCAGGTGTG<br>GTCTCGGTTACCAAATACGGTTACCTGCAGCTTTTTAGTCCTTTGTGCTCCCACGGGTCTACAGAGTC<br>CCATCTGCCCAAAGGTCTTGAAGCTTGACAGGATGTTTTCGATTACTCAGTCTCCCAGGGCACTACTG<br>GTCCGTAGGATTCGATTGGTCGGGGTAGGAGAGTTAAACAACATTTAAACAGAGTTCTCTCAAAAATGT<br>CTAAAGGGATTGTAGGTAGATAACATCCAATCACTGTTTGCACTTATCTGAAATCTTCCCTCTTGGCTG<br>CCCCCAGGTATTTACTGTGGAGAACATTGCATAGGAATGTCTGGAAAAAGCTTCTACAACTTGTTACAG<br>CCTTCACATTTGTAGAAGCTTT |
| 74 | OPA1-<br>opt_ND4-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCTCTGACCTGGCTGAGCAAGAAACACAT<br>GATCTGGATCAACACCACCACGCACAGCCTGATCATCAGCATCATCCCTCTGCTGTTCTTCAACCAGA<br>TCAACAACAACCTGTTCAGCTGCAGCCCCACCTTCAGCAGCGACCCTCTGACAACACCTCTGCTGATG<br>CTGACCACCTGGCTGCTGCCCCTCACAATCATGGCCTCTCAGAGACACCTGAGCAGCGAGCCCCTGA<br>GCCGGAAGAAACTGTACCTGAGCATGCTGATCTCCCTGCAGATCTCTCTGATCATGACCTTCACCGCC<br>ACCGAGCTGATCATGTTCTACATCTTTTTCGAGACAACGCTGATCCCCACACTGGCCATCATCACCAG<br>ATGGGGCAACCAGCCTGAGAGACTGAACGCCGGCACCTACTTTCTGTTCTACACCCTCGTGGGCAGC<br>CTGCCACTGCTGATTGCCCTGATCTACACCCACAACACCCTGGGCTCCCTGAACATCCTGCTGCTGAC<br>ACTGACAGCCCAAGAGCTGAGCAACAGCTGGGCCAACAATCTGATGTGGCTGGCCTACACAATGGCC<br>TTCATGGTCAAGATGCCCCTGTACGGCCTGCACCTGTGGCTGCCTAAAGCTCATGTGGAAGCCCCTAT<br>CGCCGGCTCTATGGTGCTGGCTGCAGTGCTGCTGAAACTCGGCGGCTACGGCATGATGCGGCTGAC<br>CCTGATTCTGAATCCCCTGACCAAGCACATGGCCTATCCATTTCTGGTGCTGAGCCTGTGGGGCATGA<br>TTATGACCAGCAGCATCTGCCTGCGGCAGACCGATCTGAAGTCCCTGATCGCCTACAGCTCCATCAG<br>CCACATGGCCCTGGTGGTCACCGCCATCCTGATTCAGACCCCTTGGAGCTTTACAGGCGCCGTGATC<br>CTGATGATTGCCCACGGCCTGACAAGCAGCCTGCTGTTTTGTCTGGCCAACAGCAACTACGAGCGGA<br>CCCACAGCAGAATCATGATCCTGTCTCAGGGCCTGCAGACCCTCCTGCCTCTTATGGCTTTTTGGTGG<br>CTGCTGGCCTCTCTGGCCAATCTGGCACTGCCTCCTACCATCAATCTGCTGGGCGAGCTGAGCGTGC<br>TGGTCACCACATTCAGCTGGTCCAATATCACCCTGCTGCTCACCGGCCTGAACATGCTGGTTACAGCC<br>CTGTACTCCCTGTACATGTTCACCACCACACAGTGGGGAAGCCTGACACACCACATCAACAATATGAA<br>GCCCAGCTTCACCCGCGAGAACACCCTGATGTTCATGCATCTGAGCCCCATTCTGCTGCTGTCCCTGA<br>ATCCTGATATCATCACCGGCTTCTCCAGCTGAGAGCACTGGGACGCCCACCGCCCCTTTCCCTCCGC<br>TGCCAGGCGAGCATGTTGTGGTAATTCTGGAACACAAGAAGAGAAATTGCTGGGTTTAGAACAAGATT<br>ATAAACGAATTCGGTGCTCAGTGATCACTTGACAGTTTTTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCTAACAATACCAATAGCTAGGACCCGGCTGCTGTGCACTGGGACTGGG<br>GATTCCACATGTTTGCCTTGGGAGTCTCAAGCTGGACTGCCA |
| 75 | OPA1-<br>opt_ND4*-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCCCTGACCTGGCTGAGCAAGAAGCACA<br>TGATCTGGATCAACACCACCACCCACAGCCTGATCATCAGCATCATCCCCCTGCTGTTCTTCAACCAG<br>ATCAACAACAACCTGTTCAGCTGCAGCCCCACCTTCAGCAGCGACCCCCTGACCACCCCCCTGCTGA<br>TGCTGACCACCTGGCTGCTGCCCCTGACCATCATGGCCAGCCAGCGCCACCTGAGCAGCGAGCCCC<br>TGAGCCGCAAGAAGCTGTACCTGAGCATGCTGATCAGCCTGCAGATCAGCCTGATCATGACCTTCACC<br>GCCACCGAGCTGATCATGTTCTACATCTTCTTCGAGACCACCCTGATCCCCACCCTGGCCATCATCAC<br>CCGCTGGGGCAACCAGCCCGAGCGCCTGAACGCCGGCACCTACTTCCTGTTCTACACCCTGGTGGG<br>CAGCCTGCCCCTGCTGATCGCCCTGATCTACACCCACAACACCCTGGGCAGCCTGAACATCCTGCTG<br>CTGACCCTGACCGCCCAGGAGCTGAGCAACAGCTGGGCCAACAACCTGATGTGGCTGGCCTACACCA<br>TGGCCTTCATGGTGAAGATGCCCCTGTACGGCCTGCACCTGTGGCTGCCCAAGGCCCACGTGGAGG<br>CCCCCATCGCCGGCAGCATGGTGCTGGCCGCCGTGCTGCTGAAGCTGGGCGGCTACGGCATGATGC<br>GCCTGACCCTGATCCTGAACCCCCTGACCAAGCACATGGCCTACCCCTTCCTGGTGCTGAGCCTGTG<br>GGGCATGATCATGACCAGCAGCATCTGCCTGCGCCAGACCGACCTGAAGAGCCTGATCGCCTACAGC |

TABLE 1-continued nucleic acid and polypeptide sequences and SEQ ID NOs

| SEQ | description | sequence |
|---|---|---|
| | | AGCATCAGCCACATGGCCCTGGTGGTGACCGCCATCCTGATCCAGACCCCCTGGAGCTTCACCGGCG<br>CCGTGATCCTGATGATCGCCCACGGCCTGACCAGCAGCCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA<br>TCAACAACATGAAGCCCAGCTTCACCCGCGAGAACACCCTGATCTTCATGCACCTGAGCCCCATCCTG<br>CTGCTGAGCCTGAACCCCGACATCATCACCGGCTTCAGCAGCTAAGAGCACTGGGACGCCCACCGCC<br>CCTTTCCCTCCGCTGCCAGGCGAGCATGTTGTGGTAATTCTGGAACACAAGAAGAGAAATTGCTGGGT<br>TTAGAACAAGATTATAAACGAATTCGGTGCTCAGTGATCACTTGACAGTTTTTTTTTTTTTTAAATATTAC<br>CCAAAATGCTCCCCAAATAAGAAATGCATCAGCTCAGTCAGTGAATACAAAAAAGGAATTATTTTTCCC<br>TTTGAGGGTCTTTTATACATCTCTCCTCCAACCCCACCCTCTATTCTGTTTCTTCCTCCTCACATGGGG<br>GTACACATACACAGCTTCCTCTTTTGGTTCCATCCTTACCACCACACCACACGCACACTCCACATGCCC<br>AGCAGAGTGGCACTTGGTGGCCAGAAAGTGTGAGCCTCATGATCTGCTGTCTGTAGTTCTGTGAGCTC<br>AGGTCCCTCAAAGGCCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCTGTGCA<br>CTGGGACTGGGGATTCCACATGTTTGCCTTGGGAGTCTCAAGCTGGACTGCCAGCCCCTGTCCTCCC<br>TTCACCCCCATTGCGTATGAGCATTTCAGAACTCCAAGGAGTCACAGGCATCTTTATAGTTCACGTTAA<br>CATATAGACACTGTTGGAAGCAGTTCCTTCTAAAAGGGTAGCCCTGGACTTAATACCAGCCGGATACC<br>TCTGGCCCCCACCCCATTACTGTACCTCTGGAGTCACTACTGTGGGTCGCCACTCCTCTGCTACACAG<br>CACGGCTTTTTCAAGGCTGTATTGAGAAGGGAAGTTAGGAAGAAGGGTGTGCTGGGCTAACCAGCCC<br>ACAGAGCTCACATTCCTGTCCCTTGGGTGAAAAATACATGTCCATCCTGATATCTCCTGAATTCAGAAA<br>TTAGCCTCCACATGTGCAATGGCTTTAAGAGCCAGAAGCAGGGTTCTGGGAATTTTGCAAGTTACCTG<br>TGGCCAGGTGTGGTCTCGGTTACCAAATACGGTTACCTGCAGCTTTTTAGTCCTTTGTGCTCCCACGG<br>GTCTACAGAGTCCCATCTGCCCAAAGGTCTTGAAGCTTGACAGGATGTTTTCGATTACTCAGTCTCCCA<br>GGGCACTACTGGTCCGTAGGATTCGATTGGTCGGGGTAGGAGAGTTAAACAACATTTAAACAGAGTTC<br>TCTCAAAAATGTCTAAAGGGATTGTAGGTAGATAACATCCAATCACTGTTTGCACTTATCTGAAATCTTC<br>CCTCTTGGCTGCCCCCAGGTATTTACTGTGGAGAACATTGCATAGGAATGTCTGGAAAAAGCTTCTAC<br>AACTTGTTACAGCCTTCACATTTGTAGAAGCTTT |
| 76 | OPA1-opt_ND4*-3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCCCTGACCTGGCTGAGCAAGAAGCACA<br>TGATCTGGATCAACACCACCACCCACAGCCTGATCATCAGCATCATCCCCCTGCTGTTCTTCAACCAG<br>ATCAACAACAACCTGTTCAGCTGCAGCCCCACCTTCAGCAGCGACCCCCTGACCACCCCCCTGCTGA<br>TGCTGACCACCTGGCTGCTGCCCCTGACCATCATGGCCAGCCAGCGCCACCTGAGCAGCGAGCCCC<br>TGAGCCGCAAGAAGCTGTACCTGAGCATGCTGATCAGCCTGCAGATCAGCCTGATCATGACCTTCACC<br>GCCACCGAGCTGATCATGTTCTACATCTTCTTCGAGACCACCCTGATCCCCACCCTGGCCATCATCAC<br>CCGCTGGGGCAACCAGCCCGAGCGCCTGAACGCCGGCACCTACTTCCTGTTCTACACCCTGGTGGG<br>CAGCCTGCCCCTGCTGATCGCCCTGATCTACACCCACAACACCCTGGGCAGCCTGAACATCCTGCTG<br>CTGACCCTGACCGCCCAGGAGCTGAGCAACAGCTGGGCCAACAACCTGATGTGGCTGGCCTACACCA<br>TGGCCTTCATGGTGAAGATGCCCCTGTACGGCCTGCACCTGTGGCTGCCCAAGGCCCACGTGGAGG<br>CCCCCATCGCCGGCAGCATGGTGCTGGCCGCCGTGCTGCTGAAGCTGGGCGGCTACGGCATGATGC<br>GCCTGACCCTGATCCTGAACCCCCTGACCAAGCACATGGCCTACCCCTTCCTGGTGCTGAGCCTGTG<br>GGGCATGATCATGACCAGCAGCATCTGCCTGCGCCAGACCGACCTGAAGAGCCTGATCGCCTACAGC<br>AGCATCAGCCACATGGCCCTGGTGGTGACCGCCATCCTGATCCAGACCCCCTGGAGCTTCACCGGCG<br>CCGTGATCCTGATGATCGCCCACGGCCTGACCAGCAGCCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA<br>TCAACAACATGAAGCCCAGCTTCACCCGCGAGAACACCCTGATGTTCATGCACCTGAGCCCCATCCTG<br>CTGCTGAGCCTGAACCCCGACATCATCACCGGCTTCAGCAGCTAAGAGCACTGGGACGCCCACCGCC<br>CCTTTCCCTCCGCTGCCAGGCGAGCATGTTGTGGTAATTCTGGAACACAAGAAGAGAAATTGCTGGGT<br>TTAGAACAAGATTATAAACGAATTCGGTGCTCAGTGATCACTTGACAGTTTTTTTTTTTTTTAAATATTAC<br>CCAAAATGCTCCCCAAATAAGAAATGCATCAGCTCAGTCAGTGAATACAAAAAAGGAATTATTTTTCCC<br>TTTGAGGGTCTTTTATACATCTCTCCTCCAACCCCACCCTCTATTCTGTTTCTTCCTCCTCACATGGGG<br>GTACACATACACAGCTTCCTCTTTTGGTTCCATCCTTACCACCACACCACACGCACACTCCACATGCCC<br>AGCAGAGTGGCACTTGGTGGCCAGAAAGTGTGAGCCTCATGATCTGCTGTCTGTAGTTCTGTGAGCTC<br>AGGTCCCTCAAAGGCCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCTGTGCA<br>CTGGGACTGGGGATTCCACATGTTTGCCTTGGGAGTCTCAAGCTGGACTGCCA |
| 77 | OPA1-ND6-3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTATGCTTTGTTTCTGTTGAGTGTGGGTTTAGTAATGGGGTTTGTGGGGTTTTCTTCTAAG<br>CCTTCTCCTATTTATGGGGGTTTAGTATTGATTGTTAGCGGTGTGGTCGGGTGTGTTATTATTCTGAAT<br>TTTGGGGGAGGTTATATGGGTTTAATGGTTTTTTTAATTTATTTAGGGGGAATGATGGTTGTCTTTGGAT<br>ATACTACAGCGATGGCTATTGAGGAGTATCCTGAGGCATGGGGGTCAGGGGTTGAGGTCTTGGTGAG<br>TGTTTTAGTGGGGTTAGCGATGGAGGTAGGATTGGTGCTGTGGGTGAAAGAGTATGATGGGGTGGTG<br>GTTGTGGTAAACTTTAATAGTGTAGGAAGCTGGATGATTTATGAAGGAGAGGGGTCAGGGTTGATTCG<br>GGAGGATCCTATTGGTGCGGGGGCTTTGTATGATTATGGGCGTTGGTTAGTAGTAGTTACTGGTTGGA<br>CATTGTTTGTTGGTGTATATATTGTAATTGAGATTGCTCGGGGGAATTAGGAGCACTGGGACGCCCAC<br>CGCCCCTTTCCCTCCGCTGCCAGGCGAGCATGTTGTGGTAATTCTGGAACACAAGAAGAGAAATTGCT |

TABLE 1-continued nucleic acid and polypeptide sequences and SEQ ID NOs

| SEQ | description | sequence |
|---|---|---|
| | | GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAAATACATGTCCATCCTGATATCTCCTGAATTC<br>AGAAATTAGCCTCCACATGTGCAATGGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC<br>CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA<br>AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 78 | OPA1-ND6-3'UTR* | GTGCTGCCCGCCTAGAAAGGGTGAAGTGGTTGTTGCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTATGCTTTGTTTCTGTTGAGTGTGGGTTTAGTAATGGGGTTTGTGGGGTTTTCTTCTAAG<br>CCTTCTCCTATTTATGGGGGTTTAGTATTGATTGTTAGCGGTGTGGTCGGGTGTGTTATTATTCTGAAT<br>TTTGGGGGAGGTTATATGGGTTTAATGGTTTTTTTAATTTATTTAGGGGGAATGATGGTTGTCTTTGGAT<br>ATACTACAGCGATGGCTATTGAGGAGTATCCTGAGGCATGGGGGTCAGGGGTTGAGGTCTTGGTGAG<br>TGTTTTAGTGGGGTTAGCGATGGAGGTAGGATTGGTGCTGTGGGTGAAAGAGTATGATGGGGTGGTG<br>GTTGTGGTAAACTTTAATAGTGTAGGAAGCTGGATGATTTATGAAGGAGAGGGGTCAGGGTTGATTCG<br>GGAGGATCCTATTGGTGCGGGGGCTTTGTATGATTATGGGCGTTGGTTAGTAGTAGTTACTGGTTGGA<br>CATTGTTTGTTGGTGTATATATTGTAATTGAGATTGCTCGGGGGAATTAGGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 79 | OPA1-opt_ND6-3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTACGCCCTGTTCCTGCTGAGCGTGGGCCTGGTGATGGGCTTCGTGGGCTTCAGCAGCA<br>AGCCCAGCCCCATCTACGGCGGCCTGGTGCTGATCGTGAGCGGCGTGGTGGGCTGCGTGATCATCC<br>TGAACTTCGGCGGCGGCTACATGGGCCTGATGGTGTTCCTGATCTACCTGGGCGGCATGATGGTGGT<br>GTTCGGCTACACCACCGCCATGGCCATCGAGGAGTACCCCGAGGCCTGGGGCAGCGGCGTGGAGGT<br>GCTGGTGAGCGTGCTGGTGGGCCTGGCCATGGAGGTGGGCCTGGTGCTGTGGGTGAAGGAGTACGA<br>CGGCGTGGTGGTGGTGGTGAACTTCAACAGCGTGGGCAGCTGGATGATCTACGAGGGCGAGGGCAG<br>CGGCCTGATCCGCGAGGACCCCATCGGCGCCGGCGCCCTGTACGACTACGGCCGCTGGCTGGTGGT<br>GGTGACCGGCTGGACCCTGTTCGTGGGCGTGTACATCGTGATCGAGATCGCCCGCGGCAACTAAGA<br>GCACTGGGACGCCCACCGCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTGCTCAGTGATCACTTGACAG<br>TTTTTTTTTTTTTTAAATATTACCCAAAATGCTCCCCAAATAAGAAATGCATCAGCTCAGTCAGTGAATAC<br>AAAAAAGGAATTATTTTTCCCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGATCTGC<br>TGTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCAGCCCCTGTCCTCCCTTCACCCCCATTGCGTATGAGCATTTCAGAACTCCAAGGAGTCACAGG<br>CATCTTTATAGTTCACGTTAACATATAGACACTGTTGGAAGCAGTTCCTTCTAAAAGGGTAGCCCTGGA<br>CTTAATACCAGCCGGATACCTCTGGCCCCCACCCCATTACTGTACCTCTGGAGTCACTACTGTGGGTC<br>GCCACTCCTCTGCTACACAGCACGGCTTTTTCAAGGCTGTATTGAGAAGGGAAGTTAGGAAGAAGGGT<br>GTGCTGGGCTAACCAGCCCACAGAGCTCACATTCCTGTCCCTTGGGTGAAAAATACATGTCCATCCTG<br>ATATCTCCTGAATTCAGAAATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATACGGTTACCTGCAGCTTTTTA<br>GTCCTTTGTGCTCCCACGGGTCTACAGAGTCCCATCTGCCCAAAGGTCTTGAAGCTTGACAGGATGTT<br>TTCGATTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAATCACTGTT<br>TGCACTTATCTGAAATCCTTTTCTTGGCTGCCCCCAGGTATTTACTGTGGAGAACATTGCATAGGAAT<br>GTCTGGAAAAAGCTTCTACAACTTGTTACAGCCTTCACATTTGTAGAAGCTTT |

TABLE 1-continued nucleic acid and polypeptide sequences and SEQ ID NOs

| SEQ | description | sequence |
|---|---|---|
| 80 | OPA1-opt_ND6-3'UTR* | GTGCTGCCCGCCTAGAAAGGGTGAAGTGGTTGTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTACGCCCTGTTCCTGCTGAGCGTGGGCCTGGTGATGGGCTTCGTGGGCTTCAGCAGCA<br>AGCCCAGCCCCATCTACGGCGGCCTGGTGCTGATCGTGAGCGGCGTGGTGGGCTGCGTGATCATCC<br>TGAACTTCGGCGGCGGCTACATGGGCCTGATGGTGTTCCTGATCTACCTGGGCGGCATGATGGTGGT<br>GTTCGGCTACACCACCGCCATGGCCATCGAGGAGTACCCCGAGGCCTGGGGCAGCGGCGTGGAGGT<br>GCTGGTGAGCGTGCTGGTGGGCCTGGCCATGGAGGTGGGCCTGGTGCTGTGGGTGAAGGAGTACGA<br>CGGCGTGGTGGTGGTGGTGAACTTCAACAGCGTGGGCAGCTGGATGATCTACGAGGGCGAGGGCAG<br>CGGCCTGATCCGCGAGGACCCCATCGGCGCCGGCGCCCTGTACGACTACGGCCGCTGGCTGGTGGT<br>GGTGACCGGCTGGACCCTGTTCGTGGGCGTGTACATCGTGATCGAGATCGCCCGCGGCAACTAAGA<br>GCACTGGGACGCCCACCGCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTGCTCAGTGATCACTTGACAG<br>TTTTTTTTTTTTTTAAATATTACCCAAAATGCTCCCCAAATAAGAAATGCATCAGCTCAGTCAGTGAATAC<br>AAAAAAGGAATTATTTTTCCCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGATCTGC<br>TGTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCA |
| 81 | OPA1-ND1-3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTCCTACTCCTCATTGTACCCATTCTAATCGCAATGGCATTCCTAATGCTTACCGAA<br>CGAAAAATTCTAGGCTATATGCAACTACGCAAAGGCCCCAACGTTGTAGGCCCCTACGGGCTACTACA<br>ACCCTTCGCTGACGCCATAAAACTCTTCACCAAAGAGCCCCTAAAACCCGCCACATCTACCATCACCC<br>TCTACATCACCGCCCCGACCTTAGCTCTCACCATCGCTCTTCTACTATGGACCCCCCTCCCCATGCCC<br>AACCCCCTGGTCAACCTCAACCTAGGCCTCCTATTTATTCTAGCCACCTCTAGCCTAGCCGTTTACTCA<br>ATCCTCTGGTCAGGGTGGGCATCAAACTCAAACTACGCCCTGATCGGCGCACTGCGAGCAGTAGCCC<br>AAACAATCTCATATGAAGTCACCCTAGCCATCATTCTACTATCAACATTACTAATGAGTGGCTCCTTTAA<br>CCTCTCCACCCTTATCACAACACAAGAACACCTCTGGTTACTCCTGCCATCATGGCCCTTGGCCATGA<br>TGTGGTTTATCTCCACACTAGCAGAGACCAACCGAACCCCCTTCGACCTTGCCGAAGGGGAGTCCGA<br>ACTAGTCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCACTCTCCC<br>CTGAACTCTACACAACATATTTGTCACCAAGACCCTACTTCTAAACCTCCCTGTTCTTATGGATTCGAAC<br>AGCATACCCCCGATTCCGCTACGACCAACTCATGCACCTCCTATGGAAAAACTTCCTACCACTCACCC<br>TAGCATTACTTATGTGGTATGTCTCCATGCCCATTACAATCTCCAGCATTCCCCCTCAAACCTAAGAGC<br>ACTGGGACGCCCACCGCCCCTTTCCCTCCGCTGCCAGGCGAGCATGTTGTGGTAATTCTGGAACACA<br>AGAAGAGAAATTGCTGGGTTTAGAACAAGATTATAAACGAATTCGGTGCTCAGTGATCACTTGACAGTT<br>TTTTTTTTTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTATTCTGTT<br>TCTTCCTCCTCACATGGGGGTACACATACACAGCTTCCTCTTTTGGTTCCATCCTTACCACCACACCAC<br>ACGCACACTCCACATGCCCAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCAGCCCCTGTCCTCCCTTCACCCCCATTGCGTATGAGCATTTCAGAACTCCAAGGAGTCACAGG<br>CATCTTTATAGTTCACGTTAACATATAGACACTGTTGGAAGCAGTTCCTTCTAAAAGGGTAGCCCTGGA<br>CTTAATACCAGCCGGATACCTCTGGCCCCCACCCCATTACTGTACCTCTGGAGTCACTACTGTGGGTC<br>GCCACTCCTCTGCTACACAGCACGGCTTTTTCAAGGCTGTATTGAGAAGGGAAGTTAGGAAGAAGGGT<br>GTGCTGGGCTAACCAGCCCACAGAGCTCACATTCCTGTCCCTTGGGTGAAAAATACATGTCCATCCTG<br>ATATCTCCTGAATTCAGAAATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATACGGTTACCTGCAGCTTTTTA<br>GTCCTTTGTGCTCCCACGGGTCTACAGAGTCCCATCTGCCCAAAGGTCTTGAAGCTTGACAGGATGTT<br>TTCGATTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAATCACTGTT<br>TGCACTTATCTGAAATCTTCCCTCTTGGCTGCCCCCAGGTATTTACTGTGGAGAACATTGCATAGGAAT<br>GTCTGGAAAAAGCTTCTACAACTTGTTACAGCCTTCACATTTGTAGAAGCTTT |
| 82 | OPA1-ND1-3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTCCTACTCCTCATTGTACCCATTCTAATCGCAATGGCATTCCTAATGCTTACCGAA<br>CGAAAAATTCTAGGCTATATGCAACTACGCAAAGGCCCCAACGTTGTAGGCCCCTACGGGCTACTACA<br>ACCCTTCGCTGACGCCATAAAAACTCTTCACCAAAGAGCCCCTAAAACCCGCCACATCTACCATCACCC<br>TCTACATCACCGCCCCGACCTTAGCTCTCACCATCGCTCTTCTACTATGGACCCCCCTCCCCATGCCC<br>AACCCCCTGGTCAACCTCAACCTAGGCCTCCTATTTATTCTAGCCACCTCTAGCCTAGCCGTTTACTCA<br>ATCCTCTGGTCAGGGTGGGCATCAAACTCAAACTACGCCCTGATCGGCGCACTGCGAGCAGTAGCCC<br>AAACAATCTCATATGAAGTCACCCTAGCCATCATTCTACTATCAACATTACTAAATGAGTGGCTCCTTTAA<br>CCTCTCCACCCTTATCACAACACAAGAACACCTCTGGTTACTCCTGCCATCATGGCCCTTGGCCATGA<br>TGTGGTTTATCTCCACACTAGCAGAGACCAACCGAACCCCCTTCGACCTTGCCGAAGGGGAGTCCGA<br>ACTAGTCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCACTCTCCC |

TABLE 1-continued

| nucleic acid and polypeptide sequences and SEQ ID NOs | | |
|---|---|---|
| SEQ | description | sequence |
| | | CTGAACTCTACACAACATATTTTGTCACCAAGACCCTACTTCTAACCTCCCTGTTCTTATGGATTCGAAC<br>AGCATACCCCCGATTCCGCTACGACCAACTCATGCACCTCCTATGGAAAAACTTCCTACCACTCACCC<br>TAGCATTACTTATGTGGTATGTCTCCATGCCCATTACAATCTCCAGCATTCCCCCTCAAACCTAAGAGC<br>ACTGGGACGCCCACCGCCCCTTTCCCTCCGCTGCCAGGCGAGCATGTTGTGGTAATTCTGGAACACA<br>AGAAGAGAAATTGCTGGGTTTAGAACAAGATTATAAACGAATTCGGTGCTCAGTGATCACTTGACAGTT<br>TTTTTTTTTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTATTCTGTT<br>TCTTCCTCCTCACATGGGGGTACACATACACAGCTTCCTCTTTTGGTTCCATCCTTACCACCACACCAC<br>ACGCACACTCCACATGCCCAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCA |
| 83 | OPA1-opt_ND1-3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTGCTGCTGCTGATCGTGCCCATCCTGATCGCCATGGCCTTCCTGATGCTGACCG<br>AGCGCAAGATCCTGGGCTACATGCAGCTGCGCAAGGGCCCCAACGTGGTGGGCCCCTACGGCCTGC<br>TGCAGCCCTTCGCCGACGCCATCAAGCTGTTCACCAAGGAGCCCCTGAAGCCCGCCACCAGCACCAT<br>CACCCTGTACATCACCGCCCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGGCCACCAGCAGCCTGGCCG<br>TGTACAGCATCCTGTGGAGCGGCTGGGCCAGCAACAGCAACTACGCCCTGATCGGCGCCCTGCGCG<br>CCGTGGCCCAGACCATCAGCTACGAGGTGACCCTGGCCATCATCCTGCTGAGCACCCTGCTGATGAG<br>CGGCAGCTTCAACCTGAGCACCCTGATCACCACCCAGGAGCACCTGTGGCTGCTGCTGCCCAGCTGG<br>CCCCTGGCCATGATGTGGTTCATCAGCACCCTGGCCGAGACCAACCGCACCCCCTTCGACCTGGCCG<br>AGGGCGAGAGCGAGCTGGTGAGCGGCTTCAACATCGAGTACGCCGCCGGCCCCTTCGCCCTGTTCT<br>TCATGGCCGAGTACACCAACATCATCATGATGAACACCCTGACCACCACCATCTTCCTGGGCACCACC<br>TACGACGCCCTGAGCCCCGAGCTGTACACCACCTACTTCGTGACCAAGACCCTGCTGCTGACCAGCC<br>TGTTCCTGTGGATCCGCACCGCCTACCCCCGCTTCCGCTACGACCAGCTGATGCACCTGCTGTGGAA<br>GAACTTCCTGCCCCTGACCCTGGCCCTGCTGATGTGGTACGTGAGCATGCCCATCACCATCAGCAGC<br>ATCCCCCCCCAGACCTAAGAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAAGATTATAAACGAATTCGGT<br>GCTCAGTGATCACTTGACAGTTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCAGCCCCTGTCCTCCCTTCACCCCCATTGCGTATGAGCATTTCA<br>GAACTCCAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATTGAGAA<br>GGGAAGTTAGGAAGAAGGGTGTGCTGGGCTAACCAGCCCACAGAGCTCACATTCCTGTCCCTTGGGT<br>GAAAAATACATGTCCATCCTGATATCTCCTGAATTCAGAAATTAGCCTCCACATGTGCAATGGCTTTAA<br>GAGCCAGAAGCAGGGTTCTGGGAATTTTGCAAGTTACCTGTGGCCAGGTGTGGTCTCGGTTACCAAAT<br>ACGGTTACCTGCAGCTTTTTAGTCCTTTGTGCTCCCACGGGTCTACAGAGTCCCATCTGCCCAAAGGT<br>CTTGAAGCTTGACAGGATGTTTTCGATTACTCAGTCTCCCAGGGCACTACTGGTCCGTAGGATTCGAT<br>TGGTCGGGGTAGGAGAGTTAAACAACATTTAAACAGAGTTCTCTCAAAAAATGTCTAAAGGGATTGTAG<br>GTAGATAACATCCAATCACTGTTTGCACTTATCTGAAATCTTCCCTCTTGGCTGCCCCCAGGTATTTAC<br>TGTGGAGAACATTGCATAGGAATGTCTGGAAAAAGCTTCTACAACTTGTTACAGCCTTCACATTTGTAG<br>AAGCTTT |
| 84 | OPA1-opt_ND1-3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTGCTGCTGCTGATCGTGCCCATCCTGATCGCCATGGCCTTCCTGATGCTGACCG<br>AGCGCAAGATCCTGGGCTACATGCAGCTGCGCAAGGGCCCCAACGTGGTGGGCCCCTACGGCCTGC<br>TGCAGCCCTTCGCCGACGCCATCAAGCTGTTCACCAAGGAGCCCCTGAAGCCCGCCACCAGCACCAT<br>CACCCTGTACATCACCGCCCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGGCCACCAGCAGCCTGGCCG<br>TGTACAGCATCCTGTGGAGCGGCTGGGCCAGCAACAGCAACTACGCCCTGATCGGCGCCCTGCGCG<br>CCGTGGCCCAGACCATCAGCTACGAGGTGACCCTGGCCATCATCCTGCTGAGCACCCTGCTGATGAG<br>CGGCAGCTTCAACCTGAGCACCCTGATCACCACCCAGGAGCACCTGTGGCTGCTGCTGCCCAGCTGG<br>CCCCTGGCCATGATGTGGTTCATCAGCACCCTGGCCGAGACCAACCGCACCCCCTTCGACCTGGCCG<br>AGGGCGAGAGCGAGCTGGTGAGCGGCTTCAACATCGAGTACGCCGCCGGCCCCTTCGCCCTGTTCT<br>TCATGGCCGAGTACACCAACATCATCATGATGAACACCCTGACCACCACCATCTTCCTGGGCACCACC<br>TACGACGCCCTGAGCCCCGAGCTGTACACCACCTACTTCGTGACCAAGACCCTGCTGCTGACCAGCC<br>TGTTCCTGTGGATCCGCACCGCCTACCCCCGCTTCCGCTACGACCAGCTGATGCACCTGCTGTGGAA<br>GAACTTCCTGCCCCTGACCCTGGCCCTGCTGATGTGGTACGTGAGCATGCCCATCACCATCAGCAGC<br>ATCCCCCCCCAGACCTAAGAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAAGATTATAAACGAATTCGGT<br>GCTCAGTGATCACTTGACAGTTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT |

TABLE 1-continued nucleic acid and polypeptide sequences and SEQ ID NOs

| SEQ | description | sequence |
|---|---|---|
| | | TCCATCCTTACCACCACACCACACGCACACTCCACATGCCCAGCAGAGTGGCACTTGGTGGCCAGAA AGTGTGAGCCTCATGATCTGCTGTCTGTAGTTCTGTGAGCTCAGGTCCCTCAAAGGCCTCGGAGCACC CCCTTCCTTGTGACTGAGCCAGGGCCTGCATTTTTGGTTTTCCCCACCCCACACATTCTCAACCATAGT CCTTCTAACAATACCAATAGCTAGGACCCGGCTGCTGTGCACTGGGACTGGGGATTCCACATGTTTGC CTTGGGAGTCTCAAGCTGGACTGCCA |
| 85 | β-actin-S primer | CGAGATCGTGCGGGACAT |
| 86 | β-actin-A primer | CAGGAAGGAGGGCTGGAAC |
| 87 | ND4-S primer | CTGCCTACGACAAACAGAC |
| 88 | ND4-A primer | AGTGCGTTCGTAGTTTGAG |
| 89 | ND6-F primer | ATGATGTATGCTTTGTTTCTG |
| 90 | ND6-R primer | CTAATTCCCCCGAGCAATCTC |
| 91 | ND6-S primer | AGTGTGGGTTTAGTAATG |
| 92 | ND6-A primer | TGCCTCAGGATACTCCTC |
| 93 | β-actin-F primer | CTCCATCCTGGCCTCGCTGT |
| 94 | β-actin-R primer | GCTGTCACCTTCACCGTTCC |
| 95 | ND6-F primer | GGGTTTTCTTCTAAGCCTTCTCC |
| 96 | ND6-R primer | CCATCATACTCTTTCACCCACAG |
| 97 | opt_ND6-F primer | CGCCTGCTGACCGGCTGCGT |
| 98 | opt_ND6-R | CCAGGCCTCGGGGTACTCCT |
| 99 | ND1-F primer | ATGGCCGCATCTCCGCACACT |
| 100 | ND1-R primer | TTAGGTTTGAGGGGGAATGCT |
| 101 | ND1-F primer | AACCTCAACCTAGGCCTCCTA |
| 102 | ND1-R primer | TGGCAGGAGTAACCAGAGGTG |
| 103 | ND1-F primer | AGGAGGCTCTGTCGTATCTTG |
| 104 | ND1-R primer | TTTTAGGGGCTCTTTGGTGAA |
| 105 | opt-ND1-F primer | GCCGCCTGCTGACCGGCTGCGT |
| 106 | opt-ND1-R primer | TGATGTACAGGGTGATGGTGCTGG |
| 107 | ND4-S primer | GCCAACAGCAACTACGAGC |
| 108 | ND4-A primer | TGATGTTGCTCCAGCTGAAG |
| 109 | opt-ND4-S primer | GCCTGACCCTGATCCTGAAC |
| 110 | opt-ND4-A primerr | GTGCGCTCGTAGTTGCTGTT |
| 111 | hsACO2 | GGGCAGTGCCTCCCCGCCCCGCCGCTGGCGTCAAGTTCAGCTCCACGTGTGCCATCAGTGGATCCG ATCCGTCCAGCCATGGCTTCCTATTCCAAGATGGTGTGACCAGACATGCTTCCTGCTCCCCGCTTAGC CCACGGAGTGACTGTGGTTGTGGTGGGGGGGTTCTTAAAATAACTTTTTAGCCCCCGTCTTCCTATTTT GAGTTTGGTTCAGATCTTAAGCAGCTCCATGCAACTGTATTTATTTTTGATGACAAGACTCCCATCTAAA GTTTTTCTCCTGCCTGATCATTTCATTGGTGGCTGAAGGATTCTAGAGAACCTTTTGTTCTTGCAAGGA AAACAAGAATCCAAAACCAGTGACTGTTCTGTGA |
| 112 | hsATR5B | GGGGTCTTTGTCCTCTGTACTGTCTCTCTCCTTGCCCCTAACCCAAAAAGCTTCATTTTTCTGTGTAGG CTGCACAAGAGCCTTGATTGAAGATATATTCTTTCTGAACAGTATTTAAGGTTTCCAATAAAATGTACAC CCCTCAG |
| 113 | hsAK2 | TGTTGGGTCCAAGAAGGAATTTCTTTCCATCCCTGTGAGGCAATGGGTGGGAATGATAGGACAGGCAA AGAGAAGCTTCCTCAGGCTAGCAAAAATATCATTTGATGTATTGATTAAAAAAGCACTTGCTTGATGTAT CTTTGGCGTGTGTGCTACTCTCATCTGTGTGTATGTGTGTTGTGTGTGTGTGTGTGTGCATGCACATAT GTGTTCACTCTGCTACTTTGTAAGTTTTAGGCTAGGTTGCTTTACCAGCTGTTTACTTCTTTTTTGTTGTT GTTTTGAGACAAGGTTTCGCTCTGCCACCCTGGCTGGAGTGCAGTGGCGTGATCTTGGCTCACGGCA ACCTCTGCCTCCTGGGGCTCAAGCAATTATCCCACCTCAGCCTCCTGAGCAGCTGGGACTACAGGTG CATGCCACAACACCTGGCTGATATTTGTATTTTTTGTAGAGACAGGATTTTGCCAAGTTGCCCAGGCTG GTCTTGAACTCCTAGGCTTAAGCAATCCACCCACCTTGGCCTCCTGAAGTGCCAGGATCACAGACGTG AGCCACTACACCCAGCCCAGCTGTTTACTTCTTTAACCATACTTTTGATTTTATTTTTTGACCAAAATGA ACTAACCCAGGTAATCTTCCAGGGACCGCAATTCCAGAACCTCATAGTATTTCTTCCATTTCCAGCAGC TGATTAGAAGTCCAGGATCATGTGAAGTCAGGCAGGGTCACAGTTCCTGATGGCACATTATGGACAGA GAATTCCATTTTGTTTTCTAACCCATGATGAAAACCCACGTGAGTCAGTGTGTGAACAGGGATCATTAA TTTTTTCCCCCTAGGTGGAAGGTVAAAGGCACTTACTTTGCAGGTTACAGAAATTACTGGGAGAGGAT ATCGTCATAAAAAGAGCCAGGCCAAATTGGAATATTTTTGTGATCTGCATCATGATGCTGAAAATAGCA ATTATTTGGGAATTGGGTTTGAAAACTGAATTGTTGCCAGAGAATTAAACCAGGTGAAAGGTCCTTTTG AATTCAGATTGTCTTCTGAACATCCAGGCTGATCATCTGAGAGCAGTCAAATCTACTTCCCCAAAAAGA GACCAGGGTAGGTTTATTTGCTTTTATTTTTAATGTTTGCCTGTGTTTccAAGTCTGAACAAAACAGTGT GTGATCTATTCTTGGATTCATTTTGATCAGTATTTATTCAAACCCAGTCTCTCTCCAGGACATAAAACTG AAATCAGATATGTTCTTTTTAAGCCCAAACCCTCTCCTTTCTAGATCCAACCCTTCACCCCTAATTTTAT GATGGCTATAGCCATGGACTTCCCCAAGAAAAGATCACCCAGAAATAAGACCACCTGTGACAGTTACC AGCTTTTATTCATAACCTTAGCTTCCCAACTATTGAGCATTTTCTAAGGTCCCTGCTGTCTTTTGGTCTC TGGTTTGATTTGTGGCAAACAGATGAAGTAACAGACTGCTATGAAGGACCACAAAAACGGCAGCCTCT GGAAAAAACCATTAGAAAGTCAGTGGCAGATCCAGTAAATAATATCGCCAGCCTCAGCATAATCTGCTG CTGACTCGATTCAGTGGACTCTAAAGTGCCCAGCCTCCTGACCTGAGCTCTCCTGCCATCTGTGAGAC TACCAGAGGTCTTATCTGCTGTCCACATGGCAACTGGGCATGAGTACCTGGCCACCTTGCTTCCCTCT TTGCCTGGTCCAAGTGAGTGTCTGCTGCCTCTGTCCTGCCTTGTTTTCCTGGCTCTAAACCAACTCCA CCCACTCTTAATGGAAACTCAGTCTGGCTTTGTGTGTTTCTGGGAAGCACATGACTTCTGGGAATGGG |

TABLE 1-continued nucleic acid and polypeptide sequences and SEQ ID NOs

| SEQ | description | sequence |
|---|---|---|
| | | CAAGGAAGAGGAGTGAAACAAAAACTGTCAGCTATGTGTGCCTGGTCTGGGATCCTTCTCTGGGTGACAGTGGCATCATGAATCTTAGAATCAGCTCCCC |
| 114 | hsALDH2 | GAATCATGCAAGCTTCCTCCCTCAGCCATTGATGGAAAGTTCAGCAAGATCAGCAACAAAACCAAGAAAAATGATCCTTGCGTGCTGAATATCTGAAAAGAGAAATTTTTCCTACAAAATCTCTTGGGTCAAGAAAGTTCTAGAATTTGAATTGATAAACATGGTGGGTTGGCTGAGGGTAAGAGTATATGAGGAACCTTTTAAACGACAACAATACTGCTAGCTTTCAGGATGATTTTTAAAAAATAGATTCAAATGTGTTATCCTCTCTCTGAAACGCTTCCTATAACTCGAGTTTATAGGGGAAGAAAAAGCTATTGTTTACAATTATATCACCATTAAGGCAACTGCTACACCCTGCTTTGTATTCTGGGCTAAGATTCATTAAAAACTAGCTGCTCTTAACTTACA |
| 115 | hsCOX10 | GAGCACTGGGACGCCCACCGCCCCTTTCCCTCCGCTGCCAGGCGAGCATGTTGTGGTAATTCTGGAACACAAGAAGAGAAATTGCTGGGTTTAGAACAAGATTATAAACGAATTCGGTGCTCAGTGATCACTTGACAGTTTTTTTTTTTTTTAAATATTACCCAAAATGCTCCCCAAATAAGAAATGCATCAGCTCAGTCAGTGAATACAAAAAAAGGAATTATTTTTCCCTTTGAGGGTCTTTATACATCTCTCCTCCAACCCCACCCTCTATTCTGTTTCTTCCTCCTCACATGGGGGTACACATACACAGCTTCCTCTTTTGGTTCCATCCTTACCACCACACCACACGCACACTCCACATGCCCAGCAGAGTGGCACTTGGTGGCCAGAAAGTGTGAGCCTCATGATCTGCTGTCTGTAGTTCTGTGAGCTCAGGTCCCTCAAAGGCCTCGGAGCACCCCCTTCCTGGTGACTGAGCCAGGGCCTGCATTTTTGGTTTTCCCCACCCCACACATTCTCAACCATAGTCCTTCTAACAATACCAATAGCTAGGACCCGGCTGCTGTGCACTGGGACTGGGGATTCCACATGTTTGCCTTGGGAGTCTCAAGCTGGACTGCCAGCCCCTGTCCTCCCTTCACCCCCATTGCGTATGAGCATTTCAGAACTCCAAGGAGTCACAGGCATCTTTATAGTTCACGTTAACATATAGACACTGTTGGAAGCAGTTCCTTCTAAAAGGGTAGCCCTGGACTTAATACCAGCCGGATACCTCTGGCCCCCACCCCATTACTGTACCTCTGGAGTCACTACTGTGGGTCGCCACTCCTCTGCTACACAGCACGGCTTTTTCAAGGCTGTATTGAGAAGGGAAGTTAGGAAGAAGGGTGTGCTGGGCTAACCAGCCCACAGAGCTCACATTCCTGTCCCTTGGGTGAAAAATACATGTCCATCCTGATATCTCCTGAATTCAGAAAATTAGCCTCCACATGTGCAATGGCTTTAAGAGCCAGAAGCAGGGTTCTGGGAATTTTGCAAGTTATCCTGTGGCCAGGTGTGGTCTCGGTTACCAAATACGGTTACCTGCAGCTTTTTAGTCCTTTGTGCTCCCACGGGTCTGCAGAGTCCCATCTGCCCAAAGGTCTTGAAGCTTGACAGGATGTTTTCATTACTCAGTCTCCCAGGGCACTGCTGGTCCGTAGGGATTCATTGGTCGGGGTGGGAGAGTTAAACAACATTTAAACAGAGTTCTCTCAAAAATGTCTAAAGGGATTGTAGGTAGATAACATCCAATCACTGTTTGCACTTATCTGAAATCTTCCCTCTTGGCTGCCCCCAGGTATTTACTGTGGAGAACATTGCATAGGAATGTCTGGAAAAAGCCTCTACAACTTGTTACAGCCTTCACATTTGTACAATTCATTGATTCTCTTTTCCTTCCACAATAAAATGGTATACAAGAAC |
| 116 | hsUQCRFS1 | GAGACTTGGACTCAAGTCATAGGCTTCTTTCAGTCTTTATGTCACCTCAGGAGACTTATTTGAGAGGAAGCCTTCTGTACTTGAAGTTGATTTGAAATATGTAAGAATTGATGATGTATTTGCAAACATTAATGTGAAATAAATTGAATTTAATGTTGAATACTTTCAGGCATTCACTTAATAAAGACACTGTTAAGCACTGTTATGCTCAGTCATACACGCGAAAGGTACAATGTCTTTTAGCTAATTCTAATTAAAAATTACAGACTGGTGTACAAGATACTTGTG |
| 117 | hsNDUFV1 | CCCACCACCCTGGCCTGCTGTCCTGCGTCTATCCATGTGGAATGCTGGACAATAAAGCGAGTGCTGCCCACCCTCCAGCTGCC |
| 118 | hsNDUFV2 | TTTATATTGAACTGTAAATATGTCACTAGAGAAATAAAATATGGACTTCCAATCTACGTAAACTTA |
| 119 | hsSOD2 | ACCACGATCGTTATGCTGAGTATGTTAAGCTCTTTATGACTGTTTTTGTAGTGGTATAGAGTACTGCAGAATACAGTAAGCTGCTCTATTGTAGCATTTCTTGATGTTGCTTAGTCACTTATTTCATAAACAACTTAATGTTCTGAATAATTTCTTACTAAACATTTTGTTATTGGGCAAGTGATTGAAAATAGTAAATGCTTTGTGTGATTGA |
| 120 | hsCOX6c | TCTTGGAATATAAAGAATTTCTTCAGGTTGAATTACCTAGAAGTTTGTCACTGACTTGTGTTCCTGAACTATGACACATGAATATGTGGGCTAAGAAATAGTTCCTCTTGATAAATAAACAATTAACAAATACTTTGGACAGTAAGTCTTTCTCAGTTCTTAATGATAATGCAGGGCACTTACTAGCATAAGAATTGGTTTGGGATTTAACTGTTTATGAAGCTAACTTGATTTCCGTGTTTTGTTAAAATTTCATTGTTCTAGCACATCTTTAACTGTGATAGTT |
| 121 | hsIRP1 | GAGACGTGCACTTGGTCGTGCGCCCAGGGAGGAAGCCGCACCACCAGCCAGCGCAGGCCCTGGTGGAGAGGCCTCCCTGGCTGCCTCTGGGAGGGGTGCTGCCTTGTAGATGGAGCAAGTGAGCACTGAGGGTCTGGTGCCAATCCTGTAGGCACAAAACCAGAAGTTTCTACATTCTCTATTTTTGTTAATCATCTTCTCTTTTTCCAGAATTTGGAAGCTAGAATGGTGGGAATGTCAGTAGTGCCAGAAAGAGAGAACCAAGCTTGTCTTTAAAGTTACTGATCACAGGACGTTGCTTTTTCACTGTTTCCTATTAATCTTCAGCTGAACACAAGCAAACCTTCTCAGGAGGTGTCTCCTACCCTCTTATTGTTCCTCTTACGCTCTGCTCAATGAAACCTTCCTCTTGAGGGTCATTTTCCTTTCTGTATTAATTATACCAGTGTTAAGTGACATAGATAAGAACTTTGCACACTTCAAATCAGAGCAGTGATTCTCTCTTCTCTCCCCTTTTCCTTCAGAGTGAATCATCCAGACTCCTCATGGATAGGTCGGGTGTTAAAGTTGTTTTGATTATGTACCTTTTGATAGATCCACATAAAAAGAAATGTGAAGTTTTCTTTTACTATCTTTTCATTTATCAAGCAGAGACCTTTGTTGGGAGGCGGTTTGGGAGAACACATTTCTAATTTGAATGAAATGAAATCTATTTTCAGTG |
| 122 | hsRPS12 | CAGAAGAAGTGACGGCTGGGGGCACAGTGGGCTGGGCGCCCCTGCAGAACATGAACCTTCCGCTCCTGGCTGCCACAGGGTCCTCCGATGCTGGCCTTTGCGCCTCTAGAGGCAGCCACTCATGGATTCAAGTCCTGGCTCCGCCTCTTCCATCAGGACCACT |
| 123 | hsATP5J2 | AGAGGACACACTCTGCACCCCCCCACCCCACGACCTTGGCCCGAGCCCCTCCGTGAGGAA |
| 124 | rnSOD2 | AGCCCTTCCGCCAGGCTGTGTGTCAGGCCCGTGGTGGGTGTTTTGTAGTAGTGTAGAGCATTGCA |
| 125 | hsOXA1L | CTTATGTTCTGTGCGCATTCTGGCAGGAATTCTGTCTCTTCAGAGACTCATCCTCAAAACAAGACTTGACACTGTGTCCTTGCCCCAGTCCTAGGAACTGTGGCACACAGAGATGTTCATTTAAAAACGGATTTCATGAAACACTCTTGTACTTATGTTTATAAGAGAGCACTGGGTAGCCAAGTGATCTTCCCATTCACAGAGTTAGTAAACCTCTGTACTACATGCTG |
| 126 | MTS-COX10 | MAASPHTLSSRLLTGCVGGSVWYLERRT |
| 127 | MTS-COX8 | MSVLTRLLLRGLTRLGSAAPVRRARIHSL |
| 128 | MTS-OPA1 | MWRLRRAAVA |
| 129 | hsCOX10 | MAASPHTLSSRLLTGCVGGSVWYLERRT |
| 130 | scRPM2 | MAFKSFIYSKGYHRSAAQKKTATSFFDSSYQYLRQNQGLVNSDPVLHASHLHPHPVVVANVNYNNVDDILHPHDLDSSINNTNNPLTHEELLYNQNVSLRSLKQQQSTNYVNNNNNNQHRYY |
| 131 | IcSirt5 | MRKRSLRCHLWSANASLSPRKDEVTSRKESENLVKGKKNKKSHLHLLLFTASKIGTDSVFDVQKSKECCKELGLLFTSLIHSIGSFPFDEEPKAAAVFLPGSLPQLTVLVLAPGSGSCPTGKSTPHLAASGRNAELLRPQNSMIVRQFTCRGTISSHLCAHLRKPHDSRNMARP |

TABLE 1-continued

| nucleic acid and polypeptide sequences and SEQ ID NOs | | |
|---|---|---|
| SEQ | description | sequence |
| 132 | tbNDUS7 | MLRRTSFNFTGRAMISRGSPEWSHRLDLKKGKKTTMMHKLGTSKPNNALQYAQMTL |
| 133 | neQCR2 | MISRSALSRGSQLALRRPAAAKTAQRGFAAAAASPAASYEPTTIAG |
| 134 | hsATP5G2 | MPELILYVAITLSVAERLVGPGHACAEPSFRSSRCSAPLCLLCSGSSSPATAPHPLKFACSKFVSTPSLVK STSQLLSRPLSAVVLKRPEILTDESLSSLAVSCPLTSLVSSRSFQTSAISRDIDTA |
| 135 | hsLACTB | MYRLMSAVTARAAAPGGLASSCGRRGVHQRAGLPPLGHGWVGGLGLGLGLALGVKLAGGLRGAAPAQS PAAPDPEASPLAEPPQEQSLAPWSPQTPAPPCSRCFARAIESSRDLL |
| 136 | spilv1 | MTVLAPLRRLHTRAAFSSYGREIALQKRFLNLNSCSAVRRYGTGFSNNLRIKKLKNAFGVVRANSTKSTSTV TTASPIKYDSSFVGKTGGEIFHDMMLKHNVKHVFGYPGGAILPVFDAIYRSPHFEFILPRHEQAAGHA |
| 137 | gmCOX2 | MILCPLEAFIVQHILTISVMGLLSCFRSTVLRKCSKGSSGMSRFLYTNNFQRNLISSGGNESYYGYFNRRSY TSLYMGTGTVGGITSARIRVPNVGCEGFMCSSHLSITQRNSRLIHSTSKIVPN |
| 138 | crATP6 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNM |
| 139 | hsOPA1 | MWRLRRAAVACEVCQSLVKHSSGIKGSLPLQKLHLVSRSIYHSHHPTLKLQRPQLRTSFQQFSSLTNLPLR KLKFSPIKYGYQPRRN |
| 140 | hsSDHD | MAVLWRLSAVCGALGGRALLLRTPVVRPAHISAFLQDRPIPEWCGVQHIHLSPSHH |
| 141 | hsADCK3 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHAHSEGPAPAYVASGPFREAGFPGQASSPLGRA NGRLFANPRDSFSAMGFQRRF |
| 142 | osP0644B06. 24-2 | MALLLRHSPKLRRAHAILGCERGTVVRHFSSSTCSSLVKEDTVSSSNLHPEYAKKIGGSDFSHDRQSGKEL QNFKVSPQEASRASNFMRASKYGMPITANGVHSLFSCGQVVPSRCF |
| 143 | *Neurospora crassa* ATP9 (ncATP9) | MASTRVLASRLASQMAASAKVARPAVRVAQVSKRTIQTGSPLQTLKRTQMTSIVNATTRQAFQKRA |
| 144 | hsGHITM | MLAARLVCLRTLPSRVFHPAFTKASPVVKNSITKNQWLLTPSRE |
| 145 | hsNDUFAB1 | MASRVLSAYVSRLPAAFAPLPRVRMLAVARPLSTALCSAGTQTRLGTLQPALVLAQVPGRVTQLCRQY |
| 146 | hsATP5G3 | MFACAKLACTPSLIRAGSRVAYRPISASVLSRPEASRTGEGSTVFNGAQNGVSQLIQREFQTSAISR |
| 147 | crATP6_ hsADCK3 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNMGGMAAILGDTIMVAKGLVKLTQAAVETHLQHL GIGGELIMAARALQSTAVEQIGMFLGKVQGQDKHEEYFAENFGGPEGEFHFSVPHAAGASTDFSSASAPD QSAPPSLGHAHSEGPAPAYVASGPFREAGFPGQASSPLGRANGRLFANPRDSFSAMGFQRRFGG |
| 148 | ncATP9_ncAT P9 | MASTRVLASRLASQMAASAKVARPAVRVAQVSKRTIQTGSPLQTLKRTQMTSIVNATTRQAFQKRAAST RVLASRLASQMAASAKVARPAVRVAQVSKRTIQTGSPLQTLKRTQMTSIVNATTRQAFQKRA |
| 149 | zmLOC10028 2174 | MALLRAAVSELRRRGRGALTPLPALSSILSSLSPRSPASTRPEPNNPHADRRHVIALRRCPPLPASAVLAPE LLHARGLLPRHWSHASPLSTSSSSSRPADKAQLTWVDKWIPEAARPY |
| 150 | ncATP9_zmL OC100282174_ spilv1_ncAT P9 | MASTRVLASRLASQMAASAKVARPAVRVAQVSKRTIQTGSPLQTLKRTQMTSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPYMTVLAPLRRLHTRAAFSSYGREIALQKRF LNLNSCSAVRRYGTGFSNNLRIKKLKNAFGVVRANSTKSTSTVTTASPIKYDSSFVGKTGGEIFHDMMLKH NVKHVFGYPGGAILPVFDAIYRSPHFEFILPRHEQAAGHAMASTRVLASRLASQMAASAKVARPAVRVAQV SKRTIQTGSPLQTLKRTQMTSIVNATTRQAFQKRA |
| 151 | zmLOC10028 2174_ hsADCK3_ crATP6_ hsTP5G3 | MALLRAASELRRRGRGALTPLPALSSLLSSISPRSPASTRPEPNNPHADRRHVIALRRCPPLPASAVLAPE LLHARGLLPRHWSHASPLSTSSSSSRPADKAQLTWVDKWIPEAARPYMAAILGDTIMVAKGLVKLTQAAVE THLQHLGIGGELIMAARALQSTAVEQIGMFLGKVQGQDKHEEYFAENFGGPEGEFHFSVPHAAGASTDFS SASAPDQSAPPSLGHAHSEGPAPAYVASGPFREAGFPGQASSPLGRANGRLFANPRDSFSAMGFQRRF MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQMNMMFACAKLACTPSLIRAGSRVAYRPISASVLSR PEASRTGEGSTVFNGAQNGVSQLICREFQTSAISR |
| 152 | zmLOC10028 2174_ hsADCK3_ hsATP5G3 | MALLRAAVSELRRRGRGALTPLPALSSLLSSLSPRSPASTRPEPNNPHADRRHVIALRRCPPLPASAVLAPE LLHARGLLPRHWSHASPLSTSSSSSRPADKAQLTWVDKWIPEAARPYMAAILGDTIMVAKGLVKLTQAAVE THLQHLGIGGELIMAARALQSTAVEQEIGMFLGKVQGQDKHEEYFAENFGGPEGEFHFSVPHAAGASTDFS SASAPDQSAPPSLGHAHSEGPAPAYVASGPFREAGFPGQASSPLGRANGRLFANPRDSFSAMGFQRRF MFACAKLACTPSLIRAGSRVAYRPISASVLSRPEASRTGEGSTVFNGAQNGVSQLIQREFQTSAISR |
| 153 | ncATP9_zmL OC100282174 | MASTRVLASRLASQMAASAKVARPAVRVAQVSKRTIQTGSPLQTLKRTQTMSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPY |
| 154 | hsADCK3_zm LOC10028217 4_crATP6_ hsATP5G3 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHARSEGPAPAYVASGPFREAGFPGQASSPLGRA NGRLFANPRDSFSAMGFQRRFMALLRAAVSELRRRGRGALTPLPALSSLLSSLSPRSPASTRPEPNNPHA DRRHVIALRRCPPLPASAVLAPELLHARGLLPRHWSHASPLSTSSSSSRPADKAQLTWVDKWIPEAARRY MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNMMFACAKLACTPSLIRAGSRVAYRPISASVLSR PEASRTGEGSTVFNGAQNGVSQLIQREFQTSAISR |
| 155 | crATP6_ hsADCK3_z mLOC100282 174_hsATP5 G3 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQMNMMAAILGDTIMVAKGLVKLTQAAVETHLQHLGIG GELIMAARALQSTAVEQIGMFLGKVQGQDKHEEYFAENFGGPEGEFHFSVPHAAGASTDFSSASAPDQSA PPSLGHAHSEGPAPAYVASGPFREAGFPGQASSPLGRANGRLFANPRDSFSAMGFQRRFMALLRAAVSE LRRRGRGALTPLPALSSLLSSLSPRSPASTRPEPNNPHADRRHVIALRRCPPLPASAVLAPELLHARGLLPR HWSHASPLSTSSSSSRPADKAQLTWVDKWIPEAAREPYMFACAKLACTPSLIRAGSRVAYRPISASVLSRPE ASRTGEGSTVFNGAQNGVSQLIQREFQTSAISR |
| 156 | hsADCK3_zm LOC10028217 4 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHAHSEGPAPAYVASGPFREAGFPGQASSPLGRA NGRLFANPRDSFSAMGFQRRFGGMALLRAAVSELRRRGRGALTPLPALSSLLSSLSPRSPASTRPEPNNP HADRRHVIALRRCPPLPASAVLAPELLHARGLLPRHWSHASPLSTSSSSSRPADKAQLTWVDKWIPEAARP YGG |

TABLE 1-continued nucleic acid and polypeptide sequences and SEQ ID NOs

| SEQ | description | sequence |
|---|---|---|
| 157 | hsADCK3_zmLOC100282174_crATP6 | MAAILGDTIMVAKGLVKLTQAAVETHLQHLGIGGELIMAARALQSTAVEQIGMFLGKVQGQDKHEEYFAENF<br>GGPEGEFHFSVPHAAGASTDFSSASAPDQSAPPSLGHAHSEGPAPAYVASGPFREAGFPGQASSPLGRA<br>NGRLFANPRDSFSAMGFQRRFGGMALLRAAVSELRRRGRGALTPLPALSSLLSSLSPRSPASTRPEPNNP<br>HADRRHVIALRRCPPLPASAVLAPELLHARGLLPRHWSHASPLSTSSSSSRPADKAQLTWVDKWIPEAARP<br>YGGMALQQAAPRVFGLLGRAPVALGQSGILTGSSGFKNQGFNGSLQSVENHVYAQAFSTSSQEEQAAPSI<br>QGASGMKLPGAGSMLLGKSRSGLRTGSMVPFAAQQMNMMGG |
| 158 | ncATP9_zmLOC100282174_spilv1_GNFP_ncATP9 | MASTRVLASRLASQMAASAKVARPAVRVAQVSKRTIQTGSPLQTLKRTQMTSIVNATTRQAFQKRAMALLR<br>AAVSELRRRGRGALTPLPALSSLLSSLSPRSPASTRPEPNNPHADRRHVIALRRCPPLPASAVLAPELLHAR<br>GLLPRHWSHASPLSTSSSSSRPADKAQLTWVDKWIPEAARPYMTVLAPLRRLHTRAAFSSYGREIALQKRF<br>LNLNSCSAVRRYGTGFSNNLRIKKLKNAFGVVRANSTKSTSTVTTASPIKYDSSFVGKTGGEIFHDMMLKH<br>NVKHVFGYPGGAILPVFDAIYRSPHFEFILPRHEQAAGHAVSGEGDATYGKLTLKFICTTGKLPVPWPTLVT<br>TLTYGVQCFSRYPDHKQHDFFKSAMPEGYVQERTIFFKDDGNYKTRAEVKFEGDTLVNRIELKGIDFKED<br>GNILGHKLEYNYNSHNVYIMADKQKNGIKVNFKIRHNIEDGSVQLADHYQQNTPIGDGPVLLPDNHYLSTQS<br>ALSKDPNEMASTRVLASRLASQMAASAKVARPAVRVAQVSKRTIQTGSPLQTLKRTQMTSIVNATTRQAFQ<br>KRA |
| 159 | ncATP9_zmLOC100282174_spilv1_IcSirt5_osP0644B06.24-2_hsATP5G2_ncATP9 | MASTRVLASRLASQMAASAKVARPAVRVAQVSKRTIQTGSPLQTLKRTQMTSIVNATTRQAFQKRAMALLR<br>AAVSELRRRGRGALTPLPALSSLLSSLSPRSPASTRPEPNNPHADRRHVIALRRCPPLPASAVLAPELLHAR<br>GLLPRHWSHASPLSTSSSSSRPADKAQLTWVDKWIPEAARPYMTVLAPLRRLHTRAAFSSYGREIALQKRF<br>LNLNSCSAVRRYGTGFSNNLRIKKLKNAFGVVRANSTKSTSTVTTASPIKYDSSFVGKTGGEIFHDMMLKH<br>NVKHVFGYPGGAILPVFDAIYRSPHFEFILPRHEQAAGHAMRKRSLRCHLWSANASLSPRKDEVTSRKESE<br>NLVKGKKNKKSHLHLLLFTASKIGTDSVPDVQKSKECCKELGLLFTSLIHSIGSFPFDEEPKAAAVFLPGSLP<br>QLTVLVLAPGSGSCPTGKSTPHLAASGRNAELLRPQNSMIVRQFTCRGTISSHLCAHLRKPHDSRNMARP<br>MALLLRHSPKLRRAHAILGCERGTVVRHFSSSTCSSLVKEDTVSSSNLHPEYAKKIGGSDFSHDRQSGKEL<br>QNFKVSPQEASRASNFRMASKYGMPITANGVHSLFSCGQVVPSRCFMPELILYVAITLSVAERLVGPGHAC<br>AEPSFRSSRCSAPLCLLCSGSSSPATAPHPLKMFACSKFVSTPSLVKSTSQLLSRPLSAVVLKRPEILTDES<br>LSSLAVSCPLTSLVSSRSFQTSAISRDIDTAMASTRVLASRLASQMAASAKVARPAVRVAQVSKRTIQTGSP<br>LQTLKRTQMTSIVNATTRQAFQKRA |
| 160 | ND4 | MLKLIVPTIMLLPLTWLSKKHMIWINTTTHSLIISIIPLLFFNQINNNLFSCSPTFSSDPLTTPLLMLTTWLLPLTI<br>MASQRHLSSEPLSRKKLYLSMLISLQISLIMTFTATELIMFYIFFETTLIPTLAIITRWGNQPERLNAGTYFLFYT<br>LVGSLPLLIALIYTHNTLGSLNILLLTLTAQELSNSWANNLMWLAYTMAFMVKMPLYGLHLWLPKAHVEAPIA<br>GSMVLAAVLLKLGGYGMMRLTLILNPLTKHMAYPFLVLSLWGMIMTSSICLRQTDLKSLIAYSSISHMALVVT<br>AILIQTPWSFTGAVILMIAHGLTSSLLFCLANSNYERTHSRIMILSQGLQTLLPLMAFWWLLASLANLALPPTIN<br>LLGELSVLVTTFSWSNITLLLTGLNMLVTALYSLYMVFTTTQWGSLTHHINNMKPSFTRENTLMFMHLSPILLL<br>SLNRPDIITGFSS |
| 161 | ND6 | MMYALFLLSVGLVMGFVGFSSKPSPIYGGLVLIVSGVVGCVIILNFGGGYMGLMVFLIYLGGMMVVFGYTTA<br>MAIEEYPEAWGSGVEVLVSVLVGLAMEVGLVLWVKEYDGVVVVVNFNSVGSWMIYEGEGSGLIREDPIGA<br>GALYDYGRWLVVVTGWTLFVGVYIVIEIARGN |
| 162 | ND1 | MANLLLLIVPILIAMAFLMLTERKILGYMQLRKGPNVVGPYGLLQPFADAIKLFTKEPLKPATSTITLYITAPTLA<br>LTIALLLWTPLPMPNPLVNLNLGLLFILATSSLAVYSILWSGWASNSNYALIGALRAVAQTISYEVTLAIILLSTL<br>LMSGSFNLSTLITTQEHLWLLLPSWPLAMMWFISTLAETNRTPFDLAEGESELVSGFNIEYAAGPFALFFMA<br>EYTNIIMMNTLTTTIFLGTTYDALSPELYTTYFVTKTLLLTSLFLWIRTAYPRFRYDQLMHLLWKNFLPLTLALL<br>MWYVSMPITISSIPPQT |

Adeno-Associated Virus (AAV)

Adeno-associated virus (AAV) is a small virus that infects humans and some other primate species. The compositions disclosed herein comprises firstly an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome can be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or Glade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10, AAV11, AAV12, AAV13, AAV14, AAV15, and AAV16, also recombinant serotypes, such as Rec2 and Rec3, recently identified from primate brain.

A preferred serotype of AAV for use in the invention is AAV2. Other serotypes of particular interest for use in the invention include AAV4, AAV5 and AAV8 which efficiently transduce tissue in the eye, such as the retinal pigmented epithelium. The serotype of AAV which is used can be an AAV serotype which is not AAV4. Reviews of AAV serotypes may be found in Choi et al (Curr Gene Ther. 2005; 5(3); 299-310) and Wu et al (Molecular Therapy. 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adenoassociated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609; Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377; Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623; Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013; Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu11 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556; Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003.

The skilled person can select an appropriate serotype, Glade, clone or isolate of AAV for use in the present invention on the basis of their common general knowledge. For instance, the AAV5 capsid has been shown to transduce primate cone photoreceptors efficiently as evidenced by the successful correction of an inherited color vision defect (Mancuso et al., Nature 2009, 461:784-7).

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within eye in LHON. Thus, AAV serotypes for use in AAV viruses administered to patients can be ones which infect cells of the neurosensory retina and retinal pigment epithelium.

Typically, the AAV genome of a naturally derived serotype or isolate or Glade of AAV comprises at least one inverted terminal repeat sequence (ITR). An ITR sequence acts in cis to provide a functional origin of replication, and allows for integration and excision of the vector from the genome of a cell. In preferred embodiments, one or more ITR sequences flank the polynucleotide sequence encoding ND4, ND6, or ND1 or a variant thereof. Preferred ITR sequences are those of AAV2, and variants thereof. The AAV genome typically also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter will be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV virus. For example, a vector comprising a full AAV genome may be used to prepare AAV virus in vitro. However, while such a vector may in principle be administered to patients, this will be done rarely in practice. Preferably the AAV genome will be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid are reviewed in Coura and Nardi (Virology Journal, 2007, 4:99), and in Choi et al and Wu et al, referenced above.

Derivatives of an AAV genome include any truncated or modified forms of an AAV genome which allow for expression of a ND4, ND6, or ND1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the polynucleotide sequence encoding ND4, ND6, ND1, or a variant thereof at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes (NB: the rep gene in the wildtype AAV genome should not to be confused with ND4, ND6, or ND1, the human gene affected in LHON). However, in some embodiments, including in vitro embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

Where a derivative genome comprises genes encoding capsid proteins i.e. VP1, VP2 and/or VP3, the derivative may be a chimeric, shuffled or capsid-modified derivative of one or more naturally occurring AAV viruses. In particular, the invention encompasses the provision of capsid protein sequences from different serotypes, clades, clones, or isolates of AAV within the same vector i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al., 2008 ARVO Abstract: D1048). The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a polynucleotide sequence comprising an AAV genome or derivative thereof and a sequence encoding ND4, ND6, ND1 or a variant thereof.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

Recombinant Nucleic Acid Sequences

Also disclosed herein are recombinant nucleic acid sequences comprising a polynucleotide sequence encoding a NADH dehydrogenase subunit-4 (ND4), NADH dehydrogenase subunit-1 (ND1) and NADH dehydrogenase subunit-6 (ND6) polypeptide or a variant thereof.

The polynucleotide sequence for ND4 is shown in SEQ ID NO: 6 and encodes the protein shown in SEQ ID NO: 160. Further nucleic acid sequences for ND4 are SEQ ID NO: 7 and 8. The polynucleotide sequence for ND6 is shown in SEQ ID NO: 9 and encodes the protein shown in SEQ ID NO: 161. A further nucleic acid sequence for ND6 is SEQ ID NO: 10. The polynucleotide sequence for ND1 is shown in SEQ ID NO: 11 and encodes the protein shown in SEQ ID NO: 162. A further nucleic acid sequence for ND1 is SEQ ID NO: 12.

A variant of any one of SEQ ID NO: 160, 161, or 162 may comprise truncations, mutants or homologues thereof, and any transcript variants thereof which encode a functional ND4, ND6, or ND1 polypeptide. Any homologues mentioned herein are typically at least 70% homologous to a relevant region of ND4, ND6, or ND1, and can functionally compensate for the polypeptide deficiency.

Homology can be measured using known methods. For example the UWGCG Package provides the BESTFIT program which can be used to calculate homology (for example used on its default settings) (Devereux et at (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et at (1990) J Mol Biol 215:403-10. Software for performing BLAST analyses is publicly available through the National Center for Biotechnology Information (http://www.ncbi.nlm.nih.gov/).

In preferred embodiments, a recombinant nucleic acid sequence may encode a polypeptide which is at least 55%, 65%, 70%, 75%, 80%, 85%, 90% and more preferably at least 95%, 97%, 99%, 99.5%, or 100% homologous to a relevant region of ND4, ND6, or ND1 (SEQ ID NO: 160, 161, or 162) over at least 20, preferably at least 30, for instance at least 40, 60, 100, 200, 300, 400 or more contiguous amino acids, or even over the entire sequence of the recombinant nucleic acid. The relevant region will be one which provides for functional activity of ND4, ND6, or ND1.

Alternatively, and preferably the recombinant nucleic acid sequence may encode a polypeptide having at least 70%, 75%, 80%, 85%, 90% and more preferably at least 95%, 97%, 99%, 99.5%, or 100% homologous to full-length ND4, ND6, or ND1 (SEQ ID NO: 160, 161, or 162) over its entire sequence. Typically the recombinant nucleic acid sequence differs from the relevant region of ND4, ND6, or ND1 (SEQ ID NO: 160, 161, or 162) by at least, or less than, 2, 5, 10, 20, 40, 50 or 60 mutations (each of which can be substitutions, insertions or deletions).

A recombinant nucleic acid ND4, ND6, or ND1 polypeptide may have a percentage identity with a particular region of SEQ ID NO: 160, 161, or 162 which is the same as any of the specific percentage homology values (i.e. it may have at least 70%, 80% or 90% and more preferably at least 95%, 97%, 99% identity) across any of the lengths of sequence mentioned above.

Variants of ND4, ND6, or ND1 (SEQ ID NO: 160, 161, or 162) also include truncations. Any truncation may be used so long as the variant is still functional. Truncations will typically be made to remove sequences that are non-essential for the protein activity and/or do not affect conformation of the folded protein, in particular folding of the active site. Appropriate truncations can routinely be identified by systematic truncation of sequences of varying length from the N- or C-terminus. Preferred truncations are N-terminal and may remove all other sequences except for the catalytic domain.

Variants of ND4, ND6, or ND1 (SEQ ID NO: 160, 161, or 162) further include mutants which have one or more, for example, 2, 3, 4, 5 to 10, 10 to 20, 20 to 40 or more, amino acid insertions, substitutions or deletions with respect to a particular region of ND4, ND6, or ND1 (SEQ ID NO: 160, 161, or 162). Deletions and insertions are made preferably outside of the catalytic domain as described below. Substitutions are also typically made in regions that are non-essential for protease activity and/or do not affect conformation of the folded protein.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the amino acids.

Similarly, preferred variants of the polynucleotide sequence of ND4, ND6, or ND1 (SEQ ID NO: 6, 9, or 11) include polynucleotides having at least 70%, 75%, 80%, 85%, 90% and more preferably at least 95%, 96%, 97%, 98%, 99%, or 99.5% homologous to a relevant region of ND4, ND6, or ND1 (SEQ ID NO: 6, 9, or 11). Preferably the variant displays these levels of homology to full-length ND4, ND6, or ND1 (SEQ ID NO: 6, 9, or 11) over its entire sequence.

Mitochondrial targeting sequences (MTSs) and three prime untranslated regions (3'UTRs) can be used to target proteins or mRNA to the mitochondria. The charge, length, and structure of the MTS can be important for protein import into the mitochondria. Particular 3'UTRs may drive mRNA localization to the mitochondrial surface and thus facilitate cotranslational protein import into the mitochondria.

The polynucleotide sequence for a mitochondrial targeting sequence can encode a polypeptide selected from hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9 (see Table 1 for SEQ ID NO). In one example, the polynucleotide sequences, COX10 (SEQ ID NO: 1, 2, or 3) can encode the mitochondrial targeting sequence, MTS-COX10 (SEQ ID NO: 126). In another example, the polynucleotide sequences, COX8 (SEQ ID NO: 4) can encode the mitochondrial targeting sequence, MTS-COX8 (SEQ ID NO: 127). In another example, the polynucleotide sequences, OPA1 (SEQ ID NO: 5) can encode the mitochondrial targeting sequence, MTS-OPA1 (SEQ ID NO: 128).

The 3'UTR nucleic acid sequence can be selected from hsACO2 (SEQ ID NO: 111), hsATP5B (SEQ ID NO: 112), hsAK2 (SEQ ID NO: 113), hsALDH2 (SEQ ID NO: 114), hsCOX10 (SEQ ID NO: 115), hsUQCRFS1 (SEQ ID NO: 116), hsNDUFV1 (SEQ ID NO: 117), hsNDUFV2 (SEQ ID NO: 118), hsSOD2 (SEQ ID NO: 119), hsCOX6c (SEQ ID NO: 120), hsIRP1 (SEQ ID NO: 121), hsMRPS12 (SEQ ID NO: 122), hsATP5J2 (SEQ ID NO: 123), rnSOD2 (SEQ ID NO: 124), and hsOXA1L (SEQ ID NO: 125). The 3'UTR nucleic acid sequence can also be a variant having at least 70%, 75%, 80%, 85%, 90% and more preferably at least 95%, 96%, 97%, 98%, 99%, 99.5%, or 100% homologous to any 3'UTR nucleic acid sequence listed here. For example, the 3'UTR nucleic acid sequence can be SEQ ID NO: 13 or 14.

Also disclosed herein are recombinant nucleic acid sequences comprising a mitochondrial targeting sequence, a mitochondrial protein coding sequence, and a 3'UTR nucleic acid sequence. For example, the recombinant nucleic acid sequence can be selected from SEQ ID NO: 15-84. The recombinant nucleic acid sequence can also be a variant having at least 70%, 75%, 80%, 85%, 90% and more preferably at least 95%, 96%, 97%, 98%, 99%, 99.5%, or 100% homologous to any recombinant nucleic acid sequence listed here.

Promoters and Regulatory Sequences

The vector of the invention also includes elements allowing for the expression of the disclosed transgene in vitro or in vivo. Thus, the vector typically comprises a promoter sequence operably linked to the polynucleotide sequence encoding the ND4, ND6, or ND1 transgene or a variant thereof.

Any suitable promoter may be used. The promoter sequence may be constitutively active i.e. operational in any host cell background, or alternatively may be active only in a specific host cell environment, thus allowing for targeted expression of the transgene in a particular cell type. The promoter may show inducible expression in response to presence of another factor, for example a factor present in a host cell. In any event, where the vector is administered for therapy, the promoter must be functional in a retinal cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters for the ND4, ND6, or ND1 transgene include the chicken beta-actin (CBA) promoter, optionally in combination with a cytomegalovirus (CME) enhancer element. In some cases, the preferred promoters for the ND4, ND6, or ND1 transgene comprises the CAG promoter. A particularly preferred promoter is a hybrid CBA/CAG promoter, for example the promoter used in the rAVE expression cassette. Examples of promoters based on human sequences that would induce retina specific gene expression include rhodospin kinase for rods and cones (Allocca et al., 2007, J Viol 81:11372-80), PR2.1 for cones only (Mancuso et al. 2009, Nature) and/or RPE65 for the retinal pigment epithelium (Bainbridge et al., 2008, N Eng J Med).

The vector of the invention may also comprise one or more additional regulatory sequences with may act pre- or post-transcriptionally. The regulatory sequence may be part of the native ND4, ND6, or ND1 gene locus or may be a heterologous regulatory sequence. The vector of the invention may comprise portions of the 5'UTR or 3'UTR from the native ND4, ND6, or ND1 transcript.

Regulatory sequences are any sequences which facilitate expression of the transgene i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal. In the context of the vector of the invention such regulatory sequences will be cis-acting. However, the invention also encompasses the use of trans-acting regulatory sequences located on additional genetic constructs.

A preferred postregulatory element for use in a vector of the invention is the woodchuck hepatitis postregulatory element (WPRE) or a variant thereof. Another regulatory sequence which may be used in a vector of the present invention is a scaffold-attachment region (SAR). Additional regulatory sequences may be selected by the skilled person on the basis of their common general knowledge.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a polynucleotide sequence encoding ND4, ND6, or ND1 or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins. This packaged viral vector typically comprises one or more AAV2 ITRs.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

In these aspects, the invention provides a method for production of a vector of the invention. The method comprises providing a vector which comprises an adeno-associated virus (AAV) genome or a derivative thereof and a polynucleotide sequence encoding ND4, ND6, or ND1 or a variant thereof in a host cell, and providing means for replication and assembly of the vector into an AAV viral particle. Preferably, the method comprises providing a vector comprising a derivative of an AAV genome and a polynucleotide sequence encoding ND4, ND6, or ND1 or a variant thereof, together with one or more additional genetic constructs encoding AAV and/or helper virus functions. Typically, the derivative of an AAV genome comprises at least one ITR. Optionally, the method further comprises a step of purifying the assembled viral particles. Additionally, the method may comprise a step of formulating the viral particles for therapeutic use.

Methods of Therapy and Medical Uses

As discussed above, the present inventors have surprisingly demonstrated that a vector of the invention may be used to address the cellular dysfunction underlying LHON. In particular, they have shown that use of the vector can correct the defect associated with LHON. This provides a means whereby the degenerative process of the disease can be treated, arrested, palliated or prevented.

The invention therefore provides a method of treating or preventing LHON in a patient in need thereof, comprising administering a therapeutically effective amount of a vector of the invention to the patient by direct retinal, subretinal or intravitreal injection. Accordingly, LHON is thereby treated or prevented in the patient.

In a related aspect, the invention provides for use of a vector of the invention in a method of treating or preventing LHON by administering said vector to a patient by direct retinal, subretinal or intravitreal injection. Additionally, the invention provides the use of a vector of the invention in the manufacture of a medicament for treating or preventing LHON by direct retinal, subretinal or intravitreal injection.

In all these embodiments, the vector of the invention may be administered in order to prevent the onset of one or more symptoms of LHON. The patient may be asymptomatic. The subject may have a predisposition to the disease. The method or use may comprise a step of identifying whether or not a subject is at risk of developing, or has, LHON. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease. Such an amount may also arrest, slow or reverse some loss of peripheral vision associated with LHON. Such an amount may also arrest, slow or reverse onset of LHON.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

The invention also provides a method of monitoring treatment or prevention of LHON in a patient comprising measuring activity ex vivo in retinal cells obtained from said patient following administration of the AAV vector of the invention by direct retinal, subretinal or intravitreal injection. This method can allow for determination of the efficacy of treatment.

Pharmaceutical Compositions

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Samples

Samples that are suitable for use in the methods described herein can be nucleic acid samples from a subject. A "nucleic acid sample" as used herein can include RNA or DNA, or a combination thereof. In another embodiment, a "polypeptide sample" (e.g., peptides or proteins, or fragments therefrom) can be used to ascertain information that an amino acid change has occurred, which is the result of a genetic variant. Nucleic acids and polypeptides can be extracted from one or more samples including but not limited to, blood, saliva, urine, mucosal scrapings of the lining of the mouth, expectorant, serum, tears, skin, tissue, or hair. A nucleic acid sample can be assayed for nucleic acid information. "Nucleic acid information," as used herein, includes a nucleic acid sequence itself, the presence/absence of genetic variation in the nucleic acid sequence, a physical property which varies depending on the nucleic acid sequence (e.g., Tm), and the amount of the nucleic acid (e.g., number of mRNA copies). A "nucleic acid" means any one of DNA, RNA, DNA including artificial nucleotides, or RNA including artificial nucleotides. As used herein, a "purified nucleic acid" includes cDNAs, fragments of genomic nucleic acids, nucleic acids produced using the polymerase chain reaction (PCR), nucleic acids formed by restriction enzyme treatment of genomic nucleic acids, recombinant nucleic acids, and chemically synthesized nucleic acid molecules. A "recombinant" nucleic acid molecule includes a nucleic acid molecule made by an artificial combination of two otherwise separated segments of sequence, e.g., by chemical synthesis or by the manipulation of isolated segments of nucleic acids by genetic engineering techniques. As used herein, a "polypeptide" includes proteins, fragments of proteins, and peptides, whether isolated from natural sources, produced by recombinant techniques, or chemically synthesized. A polypeptide may have one or more modifications, such as a post-translational modification (e.g., glycosylation, phosphorylation, etc.) or any other modification (e.g., pegylation, etc.). The polypeptide may contain one or more non-naturally-occurring amino acids (e.g., such as an amino acid with a side chain modification).

In some embodiments, the nucleic acid sample can comprise cells or tissue, for example, cell lines. Exemplary cell types from which nucleic acids can be obtained using the methods described herein include, but are not limited to, the following: a blood cell such as a B lymphocyte, T lymphocyte, leukocyte, erythrocyte, macrophage, or neutrophil; a muscle cell such as a skeletal cell, smooth muscle cell or cardiac muscle cell; a germ cell, such as a sperm or egg; an epithelial cell; a connective tissue cell, such as an adipocyte, chondrocyte; fibroblast or osteoblast; a neuron; an astrocyte; a stromal cell; an organ specific cell, such as a kidney cell, pancreatic cell, liver cell, or a keratinocyte; a stem cell; or any cell that develops therefrom. A cell from which nucleic acids can be obtained can be a blood cell or a particular type of blood cell including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Generally, any type of stem cell can be used including, without limitation, an embryonic stem cell, adult stem cell, or pluripotent stem cell.

In some embodiments, a nucleic acid sample can be processed for RNA or DNA isolation, for example, RNA or DNA in a cell or tissue sample can be separated from other components of the nucleic acid sample. Cells can be harvested from a nucleic acid sample using standard techniques, for example, by centrifuging a cell sample and resuspending the pelleted cells, for example, in a buffered solution, for example, phosphate-buffered saline (PBS). In some embodiments, after centrifuging the cell suspension to obtain a cell pellet, the cells can be lysed to extract DNA. In some embodiments, the nucleic acid sample can be concentrated and/or purified to isolate DNA. All nucleic acid samples obtained from a subject, including those subjected to any sort of further processing, are considered to be obtained from the subject. In some embodiments, standard techniques and kits known in the art can be used to extract RNA or DNA from a nucleic acid sample, including, for example, phenol extraction, a QIAAMP® Tissue Kit (Qiagen, Chatsworth, Calif.), a WIZARD® Genomic DNA purification kit (Promega), or a Qiagen Autopure method using Puregene chemistry, which can enable purification of highly stable DNA well-suited for archiving.

In some embodiments, determining the identity of an allele or determining copy number can, but need not, include obtaining a nucleic acid sample comprising RNA and/or DNA from a subject, and/or assessing the identity, copy number, presence or absence of one or more genetic variations and their chromosomal locations within the genomic DNA (i.e. subject's genome) derived from the nucleic acid sample.

The individual or organization that performs the determination need not actually carry out the physical analysis of a nucleic acid sample from a subject. In some embodiments, the methods can include using information obtained by analysis of the nucleic acid sample by a third party. In some embodiments, the methods can include steps that occur at more than one site. For example, a nucleic acid sample can be obtained from a subject at a first site, such as at a health care provider or at the subject's home in the case of a self-testing kit. The nucleic acid sample can be analyzed at the same or a second site, for example, at a laboratory or other testing facility.

Nucleic Acids

The nucleic acids and polypeptides described herein can be used in methods and kits of the present disclosure. In some embodiments, aptamers that specifically bind the nucleic acids and polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example a translated gene, or non-coding, for example a regulatory region, or any fragments, derivatives, mimetics or complements thereof. In some embodiments, nucleic acids can comprise oligonucleotides, nucleotides, polynucleotides, nucleic acid sequences, genomic sequences, complementary DNA (cDNA), antisense nucleic acids, DNA regions, probes, primers, genes, regulatory regions, introns, exons, open-reading frames, binding sites, target nucleic acids and allele-specific nucleic acids.

A "probe," as used herein, includes a nucleic acid fragment for examining a nucleic acid in a specimen using the hybridization reaction based on the complementarity of nucleic acid.

A "hybrid" as used herein, includes a double strand formed between any one of the abovementioned nucleic acid, within the same type, or across different types, including DNA-DNA, DNA-RNA, RNA-RNA or the like.

"Isolated" nucleic acids, as used herein, are separated from nucleic acids that normally flank the gene or nucleotide sequence (as in genomic sequences) and/or has been completely or partially purified from other transcribed sequences (e.g., as in an RNA library). For example, isolated nucleic acids of the disclosure can be substantially isolated with respect to the complex cellular milieu in which it naturally occurs, or culture medium when produced by recombinant techniques, or chemical precursors or other chemicals when chemically synthesized. In some instances, the isolated material can form part of a composition, for example, a crude extract containing other substances, buffer system or reagent mix. In some embodiments, the material can be purified to essential homogeneity using methods known in the art, for example, by polyacrylamide gel electrophoresis (PAGE) or column chromatography (e.g., HPLC). With regard to genomic DNA (gDNA), the term "isolated" also can refer to nucleic acids that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the gDNA of the cell from which the nucleic acid molecule is derived.

Nucleic acids can be fused to other coding or regulatory sequences can be considered isolated. For example, recombinant DNA contained in a vector is included in the definition of "isolated" as used herein. In some embodiments, isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein Such nucleic acid sequences can be detected and/or isolated by allele- or sequence-specific hybridization (e.g., under high stringency conditions). Stringency conditions and methods for nucleic acid hybridizations are well known to the skilled person (see, e.g., Current Protocols in Molecular Biology, Ausubel, F. et al., John Wiley & Sons, (1998), and Kraus, M. and Aaronson, S., Methods Enzymol., 200:546-556 (1991), the entire teachings of which are incorporated by reference herein.

Calculations of "identity" or "percent identity" between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e. % identity=# of identical positions/total # of positions×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

"Probes" or "primers" can be oligonucleotides that hybridize in a base-specific manner to a complementary strand of a nucleic acid molecule. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the complements thereof. In some embodiments, the probe or primer can be at least 70% identical, at least 80% identical, at least 85% identical, at least 90% identical, or at least 95% identical, to the contiguous nucleotide sequence or to the complement of the contiguous nucleotide sequence.

In some embodiments, a nucleic acid probe can be an oligonucleotide capable of hybridizing with a complementary region of a gene associated with a condition (e.g., LHON) containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. In some embodiments, DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained fallowing in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In some embodiments, nucleic acid can comprise one or more polymorphisms, variations, or mutations, for example, single nucleotide polymorphisms (SNPs), single nucleotide variations (SNVs), copy number variations (CNVs), for example, insertions, deletions, inversions, and translocations. In some embodiments, nucleic acids can comprise analogs, for example, phosphorothioates, phosphoramidates, methyl phosphonate, chiralmethyl phosphonates, 2-0-methyl ribonucleotides, or modified nucleic acids, for example, modified backbone residues or linkages, or nucleic acids combined with carbohydrates, lipids, polypeptide or other materials, or peptide nucleic acids (PNAs), for example, chromatin, ribosomes, and transcriptosomes. In some embodiments nucleic acids can comprise nucleic acids in various structures, for example, A DNA, B DNA, Z-form DNA, siRNA, tRNA, and ribozymes. In some embodiments, the nucleic acid may be naturally or non-naturally polymorphic, for example, having one or more sequence differences, for example, additions, deletions and/or substitutions, as compared to a reference sequence. In some embodiments, a reference sequence can be based on publicly available information, for example, the U.C. Santa Cruz Human Genome Browser Gateway (genome.ucsc.edu/cgi-bin/hgGateway) or the NCBI website (www.ncbi.nlm.nih.gov). In some embodiments, a reference sequence can be determined by a practitioner of the present disclosure using methods well known in the art, for example, by sequencing a reference nucleic acid.

In some embodiments, a probe can hybridize to an allele, SNP, SNV, or CNV as described herein. In some embodiments, the probe can bind to another marker sequence associated with LHON as described herein.

One of skill in the art would know how to design a probe so that sequence specific hybridization can occur only if a particular allele is present in a genomic sequence from a test nucleic acid sample. The disclosure can also be reduced to practice using any convenient genotyping method, including commercially available technologies and methods for genotyping particular genetic variations Control probes can also be used, for example, a probe that binds a less variable sequence, for example, a repetitive DNA associated with a centromere of a chromosome, can be used as a control. In some embodiments, probes can be obtained from commercial sources. In some embodiments, probes can be synthesized, for example, chemically or in vitro, or made from chromosomal or genomic DNA through standard techniques. In some embodiments sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as 32P or 3H, a fluorescent label, such as FITC, a chromophore label, an affinity-ligand label, an enzyme label, such as alkaline phosphatase, horseradish peroxidase, or 12 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule. A nucleotide can be directly incorporated into a probe with standard techniques, for example, nick translation, random priming, and PCR labeling. A "signal," as used herein, include a signal suitably detectable and measurable by appropriate means, including fluorescence, radioactivity, chemiluminescence, and the like.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14C, 123I, 124I, 125I, Tc99m, 32P, 33P, 35S or 3H.

Other labels can also be used in the methods of the present disclosure, for example, backbone labels. Backbone labels comprise nucleic acid stains that bind nucleic acids in a sequence independent manner. Non-limiting examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

In some embodiments, fluorophores of different colors can be chosen, for example, 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, TRITC, rhodamine, tetramethylrhodamine, R-phycoerythrin, Cy-3, Cy-5, Cy-7, Texas Red, Phar-Red, allophycocyanin (APC), and CASCADE™ blue acetylazide, such that each probe in or not in a set can be distinctly visualized. In some embodiments, fluorescently labeled probes can be viewed with a fluorescence microscope and an appropriate filter for each fluorophore, or by using dual or triple band-pass filter sets to observe multiple fluorophores. In some embodiments, techniques such as flow cytometry can be used to examine the hybridization pattern of the probes.

In other embodiments, the probes can be indirectly labeled, for example, with biotin or digoxygenin, or labeled with radioactive isotopes such as 32P and/or 3H. As a non-limiting example, a probe indirectly labeled with biotin can be detected by avidin conjugated to a detectable marker. For example, avidin can be conjugated to an enzymatic marker such as alkaline phosphatase or horseradish peroxidase. In some embodiments, enzymatic markers can be detected using colorimetric reactions using a substrate and/or a catalyst for the enzyme. In some embodiments, catalysts for alkaline phosphatase can be used, for example, 5-bromo-4-chloro-3-indolylphosphate and nitro blue tetrazolium. In some embodiments, a catalyst can be used for horseradish peroxidase, for example, diaminobenzoate.

Formulations, Routes of Administration, and Effective Doses

Yet another aspect of the present disclosure relates to formulations, routes of administration and effective doses for pharmaceutical compositions comprising an agent or combination of agents of the instant disclosure. Such pharmaceutical compositions can be used to treat a condition (e.g., LHON) as described above.

Compounds of the disclosure can be administered as pharmaceutical formulations including those suitable for oral (including buccal and sub-lingual), rectal, nasal, topical, transdermal patch, pulmonary, vaginal, suppository, or parenteral (including intraocular, intravitreal, intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, polypeptides, amino acids, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation can contain at least one preservative. General methodology on pharmaceutical dosage forms is found in Ansel et al., Pharmaceutical Dosage Forms and Drug Delivery Systems (Lippencott, Williams, & Wilkins, Baltimore Md. (1999)). It can be recognized that, while any suitable carrier known to those of ordinary skill in the art can be employed to administer the compositions of this disclosure, the type of carrier can vary depending on the mode of administration.

Compounds can also be encapsulated within liposomes using well-known technology. Biodegradable microspheres can also be employed as carriers for the pharmaceutical compositions of this disclosure. Suitable biodegradable microspheres are disclosed, for example, in U.S. Pat. Nos. 4,897,268, 5,075,109, 5,928,647, 5,811,128, 5,820,883, 5,853,763, 5,814,344 and 5,942,252.

The compound can be administered in liposomes or microspheres (or microparticles). Methods for preparing liposomes and microspheres for administration to a subject are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, and along with surfactants if required, and the material dialyzed or sonicated, as necessary. A review of known methods is provided by G. Gregoriadis, Chapter 14, “Liposomes,” Drug Carriers in Biology and Medicine, pp. 2.sup.87-341 (Academic Press, 1979).

Microspheres formed of polymers or polypeptides are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intraocular or intravitreal injection.

The compounds of the disclosure can be formulated as a sterile solution or suspension, in suitable vehicles. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington “The Science and Practice of Pharmacy” (20th Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present disclosure, and which are not biologically or otherwise undesirable.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p toluenesulfonic acid, acetic acid, fumaric acid, succinic acid, lactic acid, mandelic acid, malic acid, citric acid, tartaric acid or maleic acid. In addition, if the agent(s) contain a carboxyl group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present disclosure, and which are not biologically or otherwise undesirable. Typical esters include ethyl, methyl, isobutyl, ethylene glycol, and the like. Typical amides include unsubstituted amides, alkyl amides, dialkyl amides, and the like.

In some embodiments, an agent can be administered in combination with one or more other compounds, forms, and/or agents, e.g., as described above. Pharmaceutical compositions with one or more other active agents can be formulated to comprise certain molar ratios. For example, molar ratios of about 99:1 to about 1:99 of a first active agent to the other active agent can be used. In some subset of the embodiments, the range of molar ratios of a first active agent: other active agents are selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a first active: other active agents can be about 1:9, and in some embodiments can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant disclosure can depend, at least in part, on the condition being treated.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present disclosure can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present disclosure, or pharmaceutically acceptable salts, esters, or amides thereof, can be delivered to a subject using a number of routes or modes of administration, including oral, buccal, topical, rectal, transdermal, transmucosal, subcutaneous, intravenous, intraocular, intravitreal, and intramuscular applications, as well as by inhalation.

In some embodiments, oils or non-aqueous solvents can be used to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this disclosure can also be integrated into foodstuffs, e.g., cream cheese, butter, salad dressing, or ice cream to facilitate solubilization, administration, and/or compliance in certain subject populations.

The compounds of the disclosure can be formulated for parenteral administration (e.g., by injection, for example, intraocular or intravitreal injection) and can be presented in unit dose form in ampoules, pre-filled syringes, small volume infusion or in multi-dose containers with an added preservative. The compositions can take such forms as suspensions, solutions, or emulsions in oily or aqueous vehicles, for example, solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In some embodiments, eye disorders can be effectively treated with ophthalmic solutions, suspensions, ointments or inserts comprising an agent or combination of agents of the present disclosure. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the disclosure can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g., from 0.001% to 0.008%, preferably about 0.005% by weight. It has been found that a concentration of benzalkonium chloride of 0.005% can be sufficient to preserve the compositions of the present disclosure from microbial attack.

In some embodiments, the agents of the present disclosure are delivered in soluble rather than suspension form, which allows for more rapid and quantitative absorption to the sites of action. In general, formulations such as jellies, creams, lotions, suppositories and ointments can provide an area with more extended exposure to the agents of the present disclosure, while formulations in solution, e.g., sprays, provide more immediate, short-term exposure.

It is envisioned additionally, that the compounds of the disclosure can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, can be utilized in a formulation suitable for intra ocular implantation or injection for sustained release administration, as well any suitable biodegradable and biocompatible polymer can be used.

EXAMPLES

The following exemplary embodiments further describe the present invention. It should be understood that these examples are only intended to illustrate the invention, but not to limit the scope of the present invention. Unless otherwise indicated, the methods and conditions disclosed in e.g., sambrook et al, molecular cloning: a laboratory manual (New York: cold spring harbor laboratory press, 1989) or the conditions recommended by the manufacturer can be used in the examples below.

Example 1—ND4 Plasmid and Virus Preparation 1.1 Plasmid Preparation

The nucleotide sequence for human ND4 (SEQ ID NO: 6) was obtained based on US National Center for Biotechnology Information reference sequence yp_003024035.1. The sequences for the non-optimized mitochondrial targeting sequence COX10 is SEQ ID NO: 1. The optimized sequences for the mitochondrial targeting sequence COX10 (opt_COX10, SEQ ID NO: 2) and the coding sequence of human ND4 (opt_ND4, SEQ ID NO: 7) were designed to improve the transcription efficiency and the translation efficiency. The optimized COX10-ND4 sequence, which is about 75.89% homology to the non-optimized COX10-ND4, was followed by a three prime untranslated region (i.e., 3'UTR, SEQ ID NO: 13) to a recombinant nucleic acid, opt_COX10-opt_ND4-3'UTR (as shown in SEQ ID NO: 31).

The synthesized recombinant nucleic acid, opt_COX10-opt_ND4-3'UTR, was incorporated into an adeno-associated virus (AAV) vector by PCR amplification (FIG. 1). The opt_COX10-opt_ND4-3'UTR was cut by the EcoRI/SalI restriction enzymes to form cohesive ends, and then embedded into an AAV vector with EcoRI/SalI restriction sites, such as the pSNaV vector, to generate the pSNaV/rAAV2/2-ND4 plasmid (i.e., the pAAV2-optimized ND4 plasmid). The pAAV2-opt_ND4 plasmid was compared to the non-optimized pAAV2-ND4 plasmid.

The recon screening and identifying steps were similar to the CN102634527B: the plasmid was cultured at 37° C. in a LB plate. Blue colonies and white colonies were appeared, where white colonies were recombinant clones. The white colonies were picked, added to 100 mg/L ampicillin-containing LB culture medium, cultured at 37° C., 200 rpm for 8 hours and then the plasmid were extracted from the cultured bacterial medium based on the Biomiga plasmid extraction protocol. The identification of the plasmid was confirmed using the EcoRI/SalI restriction enzymes.

1.2 Cell Transfection

One day before transfection, HEK293 cells were inoculated to 225 $cm^2$ cell culture bottle: at the inoculation density of $3.0\times10^7$ cells/ml, the culture medium was the Dulbecco's Modified Eagle Medium (DMEM) with 10% bovine serum, at 37° C. in a 5% CO2 incubator overnight. The culture medium were replaced with fresh DMEM with 10% bovine serum on the day of transfection.

After the cells grow to 80-90%, discard the culture medium and transfect the cells with the pAAV2-ND4 and pAAV2-opt_ND4 plasmid, using the PlasmidTrans (VGTC) transfection kit. The detailed transfection protocol was described in CN102634527B example 1. The cells were collected 48 h after the transfection.

1.3 Collection, Concentration and Purification of the Recombinant Adeno-Associated Virus Virus collection: 1) dry ice ethanol bath (or liquid nitrogen) and a 37° C. water bath were prepared; 2) the transfected cells along with media were collected in a 15 ml centrifuge tube; 3) the cells were centrifuged for 3 minutes at 1000 rpm/min; the cells and supernatant were separated; the supernatant were stored separately; and the cells were re-suspended in 1 ml of PBS; 4) the cell suspension were transferred between the dry ice-ethanol bath and 37° C. water bath repeatedly, freeze thawing for four times for 10 minutes each, slightly shaking after each thawing.

Virus concentration: 1) cell debris were removed with 10,000 g centrifugation; the centrifugal supernatant was transferred to a new centrifuge tube; 2) impurities were removed by filtering with a 0.45 μm filter; 3) each ½ volume of 1M NaCl and 10% PEG 8000 solution were added in the sample, uniformly mixed, and stored at 4° C. overnight; 4) supernatant was discarded after 12,000 rpm centrifugation for 2 h; after the virus precipitate was completely dissolving in an appropriate amount of PBS solution, sterilizing the sample with a 0.22 μm filter; 5) adding benzonase nuclease was added to remove residual plasmid DNA (final concentration at 50 U/ml). The tube was inverted several times to mix thoroughly and then incubated at 37° C. for 30 minutes; 6) the sample was filtered with a 0.45 μm filtration head; the filtrate is the concentrated rAAV2 virus.

Virus purification: 1) CsCl was added to the concentrated virus solution until a density of 1.41 g/ml (refraction index at 1.372); 2) the sample was added to in the ultracentrifuge tube and filled the tube with pre-prepared 1.41 g/ml CsCl solution; 3) centrifuged at 175,000 g for 24 hours to form a density gradient. Sequential collection of different densities of the sample was performed. The enriched rAAV2 particles were collected; 4) repeating the process one more time. The virus was loaded to a 100 kDa dialysis bag and dialyzed/desalted at 4° C. overnight. The concentrated and purified recombinant adeno-associated virus were rAAV2-ND4 and rAAV2-optimized ND4.

Similarly, other mitochondrial targeting sequences (MTS), such as OPA1 (SEQ ID NO: 5) can be used to replace COX10 in the above example and create AAV with recombinant plasmids.

Example 2—Intravitreal Injection of rAAV2 in Rabbit Eyes

Twelve rabbits were divided into 2 group: rAAV2-ND4 and rAAV2-optimized ND4. Virus solution ($1\times10^{10}$ vg/0.05 mL) was punctured into the vitreous cavity from 3 mm outside the corneal limbus at the pars plana. After the intravitreal injection, the eyes were examined using slit lamp exam and fundus photography inspection. Injection for 30 days. RT-PCR detection and immunoblotting were carried out in each group respectively.

Example 3—Real-Time PCR for the Expression of ND4

The RNAs from the transfected rAAV2-ND4 and rAAV2-optimized ND4 rabbit optic nerve cells were extracted using the TRIZOL total RNA extraction kit. cDNA templates were synthesized by reverse transcription of the extracted RNA.

The NCBI conserved structural domain analysis software were used to analyze the conservative structure of ND4, ensuring that the designed primers amplified fragments were located at non-conserved region; then primers were designed according to the fluorescent quantitative PCR primer design principle:

β-actin-S: CGAGATCGTGCGGGACAT (SEQ ID NO: 85);
β-actin-A: CAGGAAGGAGGGCTGGAAC (SEQ ID NO: 86);
ND4-S: CTGCCTACGACAAACAGAC (SEQ ID NO: 87);
ND4-A: AGTGCGTTCGTAGTTTGAG (SEQ ID NO: 88);

The fluorescent quantitative PCR reaction and protocol: fluorescence quantitative PCR were measured in a real-time PCR detection system. In a 0.2 ml PCR reaction tube, SYBR green mix 12.5 μl, ddH2O 8 μl, 1 μl of each primer, and the cDNA sample 2.5 μl, were added to an overall volume of 25 μl. Each sample was used for amplification of the target gene and amplifying the reference gene β-actin, and each amplification were repeated three times. The common reagents were added together and then divided separately to minimize handling variation. The fluorescent quantitative PCR were carried out: pre-denaturation at 95° C. for 1 s, denaturation at 94° C. for 15 s, annealing at 55° C. for 15 sec, extension at 72° C. for 45 s. A total of 40 cycles of amplification reaction were performed and fluorescence signal acquisition was done at the extension phase of each cycle. After the reaction, a 94° C. to 55° C. melting curve analysis was done. By adopting a relative quantitative method research of gene expression level difference to beta-actin was used as an internal reference gene.

Figure 2:
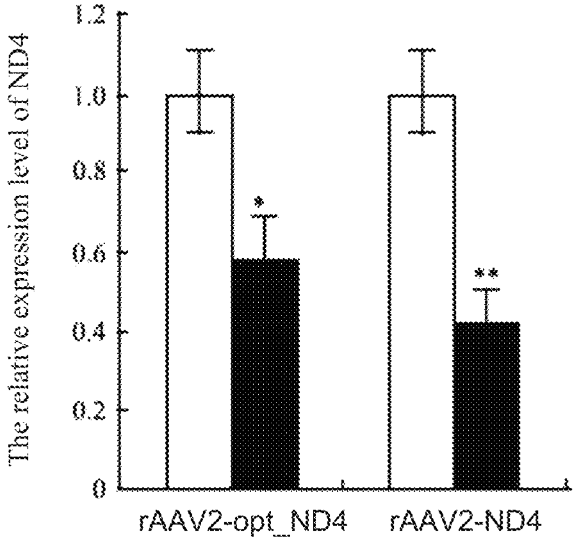
FIG. 2 shows the relative expression level comparison using qPCR between the rAAV2-opt_ND4 (left black column) and rAAV2-ND4 (right black column). β-actin is the internal reference gene (white column).

As shown in FIG. 2, the relative expression level (mRNA level) of the rAAV2-ND4 and rAAV2-optimized ND4 were $0.42\pm0.23$ and $0.57\pm0.62$, respectively ($p<0.05$, FIG. 2). The results unexpectedly show that the optimized ND4 (opt_ND4, SEQ ID NO: 7) coding nucleic acid sequence and the corresponding recombinant nucleic acid (opt_COX10-opt_ND4-3'UTR, SEQ ID NO: 31) surprisingly increased the transcription efficiency, increasing the expression of the rAAV2-optimized ND4 by about 36%. The results showed that the transcription efficiency of the rAAV2-optimized ND4 is significantly higher.

Example 4—Immunoblotting Detection of ND4 Expression

The ND4 protein was purified from the rabbit nerve cells transfected by rAAV2-optimized ND4 and rAAV2-ND4, respectively. After a 10% polyacrylamide gel electrophoresis, and transferred to a polyvinylidene difluoride membrane (Bio-Rad, HER-hercules, CA, USA) for immune detection. β-actin was used as an internal reference gene. The film strip was observed on an automatic image analysis instrument (Li-Cor; Lincoln, Nebr., USA) and analyzed using the integrated optical density of the protein band with integral normalization method, so as to obtain the same sample corresponding optical density value. The statistical analysis software SPSS 19.0 was used for the data analysis.

Figure 3:
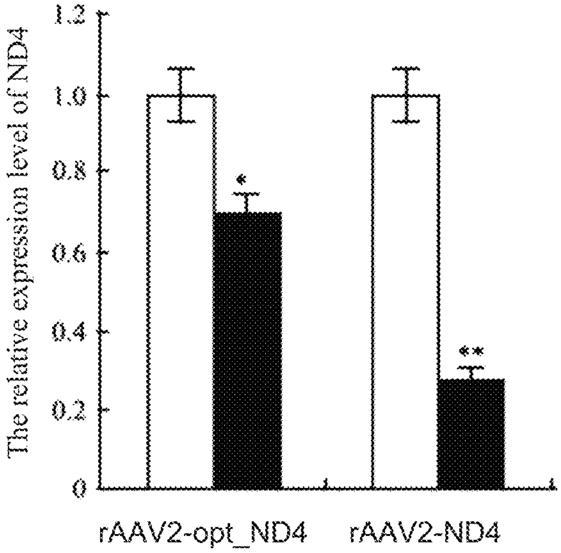
FIG. 3 shows the relative expression level comparison using immunoblotting between the rAAV2-opt_ND4 (left black column) and rAAV2-ND4 (right black column). β-actin is the internal reference gene (white column).

The results was shown in FIG. 3. The average relative protein expression level of ND4 for rAAV2-optimized ND4 (left black column) and rAAV2-ND4 was 0.32±0.11 and 0.68±0.20, respectively (p<0.01, FIG. 3). The results unexpectedly show that the optimized ND4 coding nucleic acid sequence (opt_ND4, SEQ ID NO: 7) and the corresponding recombinant nucleic acid (opt_COX10-opt_ND4-3'UTR, SEQ ID NO: 31) surprisingly increased the translation efficiency, increasing the expression of the rAAV2-optimized ND4 by about 112%. The results showed that the translation efficiency of the rAAV2-optimized ND4 is also significantly higher.

Example 5—Rabbits Intraocular Pressure and Eye-Ground Photography

Slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 4:
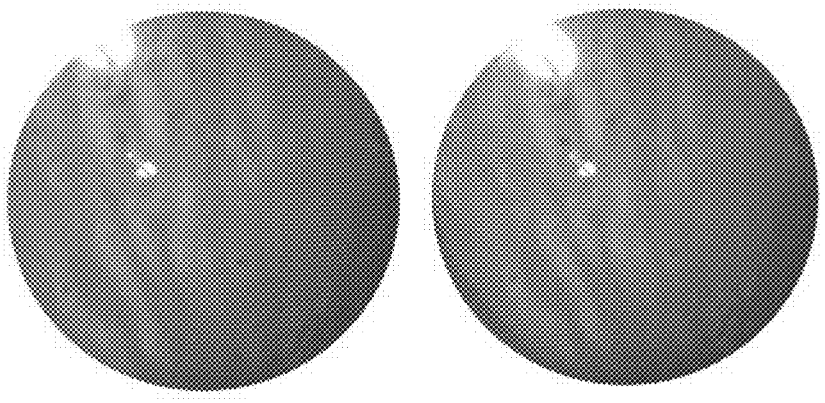
FIG. 4 shows the fundus photographic results for rabbits injected with rAAV2-opt_ND4 (right) and rAAV2-ND4 (left), respectively.

The fundus photographic results were shown in FIG. 4. No obvious damage or complication to the optic nerve and retinal vascular of the rabbits, indicating the standard intravitreal injection is safe without noticeable inflammation reaction or other complications.

Example 6—Human Clinical Trial

Two groups of patients were tested: 1) between 2011 and 2012, 9 patients received intravitreal injection of $1\times10^{10}$ vg/0.05 mL rAAV2-ND4 in a single eye, as a control group; and 2) between 2017 and January 2018, 20 patients received intravitreal injection of $1\times10^{10}$ vg/0.05 mL rAAV2-optimized ND4 in a single eye, as an experimental group. The results of the clinical trial were analyzed using the statistical analysis SPSS 19.0.

Figure 5:
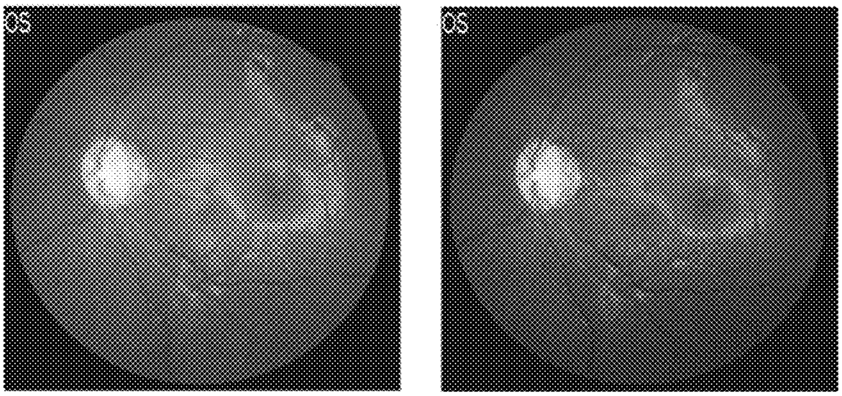
FIG. 5 shows the fundus photographic results for a patient before (left) and after (right) the injection with rAAV2-optimized ND4.

The comparison of the two groups is shown in Table 2. The fastest eyesight improving time was 1 month in the experimental group, which was significantly faster than the control group at 3 months (p<0.01); the optimal recovery of vision for the experimental group was 1.0, which was obviously higher than the control group at 0.8 (p<0.01); the average recovery of vision in the experimental group was 0.582±0.086, which was obviously higher than the control group at 0.344±0.062 (p<0.01). The fundus photographic results were shown in FIG. 5. No obvious damage or complication to the optic nerve and retinal vascular of the patients in the experimental and control groups, indicating the safety of the intravitreal injection of rAAV2-optimized ND4 and rAAV2-ND4.

TABLE 2

The comparison of rAAV2-optimized ND4 and rAAV2-ND4 in LHON gene therapy

| group | Patient number | Fastest eyesight improving time (month) | Number of patients with improved vision | optimal recovery of vision | average recovery of vision |
|---|---|---|---|---|---|
| control | 9 | 3 | 6 (67%) | 0.8 | 0.344 ± 0.062 |
| experimental | 20 | 1 | 15 (75%) | 1.0 | 0.582 ± 0.086 |
| P value | | <0.01 | <0.01 | <0.01 | <0.01 |

Example 7—OPA1 as the Mitochondrial Targeting Sequences

The COX10 and 3'UTR sequences in the recombinant nucleic acid (opt_COX10-opt_ND4-3'UTR, SEQ ID NO: 31) in examples 1-6 were replaced with another mitochondrial targeted sequence, OPA1 (SEQ ID NO: 5) and another 3'UTR sequence, 3'UTR* (SEQ ID NO: 14) respectively, to generate a new recombinant nucleic acid, OPA1-opt_ND4-3'UTR* (SEQ ID NO: 74).

Experimental methods were the same as examples 1-6, where the recombinant nucleic acid opt_COX10-opt_ND4-3'UTR (SEQ ID NO: 31) was replaced by OPA1-opt_ND4-3'UTR* (SEQ ID NO: 74). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 8—Optimized ND4 Sequence opt_ND4*

Similar experimental methods in examples 1-6 were followed using the nucleic acid, opt_COX10*-opt_ND4*-3'UTR (SEQ ID NO: 47). Follow the similar procedures as in example 1, virus tagged with a fluorescent protein, EGFP, was prepared as rAAV2-ND4-EGFP and rAAV2-opt_ND4*-EGFP.

Figure 6:
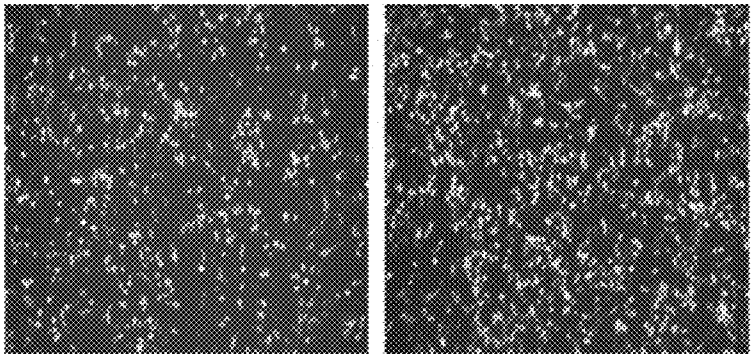
FIG. 6 shows EGFP expression levels of rAAV2-ND4 (left) and rAAV2-opt_ND4* (right).

The frozen 293T cell was resuscitated and allowed to grow in a T75 flask to about 90%. The cells were precipitated and resuspended in DMEM complete medium to a cell density of $5\times10^4$ cells/mL. The cells were resuspended. About 100 μl of the cell suspension (about 5000 cells) were added in each well of a 96 well plate. The cells were cultured and grown to 50% under 37° C. and 5% CO2. About 0.02 μl PBS was mixed with $2\times10^{10}$ vg/0.02 μl of the virus rAAV2-ND4-EGFP and rAAV2-opt_ND4*-EGFP, respectively. After 48 hours, fluorescence microscopy and RT-PCR detection and immunoblotting experiments were performed. As shown in FIG. 6, EGFP was successfully expressed, indicating that rAAV carrying the EGFP gene was successfully transfected in the 293T cells and rAAV2-ND4-EGFP and rAAV2-opt_ND4*-EGFP were successfully expressed.

Real-time PCR tests similar to example 3 was following using the following primers:

β-actin-S: CGAGATCGTGCGGGACAT (SEQ ID NO: 85);

β-actin-A: CAGGAAGGAGGGCTGGAAC (SEQ ID NO: 86);

ND4-S: GCCAACAGCAACTACGAGC (SEQ ID NO: 107);

ND4-A: TGATGTTGCTCCAGCTGAAG (SEQ ID NO: 108);

The results unexpectedly show that the optimized ND4* (opt_ND4, SEQ ID NO: 8) coding nucleic acid sequence and the corresponding recombinant nucleic acid (opt_COX10*-opt_ND4*-3'UTR, SEQ ID NO: 47) surprisingly increased the transcription efficiency, increasing the expression of the rAAV2-opt_ND4 by about 20%. The results showed that the transcription efficiency of the rAAV2-opt_ND4 is significantly higher.

Figure 7:
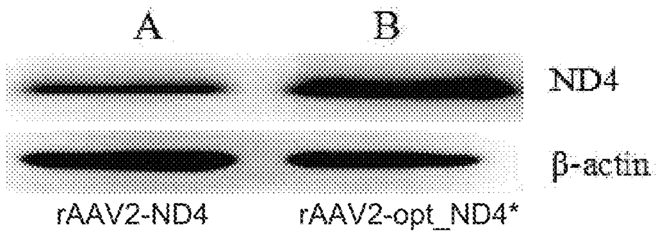
FIG. 7 shows the ND4 expression in 293T cells: rAAV2-ND4 (left) and rAAV2-opt_ND4* (right).
Figure 8:
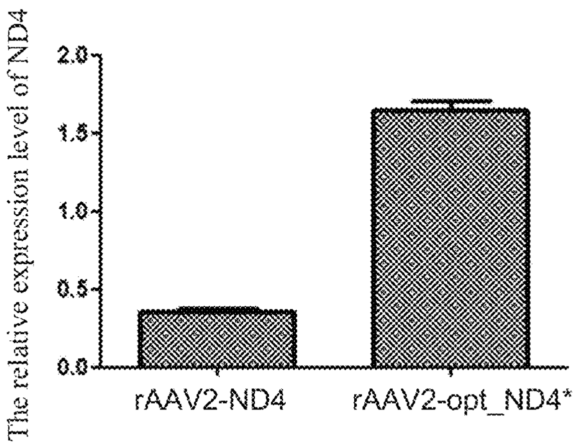
FIG. 8 shows the relative ND4 expression in 293T cells: rAAV2-ND4 (left) and rAAV2-opt_ND4* (right).

FIG. 7 shows the ND4 expression in 293T cells. The average expression of ND4 protein for rAAV2-ND4 is 0.36, while the average expression of ND4 protein for rAAV2-opt_ND4* is 1.65, which is about 4.6 times higher than the rAAV2-ND4 group ($p<0.01$) (see FIG. 8).

Figure 9:
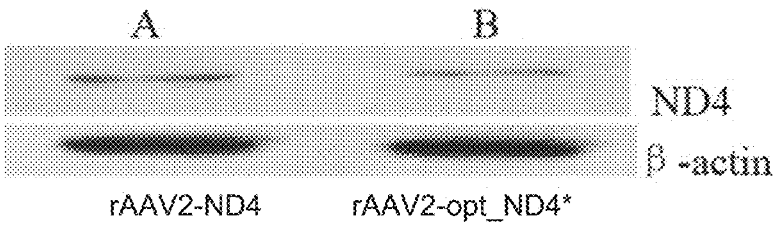
FIG. 9 shows the ND4 expression in rabbit optic nerve cells: rAAV2-ND4 (left) and rAAV2-opt_ND4* (right).
Figure 10:
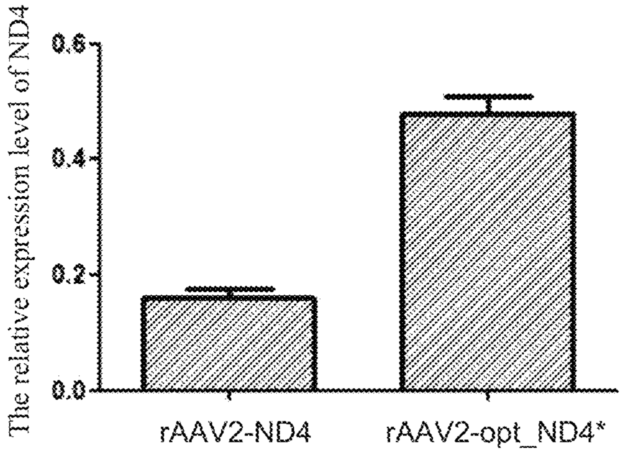
FIG. 10 shows the relative ND4 expression in rabbit optic nerve cells: rAAV2-ND4 (left) and rAAV2-opt_ND4* (right).

FIG. 9 shows the ND4 expression in rabbit optic nerve cells. The average expression of ND4 protein for rAAV2-ND4 is 0.16, while the average expression of ND4 protein for rAAV2-opt_ND4* is 0.48, which is about 3 times higher than the rAAV2-ND4 group ($p<0.01$) (see FIG. 10).

Similar to example 5, slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 11:
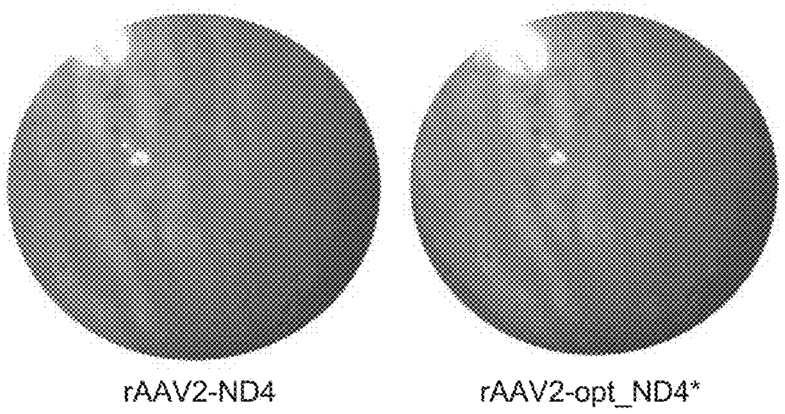
FIG. 11 shows the fundus photographic results for rAAV2-ND4 (left) and rAAV2-opt_ND4* (right).

The fundus photographic results for rAAV2-ND4 and rAAV2-opt_ND4* were shown in FIG. 11. No obvious damage or complication to the optic nerve and retinal vascular of the rabbits, indicating the standard intravitreal injection is safe without noticeable inflammation reaction or other complications.

Figure 12:
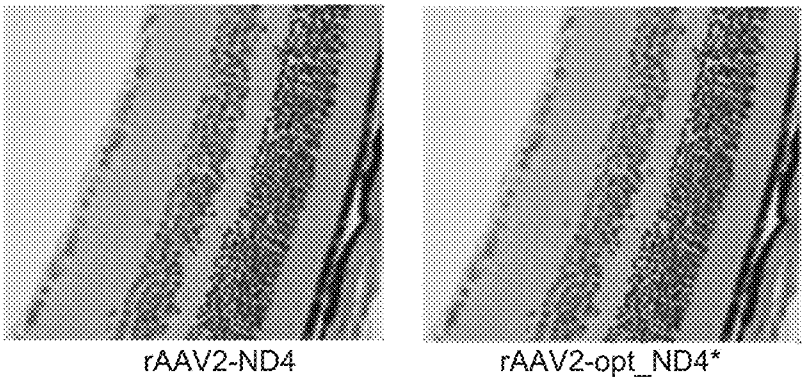
FIG. 12 shows the microscope inspection (HE staining) results for rAAV2-ND4 (left) and rAAV2-opt_ND4* (right).

Eye balls from both rabbit groups were removed after the slit lamp examination and intraocular pressure measurement. Eye balls were fixed, and dehydrated using paraffin. Tissues were pathologically sectioned along the direction of optic nerves. After further dehydration, the tissue sample was dyed using hematoxylin and eosin. The microscope inspection result is referred to FIG. 12. As shown in the HE staining results, the rabbit retinal ganglion fiber layer was not damaged and the number of ganglion cells was not reduced, indicating the intravitreal injection did not produce retinal toxicity or nerve damage, and can be used safely.

Experimental methods were the same as example 8, where the recombinant nucleic acid opt_COX10*-opt_ND4*-3'UTR (SEQ ID NO: 47) was replaced by OPA1-opt_ND4*-3'UTR* (SEQ ID NO: 76). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 9—ND6 Sequence

Similar experimental methods in examples 1-6 were followed using the nucleic acid, COX10-ND6-3'UTR (SEQ ID NO: 21), which is the combination (5' to 3') of COX10 (SEQ ID NO: 1), ND6 (SEQ ID NO: 9), and 3'UTR (SEQ ID NO: 13).

Figure 13:
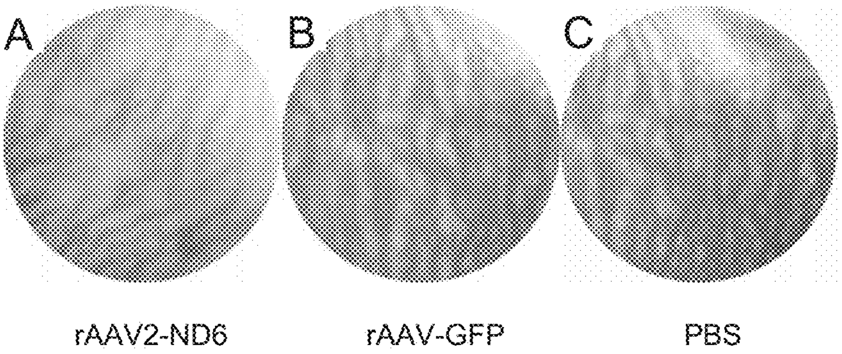
FIG. 13 shows the fundus photographic results for rabbits injected with rAAV2-ND6 (A), rAAV-GFP (B) and PBS, respectively.

The plasmid screening for COX10-ND6-3'UTR (SEQ ID NO: 21) used the following primers:

ND6-F: ATGATGTATGCTTTGTTTCTG (SEQ ID NO: 89),

ND6-R: CTAATTCCCCCGAGCAATCTC (SEQ ID NO: 90),

The transfected and screened virus rAAV2-ND6 had a viral titer of $2.0\times10^{11}$ vg/mL. Similar to example 5, slit lamp examination and intraocular pressure measurement was performed on three groups of rabbits (A: rAAV2-ND6; B: rAAV-GFP; C: PBS) at 1, 7, and 30 days after the surgery (FIG. 13). No obviously abnormality, conjunctival congestion, secretions, or endophthalmitis were observed and the intraocular pressure were not elevated in all the rabbits.

Real-time PCR tests similar to example 3 was following using the following primers:

β-actin-S: CGAGATCGTGCGGGACAT (SEQ ID NO: 85);

β-actin-A: CAGGAAGGAGGGCTGGAAC (SEQ ID NO: 86);

ND6-S: AGTGTGGGTTTAGTAATG (SEQ ID NO: 91);

ND4-A: TGCCTCAGGATACTCCTC (SEQ ID NO: 92);

The results show that the expression of ND6 for rAAV2-ND6 and control (PBS) was 0.59±0.06 and 0.41±0.03, respectively. The results showed that the transcription efficiency of the rAAV2-ND6 is higher than the control group ($p<0.01$).

Example 10—Optimized opt_ND6 Sequence

Similar experimental methods in examples 1-6 were followed using the nucleic acid, opt_COX10*-opt_ND6-3'UTR (SEQ ID NO: 51), which is the combination (5' to 3') of opt_COX10* (SEQ ID NO: 3), opt_ND6 (SEQ ID NO: 10), and 3'UTR (SEQ ID NO: 13).

Figure 14:
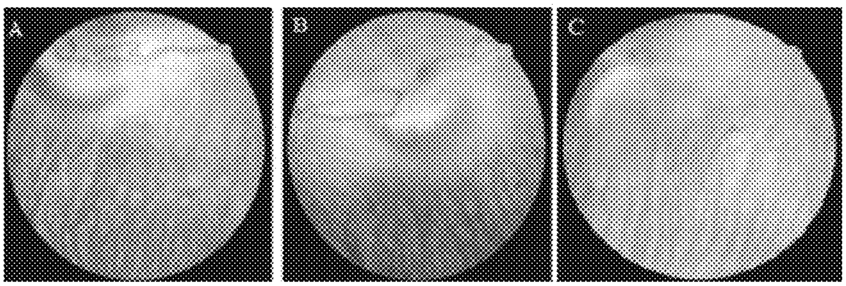
FIG. 14 shows the fundus photographic results for rabbits injected with rAAV2-opt_ND6 (A), rAAV2-ND6 (B), rAAV-EGFP (C), respectively.

Three groups of rabbits were injected: A: $10^{10}$ vg/50 μl of rAAV2-opt_ND6, B: $10^{10}$ vg/50 μl of rAAV2-ND6 (example 9), and C: $10^{10}$ vg/50 μl of rAAV2-EGFP. FIG. 14 shows the fundus photographic results for rabbits injected with rAAV2-opt_ND6 (A), rAAV2-ND6 (B), rAAV-EGFP (C), respectively. No obviously abnormality, conjunctival congestion, secretions, or endophthalmitis were observed and the intraocular pressure were not elevated in all the rabbits.

Figure 15:
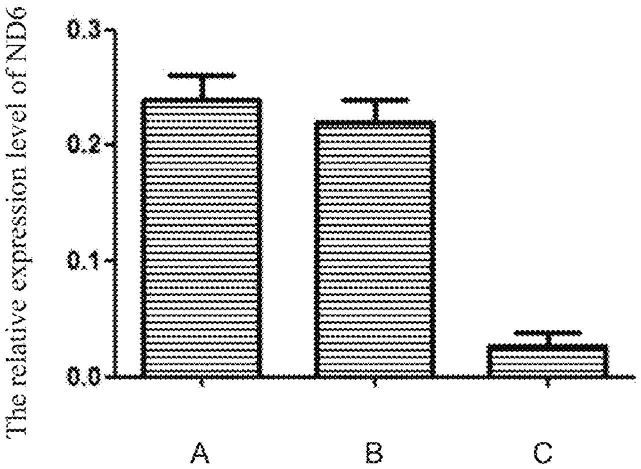
FIG. 15 shows the relative ND6 expression in rabbit optic nerve cells: rAAV2-opt_ND6 (A), rAAV2-ND6 (B), and rAAV-EGFP (C).
Figure 16:
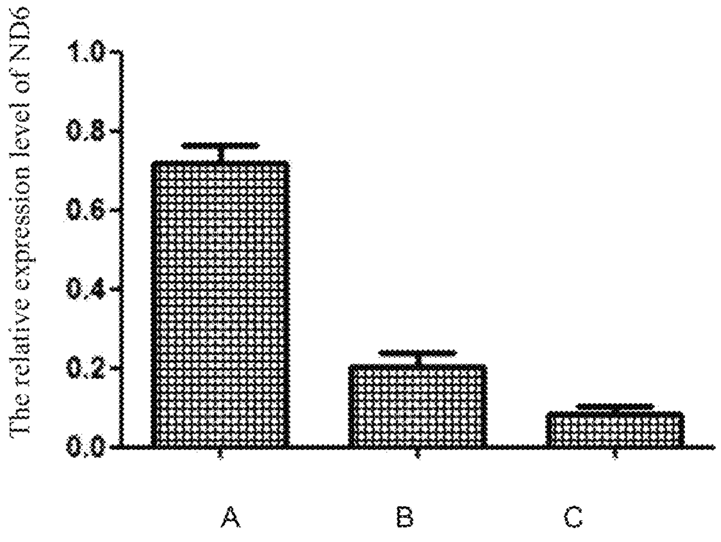
FIG. 16 shows the relative ND6 expression by western blot: rAAV2-opt_ND6 (A), rAAV2-ND6 (B), and rAAV-EGFP (C).

Real-time PCR tests similar to example 3 was following using the following primers:

β-actin-F: CTCCATCCTGGCCTCGCTGT (SEQ ID NO: 93);

β-actin-R: GCTGTCACCTTCACCGTTCC (SEQ ID NO: 94);

ND6-F: GGGTTTTCTTCTAAGCCTTCTCC (SEQ ID NO: 95);

ND6-R: CCATCATACTCTTTCACCCACAG (SEQ ID NO: 96);

opt_ND6-F: CGCCTGCTGACCGGCTGCGT (SEQ ID NO: 97);

opt_ND6-R: CCAGGCCTCGGGGTACTCCT (SEQ ID NO: 98);

As shown in FIG. 15, rAAV2-opt_ND6 (A) and rAAV2-ND6 (B) both had higher ($p<0.05$) relative ND6 expression levels than the control group (C). rAAV2-opt_ND6 (A) had a little higher relative ND6 expression levels than rAAV2-ND6 (B). As shown in the western blot in FIG. 16, rAAV2-opt_ND6 (A) had more than 3 times higher relative ND6 expression levels than rAAV2-ND6 (B).

Experimental methods were the same as example 8, where the recombinant nucleic acids, COX10-ND6-3'UTR (SEQ ID NO: 21) and opt_COX10*-opt_ND6-3'UTR (SEQ ID NO: 51), were replaced by OPA1-ND6-3'UTR (SEQ ID NO: 77) and OPA1-opt_ND6-3'UTR (SEQ ID NO: 79). It was found that, the optimized ND6 sequence has significantly improved transcription and translation efficiencies, expression levels, as well as higher efficacy and safety in treating LHON.

Example 11—ND1 and opt_ND1 Sequences

Similar experimental methods in examples 1-6 were followed using rAAV2-ND1, COX10-ND1-3'UTR (SEQ ID NO: 25), which is the combination (5' to 3') of COX10 (SEQ ID NO: 1), ND1 (SEQ ID NO: 11), and 3'UTR (SEQ ID NO: 13); and rAAV2-opt_ND1, opt_COX10*-opt_ND1-3'UTR (SEQ ID NO: 55), which is the combination (5' to 3') of opt_COX10* (SEQ ID NO: 3), opt_ND1 (SEQ ID NO: 12), and 3'UTR (SEQ ID NO: 13).

The plasmid screening for COX10-ND1-3'UTR (SEQ ID NO: 25) used the following primers:

ND1-F: ATGGCCGCATCTCCGCACACT (SEQ ID NO: 99),

ND1-R: TTAGGTTTGAGGGGGAATGCT (SEQ ID NO: 100),

The plasmid screening for opt_COX10*-opt_ND1-3'UTR (SEQ ID NO: 55) used the following primers:

ND1-F: AACCTCAACCTAGGCCTCCTA (SEQ ID NO: 101),

ND1-R: TGGCAGGAGTAACCAGAGGTG (SEQ ID NO: 102),

Three groups of rabbits were injected: A: $10^{10}$ vg/50 μl of rAAV2-opt_ND1, B: $10^{10}$ vg/50 μl of rAAV2-ND1 (example 9), and C: $10^{10}$ vg/50 μl of rAAV2-EGFP. No obviously abnormality, conjunctival congestion, secretions, or endophthalmitis were observed and the intraocular pressure were not elevated in all the rabbits.

Figure 17:
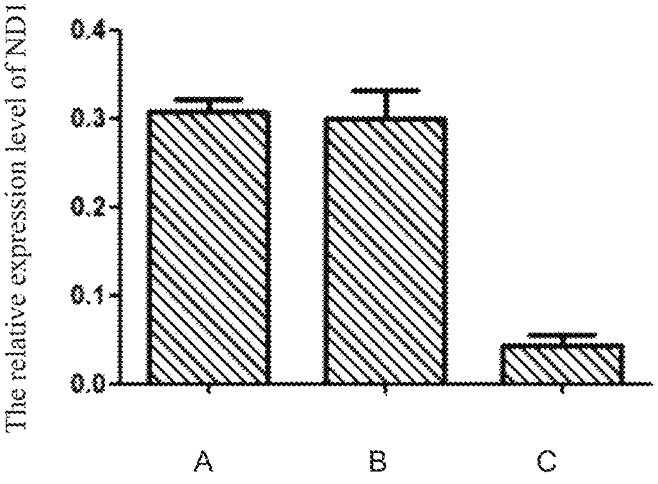
FIG. 17 shows the relative ND1 expression in rabbit optic nerve cells: rAAV2-opt_ND1 (A), rAAV2-ND1 (B), and rAAV-EGFP (C).
Figure 18:
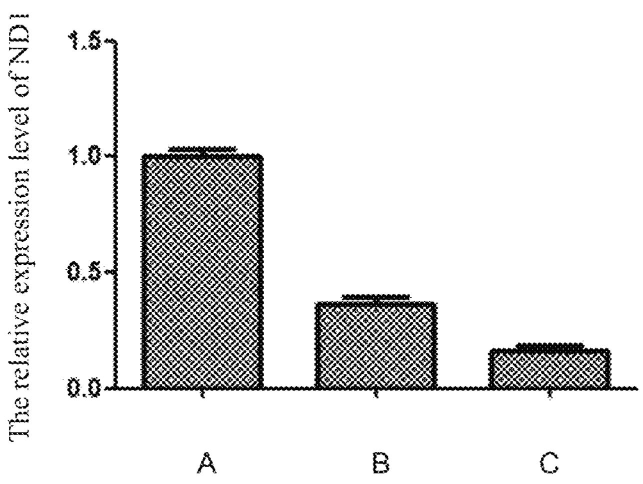
FIG. 18 shows the relative ND1 expression by western blot: rAAV2-opt_ND1 (A), rAAV2-ND1 (B), and rAAV-EGFP (C).

Real-time PCR tests similar to example 3 was following using the following primers:

ND1-F: AGGAGGCTCTGTCTGGTATCTTG (SEQ ID NO: 103);

ND1-R: TTTTAGGGGCTCTTTGGTGAA (SEQ ID NO: 104);

opt_ND1-F: GCCGCCTGCTGACCGGCTGCGT (SEQ ID NO: 105);

opt_ND1-R: TGATGTACAGGGTGATGGTGCTGG (SEQ ID NO: 106);

As shown in FIG. 17, rAAV2-opt_ND1 (A) and rAAV2-ND1 (B) both had higher ($p<0.05$) relative ND1 expression levels than the control group (C). As shown in the western blot in FIG. 18, rAAV2-opt_ND1 (A) had more than 2 times higher relative ND6 expression levels than rAAV2-ND1 (B).

Experimental methods were the same as example 8, where the recombinant nucleic acids, COX10-ND1-3'UTR (SEQ ID NO: 25) and opt_COX10*-opt_ND1-3'UTR (SEQ ID NO: 55), were replaced by OPA1-ND1-3'UTR (SEQ ID NO: 81) and OPA1-opt_ND1-3'UTR (SEQ ID NO: 83). It was found that, the optimized ND1 sequence has significantly improved transcription and translation efficiencies, expression levels, as well as higher efficacy and safety in treating LHON.

Example 12—Other Fusion Proteins

Similar experimental methods in examples 1-6 can be followed using other fusion proteins as set forth in SEQ ID NO: 15-84. And similar results are expected to be achieved.

Example 13—Formulation Development

AAV2 virus samples were used to screen different AAV formulations. The stability of the different AAV formulations were evaluated using the StepOnePlus real-time PCR system. The viral titer of each formulation under a freeze/thaw cycle condition was measured.

First, three different formulations were tested under 1, 2, 3, 4, and 5 freeze/thaw cycles and the viral titers were measured and summarized in Table 3. The three formulations tested were: A: phosphate-buffered saline (PBS); B: 1% α,α-trehalose dehydrate, 1% L-histidine monohydrochloride monohydrate, and 1% polysorbate 20; and C: 180 mM NaCl, 10 mM $NaH_2PO_4/Na_2HPO_4$, and 0.001% poloxamer 188, pH 7.3. As shown in Table 3, formulation C has the lowest relative standard deviation (RSD) after 5 freeze/thaw cycles, indicating superior stability as an AAV formulation.

TABLE 3 the viral titers of formulations A, B, and C

| viral titers | 0 cycle | 1 cycle | 2 cycles | 3 cycles | 4 cycles | 5 cycles | RSD |
|---|---|---|---|---|---|---|---|
| A | 1.15E+11 | 9.48E+10 | 6.16E+10 | 2.90E+10 | 1.56E+10 | 5.26E+09 | 83.18 |
| B | 4.25E+11 | 5.12E+11 | 6.66E+11 | 4.30E+11 | 4.77E+11 | 4.20E+11 | 19.30 |
| C | 4.96E+11 | 6.91E+11 | 7.69E+11 | 6.82E+11 | 6.83E+11 | 7.27E+11 | 13.90 |

As shown in Table 3, formulation C has the lowest relative standard deviation (RSD) after 5 freeze/thaw cycles, indicating superior stability as an AAV formulation.

Second, another group of three different formulations were tested under 1, 2, 3, 4, and 5 freeze/thaw cycles and the viral titers were measured and summarized in Table 4. The three formulations tested were: D: phosphate-buffered saline (PBS), pH 7.2-7.4; E: PBS and 0.001% poloxamer 188, pH 7.2-7.4; and F: 80 mM NaCl, 5 mM $NaH_2PO_4$, 40 mM $Na_2HPO_4$, 5 mM $KH_2PO_4$ and 0.001% poloxamer 188, 7.2-7.4.

TABLE 4 the viral titers of formulations D, E, and F

| viral titers | 0 cycle | 1 cycle | 2 cycles | 3 cycles | 4 cycles | 5 cycles | RSD |
|---|---|---|---|---|---|---|---|
| D | 1.13E+10 | 4.62E+09 | 2.25E+09 | 1.25E+09 | 1.01E+09 | 9.48E+08 | 113.25 |
| E | 4.72E+10 | 5.48E+10 | 5.33E+10 | 5.33E+10 | 4.94E+10 | 4.08E+10 | 10.53 |
| F | 6.61E+10 | 6.08E+10 | 6.47E+10 | 6.84E+10 | 6.52E+10 | 6.05E+10 | 4.81 |

As shown in Table 4, formulation F has the lowest relative standard deviation (RSD) after 5 freeze/thaw cycles, indicating superior stability as an AAV formulation. Overall, formulation F also has the lowest RSD among all tested formulations and can be used as the AAV formulation for future development.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating Leber's hereditary optic neuropathy (LHON), comprising administering a pharmaceutical composition to a patient in need thereof, wherein said pharmaceutical composition comprises a therapeutically effective amount of an adeno-associated virus (AAV) vector comprising a recombinant nucleic acid comprising:

a mitochondrial targeting sequence;

a mitochondrial protein coding sequence comprising a sequence that is:

1) at least 95% identical to SEQ ID NO: 7;

2) at least 99% identical to SEQ ID NO: 10; or 3) at least 99% identical to SEQ ID NO: 12; and a 3'UTR nucleic acid sequence, wherein the mitochondria protein coding sequence encodes an amino acid sequence that is at least 95% identical to any one of SEQ ID NO: 160-162, and wherein said pharmaceutical composition is administered via intravitreal injection.

2. The method of claim 1, further comprising administering methyl prednisolone to said patient.

3. The method of claim 2, wherein said methylprednisolone is administered daily for at least 2 days prior to said intravitreal injection of said pharmaceutical composition.

4. The method of claim 2, wherein said methylprednisolone is administered intravenously at a daily dose of about 80 mg/60 kg.

5. The method of claim 1, further comprising administering creatine phosphate sodium to said patient.

6. The method of claim 1, wherein said administering said pharmaceutical composition generates a higher average recovery of vision than a comparable pharmaceutical composition without said recombinant nucleic acid.

7. The method of claim 1, wherein said administering said pharmaceutical composition generates a higher average recovery of vision than when a comparable pharmaceutical composition comprising a recombinant nucleic acid as set forth in SEQ ID NO: 15 is administered.

8. The method of claim 1, wherein said AAV vector is a recombinant AAV2 (rAAV2) vector.

9. The method of claim 1, wherein said pharmaceutical composition comprises a pharmaceutically acceptable excipient comprising phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof.

10. The method of claim 9, wherein said pharmaceutically acceptable excipient comprises poloxamer 188.

11. The method of claim 10, wherein said pharmaceutically acceptable excipient comprises 0.0001%-0.01% poloxamer 188.

12. The method of claim 1, wherein said pharmaceutical composition has a viral titer of at least $1.0\times10^{10}$ vg/mL.

13. The method of claim 1, when said pharmaceutical composition is subject to five freeze/thaw cycles, said pharmaceutical composition retains at least 60%, 70%, 80%, or 90% of a viral titer as compared to the viral titer prior to the five freeze/thaw cycles.

14. The method of claim 1, wherein said mitochondrial targeting sequence encodes a polypeptide comprising a peptide sequence that is at least 90% identical to a sequence selected from the group consisting of SEQ ID NO: 129-159.

15. The method of claim 1, wherein said mitochondrial targeting sequence comprises a sequence that is at least 90% identical to a sequence selected from the group consisting of SEQ ID NO: 2-5.

16. The method of claim 1, wherein said mitochondrial protein is selected from the group consisting of NADH dehydrogenase 4 (ND4), NADH dehydrogenase 6 (ND6), NADH dehydrogenase 1 (ND1), and a variant thereof.

17. The method of claim 16, wherein said mitochondrial protein is ND4 or a variant thereof, and wherein said mitochondrial protein coding sequence comprises a sequence that is at least 99% identical to a sequence as set forth in SEQ ID NO: 7.

18. The method of claim 16, wherein said mitochondrial protein is ND6 or a variant thereof, and wherein said mitochondrial protein coding sequence comprises a sequence that is at least 99% identical to a sequence as set forth in SEQ ID NO: 10.

19. The method of claim 16, wherein said mitochondrial protein is ND1 or a variant thereof, and wherein said mitochondrial protein coding sequence comprises a sequence that is at least 99% identical to a sequence as set forth in SEQ ID NO: 12.

20. The method of claim 1, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

21. The method of claim 1, wherein said 3'UTR nucleic acid sequence comprises a sequence that is at least 90% identical to a sequence selected from the group consisting of SEQ ID NO: 111-125.

* * * * *

SEQUENCE LISTING

```
<160> NUMBER OF SEQ ID NOS: 162

<210> SEQ ID NO 1
<211> LENGTH: 84
<212> TYPE: DNA
<213> ORGANISM: Homo sapiens

<400> SEQUENCE: 1

atggccgcat ctccgcacac tctctcctca cgcctcctga caggttgcgt aggaggctct     60

gtctggtatc ttgaaagaag aact                                            84


<210> SEQ ID NO 2
<211> LENGTH: 84
<212> TYPE: DNA
<213> ORGANISM: Artificial Sequence
<220> FEATURE:
<223> OTHER INFORMATION: opt_COX10

<400> SEQUENCE: 2

atggccgcct ctccacacac actgagtagc agactgctga ccggctgtgt tggcggctct     60

gtgtggtatc tggaacggcg gaca                                            84


<210> SEQ ID NO 3
<211> LENGTH: 84
<212> TYPE: DNA
<213> ORGANISM: Artificial Sequence
<220> FEATURE:
<223> OTHER INFORMATION: opt_COX10*

<400> SEQUENCE: 3

atggccgcca gcccccacac cctgagcagc cgcctgctga ccggctgcgt gggcggcagc     60

gtgtggtacc tggagcgccg cacc                                            84


<210> SEQ ID NO 4
<211> LENGTH: 87
<212> TYPE: DNA
<213> ORGANISM: Artificial Sequence
<220> FEATURE:
<223> OTHER INFORMATION: COX8

<400> SEQUENCE: 4

atgtccgtcc tgacgcgcct gctgctgcgg ggcttgacac ggctcggctc ggcggctcca     60

gtgcggcgcg ccagaatcca ttcgttg                                         87


<210> SEQ ID NO 5
<211> LENGTH: 266
<212> TYPE: DNA
<213> ORGANISM: Homo sapiens

<400> SEQUENCE: 5

gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120
```

cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctg 266

<210> SEQ ID NO 6
<211> LENGTH: 1380
<212> TYPE: DNA
<213> ORGANISM: Homo sapiens

<400> SEQUENCE: 6
atgctaaaac taatcgtccc aacaattatg ttactaccac tgacatggct ttccaaaaaa 60
cacatgattt ggatcaacac aaccacccac agcctaatta ttagcatcat ccctctacta 120
ttttttaacc aaatcaacaa caacctattt agctgttccc caaccttttc ctccgacccc 180
ctaacaaccc ccctcctaat gctaactacc tggctcctac ccctcacaat catggcaagc 240
caacgccact tatccagtga accactatca cgaaaaaaac tctacctctc tatgctaatc 300
tccctacaaa tctccttaat tatgacattc acagccacag aactaatcat gttttatatc 360
ttcttcgaaa ccacacttat ccccaccttg gctatcatca cccgatgggg caaccagcca 420
gaacgcctga acgcaggcac atacttccta ttctacaccc tagtaggctc ccttccccta 480
ctcatcgcac taatttacac tcacaacacc ctaggctcac taaacattct actactcact 540
ctcactgccc aagaactatc aaactcctgg gccaacaact taatgtggct agcttacaca 600
atggctttta tggtaaagat gcctctttac ggactccact tatggctccc taaagcccat 660
gtcgaagccc ccatcgctgg gtcaatggta cttgccgcag tactcttaaa actaggcggc 720
tatggtatga tgcgcctcac actcattctc aaccccctga caaaacacat ggcctacccc 780
ttccttgtac tatccctatg ggcatgatt atgacaagct ccatctgcct acgacaaaca 840
gacctaaaat cgctcattgc atactcttca atcagccaca tggccctcgt agtaacagcc 900
attctcatcc aaaccccctg gagcttcacc ggcgcagtca ttctcatgat cgcccacggg 960
cttacatcct cattactatt ctgcctagca aactcaaact acgaacgcac tcacagtcgc 1020
atcatgatcc tctctcaagg acttcaaact ctactcccac taatggcttt ttggtggctt 1080
ctagcaagcc tcgctaacct cgccttaccc cccactatta acctactggg agaactctct 1140
gtgctagtaa ccacgttctc ctggtcaaat atcactctcc tacttacagg actcaacatg 1200
ctagtcacag ccctatactc cctctacatg tttaccacaa cacaatgggg ctcactcacc 1260
caccacatta acaacatgaa accctcattc acacgagaaa acaccctcat gttcatgcac 1320
ctatccccca ttctcctcct atccctcaac cccgacatca ttaccgggtt ttcctcttaa 1380

<210> SEQ ID NO 7
<211> LENGTH: 1380
<212> TYPE: DNA
<213> ORGANISM: Artificial Sequence
<220> FEATURE:
<223> OTHER INFORMATION: opt_ND4

<400> SEQUENCE: 7
atgctgaagc tgatcgtgcc caccatcatg ctgctgcctc tgacctggct gagcaagaaa 60
cacatgatct ggatcaacac caccacgcac agcctgatca tcagcatcat ccctctgctg 120
ttcttcaacc agatcaacaa caacctgttc agctgcagcc ccaccttcag cagcgaccct 180
ctgacaacac ctctgctgat gctgaccacc tggctgctgc ccctcacaat catggcctct 240

```
cagagacacc tgagcagcga gcccctgagc cggaagaaac tgtacctgag catgctgatc    300
tccctgcaga tctctctgat catgaccttc accgccaccg agctgatcat gttctacatc    360
tttttcgaga caacgctgat ccccacactg gccatcatca ccagatgggg caaccagcct    420
gagagactga acgccggcac ctactttctg ttctacaccc tcgtgggcag cctgccactg    480
ctgattgccc tgatctacac ccacaacacc ctgggctccc tgaacatcct gctgctgaca    540
ctgacagccc aagagctgag caacagctgg gccaacaatc tgatgtggct ggcctacaca    600
atggccttca tggtcaagat gcccctgtac ggcctgcacc tgtggctgcc taaagctcat    660
gtggaagccc ctatcgccgg ctctatggtg ctggctgcag tgctgctgaa actcggcggc    720
tacggcatga tgcggctgac cctgattctg aatcccctga ccaagcacat ggcctatcca    780
tttctggtgc tgagcctgtg ggcatgatt atgaccagca gcatctgcct gcggcagacc    840
gatctgaagt ccctgatcgc ctacagctcc atcagccaca tggccctggt ggtcaccgcc    900
atcctgattc agaccccttg gagctttaca ggcgccgtga tcctgatgat tgcccacggc    960
ctgacaagca gcctgctgtt ttgtctggcc aacagcaact acgagcggac ccacagcaga   1020
atcatgatcc tgtctcaggg cctgcagacc ctcctgcctc ttatggcttt ttggtggctg   1080
ctggcctctc tggccaatct ggcactgcct cctaccatca atctgctggg cgagctgagc   1140
gtgctggtca ccacattcag ctggtccaat atcaccctgc tgctcaccgg cctgaacatg   1200
ctggttacag ccctgtactc cctgtacatg ttcaccacca cacagtgggg aagcctgaca   1260
caccacatca acaatatgaa gcccagcttc acccgcgaga acaccctgat gttcatgcat   1320
ctgagcccca ttctgctgct gtccctgaat cctgatatca tcaccggctt ctccagctga   1380
```

<210> SEQ ID NO 8
<211> LENGTH: 1380
<212> TYPE: DNA
<213> ORGANISM: Artificial Sequence
<220> FEATURE:
<223> OTHER INFORMATION: opt_ND4*

<400> SEQUENCE: 8

```
atgctgaagc tgatcgtgcc caccatcatg ctgctgcccc tgacctggct gagcaagaag     60
cacatgatct ggatcaacac caccacccac agcctgatca tcagcatcat ccccctgctg    120
ttcttcaacc agatcaacaa caacctgttc agctgcagcc ccaccttcag cagcgacccc    180
ctgaccaccc ccctgctgat gctgaccacc tggctgctgc ccctgaccat catggccagc    240
cagcgccacc tgagcagcga gcccctgagc cgcaagaagc tgtacctgag catgctgatc    300
agcctgcaga tcagcctgat catgaccttc accgccaccg agctgatcat gttctacatc    360
ttcttcgaga ccaccctgat ccccaccctg gccatcatca cccgctgggg caaccagccc    420
gagcgcctga acgccggcac ctacttcctg ttctacaccc tggtgggcag cctgcccctg    480
ctgatcgccc tgatctacac ccacaacacc ctgggcagcc tgaacatcct gctgctgacc    540
ctgaccgccc aggagctgag caacagctgg gccaacaacc tgatgtggct ggcctacacc    600
atggccttca tggtgaagat gcccctgtac ggcctgcacc tgtggctgcc caaggcccac    660
gtggaggccc ccatcgccgg cagcatggtg ctggccgccg tgctgctgaa gctgggcggc    720
tacggcatga tgcgcctgac cctgatcctg aacccccctga ccaagcacat ggcctacccc    780
ttcctggtgc tgagcctgtg ggcatgatc atgaccagca gcatctgcct gcgccagacc    840
gacctgaaga gcctgatcgc ctacagcagc atcagccaca tggccctggt ggtgaccgcc    900
atcctgatcc agaccccctg gagcttcacc ggcgccgtga tcctgatgat cgcccacggc    960
```

```
ctgaccagca gcctgctgtt ctgcctggcc aacagcaact acgagcgcac ccacagccgc   1020

atcatgatcc tgagccaggg cctgcagacc ctgctgcccc tgatggcctt ctggtggctg   1080

ctggccagcc tggccaacct ggccctgccc cccaccatca acctgctggg cgagctgagc   1140

gtgctggtga ccaccttcag ctggagcaac atcaccctgc tgctgaccgg cctgaacatg   1200

ctggtgaccg ccctgtacag cctgtacatg ttcaccacca cccagtgggg cagcctgacc   1260

caccacatca acaacatgaa gcccagcttc acccgcgaga acaccctgat gttcatgcac   1320

ctgagcccca tcctgctgct gagcctgaac cccgacatca tcaccggctt cagcagctaa   1380
```

<210> SEQ ID NO 9
<211> LENGTH: 525
<212> TYPE: DNA
<213> ORGANISM: Homo sapiens

<400> SEQUENCE: 9

```
atgatgtatg ctttgtttct gttgagtgtg ggtttagtaa tggggtttgt ggggttttct     60

tctaagcctt ctcctattta tgggggttta gtattgattg ttagcggtgt ggtcgggtgt    120

gttattattc tgaattttgg gggaggttat atgggtttaa tggttttttt aatttattta    180

gggggaatga tggttgtctt tggatatact acagcgatgg ctattgagga gtatcctgag    240

gcatgggggt caggggttga ggtcttggtg agtgttttag tggggttagc gatggaggta    300

ggattggtgc tgtgggtgaa agagtatgat ggggtggtgg ttgtggtaaa ctttaatagt    360

gtaggaagct ggatgattta tgaaggagag gggtcagggt tgattcggga ggatcctatt    420

ggtgcggggg ctttgtatga ttatgggcgt tggttagtag tagttactgg ttggacattg    480

tttgttggtg tatatattgt aattgagatt gctcggggga attag                    525
```

<210> SEQ ID NO 10
<211> LENGTH: 525
<212> TYPE: DNA
<213> ORGANISM: Artificial Sequence
<220> FEATURE:
<223> OTHER INFORMATION: opt_ND6

<400> SEQUENCE: 10

```
atgatgtacg ccctgttcct gctgagcgtg ggcctggtga tgggcttcgt gggcttcagc     60

agcaagccca gccccatcta cggcggcctg gtgctgatcg tgagcggcgt ggtgggctgc    120

gtgatcatcc tgaacttcgg cggcggctac atgggcctga tggtgttcct gatctacctg    180

ggcggcatga tggtggtgtt cggctacacc accgccatgg ccatcgagga gtaccccgag    240

gcctggggca gcggcgtgga ggtgctggtg agcgtgctgg tgggcctggc catggaggtg    300

ggcctggtgc tgtgggtgaa ggagtacgac ggcgtggtgg tggtggtgaa cttcaacagc    360

gtgggcagct ggatgatcta cgagggcgag ggcagcggcc tgatccgcga ggaccccatc    420

ggcgccggcg ccctgtacga ctacggccgc tggctggtgg tggtgaccgg ctggaccctg    480

ttcgtgggcg tgtacatcgt gatcgagatc gcccgcggca actaa                    525
```

<210> SEQ ID NO 11
<211> LENGTH: 951
<212> TYPE: DNA
<213> ORGANISM: Homo sapiens

<400> SEQUENCE: 11

```
atggccaacc tcctactcct cattgtaccc attctaatcg caatggcatt cctaatgctt     60
```

```
accgaacgaa aaattctagg ctatatgcaa ctacgcaaag gccccaacgt tgtaggcccc    120

tacgggctac tacaaccctt cgctgacgcc ataaaactct tcaccaaaga gcccctaaaa    180

cccgccacat ctaccatcac cctctacatc accgccccga ccttagctct caccatcgct    240

cttctactat ggacccccct ccccatgccc aacccccctgg tcaacctcaa cctaggcctc    300

ctatttattc tagccacctc tagcctagcc gtttactcaa tcctctggtc agggtgggca    360

tcaaactcaa actacgccct gatcggcgca ctgcgagcag tagcccaaac aatctcatat    420

gaagtcaccc tagccatcat tctactatca acattactaa tgagtggctc ctttaacctc    480

tccaccctta tcacaacaca agaacacctc tggttactcc tgccatcatg gcccttggcc    540

atgatgtggt ttatctccac actagcagag accaaccgaa ccccccttcga ccttgccgaa    600

ggggagtccg aactagtctc aggcttcaac atcgaatacg ccgcaggccc cttcgcccta    660

ttcttcatgg ccgaatacac aaacattatt atgatgaaca ccctcaccac tacaatcttc    720

ctaggaacaa catatgacgc actctcccct gaactctaca caacatattt tgtcaccaag    780

accctacttc taacctccct gttcttatgg attcgaacag catacccccg attccgctac    840

gaccaactca tgcacctcct atggaaaaac ttcctaccac tcaccctagc attacttatg    900

tggtatgtct ccatgcccat tacaatctcc agcattcccc ctcaaaccta a             951
```

<210> SEQ ID NO 12
<211> LENGTH: 951
<212> TYPE: DNA
<213> ORGANISM: Artificial Sequence
<220> FEATURE:
<223> OTHER INFORMATION: opt_ND1

<400> SEQUENCE: 12

```
atggccaacc tgctgctgct gatcgtgccc atcctgatcg ccatggcctt cctgatgctg     60

accgagcgca agatcctggg ctacatgcag ctgcgcaagg gccccaacgt ggtgggcccc    120

tacggcctgc tgcagccctt cgccgacgcc atcaagctgt tcaccaagga gcccctgaag    180

cccgccacca gcaccatcac cctgtacatc accgccccca ccctggccct gaccatcgcc    240

ctgctgctgt ggacccccct gcccatgccc aacccccctgg tgaacctgaa cctgggcctg    300

ctgttcatcc tggccaccag cagcctggcc gtgtacagca tcctgtggag cggctgggcc    360

agcaacagca actacgccct gatcggcgcc ctgcgcgccg tggcccagac catcagctac    420

gaggtgaccc tggccatcat cctgctgagc accctgctga tgagcggcag cttcaacctg    480

agcaccctga tcaccaccca ggagcacctg tggctgctgc tgcccagctg gcccctggcc    540

atgatgtggt tcatcagcac cctggccgag accaaccgca ccccccttcga cctggccgag    600

ggcgagagcg agctggtgag cggcttcaac atcgagtacg ccgccggccc cttcgccctg    660

ttcttcatgg ccgagtacac caacatcatc atgatgaaca ccctgaccac caccatcttc    720

ctgggcacca cctacgacgc cctgagcccc gagctgtaca ccacctactt cgtgaccaag    780

accctgctgc tgaccagcct gttcctgtgg atccgcaccg cctacccccg cttccgctac    840

gaccagctga tgcacctgct gtggaagaac ttcctgcccc tgaccctggc cctgctgatg    900

tggtacgtga gcatgcccat caccatcagc agcatccccc cccagaccta a             951
```

<210> SEQ ID NO 13
<211> LENGTH: 1425
<212> TYPE: DNA
<213> ORGANISM: Homo sapiens

<400> SEQUENCE: 13

```
gagcactggg acgcccaccg cccctttccc tccgctgcca ggcgagcatg ttgtggtaat     60
tctggaacac aagaagagaa attgctgggt ttagaacaag attataaacg aattcggtgc    120
tcagtgatca cttgacagtt tttttttttt ttaaatatta cccaaaatgc tccccaaata    180
agaaatgcat cagctcagtc agtgaataca aaaaaggaat tatttttccc tttgagggtc    240
ttttatacat ctctcctcca accccaccct ctattctgtt tcttcctcct cacatggggg    300
tacacataca cagcttcctc ttttggttcc atccttacca ccacaccaca cgcacactcc    360
acatgcccag cagagtggca cttggtggcc agaaagtgtg agcctcatga tctgctgtct    420
gtagttctgt gagctcaggt ccctcaaagg cctcggagca ccccttcct tgtgactgag    480
ccagggcctg catttttggt tttccccacc ccacacattc tcaaccatag tccttctaac    540
aataccaata gctaggaccc ggctgctgtg cactgggact ggggattcca catgtttgcc    600
ttgggagtct caagctggac tgccagcccc tgtcctccct tcacccccat tgcgtatgag    660
catttcagaa ctccaaggag tcacaggcat ctttatagtt cacgttaaca tatagacact    720
gttggaagca gttccttcta aaagggtagc cctggactta ataccagccg gatacctctg    780
gcccccaccc cattactgta cctctggagt cactactgtg ggtcgccact cctctgctac    840
acagcacggc tttttcaagg ctgtattgag aagggaagtt aggaagaagg gtgtgctggg    900
ctaaccagcc cacagagctc acattcctgt cccttgggtg aaaaatacat gtccatcctg    960
atatctcctg aattcagaaa ttagcctcca catgtgcaat ggctttaaga gccagaagca   1020
gggttctggg aattttgcaa gttacctgtg gccaggtgtg gtctcggtta ccaaatacgg   1080
ttacctgcag ctttttagtc ctttgtgctc ccacgggtct acagagtccc atctgcccaa   1140
aggtcttgaa gcttgacagg atgttttcga ttactcagtc tcccagggca ctactggtcc   1200
gtaggattcg attggtcggg gtaggagagt taaacaacat ttaaacagag ttctctcaaa   1260
aatgtctaaa gggattgtag gtagataaca tccaatcact gtttgcactt atctgaaatc   1320
ttccctcttg gctgccccca ggtatttact gtggagaaca ttgcatagga atgtctggaa   1380
aaagcttcta caacttgtta cagccttcac atttgtagaa gcttt                   1425
```

<210> SEQ ID NO 14
<211> LENGTH: 625
<212> TYPE: DNA
<213> ORGANISM: Homo sapiens

<400> SEQUENCE: 14

```
gagcactggg acgcccaccg cccctttccc tccgctgcca ggcgagcatg ttgtggtaat     60
tctggaacac aagaagagaa attgctgggt ttagaacaag attataaacg aattcggtgc    120
tcagtgatca cttgacagtt tttttttttt ttaaatatta cccaaaatgc tccccaaata    180
agaaatgcat cagctcagtc agtgaataca aaaaaggaat tatttttccc tttgagggtc    240
ttttatacat ctctcctcca accccaccct ctattctgtt tcttcctcct cacatggggg    300
tacacataca cagcttcctc ttttggttcc atccttacca ccacaccaca cgcacactcc    360
acatgcccag cagagtggca cttggtggcc agaaagtgtg agcctcatga tctgctgtct    420
gtagttctgt gagctcaggt ccctcaaagg cctcggagca ccccttcct tgtgactgag    480
ccagggcctg catttttggt tttccccacc ccacacattc tcaaccatag tccttctaac    540
aataccaata gctaggaccc ggctgctgtg cactgggact ggggattcca catgtttgcc    600
ttgggagtct caagctggac tgcca                                          625
```

<210> SEQ ID NO 15
<211> LENGTH: 2889
<212> TYPE: DNA
<213> ORGANISM: Artificial Sequence
<220> FEATURE:
<223> OTHER INFORMATION: COX10-ND4-3'UTR

<400> SEQUENCE: 15

```
atggccgcat ctccgcacac tctctcctca cgcctcctga caggttgcgt aggaggctct     60
gtctggtatc ttgaaagaag aactatgcta aaactaatcg tcccaacaat tatgttacta    120
ccactgacat ggctttccaa aaaacacatg atttggatca acacaaccac ccacagccta    180
attattagca tcatccctct actatttttt aaccaaatca acaacaacct atttagctgt    240
tccccaacct tttcctccga ccccctaaca accccccctcc taatgctaac tacctggctc    300
ctacccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg ctttttggtg gcttctagca agcctcgcta acctcgcctt accccccact   1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt ttttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgccag cccctgtcct   2100
```

```
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                           2889
```

```
<210> SEQ ID NO 16
<211> LENGTH: 2089
<212> TYPE: DNA
<213> ORGANISM: Artificial Sequence
<220> FEATURE:
<223> OTHER INFORMATION: COX10-ND4-3'UTR*

<400> SEQUENCE: 16

atggccgcat ctccgcacac tctctcctca cgcctcctga caggttgcgt aggaggctct     60
gtctggtatc ttgaaagaag aactatgcta aaactaatcg tcccaacaat tatgttacta    120
ccactgacat ggctttccaa aaaacacatg atttggatca acacaaccac ccacagccta    180
attattagca tcatccctct actatttttt aaccaaatca acaacaacct atttagctgt    240
tccccaacct tttcctccga ccccctaaca acccccctcc taatgctaac tacctggctc    300
ctacccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg ctttttggtg gcttctagca agcctcgcta acctcgcctt accccccact   1200
```

```
attaacctac tgggagaact ctctgtgcta gtaaccacgt tctcctggtc aaatatcact   1260

ctcctactta caggactcaa catgctagtc acagccctat actccctcta catgtttacc   1320

acaacacaat ggggctcact cacccaccac attaacaaca tgaaaccctc attcacacga   1380

gaaaacaccc tcatgttcat gcacctatcc cccattctcc tcctatccct caaccccgac   1440

atcattaccg ggttttcctc ttaagagcac tgggacgccc accgcccctt tccctccgct   1500

gccaggcgag catgttgtgg taattctgga acacaagaag agaaattgct gggtttagaa   1560

caagattata aacgaattcg gtgctcagtg atcacttgac agtttttttt tttttaaat    1620

attacccaaa atgctcccca aataagaaat gcatcagctc agtcagtgaa tacaaaaaag   1680

gaattatttt tccctttgag ggtcttttat acatctctcc tccaacccca ccctctattc   1740

tgtttcttcc tcctcacatg gggtacaca tacacagctt cctcttttgg ttccatcctt    1800

accaccacac cacacgcaca ctccacatgc ccagcagagt ggcacttggt ggccagaaag   1860

tgtgagcctc atgatctgct gtctgtagtt ctgtgagctc aggtccctca aaggcctcgg   1920

agcacccct tccttgtgac tgagccaggg cctgcatttt tggttttccc caccccacac    1980

attctcaacc atagtccttc taacaatacc aatagctagg acccggctgc tgtgcactgg   2040

gactggggat tccacatgtt tgccttggga gtctcaagct ggactgcca               2089
```

```
<210> SEQ ID NO 17
<211> LENGTH: 2889
<212> TYPE: DNA
<213> ORGANISM: Artificial Sequence
<220> FEATURE:
<223> OTHER INFORMATION: COX10-opt_ND4-3'UTR

<400> SEQUENCE: 17

atggccgcat ctccgcacac tctctcctca cgcctcctga caggttgcgt aggaggctct     60

gtctggtatc ttgaaagaag aactatgctg aagctgatcg tgcccaccat catgctgctg    120

cctctgacct ggctgagcaa gaaacacatg atctggatca acaccaccac gcacagcctg    180

atcatcagca tcatccctct gctgttcttc aaccagatca acaacaacct gttcagctgc    240

agccccacct tcagcagcga ccctctgaca acacctctgc tgatgctgac cacctggctg    300

ctgcccctca caatcatggc ctctcagaga cacctgagca gcgagcccct gagccggaag    360

aaactgtacc tgagcatgct gatctccctg cagatctctc tgatcatgac cttcaccgcc    420

accgagctga tcatgttcta catctttttc gagacaacgc tgatccccac actggccatc    480

atcaccagat ggggcaacca gcctgagaga ctgaacgccg gcacctactt tctgttctac    540

accctcgtgg gcagcctgcc actgctgatt gccctgatct acacccacaa caccctgggc    600

tccctgaaca tcctgctgct gacactgaca gcccaagagc tgagcaacag ctgggccaac    660

aatctgatgt ggctggccta cacaatggcc ttcatggtca agatgcccct gtacggcctg    720

cacctgtggc tgcctaaagc tcatgtggaa gcccctatcg ccggctctat ggtgctggct    780

gcagtgctgc tgaaactcgg cggctacggc atgatgcggc tgaccctgat tctgaatccc    840

ctgaccaagc acatggccta tccatttctg gtgctgagcc tgtggggcat gattatgacc    900

agcagcatct gcctgcggca gaccgatctg aagtccctga tcgcctacag ctccatcagc    960

cacatggccc tggtggtcac cgccatcctg attcagaccc cttggagctt tacaggcgcc   1020

gtgatcctga tgattgccca cggcctgaca agcagcctgc tgttttgtct ggccaacagc   1080

aactacgagc ggacccacag cagaatcatg atcctgtctc agggcctgca gaccctcctg   1140

cctcttatgg ctttttggtg gctgctggcc tctctggcca atctggcact gcctcctacc   1200
```

-continued

```
atcaatctgc tgggcgagct gagcgtgctg gtcaccacat tcagctggtc caatatcacc   1260

ctgctgctca ccggcctgaa catgctggtt acagccctgt actccctgta catgttcacc   1320

accacacagt ggggaagcct gacacaccac atcaacaata tgaagcccag cttcacccgc   1380

gagaacaccc tgatgttcat gcatctgagc cccattctgc tgctgtccct gaatcctgat   1440

atcatcaccg gcttctccag ctgagagcac tgggacgccc accgcccctt tccctccgct   1500

gccaggcgag catgttgtgg taattctgga acacaagaag agaaattgct gggtttagaa   1560

caagattata aacgaattcg gtgctcagtg atcacttgac agtttttttt tttttaaat   1620

attacccaaa atgctcccca aataagaaat gcatcagctc agtcagtgaa tacaaaaaag   1680

gaattatttt tccctttgag ggtcttttat acatctctcc tccaacccca ccctctattc   1740

tgtttcttcc tcctcacatg gggtacaca tacacagctt cctcttttgg ttccatcctt   1800

accaccacac cacacgcaca ctccacatgc ccagcagagt ggcacttggt ggccagaaag   1860

tgtgagcctc atgatctgct gtctgtagtt ctgtgagctc aggtccctca aaggcctcgg   1920

agcacccct tccttgtgac tgagccaggg cctgcatttt tggttttccc cacccacac   1980

attctcaacc atagtccttc taacaatacc aatagctagg acccggctgc tgtgcactgg   2040

gactggggat tccacatgtt tgccttggga gtctcaagct ggactgccag cccctgtcct   2100

cccttcaccc ccattgcgta tgagcatttc agaactccaa ggagtcacag gcatctttat   2160

agttcacgtt aacatataga cactgttgga agcagttcct tctaaaaggg tagccctgga   2220

cttaatacca gccggatacc tctggccccc accccattac tgtacctctg gagtcactac   2280

tgtgggtcgc cactcctctg ctacacagca cggctttttc aaggctgtat tgagaaggga   2340

agttaggaag aagggtgtgc tgggctaacc agcccacaga gctcacattc ctgtcccttg   2400

ggtgaaaaat acatgtccat cctgatatct cctgaattca gaaattagcc tccacatgtg   2460

caatggcttt aagagccaga agcagggttc tgggaatttt gcaagttacc tgtggccagg   2520

tgtggtctcg gttaccaaat acggttacct gcagcttttt agtcctttgt gctcccacgg   2580

gtctacagag tcccatctgc ccaaaggtct tgaagcttga caggatgttt tcgattactc   2640

agtctcccag ggcactactg gtccgtagga ttcgattggt cggggtagga gagttaaaca   2700

acatttaaac agagttctct caaaaatgtc taaagggatt gtaggtagat aacatccaat   2760

cactgtttgc acttatctga aatcttccct cttggctgcc cccaggtatt tactgtggag   2820

aacattgcat aggaatgtct ggaaaaagct tctacaactt gttacagcct tcacatttgt   2880

agaagcttt                                                           2889
```

```
<210> SEQ ID NO 18
<211> LENGTH: 2089
<212> TYPE: DNA
<213> ORGANISM: Artificial Sequence
<220> FEATURE:
<223> OTHER INFORMATION: COX10-opt_ND4-3'UTR*

<400> SEQUENCE: 18

atggccgcat ctccgcacac tctctcctca cgcctcctga caggttgcgt aggaggctct     60

gtctggtatc ttgaaagaag aactatgctg aagctgatcg tgcccaccat catgctgctg    120

cctctgacct ggctgagcaa gaaacacatg atctggatca acaccaccac gcacagcctg    180

atcatcagca tcatccctct gctgttcttc aaccagatca acaacaacct gttcagctgc    240

agccccacct tcagcagcga ccctctgaca acacctctgc tgatgctgac cacctggctg    300
```

ctgcccctca caatcatggc ctctcagaga cacctgagca gcgagcccct gagccggaag 360
aaactgtacc tgagcatgct gatctccctg cagatctctc tgatcatgac cttcaccgcc 420
accgagctga tcatgttcta catctttttc gagacaacgc tgatccccac actggccatc 480
atcaccagat ggggcaacca gcctgagaga ctgaacgccg gcacctactt tctgttctac 540
accctcgtgg gcagcctgcc actgctgatt gccctgatct acacccacaa caccctgggc 600
tccctgaaca tcctgctgct gacactgaca gcccaagagc tgagcaacag ctgggccaac 660
aatctgatgt ggctggccta cacaatggcc ttcatggtca agatgcccct gtacggcctg 720
cacctgtggc tgcctaaagc tcatgtggaa gcccctatcg ccggctctat ggtgctggct 780
gcagtgctgc tgaaactcgg cggctacggc atgatgcggc tgaccctgat tctgaatccc 840
ctgaccaagc acatggccta tccatttctg gtgctgagcc tgtggggcat gattatgacc 900
agcagcatct gcctgcggca gaccgatctg aagtccctga tcgcctacag ctccatcagc 960
cacatggccc tggtggtcac cgccatcctg attcagaccc cttggagctt tacaggcgcc 1020
gtgatcctga tgattgccca cggcctgaca agcagcctgc tgttttgtct ggccaacagc 1080
aactacgagc ggacccacag cagaatcatg atcctgtctc agggcctgca gaccctcctg 1140
cctcttatgg ctttttggtg gctgctggcc tctctggcca atctggcact gcctcctacc 1200
atcaatctgc tgggcgagct gagcgtgctg gtcaccacat tcagctggtc caatatcacc 1260
ctgctgctca ccggcctgaa catgctggtt acagccctgt actccctgta catgttcacc 1320
accacacagt ggggaagcct gacacaccac atcaacaata tgaagcccag cttcacccgc 1380
gagaacaccc tgatgttcat gcatctgagc cccattctgc tgctgtccct gaatcctgat 1440
atcatcaccg gcttctccag ctgagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt ttttttaaat 1620
attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

<210> SEQ ID NO 19
<211> LENGTH: 2889
<212> TYPE: DNA
<213> ORGANISM: Artificial Sequence
<220> FEATURE:
<223> OTHER INFORMATION: COX10-opt_ND4*-3'UTR

<400> SEQUENCE: 19
atggccgcat ctccgcacac tctctcctca cgcctcctga caggttgcgt aggaggctct 60
gtctggtatc ttgaaagaag aactatgctg aagctgatcg tgcccaccat catgctgctg 120
cccctgacct ggctgagcaa gaagcacatg atctggatca acaccaccac ccacagcctg 180
atcatcagca tcatcccct gctgttcttc aaccagatca acaacaacct gttcagctgc 240
agccccacct tcagcagcga ccccctgacc acccccctgc tgatgctgac cacctggctg 300

```
ctgcccctga ccatcatggc cagccagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatccccac cctggccatc    480
atcacccgct ggggcaacca gcccgagcgc ctgaacgccg gcacctactt cctgttctac    540
accctggtgg gcagcctgcc cctgctgatc gccctgatct acacccacaa caccctgggc    600
agcctgaaca tcctgctgct gaccctgacc gcccaggagc tgagcaacag ctgggccaac    660
aacctgatgt ggctggccta caccatggcc ttcatggtga agatgcccct gtacggcctg    720
cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gccccccacc   1200
atcaacctgc tgggcgagct gagcgtgctg gtgaccacct tcagctggag caacatcacc   1260
ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt ttttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggtacaca tacacagctt cctcttttgg ttccatcctt    1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac  1980
attctcaacc atagtccttc taacaatacc aatagctagg acccggctgc tgtgcactgg   2040
gactggggat tccacatgtt tgccttggga gtctcaagct ggactgccag cccctgtcct   2100
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
```

-continued

```
agtctcccag ggcactactg gtccgtagga ttcgattggt cggggtagga gagttaaaca   2700

acatttaaac agagttctct caaaaatgtc taaagggatt gtaggtagat aacatccaat   2760

cactgtttgc acttatctga aatcttccct cttggctgcc cccaggtatt tactgtggag   2820

aacattgcat aggaatgtct ggaaaaagct tctacaactt gttacagcct tcacatttgt   2880

agaagcttt                                                           2889
```

<210> SEQ ID NO 20
<211> LENGTH: 2089
<212> TYPE: DNA
<213> ORGANISM: Artificial Sequence
<220> FEATURE:
<223> OTHER INFORMATION: COX10-opt_ND4*-3'UTR*

<400> SEQUENCE: 20

```
atggccgcat ctccgcacac tctctcctca cgcctcctga caggttgcgt aggaggctct     60

gtctggtatc ttgaaagaag aactatgctg aagctgatcg tgcccaccat catgctgctg    120

cccctgacct ggctgagcaa gaagcacatg atctggatca acaccaccac ccacagcctg    180

atcatcagca tcatccccct gctgttcttc aaccagatca acaacaacct gttcagctgc    240

agccccacct tcagcagcga ccccctgacc accccccctgc tgatgctgac cacctggctg   300

ctgcccctga ccatcatggc cagccagcgc cacctgagca gcgagcccct gagccgcaag    360

aagctgtacc tgagcatgct gatcagcctg cagatcagcc tgatcatgac cttcaccgcc    420

accgagctga tcatgttcta catcttcttc gagaccaccc tgatccccac cctggccatc    480

atcacccgct ggggcaacca gcccgagcgc ctgaacgccg gcacctactt cctgttctac    540

accctggtgg gcagcctgcc cctgctgatc gccctgatct acacccacaa caccctgggc    600

agcctgaaca tcctgctgct gaccctgacc gcccaggagc tgagcaacag ctgggccaac    660

aacctgatgt ggctggccta caccatggcc ttcatggtga agatgcccct gtacggcctg    720

cacctgtggc tgcccaaggc ccacgtggag gcccccatcg ccggcagcat ggtgctggcc    780

gccgtgctgc tgaagctggg cggctacggc atgatgcgcc tgaccctgat cctgaacccc    840

ctgaccaagc acatggccta cccccttcctg gtgctgagcc tgtggggcat gatcatgacc   900

agcagcatct gcctgcgcca gaccgacctg aagagcctga tcgcctacag cagcatcagc    960

cacatggccc tggtggtgac cgccatcctg atccagaccc cctggagctt caccggcgcc   1020

gtgatcctga tgatcgccca cggcctgacc agcagcctgc tgttctgcct ggccaacagc   1080

aactacgagc gcacccacag ccgcatcatg atcctgagcc agggcctgca gaccctgctg   1140

cccctgatgg ccttctggtg gctgctggcc agcctggcca acctggccct gccccccacc   1200

atcaacctgc tgggcgagct gagcgtgctg gtgaccacct tcagctggag caacatcacc   1260

ctgctgctga ccggcctgaa catgctggtg accgccctgt acagcctgta catgttcacc   1320

accacccagt ggggcagcct gacccaccac atcaacaaca tgaagcccag cttcacccgc   1380

gagaacaccc tgatgttcat gcacctgagc cccatcctgc tgctgagcct gaaccccgac   1440

atcatcaccg gcttcagcag ctaagagcac tgggacgccc accgcccctt tccctccgct   1500

gccaggcgag catgttgtgg taattctgga acacaagaag agaaattgct gggtttagaa   1560

caagattata aacgaattcg gtgctcagtg atcacttgac agtttttttt ttttttaaat   1620

attacccaaa atgctcccca aataagaaat gcatcagctc agtcagtgaa tacaaaaaag   1680

gaattatttt tccctttgag ggtcttttat acatctctcc tccaacccca ccctctattc   1740

tgtttcttcc tcctcacatg gggtacaca tacacagctt cctcttttgg ttccatcctt    1800
```

-continued accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

<210> SEQ ID NO 21
<211> LENGTH: 2034
<212> TYPE: DNA
<213> ORGANISM: Artificial Sequence
<220> FEATURE:
<223> OTHER INFORMATION: COX10-ND6-3'UTR

<400> SEQUENCE: 21
atggccgcat ctccgcacac tctctcctca cgcctcctga caggttgcgt aggaggctct 60
gtctggtatc ttgaaagaag aactatgatg tatgctttgt ttctgttgag tgtgggttta 120
gtaatggggt ttgtggggtt ttcttctaag ccttctccta tttatggggg tttagtattg 180
attgttagcg gtgtggtcgg gtgtgttatt attctgaatt ttgggggagg ttatatgggt 240
ttaatggttt ttttaattta tttaggggga atgatggttg tctttggata tactacagcg 300
atggctattg aggagtatcc tgaggcatgg gggtcagggg ttgaggtctt ggtgagtgtt 360
ttagtggggt tagcgatgga ggtaggattg gtgctgtggg tgaaagagta tgatggggtg 420
gtggttgtgg taaactttaa tagtgtagga agctggatga tttatgaagg agaggggtca 480
gggttgattc gggaggatcc tattggtgcg ggggctttgt atgattatgg gcgttggtta 540
gtagtagtta ctggttggac attgtttgtt ggtgtatata ttgtaattga gattgctcgg 600
gggaattagg agcactggga cgcccaccgc ccctttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac cccccttcctt 1080 gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gccagcccct gtcctccctt cacccccatt 1260
gcgtatgagc atttcagaac tccaaggagt cacaggcatc tttatagttc acgttaacat 1320
atagacactg ttggaagcag ttccttctaa aagggtagcc ctggacttaa taccagccgg 1380
atacctctgg cccccacccc attactgtac ctctggagtc actactgtgg gtcgccactc 1440
ctctgctaca cagcacggct ttttcaaggc tgtattgaga agggaagtta ggaagaaggg 1500
tgtgctgggc taaccagccc acagagctca cattcctgtc ccttgggtga aaaatacatg 1560
tccatcctga tatctcctga attcagaaat tagcctccac atgtgcaatg gctttaagag 1620
ccagaagcag ggttctggga attttgcaag ttacctgtgg ccaggtgtgg tctcggttac 1680
caaatacggt tacctgcagc tttttagtcc tttgtgctcc cacgggtcta cagagtccca 1740

```
tctgcccaaa ggtcttgaag cttgacagga tgttttcgat tactcagtct cccagggcac   1800

tactggtccg taggattcga ttggtcgggg taggagagtt aaacaacatt taaacagagt   1860

tctctcaaaa atgtctaaag ggattgtagg tagataacat ccaatcactg tttgcactta   1920

tctgaaatct tccctcttgg ctgcccccag gtatttactg tggagaacat tgcataggaa   1980

tgtctggaaa aagcttctac aacttgttac agccttcaca tttgtagaag cttt         2034
```

<210> SEQ ID NO 22
<211> LENGTH: 1234
<212> TYPE: DNA
<213> ORGANISM: Artificial Sequence
<220> FEATURE:
<223> OTHER INFORMATION: COX10-ND6-3'UTR*

<400> SEQUENCE: 22

```
atggccgcat ctccgcacac tctctcctca cgcctcctga caggttgcgt aggaggctct     60

gtctggtatc ttgaaagaag aactatgatg tatgctttgt ttctgttgag tgtgggttta    120

gtaatggggt ttgtggggtt ttcttctaag ccttctccta tttatggggg tttagtattg    180

attgttagcg gtgtggtcgg gtgtgttatt attctgaatt ttgggggagg ttatatgggt    240

ttaatggttt ttttaattta tttaggggga atgatggttg tctttggata tactacagcg    300

atggctattg aggagtatcc tgaggcatgg gggtcagggg ttgaggtctt ggtgagtgtt    360

ttagtggggt tagcgatgga ggtaggattg gtgctgtggg tgaaagagta tgatggggtg    420

gtggttgtgg taaactttaa tagtgtagga agctggatga tttatgaagg agaggggtca    480

gggttgattc gggaggatcc tattggtgcg ggggctttgt atgattatgg gcgttggtta    540

gtagtagtta ctggttggac attgtttgtt ggtgtatata ttgtaattga gattgctcgg    600

gggaattagg agcactggga cgcccaccgc ccctttccct ccgctgccag gcgagcatgt    660

tgtggtaatt ctggaacaca agaagagaaa ttgctgggtt tagaacaaga ttataaacga    720

attcggtgct cagtgatcac ttgacagttt tttttttttt taaatattac ccaaaatgct    780

ccccaaataa gaaatgcatc agctcagtca gtgaatacaa aaaaggaatt atttttccct    840

ttgagggtct tttatacatc tctcctccaa ccccaccctc tattctgttt cttcctcctc    900

acatgggggt acacatacac agcttcctct tttggttcca tccttaccac cacaccacac    960

gcacactcca catgcccagc agagtggcac ttggtggcca gaaagtgtga gcctcatgat   1020

ctgctgtctg tagttctgtg agctcaggtc cctcaaaggc ctcggagcac ccccttcctt   1080

gtgactgagc cagggcctgc atttttggtt ttccccaccc cacacattct caaccatagt   1140

ccttctaaca ataccaatag ctaggacccg gctgctgtgc actgggactg gggattccac   1200

atgtttgcct tgggagtctc aagctggact gcca                               1234
```

<210> SEQ ID NO 23
<211> LENGTH: 2034
<212> TYPE: DNA
<213> ORGANISM: Artificial Sequence
<220> FEATURE:
<223> OTHER INFORMATION: COX10-opt_ND6-3'UTR

<400> SEQUENCE: 23

```
atggccgcat ctccgcacac tctctcctca cgcctcctga caggttgcgt aggaggctct     60

gtctggtatc ttgaaagaag aactatgatg tacgccctgt tcctgctgag cgtgggcctg    120

gtgatgggct tcgtgggctt cagcagcaag cccagcccca tctacggcgg cctggtgctg    180

atcgtgagcg gcgtggtggg ctgcgtgatc atcctgaact tcggcggcgg ctacatgggc    240
```

ctgatggtgt tcctgatcta cctgggcggc atgatggtgg tgttcggcta caccaccgcc 300
atggccatcg aggagtaccc cgaggcctgg ggcagcggcg tggaggtgct ggtgagcgtg 360
ctggtgggcc tggccatgga ggtgggcctg gtgctgtggg tgaaggagta cgacggcgtg 420
gtggtggtgg tgaacttcaa cagcgtgggc agctggatga tctacgaggg cgagggcagc 480
ggcctgatcc gcgaggaccc catcggcgcc ggcgccctgt acgactacgg ccgctggctg 540
gtggtggtga ccggctggac cctgttcgtg ggcgtgtaca tcgtgatcga gatcgcccgc 600
ggcaactaag agcactggga cgcccaccgc ccctttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac cccctccctt 1080
gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gccagcccct gtcctccctt cacccccatt 1260
gcgtatgagc atttcagaac tccaaggagt cacaggcatc tttatagttc acgttaacat 1320
atagacactg ttggaagcag ttccttctaa aagggtagcc ctggacttaa taccagccgg 1380
atacctctgg cccccacccc attactgtac ctctggagtc actactgtgg gtcgccactc 1440
ctctgctaca cagcacggct ttttcaaggc tgtattgaga agggaagtta ggaagaaggg 1500
tgtgctgggc taaccagccc acagagctca cattcctgtc ccttgggtga aaaatacatg 1560
tccatcctga tatctcctga attcagaaat tagcctccac atgtgcaatg gctttaagag 1620
ccagaagcag ggttctggga attttgcaag ttacctgtgg ccaggtgtgg tctcggttac 1680
caaatacggt tacctgcagc tttttagtcc tttgtgctcc cacgggtcta cagagtccca 1740
tctgcccaaa ggtcttgaag cttgacagga tgttttcgat tactcagtct cccagggcac 1800
tactggtccg taggattcga ttggtcgggg taggagagtt aaacaacatt taaacagagt 1860
tctctcaaaa atgtctaaag ggattgtagg tagataacat ccaatcactg tttgcactta 1920
tctgaaatct tccctcttgg ctgcccccag gtatttactg tggagaacat tgcataggaa 1980
tgtctggaaa aagcttctac aacttgttac agccttcaca tttgtagaag cttt 2034

<210> SEQ ID NO 24
<211> LENGTH: 1234
<212> TYPE: DNA
<213> ORGANISM: Artificial Sequence
<220> FEATURE:
<223> OTHER INFORMATION: COX10-opt_ND6-3'UTR*

<400> SEQUENCE: 24
atggccgcat ctccgcacac tctctcctca cgcctcctga caggttgcgt aggaggctct 60
gtctggtatc ttgaaagaag aactatgatg tacgccctgt tcctgctgag cgtgggcctg 120
gtgatgggct tcgtgggctt cagcagcaag cccagcccca tctacggcgg cctggtgctg 180
atcgtgagcg gcgtggtggg ctgcgtgatc atcctgaact tcggcggcgg ctacatgggc 240

```
ctgatggtgt tcctgatcta cctgggcggc atgatggtgg tgttcggcta caccaccgcc    300

atggccatcg aggagtaccc cgaggcctgg ggcagcggcg tggaggtgct ggtgagcgtg    360

ctggtgggcc tggccatgga ggtgggcctg gtgctgtggg tgaaggagta cgacggcgtg    420

gtggtggtgg tgaacttcaa cagcgtgggc agctggatga tctacgaggg cgagggcagc    480

ggcctgatcc gcgaggaccc catcggcgcc ggcgccctgt acgactacgg ccgctggctg    540

gtggtggtga ccggctggac cctgttcgtg ggcgtgtaca tcgtgatcga gatcgcccgc    600

ggcaactaag agcactggga cgcccaccgc ccctttccct ccgctgccag gcgagcatgt    660

tgtggtaatt ctggaacaca agaagagaaa ttgctgggtt tagaacaaga ttataaacga    720

attcggtgct cagtgatcac ttgacagttt tttttttttt taaatattac ccaaaatgct    780

ccccaaataa gaaatgcatc agctcagtca gtgaatacaa aaaaggaatt atttttccct    840

ttgagggtct tttatacatc tctcctccaa ccccaccctc tattctgttt cttcctcctc    900

acatgggggt acacatacac agcttcctct tttggttcca tccttaccac cacaccacac    960

gcacactcca catgcccagc agagtggcac ttggtggcca gaaagtgtga gcctcatgat   1020

ctgctgtctg tagttctgtg agctcaggtc cctcaaaggc ctcggagcac cccttcctt   1080

gtgactgagc cagggcctgc atttttggtt ttccccaccc cacacattct caaccatagt   1140

ccttctaaca ataccaatag ctaggacccg gctgctgtgc actgggactg gggattccac   1200

atgtttgcct tgggagtctc aagctggact gcca                                1234
```

<210> SEQ ID NO 25
<211> LENGTH: 2460
<212> TYPE: DNA
<213> ORGANISM: Artificial Sequence
<220> FEATURE:
<223> OTHER INFORMATION: COX10-ND1-3'UTR

<400> SEQUENCE: 25

```
atggccgcat ctccgcacac tctctcctca cgcctcctga caggttgcgt aggaggctct     60

gtctggtatc ttgaaagaag aactatggcc aacctcctac tcctcattgt acccattcta    120

atcgcaatgg cattcctaat gcttaccgaa cgaaaaattc taggctatat gcaactacgc    180

aaaggcccca acgttgtagg cccctacggg ctactacaac ccttcgctga cgccataaaa    240

ctcttcacca aagagcccct aaaacccgcc acatctacca tcaccctcta catcaccgcc    300

ccgaccttag ctctcaccat cgctcttcta ctatggaccc ccctccccat gcccaacccc    360

ctggtcaacc tcaacctagg cctcctattt attctagcca cctctagcct agccgtttac    420

tcaatcctct ggtcagggtg ggcatcaaac tcaaactacg ccctgatcgg cgcactgcga    480

gcagtagccc aaacaatctc atatgaagtc accctagcca tcattctact atcaacatta    540

ctaatgagtg gctcctttaa cctctccacc cttatcacaa cacaagaaca cctctggtta    600

ctcctgccat catggccctt ggccatgatg tggtttatct ccacactagc agagaccaac    660

cgaaccccct tcgaccttgc cgaaggggag tccgaactag tctcaggctt caacatcgaa    720

tacgccgcag gccccttcgc cctattcttc atggccgaat acacaaacat tattatgatg    780

aacaccctca ccactacaat cttcctagga acaacatatg acgcactctc ccctgaactc    840

tacacaacat attttgtcac caagacccta cttctaacct ccctgttctt atggattcga    900

acagcatacc cccgattccg ctacgaccaa ctcatgcacc tcctatggaa aaacttccta    960

ccactcaccc tagcattact tatgtggtat gtctccatgc ccattacaat ctccagcatt   1020

ccccctcaaa cctaagagca ctgggacgcc caccgcccct ttccctccgc tgccaggcga   1080
```

gcatgttgtg gtaattctgg aacacaagaa gagaaattgc tgggtttaga acaagattat 1140
aaacgaattc ggtgctcagt gatcacttga cagttttttt tttttttaaa tattacccaa 1200
aatgctcccc aaataagaaa tgcatcagct cagtcagtga atacaaaaaa ggaattattt 1260
ttccctttga gggtctttta tacatctctc ctccaacccc accctctatt ctgtttcttc 1320
ctcctcacat gggggtacac atacacagct tcctcttttg gttccatcct taccaccaca 1380
ccacacgcac actccacatg cccagcagag tggcacttgg tggccagaaa gtgtgagcct 1440
catgatctgc tgtctgtagt tctgtgagct caggtccctc aaaggcctcg gagcaccccc 1500
ttccttgtga ctgagccagg gcctgcattt ttggttttcc ccaccccaca cattctcaac 1560
catagtcctt ctaacaatac caatagctag gacccggctg ctgtgcactg ggactgggga 1620
ttccacatgt ttgccttggg agtctcaagc tggactgcca gcccctgtcc tcccttcacc 1680
cccattgcgt atgagcattt cagaactcca aggagtcaca ggcatcttta tagttcacgt 1740
taacatatag acactgttgg aagcagttcc ttctaaaagg gtagccctgg acttaatacc 1800
agccggatac ctctggcccc caccccatta ctgtacctct ggagtcacta ctgtgggtcg 1860
ccactcctct gctacacagc acggcttttt caaggctgta ttgagaaggg aagttaggaa 1920
gaagggtgtg ctgggctaac cagcccacag agctcacatt cctgtccctt gggtgaaaaa 1980
tacatgtcca tcctgatatc tcctgaattc agaaattagc ctccacatgt gcaatggctt 2040
taagagccag aagcagggtt ctgggaattt tgcaagttac ctgtggccag gtgtggtctc 2100
ggttaccaaa tacggttacc tgcagctttt tagtcctttg tgctcccacg ggtctacaga 2160
gtcccatctg cccaaaggtc ttgaagcttg acaggatgtt ttcgattact cagtctccca 2220
gggcactact ggtccgtagg attcgattgg tcggggtagg agagttaaac aacatttaaa 2280
cagagttctc tcaaaaatgt ctaaagggat tgtaggtaga taacatccaa tcactgtttg 2340
cacttatctg aaatcttccc tcttggctgc ccccaggtat ttactgtgga gaacattgca 2400
taggaatgtc tggaaaaagc ttctacaact tgttacagcc ttcacatttg tagaagcttt 2460

<210> SEQ ID NO 26
<211> LENGTH: 1660
<212> TYPE: DNA
<213> ORGANISM: Artificial Sequence
<220> FEATURE:
<223> OTHER INFORMATION: COX10-ND1-3'UTR*

<400> SEQUENCE: 26
atggccgcat ctccgcacac tctctcctca cgcctcctga caggttgcgt aggaggctct 60
gtctggtatc ttgaaagaag aactatggcc aacctcctac tcctcattgt acccattcta 120
atcgcaatgg cattcctaat gcttaccgaa cgaaaaattc taggctatat gcaactacgc 180
aaaggcccca acgttgtagg cccctacggg ctactacaac ccttcgctga cgccataaaa 240
ctcttcacca aagagcccct aaaacccgcc acatctacca tcaccctcta catcaccgcc 300
ccgaccttag ctctcaccat cgctcttcta ctatggaccc ccctccccat gcccaacccc 360
ctggtcaacc tcaacctagg cctcctattt attctagcca cctctagcct agccgtttac 420
tcaatcctct ggtcagggtg ggcatcaaac tcaaactacg ccctgatcgg cgcactgcga 480
gcagtagccc aaacaatctc atatgaagtc accctagcca tcattctact atcaacatta 540
ctaatgagtg gctcctttaa cctctccacc cttatcacaa cacaagaaca cctctggtta 600
ctcctgccat catggccctt ggccatgatg tggtttatct ccacactagc agagaccaac 660

```
cgaaccccct tcgaccttgc cgaaggggag tccgaactag tctcaggctt caacatcgaa    720

tacgccgcag gccccttcgc cctattcttc atggccgaat acacaaacat tattatgatg    780

aacaccctca ccactacaat cttcctagga acaacatatg acgcactctc ccctgaactc    840

tacacaacat attttgtcac caagacccta cttctaacct ccctgttctt atggattcga    900

acagcatacc cccgattccg ctacgaccaa ctcatgcacc tcctatggaa aaacttccta    960

ccactcaccc tagcattact tatgtggtat gtctccatgc ccattacaat ctccagcatt   1020

ccccctcaaa cctaagagca ctgggacgcc caccgcccct ttccctccgc tgccaggcga   1080

gcatgttgtg gtaattctgg aacacaagaa gagaaattgc tgggtttaga acaagattat   1140

aaacgaattc ggtgctcagt gatcacttga cagttttttt tttttttaaa tattacccaa   1200

aatgctcccc aaataagaaa tgcatcagct cagtcagtga atacaaaaaa ggaattattt   1260

ttccctttga gggtctttta tacatctctc ctccaacccc accctctatt ctgtttcttc   1320

ctcctcacat gggggtacac atacacagct tcctcttttg gttccatcct taccaccaca   1380

ccacacgcac actccacatg cccagcagag tggcacttgg tggccagaaa gtgtgagcct   1440

catgatctgc tgtctgtagt tctgtgagct caggtccctc aaaggcctcg gagcaccccc   1500

ttccttgtga ctgagccagg gcctgcattt ttggttttcc ccaccccaca cattctcaac   1560

catagtcctt ctaacaatac caatagctag gacccggctg ctgtgcactg ggactgggga   1620

ttccacatgt ttgccttggg agtctcaagc tggactgcca                         1660
```

<210> SEQ ID NO 27
<211> LENGTH: 2460
<212> TYPE: DNA
<213> ORGANISM: Artificial Sequence
<220> FEATURE:
<223> OTHER INFORMATION: COX10-opt_ND1-3'UTR

<400> SEQUENCE: 27

```
atggccgcat ctccgcacac tctctcctca cgcctcctga caggttgcgt aggaggctct     60

gtctggtatc ttgaaagaag aactatggcc aacctgctgc tgctgatcgt gcccatcctg    120

atcgccatgg ccttcctgat gctgaccgag cgcaagatcc tgggctacat gcagctgcgc    180

aagggcccca acgtggtggg cccctacggc ctgctgcagc ccttcgccga cgccatcaag    240

ctgttcacca aggagcccct gaagcccgcc accagcacca tcaccctgta catcaccgcc    300

cccaccctgg ccctgaccat cgccctgctg ctgtggaccc ccctgcccat gcccaacccc    360

ctggtgaacc tgaacctggg cctgctgttc atcctggcca ccagcagcct ggccgtgtac    420

agcatcctgt ggagcggctg ggccagcaac agcaactacg ccctgatcgg cgccctgcgc    480

gccgtggccc agaccatcag ctacgaggtg accctggcca tcatcctgct gagcaccctg    540

ctgatgagcg gcagcttcaa cctgagcacc ctgatcacca cccaggagca cctgtggctg    600

ctgctgccca gctggcccct ggccatgatg tggttcatca gcaccctggc cgagaccaac    660

cgcaccccct tcgacctggc cgagggcgag agcgagctgg tgagcggctt caacatcgag    720

tacgccgccg gccccttcgc cctgttcttc atggccgagt acaccaacat catcatgatg    780

aacaccctga ccaccaccat cttcctgggc accacctacg acgccctgag ccccgagctg    840

tacaccacct acttcgtgac caagaccctg ctgctgacca gcctgttcct gtggatccgc    900

accgcctacc cccgcttccg ctacgaccag ctgatgcacc tgctgtggaa gaacttcctg    960

cccctgaccc tggccctgct gatgtggtac gtgagcatgc ccatcaccat cagcagcatc   1020

cccccccaga cctaagagca ctgggacgcc caccgcccct ttccctccgc tgccaggcga   1080
```

-continued

```
gcatgttgtg gtaattctgg aacacaagaa gagaaattgc tgggtttaga acaagattat   1140

aaacgaattc ggtgctcagt gatcacttga cagttttttt tttttttaaa tattacccaa   1200

aatgctcccc aaataagaaa tgcatcagct cagtcagtga atacaaaaaa ggaattattt   1260

ttccctttga gggtctttta tacatctctc ctccaacccc accctctatt ctgtttcttc   1320

ctcctcacat gggggtacac atacacagct tcctcttttg gttccatcct taccaccaca   1380

ccacacgcac actccacatg cccagcagag tggcacttgg tggccagaaa gtgtgagcct   1440

catgatctgc tgtctgtagt tctgtgagct caggtccctc aaaggcctcg gagcaccccc   1500

ttccttgtga ctgagccagg gcctgcattt ttggttttcc ccaccccaca cattctcaac   1560

catagtcctt ctaacaatac caatagctag gacccggctg ctgtgcactg ggactgggga   1620

ttccacatgt ttgccttggg agtctcaagc tggactgcca gcccctgtcc tcccttcacc   1680

cccattgcgt atgagcattt cagaactcca aggagtcaca ggcatcttta tagttcacgt   1740

taacatatag acactgttgg aagcagttcc ttctaaaagg gtagccctgg acttaatacc   1800

agccggatac ctctggcccc caccccatta ctgtacctct ggagtcacta ctgtgggtcg   1860

ccactcctct gctacacagc acggcttttt caaggctgta ttgagaaggg aagttaggaa   1920

gaagggtgtg ctgggctaac cagcccacag agctcacatt cctgtccctt gggtgaaaaa   1980

tacatgtcca tcctgatatc tcctgaattc agaaattagc ctccacatgt gcaatggctt   2040

taagagccag aagcagggtt ctgggaattt tgcaagttac ctgtggccag gtgtggtctc   2100

ggttaccaaa tacggttacc tgcagctttt tagtcctttg tgctcccacg ggtctacaga   2160

gtcccatctg cccaaaggtc ttgaagcttg acaggatgtt ttcgattact cagtctccca   2220

gggcactact ggtccgtagg attcgattgg tcggggtagg agagttaaac aacatttaaa   2280

cagagttctc tcaaaaatgt ctaaagggat tgtaggtaga taacatccaa tcactgtttg   2340

cacttatctg aaatcttccc tcttggctgc ccccaggtat ttactgtgga gaacattgca   2400

taggaatgtc tggaaaaagc ttctacaact tgttacagcc ttcacatttg tagaagcttt   2460

<210> SEQ ID NO 28
<211> LENGTH: 1660
<212> TYPE: DNA
<213> ORGANISM: Artificial Sequence
<220> FEATURE:
<223> OTHER INFORMATION: COX10-opt_ND1-3'UTR*

<400> SEQUENCE: 28

atggccgcat ctccgcacac tctctcctca cgcctcctga caggttgcgt aggaggctct     60

gtctggtatc ttgaaagaag aactatggcc aacctgctgc tgctgatcgt gcccatcctg    120

atcgccatgg ccttcctgat gctgaccgag cgcaagatcc tgggctacat gcagctgcgc    180

aagggcccca acgtggtggg cccctacggc ctgctgcagc ccttcgccga cgccatcaag    240

ctgttcacca aggagcccct gaagcccgcc accagcacca tcaccctgta catcaccgcc    300

cccaccctgg ccctgaccat cgccctgctg ctgtggaccc ccctgcccat gcccaacccc    360

ctggtgaacc tgaacctggg cctgctgttc atcctggcca ccagcagcct ggccgtgtac    420

agcatcctgt ggagcggctg ggccagcaac agcaactacg ccctgatcgg cgccctgcgc    480

gccgtggccc agaccatcag ctacgaggtg accctggcca tcatcctgct gagcaccctg    540

ctgatgagcg gcagcttcaa cctgagcacc ctgatcacca cccaggagca cctgtggctg    600

ctgctgccca gctggcccct ggccatgatg tggttcatca gcaccctggc cgagaccaac    660
```

```
cgcacccccct tcgacctggc cgagggcgag agcgagctgg tgagcggctt caacatcgag    720

tacgccgccg gccccttcgc cctgttcttc atggccgagt acaccaacat catcatgatg    780

aacaccctga ccaccaccat cttcctgggc accacctacg acgccctgag ccccgagctg    840

tacaccacct acttcgtgac caagaccctg ctgctgacca gcctgttcct gtggatccgc    900

accgcctacc cccgcttccg ctacgaccag ctgatgcacc tgctgtggaa gaacttcctg    960

cccctgaccc tggccctgct gatgtggtac gtgagcatgc ccatcaccat cagcagcatc   1020

ccccccccaga cctaagagca ctgggacgcc caccgcccct ttccctccgc tgccaggcga   1080

gcatgttgtg gtaattctgg aacacaagaa gagaaattgc tgggtttaga acaagattat   1140

aaacgaattc ggtgctcagt gatcacttga cagttttttt ttttttttaaa tattacccaa   1200

aatgctcccc aaataagaaa tgcatcagct cagtcagtga atacaaaaaa ggaattattt   1260

ttccctttga gggtctttta tacatctctc ctccaacccc accctctatt ctgtttcttc   1320

ctcctcacat gggggtacac atacacagct tcctcttttg gttccatcct taccaccaca   1380

ccacacgcac actccacatg cccagcagag tggcacttgg tggccagaaa gtgtgagcct   1440

catgatctgc tgtctgtagt tctgtgagct caggtccctc aaaggcctcg gagcaccccc   1500

ttccttgtga ctgagccagg gcctgcattt ttggttttcc ccaccccaca cattctcaac   1560

catagtcctt ctaacaatac caatagctag gacccggctg ctgtgcactg ggactgggga   1620

ttccacatgt ttgccttggg agtctcaagc tggactgcca                         1660
```

<210> SEQ ID NO 29
<211> LENGTH: 2889
<212> TYPE: DNA
<213> ORGANISM: Artificial Sequence
<220> FEATURE:
<223> OTHER INFORMATION: opt_COX10-ND4-3'UTR

<400> SEQUENCE: 29

```
atggccgcct ctccacacac actgagtagc agactgctga ccggctgtgt tggcggctct     60

gtgtggtatc tggaacggcg gacaatgcta aaactaatcg tcccaacaat tatgttacta    120

ccactgacat ggctttccaa aaaacacatg atttggatca acacaaccac ccacagccta    180

attattagca tcatccctct actatttttt aaccaaatca acaacaacct atttagctgt    240

tccccaacct tttcctccga ccccctaaca accccccctcc taatgctaac tacctggctc    300

ctacccctca caatcatggc aagccaacgc cacttatcca gtgaaccact atcacgaaaa    360

aaactctacc tctctatgct aatctcccta caaatctcct taattatgac attcacagcc    420

acagaactaa tcatgtttta tatcttcttc gaaaccacac ttatccccac cttggctatc    480

atcacccgat ggggcaacca gccagaacgc ctgaacgcag gcacatactt cctattctac    540

accctagtag gctcccttcc cctactcatc gcactaattt acactcacaa caccctaggc    600

tcactaaaca ttctactact cactctcact gcccaagaac tatcaaactc ctgggccaac    660

aacttaatgt ggctagctta cacaatggct tttatggtaa agatgcctct ttacggactc    720

cacttatggc tccctaaagc ccatgtcgaa gcccccatcg ctgggtcaat ggtacttgcc    780

gcagtactct taaaactagg cggctatggt atgatgcgcc tcacactcat tctcaacccc    840

ctgacaaaac acatggccta ccccttcctt gtactatccc tatggggcat gattatgaca    900

agctccatct gcctacgaca aacagaccta aaatcgctca ttgcatactc ttcaatcagc    960

cacatggccc tcgtagtaac agccattctc atccaaaccc cctggagctt caccggcgca   1020

gtcattctca tgatcgccca cgggcttaca tcctcattac tattctgcct agcaaactca   1080
```

aactacgaac gcactcacag tcgcatcatg atcctctctc aaggacttca aactctactc 1140
ccactaatgg ctttttggtg gcttctagca agcctcgcta acctcgcctt accccccact 1200
attaacctac tgggagaact ctctgtgcta gtaaccacgt tctcctggtc aaatatcact 1260
ctcctactta caggactcaa catgctagtc acagccctat actccctcta catgtttacc 1320
acaacacaat ggggctcact cacccaccac attaacaaca tgaaaccctc attcacacga 1380
gaaaacaccc tcatgttcat gcacctatcc cccattctcc tcctatccct caaccccgac 1440
atcattaccg ggttttcctc ttaagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt ttttttaaat 1620
attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgccag cccctgtcct 2100
cccttcaccc ccattgcgta tgagcatttc agaactccaa ggagtcacag gcatctttat 2160
agttcacgtt aacatataga cactgttgga agcagttcct tctaaaaggg tagccctgga 2220
cttaatacca gccggatacc tctggccccc accccattac tgtacctctg gagtcactac 2280
tgtgggtcgc cactcctctg ctacacagca cggcttttc aaggctgtat tgagaaggga 2340
agttaggaag aagggtgtgc tgggctaacc agcccacaga gctcacattc ctgtcccttg 2400
ggtgaaaaat acatgtccat cctgatatct cctgaattca gaaattagcc tccacatgtg 2460
caatggcttt aagagccaga agcagggttc tgggaatttt gcaagttacc tgtggccagg 2520
tgtggtctcg gttaccaaat acggttacct gcagcttttt agtcctttgt gctcccacgg 2580
gtctacagag tcccatctgc ccaaaggtct tgaagcttga caggatgttt tcgattactc 2640
agtctcccag ggcactactg gtccgtagga ttcgattggt cggggtagga gagttaaaca 2700
acatttaaac agagttctct caaaaatgtc taaagggatt gtaggtagat aacatccaat 2760
cactgtttgc acttatctga aatcttccct cttggctgcc cccaggtatt tactgtggag 2820
aacattgcat aggaatgtct ggaaaaagct tctacaactt gttacagcct tcacatttgt 2880
agaagcttt 2889

<210> SEQ ID NO 30
<211> LENGTH: 2089
<212> TYPE: DNA
<213> ORGANISM: Artificial Sequence
<220> FEATURE:
<223> OTHER INFORMATION: opt_COX10-ND4-3'UTR*

<400> SEQUENCE: 30
atggccgcct ctccacacac actgagtagc agactgctga ccggctgtgt tggcggctct 60
gtgtggtatc tggaacggcg gacaatgcta aaactaatcg tcccaacaat tatgttacta 120
ccactgacat ggctttccaa aaaacacatg atttggatca acacaaccac ccacagccta 180

```
attattagca tcatccctct actatttttt aaccaaatca acaacaacct atttagctgt    240
tccccaacct tttcctccga ccccctaaca accccccctcc taatgctaac tacctggctc    300
ctacccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cggcttaca tcctcattac tattctgcct agcaaactca   1080
aactacgaac gcactcacag tcgcatcatg atcctctctc aaggacttca aactctactc   1140
ccactaatgg ctttttggtg gcttctagca agcctcgcta acctcgcctt acccccccact   1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agttttttttt tttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgcca                2089
```

<210> SEQ ID NO 31
<211> LENGTH: 2889
<212> TYPE: DNA
<213> ORGANISM: Artificial Sequence
<220> FEATURE:
<223> OTHER INFORMATION: opt_COX10-opt_ND4-3'UTR

<400> SEQUENCE: 31

```
atggccgcct ctccacacac actgagtagc agactgctga ccggctgtgt tggcggctct     60
gtgtggtatc tggaacggcg gacaatgctg aagctgatcg tgcccaccat catgctgctg    120
cctctgacct ggctgagcaa gaaacacatg atctggatca acaccaccac gcacagcctg    180
```

```
atcatcagca tcatccctct gctgttcttc aaccagatca acaacaacct gttcagctgc    240
agccccacct tcagcagcga ccctctgaca acacctctgc tgatgctgac cacctggctg    300
ctgcccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catctttttc gagacaacgc tgatccccac actggccatc    480
atcaccagat ggggcaacca gcctgagaga ctgaacgccg gcacctactt tctgttctac    540
accctcgtgg gcagcctgcc actgctgatt gccctgatct acacccacaa caccctgggc    600
tccctgaaca tcctgctgct gacactgaca gcccaagagc tgagcaacag ctgggccaac    660
aatctgatgt ggctggccta cacaatggcc ttcatggtca agatgcccct gtacggcctg    720
cacctgtggc tgcctaaagc tcatgtggaa gcccctatcg ccggctctat ggtgctggct    780
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt tacaggcgcc   1020
gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg ctttttggtg gctgctggcc tctctggcca atctggcact gcctcctacc   1200
atcaatctgc tgggcgagct gagcgtgctg gtcaccacat tcagctggtc caatatcacc   1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt tttttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgccag cccctgtcct   2100
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
```

-continued

```
tgtggtctcg gttaccaaat acggttacct gcagcttttt agtcctttgt gctcccacgg   2580

gtctacagag tcccatctgc ccaaaggtct tgaagcttga caggatgttt tcgattactc   2640

agtctcccag ggcactactg gtccgtagga ttcgattggt cggggtagga gagttaaaca   2700

acatttaaac agagttctct caaaaatgtc taaagggatt gtaggtagat aacatccaat   2760

cactgtttgc acttatctga aatcttccct cttggctgcc cccaggtatt tactgtggag   2820

aacattgcat aggaatgtct ggaaaaagct tctacaactt gttacagcct tcacatttgt   2880

agaagcttt                                                           2889
```

<210> SEQ ID NO 32
<211> LENGTH: 2089
<212> TYPE: DNA
<213> ORGANISM: Artificial Sequence
<220> FEATURE:
<223> OTHER INFORMATION: opt_COX10-opt_ND4-3'UTR*

<400> SEQUENCE: 32

```
atggccgcct ctccacacac actgagtagc agactgctga ccggctgtgt tggcggctct     60

gtgtggtatc tggaacggcg gacaatgctg aagctgatcg tgcccaccat catgctgctg    120

cctctgacct ggctgagcaa gaaacacatg atctggatca acaccaccac gcacagcctg    180

atcatcagca tcatccctct gctgttcttc aaccagatca acaacaacct gttcagctgc    240

agccccacct tcagcagcga ccctctgaca acacctctgc tgatgctgac cacctggctg    300

ctgcccctca caatcatggc ctctcagaga cacctgagca gcgagcccct gagccggaag    360

aaactgtacc tgagcatgct gatctccctg cagatctctc tgatcatgac cttcaccgcc    420

accgagctga tcatgttcta catctttttc gagacaacgc tgatccccac actggccatc    480

atcaccagat ggggcaacca gcctgagaga ctgaacgccg gcacctactt tctgttctac    540

accctcgtgg gcagcctgcc actgctgatt gccctgatct acacccacaa caccctgggc    600

tccctgaaca tcctgctgct gacactgaca gcccaagagc tgagcaacag ctgggccaac    660

aatctgatgt ggctggccta cacaatggcc ttcatggtca agatgcccct gtacggcctg    720

cacctgtggc tgcctaaagc tcatgtggaa gcccctatcg ccggctctat ggtgctggct    780

gcagtgctgc tgaaactcgg cggctacggc atgatgcggc tgaccctgat tctgaatccc    840

ctgaccaagc acatggccta tccatttctg gtgctgagcc tgtggggcat gattatgacc    900

agcagcatct gcctgcggca gaccgatctg aagtccctga tcgcctacag ctccatcagc    960

cacatggccc tggtggtcac cgccatcctg attcagaccc cttggagctt tacaggcgcc   1020

gtgatcctga tgattgccca cggcctgaca agcagcctgc tgttttgtct ggccaacagc   1080

aactacgagc ggacccacag cagaatcatg atcctgtctc agggcctgca gaccctcctg   1140

cctcttatgg ctttttggtg gctgctggcc tctctggcca atctggcact gcctcctacc   1200

atcaatctgc tgggcgagct gagcgtgctg gtcaccacat tcagctggtc caatatcacc   1260

ctgctgctca ccggcctgaa catgctggtt acagccctgt actccctgta catgttcacc   1320

accacacagt ggggaagcct gacacaccac atcaacaata tgaagcccag cttcacccgc   1380

gagaacaccc tgatgttcat gcatctgagc cccattctgc tgctgtccct gaatcctgat   1440

atcatcaccg gcttctccag ctgagagcac tgggacgccc accgcccctt tccctccgct   1500

gccaggcgag catgttgtgg taattctgga acacaagaag agaaattgct gggtttagaa   1560

caagattata aacgaattcg gtgctcagtg atcacttgac agtttttttt ttttttaaat   1620

attacccaaa atgctcccca aataagaaat gcatcagctc agtcagtgaa tacaaaaaag   1680
```

gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

<210> SEQ ID NO 33
<211> LENGTH: 2889
<212> TYPE: DNA
<213> ORGANISM: Artificial Sequence
<220> FEATURE:
<223> OTHER INFORMATION: opt_COX10-opt_ND4*-3'UTR

<400> SEQUENCE: 33
atggccgcct ctccacacac actgagtagc agactgctga ccggctgtgt tggcggctct 60
gtgtggtatc tggaacggcg gacaatgctg aagctgatcg tgcccaccat catgctgctg 120
cccctgacct ggctgagcaa gaagcacatg atctggatca acaccaccac ccacagcctg 180
atcatcagca tcatcccccct gctgttcttc aaccagatca acaacaacct gttcagctgc 240
agccccacct tcagcagcga ccccctgacc accccccctgc tgatgctgac cacctggctg 300
ctgcccctga ccatcatggc cagccagcgc cacctgagca gcgagcccct gagccgcaag 360
aagctgtacc tgagcatgct gatcagcctg cagatcagcc tgatcatgac cttcaccgcc 420
accgagctga tcatgttcta catcttcttc gagaccaccc tgatccccac cctggccatc 480
atcacccgct ggggcaacca gcccgagcgc ctgaacgccg gcacctactt cctgttctac 540
accctggtgg gcagcctgcc cctgctgatc gccctgatct acacccacaa caccctgggc 600
agcctgaaca tcctgctgct gaccctgacc gcccaggagc tgagcaacag ctgggccaac 660
aacctgatgt ggctggccta caccatggcc ttcatggtga agatgcccct gtacggcctg 720
cacctgtggc tgcccaaggc ccacgtggag gcccccatcg ccggcagcat ggtgctggcc 780
gccgtgctgc tgaagctggg cggctacggc atgatgcgcc tgaccctgat cctgaacccc 840
ctgaccaagc acatggccta ccccttcctg gtgctgagcc tgtggggcat gatcatgacc 900
agcagcatct gcctgcgcca gaccgacctg aagagcctga tcgcctacag cagcatcagc 960
cacatggccc tggtggtgac cgccatcctg atccagaccc cctggagctt caccggcgcc 1020
gtgatcctga tgatcgccca cggcctgacc agcagcctgc tgttctgcct ggccaacagc 1080
aactacgagc gcacccacag ccgcatcatg atcctgagcc agggcctgca gaccctgctg 1140
cccctgatgg ccttctggtg gctgctggcc agcctggcca acctggccct gccccccacc 1200
atcaacctgc tgggcgagct gagcgtgctg gtgaccacct tcagctggag caacatcacc 1260
ctgctgctga ccggcctgaa catgctggtg accgccctgt acagcctgta catgttcacc 1320
accacccagt ggggcagcct gacccaccac atcaacaaca tgaagcccag cttcacccgc 1380
gagaacaccc tgatgttcat gcacctgagc cccatcctgc tgctgagcct gaaccccgac 1440
atcatcaccg gcttcagcag ctaagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt tttttaaat 1620 attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgccag cccctgtcct 2100
cccttcaccc ccattgcgta tgagcatttc agaactccaa ggagtcacag gcatctttat 2160
agttcacgtt aacatataga cactgttgga agcagttcct tctaaaaggg tagccctgga 2220
cttaatacca gccggatacc tctggccccc accccattac tgtacctctg gagtcactac 2280
tgtgggtcgc cactcctctg ctacacagca cggctttttc aaggctgtat tgagaaggga 2340
agttaggaag aagggtgtgc tgggctaacc agcccacaga gctcacattc ctgtcccttg 2400
ggtgaaaaat acatgtccat cctgatatct cctgaattca gaaattagcc tccacatgtg 2460
caatggcttt aagagccaga agcagggttc tgggaatttt gcaagttacc tgtggccagg 2520
tgtggtctcg gttaccaaat acggttacct gcagcttttt agtcctttgt gctcccacgg 2580
gtctacagag tcccatctgc ccaaaggtct tgaagcttga caggatgttt tcgattactc 2640
agtctcccag ggcactactg gtccgtagga ttcgattggt cggggtagga gagttaaaca 2700
acatttaaac agagttctct caaaaatgtc taaagggatt gtaggtagat aacatccaat 2760
cactgtttgc acttatctga aatcttccct cttggctgcc cccaggtatt tactgtggag 2820
aacattgcat aggaatgtct ggaaaaagct tctacaactt gttacagcct tcacatttgt 2880
agaagcttt 2889

<210> SEQ ID NO 34
<211> LENGTH: 2089
<212> TYPE: DNA
<213> ORGANISM: Artificial Sequence
<220> FEATURE:
<223> OTHER INFORMATION: opt_COX10-opt_ND4*-3'UTR*

<400> SEQUENCE: 34
atggccgcct ctccacacac actgagtagc agactgctga ccggctgtgt tggcggctct 60
gtgtggtatc tggaacggcg gacaatgctg aagctgatcg tgcccaccat catgctgctg 120
cccctgacct ggctgagcaa gaagcacatg atctggatca acaccaccac ccacagcctg 180
atcatcagca tcatcccct gctgttcttc aaccagatca acaacaacct gttcagctgc 240
agccccacct tcagcagcga ccccctgacc accccctgc tgatgctgac cacctggctg 300
ctgcccctga ccatcatggc cagccagcgc cacctgagca gcgagcccct gagccgcaag 360
aagctgtacc tgagcatgct gatcagcctg cagatcagcc tgatcatgac cttcaccgcc 420
accgagctga tcatgttcta catcttcttc gagaccaccc tgatccccac cctggccatc 480
atcacccgct ggggcaacca gcccgagcgc ctgaacgccg gcacctactt cctgttctac 540
accctggtgg gcagcctgcc cctgctgatc gccctgatct acacccacaa caccctgggc 600
agcctgaaca tcctgctgct gaccctgacc gcccaggagc tgagcaacag ctgggccaac 660
aacctgatgt ggctggccta caccatggcc ttcatggtga agatgcccct gtacggcctg 720
cacctgtggc tgcccaaggc ccacgtggag gcccccatcg ccggcagcat ggtgctggcc 780

```
gccgtgctgc tgaagctggg cggctacggc atgatgcgcc tgaccctgat cctgaacccc    840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gcccccccacc   1200
atcaacctgc tgggcgagct gagcgtgctg gtgaccacct tcagctggag caacatcacc   1260
ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt tttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgcca               2089
```

<210> SEQ ID NO 35
<211> LENGTH: 2034
<212> TYPE: DNA
<213> ORGANISM: Artificial Sequence
<220> FEATURE:
<223> OTHER INFORMATION: opt_COX10-ND6-3'UTR

<400> SEQUENCE: 35

```
atggccgcct ctccacacac actgagtagc agactgctga ccggctgtgt tggcggctct     60
gtgtggtatc tggaacggcg gacaatgatg tatgctttgt ttctgttgag tgtgggttta    120
gtaatggggt ttgtggggtt ttcttctaag ccttctccta tttatggggg tttagtattg    180
attgttagcg gtgtggtcgg gtgtgttatt attctgaatt ttgggggagg ttatatgggt    240
ttaatggttt ttttaattta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agaggggtca    480
gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc ccctttccct ccgctgccag gcgagcatgt    660
tgtggtaatt ctggaacaca agaagagaaa ttgctgggtt tagaacaaga ttataaacga    720
```

```
attcggtgct cagtgatcac ttgacagttt tttttttttt taaatattac ccaaaatgct    780

ccccaaataa gaaatgcatc agctcagtca gtgaatacaa aaaaggaatt atttttccct    840

ttgagggtct tttatacatc tctcctccaa ccccaccctc tattctgttt cttcctcctc    900

acatgggggt acacatacac agcttcctct tttggttcca tccttaccac cacaccacac    960

gcacactcca catgcccagc agagtggcac ttggtggcca gaaagtgtga gcctcatgat   1020

ctgctgtctg tagttctgtg agctcaggtc cctcaaaggc ctcggagcac ccccttcctt   1080

gtgactgagc cagggcctgc atttttggtt ttccccaccc cacacattct caaccatagt   1140

ccttctaaca ataccaatag ctaggacccg gctgctgtgc actgggactg gggattccac   1200

atgtttgcct tgggagtctc aagctggact gccagcccct gtcctccctt cacccccatt   1260

gcgtatgagc atttcagaac tccaaggagt cacaggcatc tttatagttc acgttaacat   1320

atagacactg ttggaagcag ttccttctaa aagggtagcc ctggacttaa taccagccgg   1380

atacctctgg cccccacccc attactgtac ctctggagtc actactgtgg gtcgccactc   1440

ctctgctaca cagcacggct ttttcaaggc tgtattgaga agggaagtta ggaagaaggg   1500

tgtgctgggc taaccagccc acagagctca cattcctgtc ccttgggtga aaaatacatg   1560

tccatcctga tatctcctga attcagaaat tagcctccac atgtgcaatg gctttaagag   1620

ccagaagcag ggttctggga attttgcaag ttacctgtgg ccaggtgtgg tctcggttac   1680

caaatacggt tacctgcagc tttttagtcc tttgtgctcc cacgggtcta cagagtccca   1740

tctgcccaaa ggtcttgaag cttgacagga tgttttcgat tactcagtct cccagggcac   1800

tactggtccg taggattcga ttggtcgggg taggagagtt aaacaacatt taaacagagt   1860

tctctcaaaa atgtctaaag ggattgtagg tagataacat ccaatcactg tttgcactta   1920

tctgaaatct tccctcttgg ctgcccccag gtatttactg tggagaacat tgcataggaa   1980

tgtctggaaa aagcttctac aacttgttac agccttcaca tttgtagaag cttt         2034
```

<210> SEQ ID NO 36
<211> LENGTH: 1234
<212> TYPE: DNA
<213> ORGANISM: Artificial Sequence
<220> FEATURE:
<223> OTHER INFORMATION: opt_COX10-ND6-3'UTR*

<400> SEQUENCE: 36

```
atggccgcct ctccacacac actgagtagc agactgctga ccggctgtgt tggcggctct     60

gtgtggtatc tggaacggcg gacaatgatg tatgctttgt ttctgttgag tgtgggttta    120

gtaatggggt ttgtggggtt ttcttctaag ccttctccta tttatggggg tttagtattg    180

attgttagcg gtgtggtcgg gtgtgttatt attctgaatt ttgggggagg ttatatgggt    240

ttaatggttt ttttaattta tttaggggga atgatggttg tctttggata tactacagcg    300

atggctattg aggagtatcc tgaggcatgg gggtcagggg ttgaggtctt ggtgagtgtt    360

ttagtggggt tagcgatgga ggtaggattg gtgctgtggg tgaaagagta tgatggggtg    420

gtggttgtgg taaactttaa tagtgtagga agctggatga tttatgaagg agaggggtca    480

gggttgattc gggaggatcc tattggtgcg ggggctttgt atgattatgg gcgttggtta    540

gtagtagtta ctggttggac attgtttgtt ggtgtatata ttgtaattga gattgctcgg    600

gggaattagg agcactggga cgcccaccgc ccctttccct ccgctgccag gcgagcatgt    660

tgtggtaatt ctggaacaca agaagagaaa ttgctgggtt tagaacaaga ttataaacga    720

attcggtgct cagtgatcac ttgacagttt tttttttttt taaatattac ccaaaatgct    780
```

ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac cccccttcctt 1080 gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gcca 1234

<210> SEQ ID NO 37
<211> LENGTH: 2034
<212> TYPE: DNA
<213> ORGANISM: Artificial Sequence
<220> FEATURE:
<223> OTHER INFORMATION: opt_COX10-opt_ND6-3'UTR

<400> SEQUENCE: 37
atggccgcct ctccacacac actgagtagc agactgctga ccggctgtgt tggcggctct 60
gtgtggtatc tggaacggcg gacaatgatg tacgccctgt tcctgctgag cgtgggcctg 120
gtgatgggct tcgtgggctt cagcagcaag cccagcccca tctacggcgg cctggtgctg 180
atcgtgagcg gcgtggtggg ctgcgtgatc atcctgaact tcggcggcgg ctacatgggc 240
ctgatggtgt tcctgatcta cctgggcggc atgatggtgg tgttcggcta caccaccgcc 300
atggccatcg aggagtaccc cgaggcctgg ggcagcggcg tggaggtgct ggtgagcgtg 360
ctggtgggcc tggccatgga ggtgggcctg gtgctgtggg tgaaggagta cgacggcgtg 420
gtggtggtgg tgaacttcaa cagcgtgggc agctggatga tctacgaggg cgagggcagc 480
ggcctgatcc gcgaggaccc catcggcgcc ggcgccctgt acgactacgg ccgctggctg 540
gtggtggtga ccggctggac cctgttcgtg ggcgtgtaca tcgtgatcga gatcgcccgc 600
ggcaactaag agcactggga cgcccaccgc ccctttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac cccccttcctt 1080 gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gccagcccct gtcctccctt cacccccatt 1260
gcgtatgagc atttcagaac tccaaggagt cacaggcatc tttatagttc acgttaacat 1320
atagacactg ttggaagcag ttccttctaa aagggtagcc ctggacttaa taccagccgg 1380
atacctctgg cccccacccc attactgtac ctctggagtc actactgtgg gtcgccactc 1440
ctctgctaca cagcacggct ttttcaaggc tgtattgaga agggaagtta ggaagaaggg 1500
tgtgctgggc taaccagccc acagagctca cattcctgtc ccttgggtga aaaatacatg 1560
tccatcctga tatctcctga attcagaaat tagcctccac atgtgcaatg gctttaagag 1620
ccagaagcag ggttctggga attttgcaag ttacctgtgg ccaggtgtgg tctcggttac 1680
caaatacggt tacctgcagc tttttagtcc tttgtgctcc cacgggtcta cagagtccca 1740
tctgcccaaa ggtcttgaag cttgacagga tgttttcgat tactcagtct cccagggcac 1800
tactggtccg taggattcga ttggtcgggg taggagagtt aaacaacatt taaacagagt 1860
tctctcaaaa atgtctaaag ggattgtagg tagataacat ccaatcactg tttgcactta 1920
tctgaaatct tccctcttgg ctgcccccag gtatttactg tggagaacat tgcataggaa 1980
tgtctggaaa aagcttctac aacttgttac agccttcaca tttgtagaag cttt 2034

<210> SEQ ID NO 38
<211> LENGTH: 1234
<212> TYPE: DNA
<213> ORGANISM: Artificial Sequence
<220> FEATURE:
<223> OTHER INFORMATION: opt_COX10-opt_ND6-3'UTR*

<400> SEQUENCE: 38
atggccgcct ctccacacac actgagtagc agactgctga ccggctgtgt tggcggctct 60
gtgtggtatc tggaacggcg gacaatgatg tacgccctgt tcctgctgag cgtgggcctg 120
gtgatgggct tcgtgggctt cagcagcaag cccagcccca tctacggcgg cctggtgctg 180
atcgtgagcg gcgtggtggg ctgcgtgatc atcctgaact tcggcggcgg ctacatgggc 240
ctgatggtgt tcctgatcta cctgggcggc atgatggtgg tgttcggcta caccaccgcc 300
atggccatcg aggagtaccc cgaggcctgg ggcagcggcg tggaggtgct ggtgagcgtg 360
ctggtgggcc tggccatgga ggtgggcctg gtgctgtggg tgaaggagta cgacggcgtg 420
gtggtggtgg tgaacttcaa cagcgtgggc agctggatga tctacgaggg cgagggcagc 480
ggcctgatcc gcgaggaccc catcggcgcc ggcgccctgt acgactacgg ccgctggctg 540
gtggtggtga ccggctggac cctgttcgtg ggcgtgtaca tcgtgatcga gatcgcccgc 600
ggcaactaag agcactggga cgcccaccgc ccctttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac ccccttcctt 1080
gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gcca 1234

<210> SEQ ID NO 39
<211> LENGTH: 2460
<212> TYPE: DNA
<213> ORGANISM: Artificial Sequence
<220> FEATURE:
<223> OTHER INFORMATION: opt_COX10-ND1-3'UTR

<400> SEQUENCE: 39
atggccgcct ctccacacac actgagtagc agactgctga ccggctgtgt tggcggctct 60

```
gtgtggtatc tggaacggcg gacaatggcc aacctcctac tcctcattgt acccattcta    120
atcgcaatgg cattcctaat gcttaccgaa cgaaaaattc taggctatat gcaactacgc    180
aaaggcccca acgttgtagg cccctacggg ctactacaac ccttcgctga cgccataaaa    240
ctcttcacca aagagcccct aaaacccgcc acatctacca tcaccctcta catcaccgcc    300
ccgaccttag ctctcaccat cgctcttcta ctatggaccc ccctccccat gcccaacccc    360
ctggtcaacc tcaacctagg cctcctattt attctagcca cctctagcct agccgtttac    420
tcaatcctct ggtcagggtg ggcatcaaac tcaaactacg ccctgatcgg cgcactgcga    480
gcagtagccc aaacaatctc atatgaagtc accctagcca tcattctact atcaacatta    540
ctaatgagtg gctcctttaa cctctccacc cttatcacaa cacaagaaca cctctggtta    600
ctcctgccat catggccctt ggccatgatg tggtttatct ccacactagc agagaccaac    660
cgaaccccct tcgaccttgc cgaaggggag tccgaactag tctcaggctt caacatcgaa    720
tacgccgcag gccccttcgc cctattcttc atggccgaat acacaaacat tattatgatg    780
aacaccctca ccactacaat cttcctagga acaacatatg acgcactctc ccctgaactc    840
tacacaacat attttgtcac caagacccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt   1020
ccccctcaaa cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt ttttttaaa tattacccaa   1200
aatgctcccc aaataagaaa tgcatcagct cagtcagtga atacaaaaaa ggaattattt   1260
ttccctttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca gcccctgtcc tcccttcacc   1680
cccattgcgt atgagcattt cagaactcca aggagtcaca ggcatcttta tagttcacgt   1740
taacatatag acactgttgg aagcagttcc ttctaaaagg gtagccctgg acttaatacc   1800
agccggatac ctctggcccc caccccatta ctgtacctct ggagtcacta ctgtgggtcg   1860
ccactcctct gctacacagc acggcttttt caaggctgta ttgagaaggg aagttaggaa   1920
gaagggtgtg ctgggctaac cagcccacag agctcacatt cctgtccctt gggtgaaaaa   1980
tacatgtcca tcctgatatc tcctgaattc agaaattagc ctccacatgt gcaatggctt   2040
taagagccag aagcagggtt ctgggaattt tgcaagttac ctgtggccag gtgtggtctc   2100
ggttaccaaa tacggttacc tgcagctttt tagtcctttg tgctcccacg ggtctacaga   2160
gtcccatctg cccaaaggtc ttgaagcttg acaggatgtt ttcgattact cagtctccca   2220
gggcactact ggtccgtagg attcgattgg tcggggtagg agagttaaac aacatttaaa   2280
cagagttctc tcaaaaatgt ctaaagggat tgtaggtaga taacatccaa tcactgtttg   2340
cacttatctg aaatcttccc tcttggctgc ccccaggtat ttactgtgga gaacattgca   2400
```

-continued taggaatgtc tggaaaaagc ttctacaact tgttacagcc ttcacatttg tagaagcttt 2460

<210> SEQ ID NO 40
<211> LENGTH: 1660
<212> TYPE: DNA
<213> ORGANISM: Artificial Sequence
<220> FEATURE:
<223> OTHER INFORMATION: opt_COX10-ND1-3'UTR*

<400> SEQUENCE: 40
atggccgcct ctccacacac actgagtagc agactgctga ccggctgtgt tggcggctct 60
gtgtggtatc tggaacggcg gacaatggcc aacctcctac tcctcattgt acccattcta 120
atcgcaatgg cattcctaat gcttaccgaa cgaaaaattc taggctatat gcaactacgc 180
aaaggcccca acgttgtagg cccctacggg ctactacaac ccttcgctga cgccataaaa 240
ctcttcacca aagagcccct aaaacccgcc acatctacca tcaccctcta catcaccgcc 300
ccgaccttag ctctcaccat cgctcttcta ctatggaccc ccctccccat gcccaacccc 360
ctggtcaacc tcaacctagg cctcctattt attctagcca cctctagcct agccgtttac 420
tcaatcctct ggtcagggtg ggcatcaaac tcaaactacg ccctgatcgg cgcactgcga 480
gcagtagccc aaacaatctc atatgaagtc accctagcca tcattctact atcaacatta 540
ctaatgagtg gctcctttaa cctctccacc cttatcacaa cacaagaaca cctctggtta 600
ctcctgccat catggccctt ggccatgatg tggtttatct ccacactagc agagaccaac 660 cgaacccccct tcgaccttgc cgaaggggag tccgaactag tctcaggctt caacatcgaa 720
tacgccgcag gccccttcgc cctattcttc atggccgaat acacaaacat tattatgatg 780
aacaccctca ccactacaat cttcctagga acaacatatg acgcactctc ccctgaactc 840
tacacaacat attttgtcac caagacccta cttctaacct ccctgttctt atggattcga 900
acagcatacc cccgattccg ctacgaccaa ctcatgcacc tcctatggaa aaacttccta 960
ccactcaccc tagcattact tatgtggtat gtctccatgc ccattacaat ctccagcatt 1020
ccccctcaaa cctaagagca ctgggacgcc caccgcccct ttccctccgc tgccaggcga 1080
gcatgttgtg gtaattctgg aacacaagaa gagaaattgc tgggtttaga acaagattat 1140
aaacgaattc ggtgctcagt gatcacttga cagttttttt tttttttaaa tattacccaa 1200
aatgctcccc aaataagaaa tgcatcagct cagtcagtga atacaaaaaa ggaattattt 1260
ttccctttga gggtctttta tacatctctc ctccaacccc accctctatt ctgtttcttc 1320
ctcctcacat gggggtacac atacacagct tcctcttttg gttccatcct taccaccaca 1380
ccacacgcac actccacatg cccagcagag tggcacttgg tggccagaaa gtgtgagcct 1440
catgatctgc tgtctgtagt tctgtgagct caggtccctc aaaggcctcg gagcaccccc 1500
ttccttgtga ctgagccagg gcctgcattt ttggttttcc ccacccccaca cattctcaac 1560 catagtcctt ctaacaatac caatagctag gacccggctg ctgtgcactg ggactgggga 1620
ttccacatgt ttgccttggg agtctcaagc tggactgcca 1660

<210> SEQ ID NO 41
<211> LENGTH: 2460
<212> TYPE: DNA
<213> ORGANISM: Artificial Sequence
<220> FEATURE:
<223> OTHER INFORMATION: opt_COX10-opt_ND1-3'UTR

<400> SEQUENCE: 41
atggccgcct ctccacacac actgagtagc agactgctga ccggctgtgt tggcggctct 60

```
gtgtggtatc tggaacggcg gacaatggcc aacctgctgc tgctgatcgt gcccatcctg    120
atcgccatgg ccttcctgat gctgaccgag cgcaagatcc tgggctacat gcagctgcgc    180
aagggcccca acgtggtggg cccctacggc ctgctgcagc ccttcgccga cgccatcaag    240
ctgttcacca aggagcccct gaagcccgcc accagcacca tcaccctgta catcaccgcc    300
cccaccctgg ccctgaccat cgccctgctg ctgtggaccc ccctgcccat gcccaacccc    360
ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660
cgcacccccct tcgacctggc cgagggcgag agcgagctgg tgagcggctt caacatcgag    720
tacgccgccg gccccttcgc cctgttcttc atggccgagt acaccaacat catcatgatg    780
aacaccctga ccaccaccat cttcctgggc accacctacg acgccctgag ccccgagctg    840
tacaccacct acttcgtgac caagaccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020
ccccccccaga cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt tttttttaaa tattacccaa   1200
aatgctcccc aaataagaaa tgcatcagct cagtcagtga atacaaaaaa ggaattattt   1260
ttccctttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccacccccaca cattctcaac   1560
catagtcctt ctaacaatac caatagctag gacccggctg ctgtgcactg ggactgggga   1620
ttccacatgt ttgccttggg agtctcaagc tggactgcca gcccctgtcc tcccttcacc   1680
cccattgcgt atgagcattt cagaactcca aggagtcaca ggcatcttta tagttcacgt   1740
taacatatag acactgttgg aagcagttcc ttctaaaagg gtagccctgg acttaatacc   1800
agccggatac ctctggcccc caccccatta ctgtacctct ggagtcacta ctgtgggtcg   1860
ccactcctct gctacacagc acggcttttt caaggctgta ttgagaaggg aagttaggaa   1920
gaagggtgtg ctgggctaac cagcccacag agctcacatt cctgtccctt gggtgaaaaa   1980
tacatgtcca tcctgatatc tcctgaattc agaaattagc ctccacatgt gcaatggctt   2040
taagagccag aagcagggtt ctgggaattt tgcaagttac ctgtggccag gtgtggtctc   2100
ggttaccaaa tacggttacc tgcagctttt tagtcctttg tgctcccacg ggtctacaga   2160
gtcccatctg cccaaaggtc ttgaagcttg acaggatgtt ttcgattact cagtctccca   2220
gggcactact ggtccgtagg attcgattgg tcggggtagg agagttaaac aacatttaaa   2280
cagagttctc tcaaaaatgt ctaaagggat tgtaggtaga taacatccaa tcactgtttg   2340
cacttatctg aaatcttccc tcttggctgc ccccaggtat ttactgtgga gaacattgca   2400
```

-continued

```
taggaatgtc tggaaaaagc ttctacaact tgttacagcc ttcacatttg tagaagcttt   2460


<210> SEQ ID NO 42
<211> LENGTH: 1660
<212> TYPE: DNA
<213> ORGANISM: Artificial Sequence
<220> FEATURE:
<223> OTHER INFORMATION: opt_COX10-opt_ND1-3'UTR*

<400> SEQUENCE: 42

atggccgcct ctccacacac actgagtagc agactgctga ccggctgtgt tggcggctct     60

gtgtggtatc tggaacggcg gacaatggcc aacctgctgc tgctgatcgt gcccatcctg    120

atcgccatgg ccttcctgat gctgaccgag cgcaagatcc tgggctacat gcagctgcgc    180

aagggcccca acgtggtggg cccctacggc ctgctgcagc ccttcgccga cgccatcaag    240

ctgttcacca aggagcccct gaagcccgcc accagcacca tcaccctgta catcaccgcc    300

cccaccctgg ccctgaccat cgccctgctg ctgtggaccc ccctgcccat gcccaacccc    360

ctggtgaacc tgaacctggg cctgctgttc atcctggcca ccagcagcct ggccgtgtac    420

agcatcctgt ggagcggctg ggccagcaac agcaactacg ccctgatcgg cgccctgcgc    480

gccgtggccc agaccatcag ctacgaggtg accctggcca tcatcctgct gagcaccctg    540

ctgatgagcg gcagcttcaa cctgagcacc ctgatcacca cccaggagca cctgtggctg    600

ctgctgccca gctggcccct ggccatgatg tggttcatca gcaccctggc cgagaccaac    660

cgcacccccct tcgacctggc cgagggcgag agcgagctgg tgagcggctt caacatcgag    720

tacgccgccg gccccttcgc cctgttcttc atggccgagt acaccaacat catcatgatg    780

aacaccctga ccaccaccat cttcctgggc accacctacg acgccctgag ccccgagctg    840

tacaccacct acttcgtgac caagaccctg ctgctgacca gcctgttcct gtggatccgc    900

accgcctacc cccgcttccg ctacgaccag ctgatgcacc tgctgtggaa gaacttcctg    960

cccctgaccc tggccctgct gatgtggtac gtgagcatgc ccatcaccat cagcagcatc   1020

cccccccaga cctaagagca ctgggacgcc caccgcccct ttccctccgc tgccaggcga   1080

gcatgttgtg gtaattctgg aacacaagaa gagaaattgc tgggtttaga acaagattat   1140

aaacgaattc ggtgctcagt gatcacttga cagttttttt ttttttaaa tattacccaa   1200

aatgctcccc aaataagaaa tgcatcagct cagtcagtga atacaaaaaa ggaattattt   1260

ttccctttga gggtctttta tacatctctc ctccaacccc accctctatt ctgtttcttc   1320

ctcctcacat gggggtacac atacacagct tcctcttttg gttccatcct taccaccaca   1380

ccacacgcac actccacatg cccagcagag tggcacttgg tggccagaaa gtgtgagcct   1440

catgatctgc tgtctgtagt tctgtgagct caggtccctc aaaggcctcg gagcaccccc   1500

ttccttgtga ctgagccagg gcctgcattt ttggttttcc ccaccccaca cattctcaac   1560

catagtcctt ctaacaatac caatagctag gacccggctg ctgtgcactg ggactgggga   1620

ttccacatgt ttgccttggg agtctcaagc tggactgcca                         1660


<210> SEQ ID NO 43
<211> LENGTH: 2889
<212> TYPE: DNA
<213> ORGANISM: Artificial Sequence
<220> FEATURE:
<223> OTHER INFORMATION: opt_COX10*-ND4-3'UTR

<400> SEQUENCE: 43

atggccgcca gcccccacac cctgagcagc cgcctgctga ccggctgcgt gggcggcagc     60
```

```
gtgtggtacc tggagcgccg caccatgcta aaactaatcg tcccaacaat tatgttacta    120
ccactgacat ggctttccaa aaaacacatg atttggatca acacaaccac ccacagccta    180
attattagca tcatccctct actatttttt aaccaaatca acaacaacct atttagctgt    240
tccccaacct tttcctccga cccccctaaca acccccctcc taatgctaac tacctggctc    300
ctacccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg ctttttggtg gcttctagca agcctcgcta acctcgcctt acccccact    1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt ttttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggtacaca tacacagctt cctcttttgg ttccatcctt    1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgccag cccctgtcct   2100
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
```

-continued

```
ggtgaaaaat acatgtccat cctgatatct cctgaattca gaaattagcc tccacatgtg   2460

caatggcttt aagagccaga agcagggttc tgggaatttt gcaagttacc tgtggccagg   2520

tgtggtctcg gttaccaaat acggttacct gcagcttttt agtcctttgt gctcccacgg   2580

gtctacagag tcccatctgc ccaaaggtct tgaagcttga caggatgttt tcgattactc   2640

agtctcccag ggcactactg gtccgtagga ttcgattggt cggggtagga gagttaaaca   2700

acatttaaac agagttctct caaaaatgtc taaagggatt gtaggtagat aacatccaat   2760

cactgtttgc acttatctga aatcttccct cttggctgcc cccaggtatt tactgtggag   2820

aacattgcat aggaatgtct ggaaaaagct tctacaactt gttacagcct tcacatttgt   2880

agaagcttt                                                           2889
```

```
<210> SEQ ID NO 44
<211> LENGTH: 2089
<212> TYPE: DNA
<213> ORGANISM: Artificial Sequence
<220> FEATURE:
<223> OTHER INFORMATION: opt_COX10*-ND4-3'UTR*

<400> SEQUENCE: 44

atggccgcca gcccccacac cctgagcagc cgcctgctga ccggctgcgt gggcggcagc     60

gtgtggtacc tggagcgccg caccatgcta aaactaatcg tcccaacaat tatgttacta    120

ccactgacat ggctttccaa aaaacacatg atttggatca acacaaccac ccacagccta    180

attattagca tcatccctct actatttttt aaccaaatca acaacaacct atttagctgt    240

tccccaacct tttcctccga cccccctaaca accccccctcc taatgctaac tacctggctc    300

ctacccctca caatcatggc aagccaacgc cacttatcca gtgaaccact atcacgaaaa    360

aaactctacc tctctatgct aatctcccta caaatctcct taattatgac attcacagcc    420

acagaactaa tcatgtttta tatcttcttc gaaaccacac ttatccccac cttggctatc    480

atcacccgat ggggcaacca gccagaacgc ctgaacgcag gcacatactt cctattctac    540

accctagtag gctcccttcc cctactcatc gcactaattt acactcacaa caccctaggc    600

tcactaaaca ttctactact cactctcact gcccaagaac tatcaaactc ctgggccaac    660

aacttaatgt ggctagctta cacaatggct tttatggtaa agatgcctct ttacggactc    720

cacttatggc tccctaaagc ccatgtcgaa gcccccatcg ctgggtcaat ggtacttgcc    780

gcagtactct taaaactagg cggctatggt atgatgcgcc tcacactcat tctcaacccc    840

ctgacaaaac acatggccta ccccttcctt gtactatccc tatggggcat gattatgaca    900

agctccatct gcctacgaca aacagaccta aaatcgctca ttgcatactc ttcaatcagc    960

cacatggccc tcgtagtaac agccattctc atccaaaccc cctggagctt caccggcgca   1020

gtcattctca tgatcgccca cgggcttaca tcctcattac tattctgcct agcaaactca   1080

aactacgaac gcactcacag tcgcatcatg atcctctctc aaggacttca aactctactc   1140

ccactaatgg ctttttggtg gcttctagca agcctcgcta acctcgcctt accccccact   1200

attaacctac tgggagaact ctctgtgcta gtaaccacgt tctcctggtc aaatatcact   1260

ctcctactta caggactcaa catgctagtc acagccctat actccctcta catgtttacc   1320

acaacacaat ggggctcact cacccaccac attaacaaca tgaaaccctc attcacacga   1380

gaaaacaccc tcatgttcat gcacctatcc cccattctcc tcctatccct caaccccgac   1440

atcattaccg ggttttcctc ttaagagcac tgggacgccc accgcccctt tccctccgct   1500

gccaggcgag catgttgtgg taattctgga acacaagaag agaaattgct gggtttagaa   1560
```

caagattata aacgaattcg gtgctcagtg atcacttgac agtttttttt ttttttaaat 1620
attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

<210> SEQ ID NO 45
<211> LENGTH: 2889
<212> TYPE: DNA
<213> ORGANISM: Artificial Sequence
<220> FEATURE:
<223> OTHER INFORMATION: opt_COX10*-opt_ND4-3'UTR

<400> SEQUENCE: 45
atggccgcca gcccccacac cctgagcagc cgcctgctga ccggctgcgt gggcggcagc 60
gtgtggtacc tggagcgccg caccatgctg aagctgatcg tgcccaccat catgctgctg 120
cctctgacct ggctgagcaa gaaacacatg atctggatca acaccaccac gcacagcctg 180
atcatcagca tcatccctct gctgttcttc aaccagatca acaacaacct gttcagctgc 240
agccccacct tcagcagcga ccctctgaca acacctctgc tgatgctgac cacctggctg 300
ctgcccctca caatcatggc ctctcagaga cacctgagca gcgagcccct gagccggaag 360
aaactgtacc tgagcatgct gatctccctg cagatctctc tgatcatgac cttcaccgcc 420
accgagctga tcatgttcta catctttttc gagacaacgc tgatccccac actggccatc 480
atcaccagat ggggcaacca gcctgagaga ctgaacgccg gcacctactt tctgttctac 540
accctcgtgg gcagcctgcc actgctgatt gccctgatct acacccacaa caccctgggc 600
tccctgaaca tcctgctgct gacactgaca gcccaagagc tgagcaacag ctgggccaac 660
aatctgatgt ggctggccta cacaatggcc ttcatggtca agatgcccct gtacggcctg 720
cacctgtggc tgcctaaagc tcatgtggaa gcccctatcg ccggctctat ggtgctggct 780
gcagtgctgc tgaaactcgg cggctacggc atgatgcggc tgaccctgat tctgaatccc 840
ctgaccaagc acatggccta tccatttctg gtgctgagcc tgtggggcat gattatgacc 900
agcagcatct gcctgcggca gaccgatctg aagtccctga tcgcctacag ctccatcagc 960
cacatggccc tggtggtcac cgccatcctg attcagaccc cttggagctt tacaggcgcc 1020
gtgatcctga tgattgccca cggcctgaca agcagcctgc tgttttgtct ggccaacagc 1080
aactacgagc ggacccacag cagaatcatg atcctgtctc agggcctgca gaccctcctg 1140
cctcttatgg ctttttggtg gctgctggcc tctctggcca atctggcact gcctcctacc 1200
atcaatctgc tgggcgagct gagcgtgctg gtcaccacat tcagctggtc caatatcacc 1260
ctgctgctca ccggcctgaa catgctggtt acagccctgt actccctgta catgttcacc 1320
accacacagt ggggaagcct gacacaccac atcaacaata tgaagcccag cttcacccgc 1380
gagaacaccc tgatgttcat gcatctgagc cccattctgc tgctgtccct gaatcctgat 1440
atcatcaccg gcttctccag ctgagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt ttttttaaat 1620
attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgccag cccctgtcct 2100
cccttcaccc ccattgcgta tgagcatttc agaactccaa ggagtcacag gcatctttat 2160
agttcacgtt aacatataga cactgttgga agcagttcct tctaaaaggg tagccctgga 2220
cttaatacca gccggatacc tctggccccc accccattac tgtacctctg gagtcactac 2280
tgtgggtcgc cactcctctg ctacacagca cggctttttc aaggctgtat tgagaaggga 2340
agttaggaag aagggtgtgc tgggctaacc agcccacaga gctcacattc ctgtcccttg 2400
ggtgaaaaat acatgtccat cctgatatct cctgaattca gaaattagcc tccacatgtg 2460
caatggcttt aagagccaga agcagggttc tgggaatttt gcaagttacc tgtggccagg 2520
tgtggtctcg gttaccaaat acggttacct gcagcttttt agtcctttgt gctcccacgg 2580
gtctacagag tcccatctgc ccaaaggtct tgaagcttga caggatgttt tcgattactc 2640
agtctcccag ggcactactg gtccgtagga ttcgattggt cggggtagga gagttaaaca 2700
acatttaaac agagttctct caaaaatgtc taaagggatt gtaggtagat aacatccaat 2760
cactgtttgc acttatctga aatcttccct cttggctgcc cccaggtatt tactgtggag 2820
aacattgcat aggaatgtct ggaaaaagct tctacaactt gttacagcct tcacatttgt 2880
agaagcttt 2889

<210> SEQ ID NO 46
<211> LENGTH: 2089
<212> TYPE: DNA
<213> ORGANISM: Artificial Sequence
<220> FEATURE:
<223> OTHER INFORMATION: opt_COX10*-opt_ND4-3'UTR*

<400> SEQUENCE: 46
atggccgcca gcccccacac cctgagcagc cgcctgctga ccggctgcgt gggcggcagc 60
gtgtggtacc tggagcgccg caccatgctg aagctgatcg tgcccaccat catgctgctg 120
cctctgacct ggctgagcaa gaaacacatg atctggatca acaccaccac gcacagcctg 180
atcatcagca tcatccctct gctgttcttc aaccagatca acaacaacct gttcagctgc 240
agccccacct tcagcagcga ccctctgaca acacctctgc tgatgctgac cacctggctg 300
ctgcccctca caatcatggc ctctcagaga cacctgagca gcgagcccct gagccggaag 360
aaactgtacc tgagcatgct gatctccctg cagatctctc tgatcatgac cttcaccgcc 420
accgagctga tcatgttcta catctttttc gagacaacgc tgatccccac actggccatc 480
atcaccagat ggggcaacca gcctgagaga ctgaacgccg gcacctactt tctgttctac 540
accctcgtgg gcagcctgcc actgctgatt gccctgatct acacccacaa caccctgggc 600
tccctgaaca tcctgctgct gacactgaca gcccaagagc tgagcaacag ctgggccaac 660
aatctgatgt ggctggccta cacaatggcc ttcatggtca agatgcccct gtacggcctg 720
cacctgtggc tgcctaaagc tcatgtggaa gcccctatcg ccggctctat ggtgctggct 780
gcagtgctgc tgaaactcgg cggctacggc atgatgcggc tgaccctgat tctgaatccc 840
ctgaccaagc acatggccta tccatttctg gtgctgagcc tgtggggcat gattatgacc 900
agcagcatct gcctgcggca gaccgatctg aagtccctga tcgcctacag ctccatcagc 960
cacatggccc tggtggtcac cgccatcctg attcagaccc cttggagctt tacaggcgcc 1020
gtgatcctga tgattgccca cggcctgaca agcagcctgc tgttttgtct ggccaacagc 1080
aactacgagc ggacccacag cagaatcatg atcctgtctc agggcctgca gaccctcctg 1140
cctcttatgg ctttttggtg gctgctggcc tctctggcca atctggcact gcctcctacc 1200
atcaatctgc tgggcgagct gagcgtgctg gtcaccacat tcagctggtc caatatcacc 1260
ctgctgctca ccggcctgaa catgctggtt acagccctgt actccctgta catgttcacc 1320
accacacagt ggggaagcct gacacaccac atcaacaata tgaagcccag cttcacccgc 1380
gagaacaccc tgatgttcat gcatctgagc cccattctgc tgctgtccct gaatcctgat 1440
atcatcaccg gcttctccag ctgagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt tttttaaat 1620 attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

<210> SEQ ID NO 47
<211> LENGTH: 2889
<212> TYPE: DNA
<213> ORGANISM: Artificial Sequence
<220> FEATURE:
<223> OTHER INFORMATION: opt_COX10*-opt_ND4*-3'UTR

<400> SEQUENCE: 47
atggccgcca gcccccacac cctgagcagc cgcctgctga ccggctgcgt gggcggcagc 60
gtgtggtacc tggagcgccg caccatgctg aagctgatcg tgcccaccat catgctgctg 120
cccctgacct ggctgagcaa gaagcacatg atctggatca acaccaccac ccacagcctg 180
atcatcagca tcatcccccct gctgttcttc aaccagatca acaacaacct gttcagctgc 240
agccccacct tcagcagcga cccccctgacc accccccctgc tgatgctgac cacctggctg 300
ctgcccctga ccatcatggc cagccagcgc cacctgagca gcgagcccct gagccgcaag 360
aagctgtacc tgagcatgct gatcagcctg cagatcagcc tgatcatgac cttcaccgcc 420
accgagctga tcatgttcta catcttcttc gagaccaccc tgatccccac cctggccatc 480
atcacccgct ggggcaacca gcccgagcgc ctgaacgccg gcacctactt cctgttctac 540
accctggtgg gcagcctgcc cctgctgatc gccctgatct acacccacaa caccctgggc 600

-continued

```
agcctgaaca tcctgctgct gaccctgacc gcccaggagc tgagcaacag ctgggccaac    660
aacctgatgt ggctggccta caccatggcc ttcatggtga agatgcccct gtacggcctg    720
cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gcccccccacc   1200
atcaacctgc tgggcgagct gagcgtgctg gtgaccacct tcagctggag caacatcacc   1260
ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt tttttttaaat   1620
attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg gggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgccag cccctgtcct   2100
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                            2889
```

<210> SEQ ID NO 48
<211> LENGTH: 2089
<212> TYPE: DNA
<213> ORGANISM: Artificial Sequence
<220> FEATURE:
<223> OTHER INFORMATION: opt_COX10*-opt_ND4*-3'UTR*

<400> SEQUENCE: 48
atggccgcca gcccccacac cctgagcagc cgcctgctga ccggctgcgt gggcggcagc 60
gtgtggtacc tggagcgccg caccatgctg aagctgatcg tgcccaccat catgctgctg 120
cccctgacct ggctgagcaa gaagcacatg atctggatca acaccaccac ccacagcctg 180
atcatcagca tcatccccct gctgttcttc aaccagatca acaacaacct gttcagctgc 240
agccccacct tcagcagcga cccccctgacc accccccctgc tgatgctgac cacctggctg 300
ctgcccctga ccatcatggc cagccagcgc cacctgagca gcgagcccct gagccgcaag 360
aagctgtacc tgagcatgct gatcagcctg cagatcagcc tgatcatgac cttcaccgcc 420
accgagctga tcatgttcta catcttcttc gagaccaccc tgatccccac cctggccatc 480
atcacccgct ggggcaacca gcccgagcgc ctgaacgccg gcacctactt cctgttctac 540
accctggtgg gcagcctgcc cctgctgatc gccctgatct acacccacaa caccctgggc 600
agcctgaaca tcctgctgct gaccctgacc gcccaggagc tgagcaacag ctgggccaac 660
aacctgatgt ggctggccta caccatggcc ttcatggtga agatgcccct gtacggcctg 720
cacctgtggc tgcccaaggc ccacgtggag gcccccatcg ccggcagcat ggtgctggcc 780
gccgtgctgc tgaagctggg cggctacggc atgatgcgcc tgaccctgat cctgaacccc 840
ctgaccaagc acatggccta ccccttcctg gtgctgagcc tgtggggcat gatcatgacc 900
agcagcatct gcctgcgcca gaccgacctg aagagcctga tcgcctacag cagcatcagc 960
cacatggccc tggtggtgac cgccatcctg atccagaccc cctggagctt caccggcgcc 1020
gtgatcctga tgatcgccca cggcctgacc agcagcctgc tgttctgcct ggccaacagc 1080
aactacgagc gcacccacag ccgcatcatg atcctgagcc agggcctgca gaccctgctg 1140
cccctgatgg ccttctggtg gctgctggcc agcctggcca acctggccct gcccccccacc 1200 atcaacctgc tgggcgagct gagcgtgctg gtgaccacct tcagctggag caacatcacc 1260
ctgctgctga ccggcctgaa catgctggtg accgccctgt acagcctgta catgttcacc 1320
accacccagt ggggcagcct gacccaccac atcaacaaca tgaagcccag cttcacccgc 1380
gagaacaccc tgatgttcat gcacctgagc cccatcctgc tgctgagcct gaaccccgac 1440
atcatcaccg gcttcagcag ctaagagcac tgggacgccc accgcccctt tccctccgct 1500
gccaggcgag catgttgtgg taattctgga acacaagaag agaaattgct gggtttagaa 1560
caagattata aacgaattcg gtgctcagtg atcacttgac agtttttttt ttttttaaat 1620
attacccaaa atgctcccca aataagaaat gcatcagctc agtcagtgaa tacaaaaaag 1680
gaattatttt tccctttgag ggtcttttat acatctctcc tccaacccca ccctctattc 1740
tgtttcttcc tcctcacatg gggtacaca tacacagctt cctcttttgg ttccatcctt 1800
accaccacac cacacgcaca ctccacatgc ccagcagagt ggcacttggt ggccagaaag 1860
tgtgagcctc atgatctgct gtctgtagtt ctgtgagctc aggtccctca aaggcctcgg 1920 agcacccccct tccttgtgac tgagccaggg cctgcatttt tggttttccc caccccacac 1980
attctcaacc atagtccttc taacaatacc aatagctagg acccggctgc tgtgcactgg 2040
gactggggat tccacatgtt tgccttggga gtctcaagct ggactgcca 2089

```
<210> SEQ ID NO 49
<211> LENGTH: 2034
<212> TYPE: DNA
<213> ORGANISM: Artificial Sequence
<220> FEATURE:
<223> OTHER INFORMATION: opt_COX10*-ND6-3'UTR

<400> SEQUENCE: 49

atggccgcca gcccccacac cctgagcagc cgcctgctga ccggctgcgt gggcggcagc      60

gtgtggtacc tggagcgccg caccatgatg tatgctttgt ttctgttgag tgtgggttta     120

gtaatggggt ttgtggggtt ttcttctaag ccttctccta tttatggggg tttagtattg     180

attgttagcg gtgtggtcgg gtgtgttatt attctgaatt ttgggggagg ttatatgggt     240

ttaatggttt ttttaattta tttaggggga atgatggttg tctttggata tactacagcg     300

atggctattg aggagtatcc tgaggcatgg gggtcagggg ttgaggtctt ggtgagtgtt     360

ttagtggggt tagcgatgga ggtaggattg gtgctgtggg tgaaagagta tgatggggtg     420

gtggttgtgg taaactttaa tagtgtagga agctggatga tttatgaagg agaggggtca     480

gggttgattc gggaggatcc tattggtgcg ggggctttgt atgattatgg gcgttggtta     540

gtagtagtta ctggttggac attgtttgtt ggtgtatata ttgtaattga gattgctcgg     600

gggaattagg agcactggga cgcccaccgc ccctttccct ccgctgccag gcgagcatgt     660

tgtggtaatt ctggaacaca agaagagaaa ttgctgggtt tagaacaaga ttataaacga     720

attcggtgct cagtgatcac ttgacagttt tttttttttt taaatattac ccaaaatgct     780

ccccaaataa gaaatgcatc agctcagtca gtgaatacaa aaaaggaatt atttttccct     840

ttgagggtct tttatacatc tctcctccaa ccccaccctc tattctgttt cttcctcctc     900

acatgggggt acacatacac agcttcctct tttggttcca tccttaccac cacaccacac     960

gcacactcca catgcccagc agagtggcac ttggtggcca gaaagtgtga gcctcatgat    1020

ctgctgtctg tagttctgtg agctcaggtc cctcaaaggc ctcggagcac ccccttcctt    1080

gtgactgagc cagggcctgc atttttggtt ttccccaccc cacacattct caaccatagt    1140

ccttctaaca ataccaatag ctaggacccg gctgctgtgc actgggactg gggattccac    1200

atgtttgcct tgggagtctc aagctggact gccagcccct gtcctccctt cacccccatt    1260

gcgtatgagc atttcagaac tccaaggagt cacaggcatc tttatagttc acgttaacat    1320

atagacactg ttggaagcag ttccttctaa aagggtagcc ctggacttaa taccagccgg    1380

atacctctgg cccccacccc attactgtac ctctggagtc actactgtgg gtcgccactc    1440

ctctgctaca cagcacggct ttttcaaggc tgtattgaga agggaagtta ggaagaaggg    1500

tgtgctgggc taaccagccc acagagctca cattcctgtc ccttgggtga aaaatacatg    1560

tccatcctga tatctcctga attcagaaat tagcctccac atgtgcaatg gctttaagag    1620

ccagaagcag ggttctggga attttgcaag ttacctgtgg ccaggtgtgg tctcggttac    1680

caaatacggt tacctgcagc tttttagtcc tttgtgctcc cacgggtcta cagagtccca    1740

tctgcccaaa ggtcttgaag cttgacagga tgttttcgat tactcagtct cccagggcac    1800

tactggtccg taggattcga ttggtcgggg taggagagtt aaacaacatt taaacagagt    1860

tctctcaaaa atgtctaaag ggattgtagg tagataacat ccaatcactg tttgcactta    1920

tctgaaatct tccctcttgg ctgcccccag gtatttactg tggagaacat tgcataggaa    1980

tgtctggaaa aagcttctac aacttgttac agccttcaca tttgtagaag cttt          2034
```

<210> SEQ ID NO 50
<211> LENGTH: 1234
<212> TYPE: DNA
<213> ORGANISM: Artificial Sequence
<220> FEATURE:
<223> OTHER INFORMATION: opt_COX10*-ND6-3'UTR*

<400> SEQUENCE: 50
atggccgcca gcccccacac cctgagcagc cgcctgctga ccggctgcgt gggcggcagc 60
gtgtggtacc tggagcgccg caccatgatg tatgctttgt ttctgttgag tgtgggttta 120
gtaatggggt ttgtggggtt ttcttctaag ccttctccta tttatggggg tttagtattg 180
attgttagcg gtgtggtcgg gtgtgttatt attctgaatt ttgggggagg ttatatgggt 240
ttaatggttt ttttaattta tttaggggga atgatggttg tctttggata tactacagcg 300
atggctattg aggagtatcc tgaggcatgg gggtcagggg ttgaggtctt ggtgagtgtt 360
ttagtggggt tagcgatgga ggtaggattg gtgctgtggg tgaaagagta tgatggggtg 420
gtggttgtgg taaactttaa tagtgtagga agctggatga tttatgaagg agaggggtca 480
gggttgattc gggaggatcc tattggtgcg ggggctttgt atgattatgg gcgttggtta 540
gtagtagtta ctggttggac attgtttgtt ggtgtatata ttgtaattga gattgctcgg 600
gggaattagg agcactggga cgcccaccgc cccttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac ccccttcctt 1080
gtgactgagc cagggcctgc atttttggtt ttccccaccc cacacattct caaccatagt 1140
ccttctaaca ataccaatag ctaggacccg gctgctgtgc actgggactg ggattccac 1200 atgtttgcct tgggagtctc aagctggact gcca 1234

<210> SEQ ID NO 51
<211> LENGTH: 2034
<212> TYPE: DNA
<213> ORGANISM: Artificial Sequence
<220> FEATURE:
<223> OTHER INFORMATION: opt_COX10*-opt_ND6-3'UTR

<400> SEQUENCE: 51
atggccgcca gcccccacac cctgagcagc cgcctgctga ccggctgcgt gggcggcagc 60
gtgtggtacc tggagcgccg caccatgatg tacgccctgt tcctgctgag cgtgggcctg 120
gtgatgggct tcgtgggctt cagcagcaag cccagcccca tctacggcgg cctggtgctg 180
atcgtgagcg gcgtggtggg ctgcgtgatc atcctgaact tcggcggcgg ctacatgggc 240
ctgatggtgt tcctgatcta cctgggcggc atgatggtgg tgttcggcta caccaccgcc 300
atggccatcg aggagtaccc cgaggcctgg ggcagcggcg tggaggtgct ggtgagcgtg 360
ctggtgggcc tggccatgga ggtgggcctg gtgctgtggg tgaaggagta cgacggcgtg 420
gtggtggtgg tgaacttcaa cagcgtgggc agctggatga tctacgaggg cgagggcagc 480
ggcctgatcc gcgaggaccc catcggcgcc ggcgccctgt acgactacgg ccgctggctg 540

-continued gtggtggtga ccggctggac cctgttcgtg ggcgtgtaca tcgtgatcga gatcgcccgc 600
ggcaactaag agcactggga cgcccaccgc ccctttccct ccgctgccag gcgagcatgt 660
tgtggtaatt ctggaacaca agaagagaaa ttgctgggtt tagaacaaga ttataaacga 720
attcggtgct cagtgatcac ttgacagttt tttttttttt taaatattac ccaaaatgct 780
ccccaaataa gaaatgcatc agctcagtca gtgaatacaa aaaaggaatt atttttccct 840
ttgagggtct tttatacatc tctcctccaa ccccaccctc tattctgttt cttcctcctc 900
acatgggggt acacatacac agcttcctct tttggttcca tccttaccac cacaccacac 960
gcacactcca catgcccagc agagtggcac ttggtggcca gaaagtgtga gcctcatgat 1020
ctgctgtctg tagttctgtg agctcaggtc cctcaaaggc ctcggagcac ccccttcctt 1080
gtgactgagc cagggcctgc atttttggtt ttccccaccc cacacattct caaccatagt 1140
ccttctaaca ataccaatag ctaggacccg gctgctgtgc actgggactg gggattccac 1200
atgtttgcct tgggagtctc aagctggact gccagcccct gtcctccctt cacccccatt 1260
gcgtatgagc atttcagaac tccaaggagt cacaggcatc tttatagttc acgttaacat 1320
atagacactg ttggaagcag ttccttctaa aagggtagcc ctggacttaa taccagccgg 1380
atacctctgg cccccacccc attactgtac ctctggagtc actactgtgg gtcgccactc 1440
ctctgctaca cagcacggct ttttcaaggc tgtattgaga agggaagtta ggaagaaggg 1500
tgtgctgggc taaccagccc acagagctca cattcctgtc ccttgggtga aaaatacatg 1560
tccatcctga tatctcctga attcagaaat tagcctccac atgtgcaatg gctttaagag 1620
ccagaagcag ggttctggga attttgcaag ttacctgtgg ccaggtgtgg tctcggttac 1680
caaatacggt tacctgcagc tttttagtcc tttgtgctcc cacgggtcta cagagtccca 1740
tctgcccaaa ggtcttgaag cttgacagga tgttttcgat tactcagtct cccagggcac 1800
tactggtccg taggattcga ttggtcgggg taggagagtt aaacaacatt taaacagagt 1860
tctctcaaaa atgtctaaag ggattgtagg tagataacat ccaatcactg tttgcactta 1920
tctgaaatct tccctcttgg ctgcccccag gtatttactg tggagaacat tgcataggaa 1980
tgtctggaaa aagcttctac aacttgttac agccttcaca tttgtagaag cttt 2034

<210> SEQ ID NO 52
<211> LENGTH: 1234
<212> TYPE: DNA
<213> ORGANISM: Artificial Sequence
<220> FEATURE:
<223> OTHER INFORMATION: opt_COX10*-opt_ND6-3'UTR*

<400> SEQUENCE: 52
atggccgcca gcccccacac cctgagcagc cgcctgctga ccggctgcgt gggcggcagc 60
gtgtggtacc tggagcgccg caccatgatg tacgccctgt tcctgctgag cgtgggcctg 120
gtgatgggct tcgtgggctt cagcagcaag cccagcccca tctacggcgg cctggtgctg 180
atcgtgagcg gcgtggtggg ctgcgtgatc atcctgaact tcggcggcgg ctacatgggc 240
ctgatggtgt tcctgatcta cctgggcggc atgatggtgg tgttcggcta caccaccgcc 300
atggccatcg aggagtaccc cgaggcctgg ggcagcggcg tggaggtgct ggtgagcgtg 360
ctggtgggcc tggccatgga ggtgggcctg gtgctgtggg tgaaggagta cgacggcgtg 420
gtggtggtgg tgaacttcaa cagcgtgggc agctggatga tctacgaggg cgagggcagc 480
ggcctgatcc gcgaggaccc catcggcgcc ggcgccctgt acgactacgg ccgctggctg 540
gtggtggtga ccggctggac cctgttcgtg ggcgtgtaca tcgtgatcga gatcgcccgc 600

```
ggcaactaag agcactggga cgcccaccgc ccctttccct ccgctgccag gcgagcatgt    660

tgtggtaatt ctggaacaca agaagagaaa ttgctgggtt tagaacaaga ttataaacga    720

attcggtgct cagtgatcac ttgacagttt tttttttttt taaatattac ccaaaatgct    780

ccccaaataa gaaatgcatc agctcagtca gtgaatacaa aaaaggaatt atttttccct    840

ttgagggtct tttatacatc tctcctccaa ccccaccctc tattctgttt cttcctcctc    900

acatgggggt acacatacac agcttcctct tttggttcca tccttaccac cacaccacac    960

gcacactcca catgcccagc agagtggcac ttggtggcca gaaagtgtga gcctcatgat   1020

ctgctgtctg tagttctgtg agctcaggtc cctcaaaggc ctcggagcac cccctccctt   1080

gtgactgagc cagggcctgc atttttggtt ttccccaccc cacacattct caaccatagt   1140

ccttctaaca ataccaatag ctaggacccg gctgctgtgc actgggactg gggattccac   1200

atgtttgcct tgggagtctc aagctggact gcca                               1234
```

<210> SEQ ID NO 53
<211> LENGTH: 2460
<212> TYPE: DNA
<213> ORGANISM: Artificial Sequence
<220> FEATURE:
<223> OTHER INFORMATION: opt_COX10*-ND1-3'UTR

<400> SEQUENCE: 53

```
atggccgcca gcccccacac cctgagcagc cgcctgctga ccggctgcgt gggcggcagc     60

gtgtggtacc tggagcgccg caccatggcc aacctcctac tcctcattgt acccattcta    120

atcgcaatgg cattcctaat gcttaccgaa cgaaaaattc taggctatat gcaactacgc    180

aaaggcccca acgttgtagg cccctacggg ctactacaac ccttcgctga cgccataaaa    240

ctcttcacca aagagcccct aaaacccgcc acatctacca tcaccctcta catcaccgcc    300

ccgaccttag ctctcaccat cgctcttcta ctatggaccc ccctccccat gcccaacccc    360

ctggtcaacc tcaacctagg cctcctattt attctagcca cctctagcct agccgtttac    420

tcaatcctct ggtcagggtg ggcatcaaac tcaaactacg ccctgatcgg cgcactgcga    480

gcagtagccc aaacaatctc atatgaagtc accctagcca tcattctact atcaacatta    540

ctaatgagtg gctcctttaa cctctccacc cttatcacaa cacaagaaca cctctggtta    600

ctcctgccat catggccctt ggccatgatg tggtttatct ccacactagc agagaccaac    660

cgaacccccct tcgaccttgc cgaaggggag tccgaactag tctcaggctt caacatcgaa    720

tacgccgcag gccccttcgc cctattcttc atggccgaat acacaaacat tattatgatg    780

aacaccctca ccactacaat cttcctagga acaacatatg acgcactctc ccctgaactc    840

tacacaacat attttgtcac caagacccta cttctaacct ccctgttctt atggattcga    900

acagcatacc cccgattccg ctacgaccaa ctcatgcacc tcctatggaa aaacttccta    960

ccactcaccc tagcattact tatgtggtat gtctccatgc ccattacaat ctccagcatt   1020

ccccctcaaa cctaagagca ctgggacgcc caccgcccct ttccctccgc tgccaggcga   1080

gcatgttgtg gtaattctgg aacacaagaa gagaaattgc tgggtttaga acaagattat   1140

aaacgaattc ggtgctcagt gatcacttga cagttttttt tttttttaaa tattacccaa   1200

aatgctcccc aaataagaaa tgcatcagct cagtcagtga atacaaaaaa ggaattattt   1260

ttccctttga gggtctttta tacatctctc ctccaacccc accctctatt ctgtttcttc   1320

ctcctcacat gggggtacac atacacagct tcctcttttg gttccatcct taccaccaca   1380
```

-continued ccacacgcac actccacatg cccagcagag tggcacttgg tggccagaaa gtgtgagcct 1440
catgatctgc tgtctgtagt tctgtgagct caggtccctc aaaggcctcg gagcaccccc 1500
ttccttgtga ctgagccagg gcctgcattt ttggttttcc ccaccccaca cattctcaac 1560
catagtcctt ctaacaatac caatagctag gacccggctg ctgtgcactg ggactgggga 1620
ttccacatgt ttgccttggg agtctcaagc tggactgcca gcccctgtcc tcccttcacc 1680
cccattgcgt atgagcattt cagaactcca aggagtcaca ggcatcttta tagttcacgt 1740
taacatatag acactgttgg aagcagttcc ttctaaaagg gtagccctgg acttaatacc 1800
agccggatac ctctggcccc caccccatta ctgtacctct ggagtcacta ctgtgggtcg 1860
ccactcctct gctacacagc acggcttttt caaggctgta ttgagaaggg aagttaggaa 1920
gaagggtgtg ctgggctaac cagcccacag agctcacatt cctgtccctt gggtgaaaaa 1980
tacatgtcca tcctgatatc tcctgaattc agaaattagc ctccacatgt gcaatggctt 2040
taagagccag aagcagggtt ctgggaattt tgcaagttac ctgtggccag gtgtggtctc 2100
ggttaccaaa tacggttacc tgcagctttt tagtcctttg tgctcccacg ggtctacaga 2160
gtcccatctg cccaaaggtc ttgaagcttg acaggatgtt ttcgattact cagtctccca 2220
gggcactact ggtccgtagg attcgattgg tcggggtagg agagttaaac aacatttaaa 2280
cagagttctc tcaaaaatgt ctaaagggat tgtaggtaga taacatccaa tcactgtttg 2340
cacttatctg aaatcttccc tcttggctgc ccccaggtat ttactgtgga gaacattgca 2400
taggaatgtc tggaaaaagc ttctacaact tgttacagcc ttcacatttg tagaagcttt 2460

<210> SEQ ID NO 54
<211> LENGTH: 1660
<212> TYPE: DNA
<213> ORGANISM: Artificial Sequence
<220> FEATURE:
<223> OTHER INFORMATION: opt_COX10*-ND1-3'UTR*

<400> SEQUENCE: 54
atggccgcca gcccccacac cctgagcagc cgcctgctga ccggctgcgt gggcggcagc 60
gtgtggtacc tggagcgccg caccatggcc aacctcctac tcctcattgt acccattcta 120
atcgcaatgg cattcctaat gcttaccgaa cgaaaaattc taggctatat gcaactacgc 180
aaaggcccca acgttgtagg cccctacggg ctactacaac ccttcgctga cgccataaaa 240
ctcttcacca aagagcccct aaaacccgcc acatctacca tcaccctcta catcaccgcc 300
ccgaccttag ctctcaccat cgctcttcta ctatggaccc ccctccccat gcccaacccc 360
ctggtcaacc tcaacctagg cctcctattt attctagcca cctctagcct agccgtttac 420
tcaatcctct ggtcagggtg ggcatcaaac tcaaactacg ccctgatcgg cgcactgcga 480
gcagtagccc aaacaatctc atatgaagtc accctagcca tcattctact atcaacatta 540
ctaatgagtg gctcctttaa cctctccacc cttatcacaa cacaagaaca cctctggtta 600
ctcctgccat catggccctt ggccatgatg tggtttatct ccacactagc agagaccaac 660
cgaaccccct tcgaccttgc cgaaggggag tccgaactag tctcaggctt caacatcgaa 720
tacgccgcag gccccttcgc cctattcttc atggccgaat acacaaacat tattatgatg 780
aacaccctca ccactacaat cttcctagga acaacatatg acgcactctc ccctgaactc 840
tacacaacat attttgtcac caagacccta cttctaacct ccctgttctt atggattcga 900
acagcatacc cccgattccg ctacgaccaa ctcatgcacc tcctatggaa aaacttccta 960
ccactcaccc tagcattact tatgtggtat gtctccatgc ccattacaat ctccagcatt 1020

```
ccccctcaaa cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt ttttttaaa tattacccaa    1200
aatgctcccc aaataagaaa tgcatcagct cagtcagtga atacaaaaaa ggaattattt   1260
ttccctttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca                         1660
```

<210> SEQ ID NO 55
<211> LENGTH: 2460
<212> TYPE: DNA
<213> ORGANISM: Artificial Sequence
<220> FEATURE:
<223> OTHER INFORMATION: opt_COX10*-opt_ND1-3'UTR

<400> SEQUENCE: 55

```
atggccgcca gcccccacac cctgagcagc cgcctgctga ccggctgcgt gggcggcagc     60
gtgtggtacc tggagcgccg caccatggcc aacctgctgc tgctgatcgt gcccatcctg    120
atcgccatgg ccttcctgat gctgaccgag cgcaagatcc tgggctacat gcagctgcgc    180
aagggcccca acgtggtggg cccctacggc ctgctgcagc ccttcgccga cgccatcaag    240
ctgttcacca aggagcccct gaagcccgcc accagcacca tcaccctgta catcaccgcc    300
cccaccctgg ccctgaccat cgccctgctg ctgtggaccc ccctgcccat gcccaacccc    360
ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660
cgcacccccct tcgacctggc cgagggcgag agcgagctgg tgagcggctt caacatcgag    720
tacgccgccg gccccttcgc cctgttcttc atggccgagt acaccaacat catcatgatg    780
aacaccctga ccaccaccat cttcctgggc accacctacg acgccctgag ccccgagctg    840
tacaccacct acttcgtgac caagaccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020
ccccccaga cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt ttttttaaa tattacccaa    1200
aatgctcccc aaataagaaa tgcatcagct cagtcagtga atacaaaaaa ggaattattt   1260
ttccctttga gggtctttta tacatctctc ctccaacccc accctctatt ctgtttcttc   1320
ctcctcacat gggggtacac atacacagct tcctcttttg gttccatcct taccaccaca   1380
```

ccacacgcac actccacatg cccagcagag tggcacttgg tggccagaaa gtgtgagcct 1440
catgatctgc tgtctgtagt tctgtgagct caggtccctc aaaggcctcg gagcaccccc 1500
ttccttgtga ctgagccagg gcctgcattt ttggttttcc ccaccccaca cattctcaac 1560
catagtcctt ctaacaatac caatagctag gacccggctg ctgtgcactg ggactgggga 1620
ttccacatgt ttgccttggg agtctcaagc tggactgcca gcccctgtcc tcccttcacc 1680
cccattgcgt atgagcattt cagaactcca aggagtcaca ggcatcttta tagttcacgt 1740
taacatatag acactgttgg aagcagttcc ttctaaaagg gtagccctgg acttaatacc 1800
agccggatac ctctggcccc caccccatta ctgtacctct ggagtcacta ctgtgggtcg 1860
ccactcctct gctacacagc acggcttttt caaggctgta ttgagaaggg aagttaggaa 1920
gaagggtgtg ctgggctaac cagcccacag agctcacatt cctgtccctt gggtgaaaaa 1980
tacatgtcca tcctgatatc tcctgaattc agaaattagc ctccacatgt gcaatggctt 2040
taagagccag aagcagggtt ctgggaattt tgcaagttac ctgtggccag gtgtggtctc 2100
ggttaccaaa tacggttacc tgcagctttt tagtcctttg tgctcccacg ggtctacaga 2160
gtcccatctg cccaaaggtc ttgaagcttg acaggatgtt ttcgattact cagtctccca 2220
gggcactact ggtccgtagg attcgattgg tcggggtagg agagttaaac aacatttaaa 2280
cagagttctc tcaaaaatgt ctaaagggat tgtaggtaga taacatccaa tcactgtttg 2340
cacttatctg aaatcttccc tcttggctgc ccccaggtat ttactgtgga gaacattgca 2400
taggaatgtc tggaaaaagc ttctacaact tgttacagcc ttcacatttg tagaagcttt 2460

<210> SEQ ID NO 56
<211> LENGTH: 1660
<212> TYPE: DNA
<213> ORGANISM: Artificial Sequence
<220> FEATURE:
<223> OTHER INFORMATION: opt_COX10*-opt_ND1-3'UTR*

<400> SEQUENCE: 56
atggccgcca gcccccacac cctgagcagc cgcctgctga ccggctgcgt gggcggcagc 60
gtgtggtacc tggagcgccg caccatggcc aacctgctgc tgctgatcgt gcccatcctg 120
atcgccatgg ccttcctgat gctgaccgag cgcaagatcc tgggctacat gcagctgcgc 180
aagggcccca acgtggtggg cccctacggc ctgctgcagc ccttcgccga cgccatcaag 240
ctgttcacca aggagcccct gaagcccgcc accagcacca tcaccctgta catcaccgcc 300
cccaccctgg ccctgaccat cgccctgctg ctgtggaccc ccctgcccat gcccaacccc 360
ctggtgaacc tgaacctggg cctgctgttc atcctggcca ccagcagcct ggccgtgtac 420
agcatcctgt ggagcggctg ggccagcaac agcaactacg ccctgatcgg cgccctgcgc 480
gccgtggccc agaccatcag ctacgaggtg accctggcca tcatcctgct gagcaccctg 540
ctgatgagcg gcagcttcaa cctgagcacc ctgatcacca cccaggagca cctgtggctg 600
ctgctgccca gctggcccct ggccatgatg tggttcatca gcaccctggc cgagaccaac 660 cgcacccccct tcgacctggc cgagggcgag agcgagctgg tgagcggctt caacatcgag 720
tacgccgccg gccccttcgc cctgttcttc atggccgagt acaccaacat catcatgatg 780
aacaccctga ccaccaccat cttcctgggc accacctacg acgccctgag ccccgagctg 840
tacaccacct acttcgtgac caagaccctg ctgctgacca gcctgttcct gtggatccgc 900
accgcctacc cccgcttccg ctacgaccag ctgatgcacc tgctgtggaa gaacttcctg 960
cccctgaccc tggccctgct gatgtggtac gtgagcatgc ccatcaccat cagcagcatc 1020

-continued cccccccaga cctaagagca ctgggacgcc caccgcccct ttccctccgc tgccaggcga 1080
gcatgttgtg gtaattctgg aacacaagaa gagaaattgc tgggtttaga acaagattat 1140
aaacgaattc ggtgctcagt gatcacttga cagttttttt tttttttaaa tattacccaa 1200
aatgctcccc aaataagaaa tgcatcagct cagtcagtga atacaaaaaa ggaattattt 1260
ttccctttga gggtctttta tacatctctc ctccaacccc accctctatt ctgtttcttc 1320
ctcctcacat gggggtacac atacacagct tcctcttttg gttccatcct taccaccaca 1380
ccacacgcac actccacatg cccagcagag tggcacttgg tggccagaaa gtgtgagcct 1440
catgatctgc tgtctgtagt tctgtgagct caggtccctc aaaggcctcg gagcaccccc 1500
ttccttgtga ctgagccagg gcctgcattt ttggttttcc ccaccccaca cattctcaac 1560
catagtcctt ctaacaatac caatagctag gacccggctg ctgtgcactg ggactgggga 1620
ttccacatgt ttgccttggg agtctcaagc tggactgcca 1660

<210> SEQ ID NO 57
<211> LENGTH: 2892
<212> TYPE: DNA
<213> ORGANISM: Artificial Sequence
<220> FEATURE:
<223> OTHER INFORMATION: COX8-ND4-3'UTR

<400> SEQUENCE: 57
atgtccgtcc tgacgcgcct gctgctgcgg ggcttgacac ggctcggctc ggcggctcca 60
gtgcggcgcg ccagaatcca ttcgttgatg ctaaaactaa tcgtcccaac aattatgtta 120
ctaccactga catggctttc caaaaaacac atgatttgga tcaacacaac cacccacagc 180
ctaattatta gcatcatccc tctactattt tttaaccaaa tcaacaacaa cctatttagc 240
tgttccccaa ccttttcctc cgaccccta acaacccccc tcctaatgct aactacctgg 300
ctcctacccc tcacaatcat ggcaagccaa cgccacttat ccagtgaacc actatcacga 360
aaaaaactct acctctctat gctaatctcc ctacaaatct ccttaattat gacattcaca 420
gccacagaac taatcatgtt ttatatcttc ttcgaaacca cacttatccc caccttggct 480
atcatcaccc gatggggcaa ccagccagaa cgcctgaacg caggcacata cttcctattc 540
tacaccctag taggctccct tcccctactc atcgcactaa tttacactca caacaccta 600 ggctcactaa acattctact actcactctc actgcccaag aactatcaaa ctcctgggcc 660
aacaacttaa tgtggctagc ttacacaatg gcttttatgg taaagatgcc tctttacgga 720
ctccacttat ggctccctaa agcccatgtc gaagccccca tcgctgggtc aatggtactt 780
gccgcagtac tcttaaaact aggcggctat ggtatgatgc gcctcacact cattctcaac 840
cccctgacaa aacacatggc ctacccttc cttgtactat ccctatgggg catgattatg 900
acaagctcca tctgcctacg acaaacagac ctaaaatcgc tcattgcata ctcttcaatc 960
agccacatgg ccctcgtagt aacagccatt ctcatccaaa ccccctggag cttcaccggc 1020
gcagtcattc tcatgatcgc ccacgggctt acatcctcat tactattctg cctagcaaac 1080
tcaaactacg aacgcactca cagtcgcatc atgatcctct ctcaaggact tcaaactcta 1140
ctcccactaa tggctttttg gtggcttcta gcaagcctcg ctaacctcgc cttacccccc 1200
actattaacc tactgggaga actctctgtg ctagtaacca cgttctcctg gtcaaatatc 1260
actctcctac ttacaggact caacatgcta gtcacagccc tatactccct ctacatgttt 1320
accacaacac aatggggctc actcacccac cacattaaca acatgaaacc ctcattcaca 1380

```
cgagaaaaca ccctcatgtt catgcaccta tcccccattc tcctcctatc cctcaacccc   1440

gacatcatta ccgggttttc ctcttaagag cactgggacg cccaccgccc ctttccctcc   1500

gctgccaggc gagcatgttg tggtaattct ggaacacaag aagagaaatt gctgggttta   1560

gaacaagatt ataaacgaat tcggtgctca gtgatcactt gacagttttt ttttttttta   1620

aatattaccc aaaatgctcc ccaaataaga aatgcatcag ctcagtcagt gaatacaaaa   1680

aaggaattat ttttcccttt gagggtcttt tatacatctc tcctccaacc ccaccctcta   1740

ttctgtttct tcctcctcac atgggggtac acatacacag cttcctcttt tggttccatc   1800

cttaccacca caccacacgc acactccaca tgcccagcag agtggcactt ggtggccaga   1860

aagtgtgagc ctcatgatct gctgtctgta gttctgtgag ctcaggtccc tcaaaggcct   1920

cggagcaccc ccttccttgt gactgagcca gggcctgcat tttggtttt ccccacccca   1980

cacattctca accatagtcc ttctaacaat accaatagct aggacccggc tgctgtgcac   2040

tgggactggg gattccacat gtttgccttg ggagtctcaa gctggactgc cagcccctgt   2100

cctcccttca cccccattgc gtatgagcat ttcagaactc caaggagtca caggcatctt   2160

tatagttcac gttaacatat agacactgtt ggaagcagtt ccttctaaaa gggtagccct   2220

ggacttaata ccagccggat acctctggcc cccaccccat tactgtacct ctggagtcac   2280

tactgtgggt cgccactcct ctgctacaca gcacggcttt ttcaaggctg tattgagaag   2340

ggaagttagg aagaagggtg tgctgggcta accagcccac agagctcaca ttcctgtccc   2400

ttgggtgaaa aatacatgtc catcctgata tctcctgaat tcagaaatta gcctccacat   2460

gtgcaatggc tttaagagcc agaagcaggg ttctgggaat tttgcaagtt acctgtggcc   2520

aggtgtggtc tcggttacca aatacggtta cctgcagctt tttagtcctt tgtgctccca   2580

cgggtctaca gagtcccatc tgcccaaagg tcttgaagct tgacaggatg ttttcgatta   2640

ctcagtctcc cagggcacta ctggtccgta ggattcgatt ggtcggggta ggagagttaa   2700

acaacattta aacagagttc tctcaaaaat gtctaaaggg attgtaggta gataacatcc   2760

aatcactgtt tgcacttatc tgaaatcttc cctcttggct gcccccaggt atttactgtg   2820

gagaacattg cataggaatg tctggaaaaa gcttctacaa cttgttacag ccttcacatt   2880

tgtagaagct tt                                                       2892
```

<210> SEQ ID NO 58
<211> LENGTH: 2092
<212> TYPE: DNA
<213> ORGANISM: Artificial Sequence
<220> FEATURE:
<223> OTHER INFORMATION: COX8-ND4-3'UTR*

<400> SEQUENCE: 58

```
atgtccgtcc tgacgcgcct gctgctgcgg ggcttgacac ggctcggctc ggcggctcca     60

gtgcggcgcg ccagaatcca ttcgttgatg ctaaaactaa tcgtcccaac aattatgtta    120

ctaccactga catggctttc caaaaaacac atgatttgga tcaacacaac cacccacagc    180

ctaattatta gcatcatccc tctactattt tttaaccaaa tcaacaacaa cctatttagc    240

tgttccccaa ccttttcctc cgaccccta acaacccccc tcctaatgct aactacctgg    300

ctcctacccc tcacaatcat ggcaagccaa cgccacttat ccagtgaacc actatcacga    360

aaaaaactct acctctctat gctaatctcc ctacaaatct ccttaattat gacattcaca    420

gccacagaac taatcatgtt ttatatcttc ttcgaaacca cacttatccc caccttggct    480

atcatcaccc gatggggcaa ccagccagaa cgcctgaacg caggcacata cttcctattc    540
```

```
tacaccctag taggctccct tcccctactc atcgcactaa tttacactca caacacccta    600
ggctcactaa acattctact actcactctc actgcccaag aactatcaaa ctcctgggcc    660
aacaacttaa tgtggctagc ttacacaatg gcttttatgg taaagatgcc tctttacgga    720
ctccacttat ggctccctaa agcccatgtc gaagccccca tcgctgggtc aatggtactt    780
gccgcagtac tcttaaaact aggcggctat ggtatgatgc gcctcacact cattctcaac    840
cccctgacaa aacacatggc ctacccctc cttgtactat ccctatgggg catgattatg    900
acaagctcca tctgcctacg acaaacagac ctaaaatcgc tcattgcata ctcttcaatc    960
agccacatgg ccctcgtagt aacagccatt ctcatccaaa ccccctggag cttcaccggc   1020
gcagtcattc tcatgatcgc ccacgggctt acatcctcat tactattctg cctagcaaac   1080
tcaaactacg aacgcactca cagtcgcatc atgatcctct ctcaaggact tcaaactcta   1140
ctcccactaa tggctttttg gtggcttcta gcaagcctcg ctaacctcgc cttacccccc   1200
actattaacc tactgggaga actctctgtg ctagtaacca cgttctcctg gtcaaatatc   1260
actctcctac ttacaggact caacatgcta gtcacagccc tatactccct ctacatgttt   1320
accacaacac aatggggctc actcacccac cacattaaca acatgaaacc ctcattcaca   1380
cgagaaaaca ccctcatgtt catgcaccta tcccccattc tcctccctatc cctcaacccc   1440
gacatcatta ccgggttttc ctcttaagag cactgggacg cccaccgccc ctttccctcc   1500
gctgccaggc gagcatgttg tggtaattct ggaacacaag aagagaaatt gctgggttta   1560
gaacaagatt ataaacgaat tcggtgctca gtgatcactt gacagttttt ttttttttta   1620
aatattaccc aaaatgctcc ccaaataaga aatgcatcag ctcagtcagt gaatacaaaa   1680
aaggaattat ttttcccttt gagggtcttt tatacatctc tcctccaacc ccaccctcta   1740
ttctgtttct tcctcctcac atgggggtac acatacacag cttcctcttt tggttccatc   1800
cttaccacca caccacacgc acactccaca tgcccagcag agtggcactt ggtggccaga   1860
aagtgtgagc ctcatgatct gctgtctgta gttctgtgag ctcaggtccc tcaaaggcct   1920
cggagcaccc ccttccttgt gactgagcca gggcctgcat ttttggtttt ccccacccca   1980
cacattctca accatagtcc ttctaacaat accaatagct aggacccggc tgctgtgcac   2040
tgggactggg gattccacat gtttgccttg ggagtctcaa gctggactgc ca            2092
```

<210> SEQ ID NO 59
<211> LENGTH: 2892
<212> TYPE: DNA
<213> ORGANISM: Artificial Sequence
<220> FEATURE:
<223> OTHER INFORMATION: COX8-opt_ND4-3'UTR

<400> SEQUENCE: 59

```
atgtccgtcc tgacgcgcct gctgctgcgg ggcttgacac ggctcggctc ggcggctcca     60
gtgcggcgcg ccagaatcca ttcgttgatg ctgaagctga tcgtgcccac catcatgctg    120
ctgcctctga cctggctgag caagaaacac atgatctgga tcaacaccac cacgcacagc    180
ctgatcatca gcatcatccc tctgctgttc ttcaaccaga tcaacaacaa cctgttcagc    240
tgcagcccca ccttcagcag cgaccctctg acaacacctc tgctgatgct gaccacctgg    300
ctgctgcccc tcacaatcat ggcctctcag agacacctga gcagcgagcc cctgagccgg    360
aagaaactgt acctgagcat gctgatctcc ctgcagatct ctctgatcat gaccttcacc    420
gccaccgagc tgatcatgtt ctacatcttt ttcgagacaa cgctgatccc cacactggcc    480
```

-continued

```
atcatcacca gatggggcaa ccagcctgag agactgaacg ccggcaccta ctttctgttc    540
tacaccctcg tgggcagcct gccactgctg attgccctga tctacaccca caacaccctg    600
ggctccctga acatcctgct gctgacactg acagcccaag agctgagcaa cagctgggcc    660
aacaatctga tgtggctggc ctacacaatg gccttcatgg tcaagatgcc cctgtacggc    720
ctgcacctgt ggctgcctaa agctcatgtg gaagccccta tcgccggctc tatggtgctg    780
gctgcagtgc tgctgaaact cggcggctac ggcatgatgc ggctgaccct gattctgaat    840
cccctgacca agcacatggc ctatccattt ctggtgctga gcctgtgggg catgattatg    900
accagcagca tctgcctgcg gcagaccgat ctgaagtccc tgatcgccta cagctccatc    960
agccacatgg ccctggtggt caccgccatc ctgattcaga ccccttggag ctttacaggc   1020
gccgtgatcc tgatgattgc ccacggcctg acaagcagcc tgctgttttg tctggccaac   1080
agcaactacg agcggaccca cagcagaatc atgatcctgt ctcagggcct gcagaccctc   1140
ctgcctctta tggctttttg gtggctgctg gcctctctgg ccaatctggc actgcctcct   1200
accatcaatc tgctgggcga gctgagcgtg ctggtcacca cattcagctg gtccaatatc   1260
accctgctgc tcaccggcct gaacatgctg gttacagccc tgtactccct gtacatgttc   1320
accaccacac agtggggaag cctgacacac cacatcaaca atatgaagcc cagcttcacc   1380
cgcgagaaca ccctgatgtt catgcatctg agccccattc tgctgctgtc cctgaatcct   1440
gatatcatca ccggcttctc cagctgagag cactgggacg cccaccgccc ctttccctcc   1500
gctgccaggc gagcatgttg tggtaattct ggaacacaag aagagaaatt gctgggttta   1560
gaacaagatt ataaacgaat tcggtgctca gtgatcactt gacagttttt ttttttttta   1620
aatattaccc aaaatgctcc ccaaataaga aatgcatcag ctcagtcagt gaatacaaaa   1680
aaggaattat ttttcccttt gagggtcttt tatacatctc tcctccaacc ccaccctcta   1740
ttctgtttct tcctcctcac atgggggtac acatacacag cttcctcttt tggttccatc   1800
cttaccacca caccacacgc acactccaca tgcccagcag agtggcactt ggtggccaga   1860
aagtgtgagc ctcatgatct gctgtctgta gttctgtgag ctcaggtccc tcaaaggcct   1920
cggagcaccc ccttccttgt gactgagcca gggcctgcat ttttggtttt ccccacccca   1980
cacattctca accatagtcc ttctaacaat accaatagct aggacccggc tgctgtgcac   2040
tgggactggg gattccacat gtttgccttg ggagtctcaa gctggactgc cagcccctgt   2100
cctcccttca cccccattgc gtatgagcat ttcagaactc caaggagtca caggcatctt   2160
tatagttcac gttaacatat agacactgtt ggaagcagtt ccttctaaaa gggtagccct   2220
ggacttaata ccagccggat acctctggcc cccaccccat tactgtacct ctggagtcac   2280
tactgtgggt cgccactcct ctgctacaca gcacggcttt ttcaaggctg tattgagaag   2340
ggaagttagg aagaagggtg tgctgggcta accagcccac agagctcaca ttcctgtccc   2400
ttgggtgaaa aatacatgtc catcctgata tctcctgaat tcagaaatta gcctccacat   2460
gtgcaatggc tttaagagcc agaagcaggg ttctgggaat tttgcaagtt acctgtggcc   2520
aggtgtggtc tcggttacca aatacggtta cctgcagctt tttagtcctt tgtgctccca   2580
cgggtctaca gagtcccatc tgcccaaagg tcttgaagct tgacaggatg ttttcgatta   2640
ctcagtctcc cagggcacta ctggtccgta ggattcgatt ggtcggggta ggagagttaa   2700
acaacattta aacagagttc tctcaaaaat gtctaaaggg attgtaggta gataacatcc   2760
aatcactgtt tgcacttatc tgaaatcttc cctcttggct gcccccaggt atttactgtg   2820
gagaacattg cataggaatg tctggaaaaa gcttctacaa cttgttacag ccttcacatt   2880
```

-continued

```
tgtagaagct tt                                                       2892


<210> SEQ ID NO 60
<211> LENGTH: 2092
<212> TYPE: DNA
<213> ORGANISM: Artificial Sequence
<220> FEATURE:
<223> OTHER INFORMATION: COX8-opt_ND4-3'UTR*

<400> SEQUENCE: 60

atgtccgtcc tgacgcgcct gctgctgcgg ggcttgacac ggctcggctc ggcggctcca     60

gtgcggcgcg ccagaatcca ttcgttgatg ctgaagctga tcgtgcccac catcatgctg    120

ctgcctctga cctggctgag caagaaacac atgatctgga tcaacaccac cacgcacagc    180

ctgatcatca gcatcatccc tctgctgttc ttcaaccaga tcaacaacaa cctgttcagc    240

tgcagcccca ccttcagcag cgaccctctg acaacacctc tgctgatgct gaccacctgg    300

ctgctgcccc tcacaatcat ggcctctcag agacacctga gcagcgagcc cctgagccgg    360

aagaaactgt acctgagcat gctgatctcc ctgcagatct ctctgatcat gaccttcacc    420

gccaccgagc tgatcatgtt ctacatcttt ttcgagacaa cgctgatccc cacactggcc    480

atcatcacca gatggggcaa ccagcctgag agactgaacg ccggcaccta ctttctgttc    540

tacaccctcg tgggcagcct gccactgctg attgccctga tctacaccca caacaccctg    600

ggctccctga acatcctgct gctgacactg acagcccaag agctgagcaa cagctgggcc    660

aacaatctga tgtggctggc ctacacaatg gccttcatgg tcaagatgcc cctgtacggc    720

ctgcacctgt ggctgcctaa agctcatgtg gaagccccta tcgccggctc tatggtgctg    780

gctgcagtgc tgctgaaact cggcggctac ggcatgatgc ggctgaccct gattctgaat    840

cccctgacca agcacatggc ctatccattt ctggtgctga gcctgtgggg catgattatg    900

accagcagca tctgcctgcg gcagaccgat ctgaagtccc tgatcgccta cagctccatc    960

agccacatgg ccctggtggt caccgccatc ctgattcaga ccccttggag ctttacaggc   1020

gccgtgatcc tgatgattgc ccacggcctg acaagcagcc tgctgttttg tctggccaac   1080

agcaactacg agcggaccca cagcagaatc atgatcctgt ctcagggcct gcagaccctc   1140

ctgcctctta tggctttttg gtggctgctg gcctctctgg ccaatctggc actgcctcct   1200

accatcaatc tgctgggcga gctgagcgtg ctggtcacca cattcagctg gtccaatatc   1260

accctgctgc tcaccggcct gaacatgctg gttacagccc tgtactccct gtacatgttc   1320

accaccacac agtggggaag cctgacacac cacatcaaca atatgaagcc cagcttcacc   1380

cgcgagaaca ccctgatgtt catgcatctg agccccattc tgctgctgtc cctgaatcct   1440

gatatcatca ccggcttctc cagctgagag cactgggacg cccaccgccc ctttccctcc   1500

gctgccaggc gagcatgttg tggtaattct ggaacacaag aagagaaatt gctgggttta   1560

gaacaagatt ataaacgaat tcggtgctca gtgatcactt gacagttttt ttttttttta   1620

aatattaccc aaaatgctcc ccaaataaga aatgcatcag ctcagtcagt gaatacaaaa   1680

aaggaattat ttttcccttt gagggtcttt tatacatctc tcctccaacc ccaccctcta   1740

ttctgtttct tcctcctcac atgggggtac acatacacag cttcctcttt tggttccatc   1800

cttaccacca caccacacgc acactccaca tgcccagcag agtggcactt ggtggccaga   1860

aagtgtgagc ctcatgatct gctgtctgta gttctgtgag ctcaggtccc tcaaaggcct   1920

cggagcaccc ccttccttgt gactgagcca gggcctgcat tttggtttt ccccacccca   1980
```

cacattctca accatagtcc ttctaacaat accaatagct aggacccggc tgctgtgcac 2040
tgggactggg gattccacat gtttgccttg ggagtctcaa gctggactgc ca 2092

<210> SEQ ID NO 61
<211> LENGTH: 2892
<212> TYPE: DNA
<213> ORGANISM: Artificial Sequence
<220> FEATURE:
<223> OTHER INFORMATION: COX8-opt_ND4*-3'UTR

<400> SEQUENCE: 61
atgtccgtcc tgacgcgcct gctgctgcgg ggcttgacac ggctcggctc ggcggctcca 60
gtgcggcgcg ccagaatcca ttcgttgatg ctgaagctga tcgtgcccac catcatgctg 120
ctgcccctga cctggctgag caagaagcac atgatctgga tcaacaccac cacccacagc 180
ctgatcatca gcatcatccc cctgctgttc ttcaaccaga tcaacaacaa cctgttcagc 240
tgcagcccca ccttcagcag cgacccccctg accaccccc tgctgatgct gaccacctgg 300
ctgctgcccc tgaccatcat ggccagccag cgccacctga gcagcgagcc cctgagccgc 360
aagaagctgt acctgagcat gctgatcagc ctgcagatca gcctgatcat gaccttcacc 420
gccaccgagc tgatcatgtt ctacatcttc ttcgagacca ccctgatccc caccctggcc 480
atcatcaccc gctggggcaa ccagcccgag cgcctgaacg ccggcaccta cttcctgttc 540
tacaccctgg tgggcagcct gcccctgctg atcgccctga tctacaccca caacaccctg 600
ggcagcctga acatcctgct gctgaccctg accgcccagg agctgagcaa cagctgggcc 660
aacaacctga tgtggctggc ctacaccatg gccttcatgg tgaagatgcc cctgtacggc 720
ctgcacctgt ggctgcccaa ggcccacgtg gaggccccca tcgccggcag catggtgctg 780
gccgccgtgc tgctgaagct gggcggctac ggcatgatgc gcctgaccct gatcctgaac 840
cccctgacca agcacatggc ctacccttc ctggtgctga gcctgtgggg catgatcatg 900
accagcagca tctgcctgcg ccagaccgac ctgaagagcc tgatcgccta cagcagcatc 960
agccacatgg ccctggtggt gaccgccatc ctgatccaga cccccctggag cttcaccggc 1020 gccgtgatcc tgatgatcgc ccacggcctg accagcagcc tgctgttctg cctggccaac 1080
agcaactacg agcgcaccca cagccgcatc atgatcctga gccagggcct gcagaccctg 1140
ctgcccctga tggccttctg gtggctgctg gccagcctgg ccaacctggc cctgcccccc 1200
accatcaacc tgctgggcga gctgagcgtg ctggtgacca ccttcagctg gagcaacatc 1260
accctgctgc tgaccggcct gaacatgctg gtgaccgccc tgtacagcct gtacatgttc 1320
accaccaccc agtggggcag cctgacccac cacatcaaca acatgaagcc cagcttcacc 1380
cgcgagaaca ccctgatgtt catgcacctg agccccatcc tgctgctgag cctgaacccc 1440
gacatcatca ccggcttcag cagctaagag cactgggacg cccaccgccc ctttccctcc 1500
gctgccaggc gagcatgttg tggtaattct ggaacacaag aagagaaatt gctgggttta 1560
gaacaagatt ataaacgaat tcggtgctca gtgatcactt gacagttttt ttttttttta 1620
aatattaccc aaaatgctcc ccaaataaga aatgcatcag ctcagtcagt gaatacaaaa 1680
aaggaattat ttttcccttt gagggtcttt tatacatctc tcctccaacc ccaccctcta 1740
ttctgtttct tcctcctcac atgggggtac acatacacag cttcctcttt tggttccatc 1800
cttaccacca caccacacgc acactccaca tgcccagcag agtggcactt ggtggccaga 1860
aagtgtgagc ctcatgatct gctgtctgta gttctgtgag ctcaggtccc tcaaaggcct 1920
cggagcaccc ccttccttgt gactgagcca gggcctgcat tttggtttt ccccacccca 1980

```
cacattctca accatagtcc ttctaacaat accaatagct aggacccggc tgctgtgcac   2040

tgggactggg gattccacat gtttgccttg ggagtctcaa gctggactgc cagcccctgt   2100

cctcccttca cccccattgc gtatgagcat ttcagaactc caaggagtca caggcatctt   2160

tatagttcac gttaacatat agacactgtt ggaagcagtt ccttctaaaa gggtagccct   2220

ggacttaata ccagccggat acctctggcc cccaccccat tactgtacct ctggagtcac   2280

tactgtgggt cgccactcct ctgctacaca gcacggcttt ttcaaggctg tattgagaag   2340

ggaagttagg aagaagggtg tgctgggcta accagcccac agagctcaca ttcctgtccc   2400

ttgggtgaaa aatacatgtc catcctgata tctcctgaat tcagaaatta gcctccacat   2460

gtgcaatggc tttaagagcc agaagcaggg ttctgggaat tttgcaagtt acctgtggcc   2520

aggtgtggtc tcggttacca aatacggtta cctgcagctt tttagtcctt tgtgctccca   2580

cgggtctaca gagtcccatc tgcccaaagg tcttgaagct tgacaggatg ttttcgatta   2640

ctcagtctcc cagggcacta ctggtccgta ggattcgatt ggtcggggta ggagagttaa   2700

acaacattta aacagagttc tctcaaaaat gtctaaaggg attgtaggta gataacatcc   2760

aatcactgtt tgcacttatc tgaaatcttc cctcttggct gcccccaggt atttactgtg   2820

gagaacattg cataggaatg tctggaaaaa gcttctacaa cttgttacag ccttcacatt   2880

tgtagaagct tt                                                       2892
```

<210> SEQ ID NO 62
<211> LENGTH: 2092
<212> TYPE: DNA
<213> ORGANISM: Artificial Sequence
<220> FEATURE:
<223> OTHER INFORMATION: COX8-opt_ND4*-3'UTR*

<400> SEQUENCE: 62

```
atgtccgtcc tgacgcgcct gctgctgcgg ggcttgacac ggctcggctc ggcggctcca     60

gtgcggcgcg ccagaatcca ttcgttgatg ctgaagctga tcgtgcccac catcatgctg    120

ctgcccctga cctggctgag caagaagcac atgatctgga tcaacaccac cacccacagc    180

ctgatcatca gcatcatccc cctgctgttc ttcaaccaga tcaacaacaa cctgttcagc    240

tgcagcccca ccttcagcag cgacccctg accacccccc tgctgatgct gaccacctgg     300

ctgctgcccc tgaccatcat ggccagccag cgccacctga gcagcgagcc cctgagccgc    360

aagaagctgt acctgagcat gctgatcagc ctgcagatca gcctgatcat gaccttcacc    420

gccaccgagc tgatcatgtt ctacatcttc ttcgagacca ccctgatccc caccctggcc    480

atcatcaccc gctggggcaa ccagcccgag cgcctgaacg ccggcaccta cttcctgttc    540

tacaccctgg tgggcagcct gcccctgctg atcgccctga tctacaccca caacaccctg    600

ggcagcctga acatcctgct gctgaccctg accgcccagg agctgagcaa cagctgggcc    660

aacaacctga tgtggctggc ctacaccatg gccttcatgg tgaagatgcc cctgtacggc    720

ctgcacctgt ggctgcccaa ggcccacgtg gaggccccca tcgccggcag catggtgctg    780

gccgccgtgc tgctgaagct gggcggctac ggcatgatgc gcctgaccct gatcctgaac    840

cccctgacca agcacatggc ctaccccttc ctggtgctga gcctgtgggg catgatcatg    900

accagcagca tctgcctgcg ccagaccgac ctgaagagcc tgatcgccta cagcagcatc    960

agccacatgg ccctggtggt gaccgccatc ctgatccaga ccccctggag cttcaccggc   1020

gccgtgatcc tgatgatcgc ccacggcctg accagcagcc tgctgttctg cctggccaac   1080
```

-continued

```
agcaactacg agcgcaccca cagccgcatc atgatcctga gccagggcct gcagaccctg   1140

ctgcccctga tggccttctg gtggctgctg gccagcctgg ccaacctggc cctgcccccc   1200

accatcaacc tgctgggcga gctgagcgtg ctggtgacca ccttcagctg gagcaacatc   1260

accctgctgc tgaccggcct gaacatgctg gtgaccgccc tgtacagcct gtacatgttc   1320

accaccaccc agtggggcag cctgacccac cacatcaaca acatgaagcc cagcttcacc   1380

cgcgagaaca ccctgatgtt catgcacctg agccccatcc tgctgctgag cctgaacccc   1440

gacatcatca ccggcttcag cagctaagag cactgggacg cccaccgccc ctttccctcc   1500

gctgccaggc gagcatgttg tggtaattct ggaacacaag aagagaaatt gctgggttta   1560

gaacaagatt ataaacgaat tcggtgctca gtgatcactt gacagttttt ttttttttta   1620

aatattaccc aaaatgctcc ccaaataaga aatgcatcag ctcagtcagt gaatacaaaa   1680

aaggaattat ttttcccttt gagggtcttt tatacatctc tcctccaacc ccaccctcta   1740

ttctgtttct tcctcctcac atgggggtac acatacacag cttcctcttt tggttccatc   1800

cttaccacca caccacacgc acactccaca tgcccagcag agtggcactt ggtggccaga   1860

aagtgtgagc ctcatgatct gctgtctgta gttctgtgag ctcaggtccc tcaaaggcct   1920

cggagcaccc ccttccttgt gactgagcca gggcctgcat tttggtttt ccccacccca    1980

cacattctca accatagtcc ttctaacaat accaatagct aggacccggc tgctgtgcac   2040

tgggactggg gattccacat gtttgccttg ggagtctcaa gctggactgc ca           2092
```

<210> SEQ ID NO 63
<211> LENGTH: 2037
<212> TYPE: DNA
<213> ORGANISM: Artificial Sequence
<220> FEATURE:
<223> OTHER INFORMATION: COX8-ND6-3'UTR

<400> SEQUENCE: 63

```
atgtccgtcc tgacgcgcct gctgctgcgg ggcttgacac ggctcggctc ggcggctcca     60

gtgcggcgcg ccagaatcca ttcgttgatg atgtatgctt tgtttctgtt gagtgtgggt    120

ttagtaatgg ggtttgtggg gttttcttct aagccttctc ctatttatgg gggtttagta    180

ttgattgtta gcggtgtggt cgggtgtgtt attattctga attttggggg aggttatatg    240

ggtttaatgg ttttttttaat ttatttaggg ggaatgatgg ttgtctttgg atatactaca    300

gcgatggcta ttgaggagta tcctgaggca tgggggtcag ggggttgaggt cttggtgagt    360

gttttagtgg ggttagcgat ggaggtagga ttggtgctgt gggtgaaaga gtatgatggg    420

gtggtggttg tggtaaactt taatagtgta ggaagctgga tgatttatga aggagagggg    480

tcagggttga ttcgggagga tcctattggt gcgggggctt tgtatgatta tgggcgttgg    540

ttagtagtag ttactggttg gacattgttt gttggtgtat atattgtaat tgagattgct    600

cgggggaatt aggagcactg ggacgcccac cgcccctttc cctccgctgc caggcgagca    660

tgttgtggta attctggaac acaagaagag aaattgctgg gtttagaaca agattataaa    720

cgaattcggt gctcagtgat cacttgacag tttttttttt ttttaaatat tacccaaaat    780

gctccccaaa taagaaatgc atcagctcag tcagtgaata caaaaaagga attatttttc    840

cctttgaggg tcttttatac atctctcctc caaccccacc ctctattctg tttcttcctc    900

ctcacatggg ggtacacata cacagcttcc tcttttggtt ccatccttac caccacacca    960

cacgcacact ccacatgccc agcagagtgg cacttggtgg ccagaaagtg tgagcctcat   1020

gatctgctgt ctgtagttct gtgagctcag gtccctcaaa ggcctcggag cacccccttc   1080
```

```
cttgtgactg agccagggcc tgcatttttg gttttcccca ccccacacat tctcaaccat   1140
agtccttcta acaataccaa tagctaggac ccggctgctg tgcactggga ctggggattc   1200
cacatgtttg ccttgggagt ctcaagctgg actgccagcc cctgtcctcc cttcaccccc   1260
attgcgtatg agcatttcag aactccaagg agtcacaggc atctttatag ttcacgttaa   1320
catatagaca ctgttggaag cagttccttc taaaagggta gccctggact taataccagc   1380
cggatacctc tggcccccac cccattactg tacctctgga gtcactactg tgggtcgcca   1440
ctcctctgct acacagcacg gctttttcaa ggctgtattg agaagggaag ttaggaagaa   1500
gggtgtgctg ggctaaccag cccacagagc tcacattcct gtcccttggg tgaaaaatac   1560
atgtccatcc tgatatctcc tgaattcaga aattagcctc cacatgtgca atggctttaa   1620
gagccagaag cagggttctg ggaattttgc aagttacctg tggccaggtg tggtctcggt   1680
taccaaatac ggttacctgc agctttttag tcctttgtgc tcccacgggt ctacagagtc   1740
ccatctgccc aaaggtcttg aagcttgaca ggatgttttc gattactcag tctcccaggg   1800
cactactggt ccgtaggatt cgattggtcg gggtaggaga gttaaacaac atttaaacag   1860
agttctctca aaaatgtcta aagggattgt aggtagataa catccaatca ctgtttgcac   1920
ttatctgaaa tcttccctct tggctgcccc caggtattta ctgtggagaa cattgcatag   1980
gaatgtctgg aaaaagcttc tacaacttgt tacagccttc acatttgtag aagcttt      2037
```

<210> SEQ ID NO 64
<211> LENGTH: 1237
<212> TYPE: DNA
<213> ORGANISM: Artificial Sequence
<220> FEATURE:
<223> OTHER INFORMATION: COX8-ND6-3'UTR*

<400> SEQUENCE: 64

```
atgtccgtcc tgacgcgcct gctgctgcgg ggcttgacac ggctcggctc ggcggctcca     60
gtgcggcgcg ccagaatcca ttcgttgatg atgtatgctt tgtttctgtt gagtgtgggt    120
ttagtaatgg ggtttgtggg gttttcttct aagccttctc ctatttatgg gggtttagta    180
ttgattgtta gcggtgtggt cgggtgtgtt attattctga attttggggg aggttatatg    240
ggtttaatgg ttttttttaat ttatttaggg ggaatgatgg ttgtctttgg atatactaca    300
gcgatggcta ttgaggagta tcctgaggca tgggggtcag ggggttgaggt cttggtgagt    360
gttttagtgg ggttagcgat ggaggtagga ttggtgctgt gggtgaaaga gtatgatggg    420
gtggtggttg tggtaaactt taatagtgta ggaagctgga tgatttatga aggagagggg    480
tcagggttga ttcgggagga tcctattggt gcgggggctt tgtatgatta tgggcgttgg    540
ttagtagtag ttactggttg gacattgttt gttggtgtat atattgtaat tgagattgct    600
cgggggaatt aggagcactg ggacgcccac cgcccctttc cctccgctgc caggcgagca    660
tgttgtggta attctggaac acaagaagag aaattgctgg gtttagaaca agattataaa    720
cgaattcggt gctcagtgat cacttgacag tttttttttt ttttaaatat tacccaaaat    780
gctccccaaa taagaaatgc atcagctcag tcagtgaata caaaaaagga attatttttc    840
cctttgaggg tcttttatac atctctcctc caaccccacc ctctattctg tttcttcctc    900
ctcacatggg ggtacacata cacagcttcc tcttttggtt ccatccttac caccacacca    960
cacgcacact ccacatgccc agcagagtgg cacttggtgg ccagaaagtg tgagcctcat   1020
gatctgctgt ctgtagttct gtgagctcag gtccctcaaa ggcctcggag cacccccttc   1080
```

cttgtgactg agccagggcc tgcatttttg gttttcccca ccccacacat tctcaaccat 1140
agtccttcta acaataccaa tagctaggac ccggctgctg tgcactggga ctggggattc 1200
cacatgtttg ccttgggagt ctcaagctgg actgcca 1237

<210> SEQ ID NO 65
<211> LENGTH: 2037
<212> TYPE: DNA
<213> ORGANISM: Artificial Sequence
<220> FEATURE:
<223> OTHER INFORMATION: COX8-opt_ND6-3'UTR

<400> SEQUENCE: 65
atgtccgtcc tgacgcgcct gctgctgcgg ggcttgacac ggctcggctc ggcggctcca 60
gtgcggcgcg ccagaatcca ttcgttgatg atgtacgccc tgttcctgct gagcgtgggc 120
ctggtgatgg gcttcgtggg cttcagcagc aagcccagcc ccatctacgg cggcctggtg 180
ctgatcgtga gcggcgtggt gggctgcgtg atcatcctga acttcggcgg cggctacatg 240
ggcctgatgg tgttcctgat ctacctgggc ggcatgatgg tggtgttcgg ctacaccacc 300
gccatggcca tcgaggagta ccccgaggcc tggggcagcg gcgtggaggt gctggtgagc 360
gtgctggtgg gcctggccat ggaggtgggc ctggtgctgt gggtgaagga gtacgacggc 420
gtggtggtgg tggtgaactt caacagcgtg ggcagctgga tgatctacga gggcgagggc 480
agcggcctga tccgcgagga ccccatcggc gccggcgccc tgtacgacta cggccgctgg 540
ctggtggtgg tgaccggctg gaccctgttc gtgggcgtgt acatcgtgat cgagatcgcc 600
cgcggcaact aagagcactg ggacgcccac cgcccctttc cctccgctgc caggcgagca 660
tgttgtggta attctggaac acaagaagag aaattgctgg gtttagaaca agattataaa 720
cgaattcggt gctcagtgat cacttgacag tttttttttt ttttaaatat tacccaaaat 780
gctccccaaa taagaaatgc atcagctcag tcagtgaata caaaaaagga attatttttc 840
cctttgaggg tcttttatac atctctcctc caaccccacc ctctattctg tttcttcctc 900
ctcacatggg ggtacacata cacagcttcc tcttttggtt ccatccttac caccacacca 960
cacgcacact ccacatgccc agcagagtgg cacttggtgg ccagaaagtg tgagcctcat 1020
gatctgctgt ctgtagttct gtgagctcag gtccctcaaa ggcctcggag cacccccttc 1080
cttgtgactg agccagggcc tgcatttttg gttttcccca ccccacacat tctcaaccat 1140
agtccttcta acaataccaa tagctaggac ccggctgctg tgcactggga ctggggattc 1200
cacatgtttg ccttgggagt ctcaagctgg actgccagcc cctgtcctcc cttcaccccc 1260
attgcgtatg agcatttcag aactccaagg agtcacaggc atctttatag ttcacgttaa 1320
catatagaca ctgttggaag cagttccttc taaaagggta gccctggact taataccagc 1380
cggatacctc tggcccccac cccattactg tacctctgga gtcactactg tgggtcgcca 1440
ctcctctgct acacagcacg gctttttcaa ggctgtattg agaagggaag ttaggaagaa 1500
gggtgtgctg ggctaaccag cccacagagc tcacattcct gtcccttggg tgaaaaatac 1560
atgtccatcc tgatatctcc tgaattcaga aattagcctc cacatgtgca atggctttaa 1620
gagccagaag cagggttctg ggaattttgc aagttacctg tggccaggtg tggtctcggt 1680
taccaaatac ggttacctgc agctttttag tcctttgtgc tcccacgggt ctacagagtc 1740
ccatctgccc aaaggtcttg aagcttgaca ggatgtttc gattactcag tctcccaggg 1800
cactactggt ccgtaggatt cgattggtcg gggtaggaga gttaaacaac atttaaacag 1860
agttctctca aaaatgtcta aagggattgt aggtagataa catccaatca ctgtttgcac 1920
ttatctgaaa tcttccctct tggctgcccc caggtattta ctgtggagaa cattgcatag 1980
gaatgtctgg aaaaagcttc tacaacttgt tacagccttc acatttgtag aagcttt 2037

<210> SEQ ID NO 66
<211> LENGTH: 1237
<212> TYPE: DNA
<213> ORGANISM: Artificial Sequence
<220> FEATURE:
<223> OTHER INFORMATION: COX8-opt_ND6-3'UTR*

<400> SEQUENCE: 66
atgtccgtcc tgacgcgcct gctgctgcgg ggcttgacac ggctcggctc ggcggctcca 60
gtgcggcgcg ccagaatcca ttcgttgatg atgtacgccc tgttcctgct gagcgtgggc 120
ctggtgatgg gcttcgtggg cttcagcagc aagcccagcc ccatctacgg cggcctggtg 180
ctgatcgtga gcggcgtggt gggctgcgtg atcatcctga acttcggcgg cggctacatg 240
ggcctgatgg tgttcctgat ctacctgggc ggcatgatgg tggtgttcgg ctacaccacc 300
gccatggcca tcgaggagta ccccgaggcc tggggcagcg gcgtggaggt gctggtgagc 360
gtgctggtgg gcctggccat ggaggtgggc ctggtgctgt gggtgaagga gtacgacggc 420
gtggtggtgg tggtgaactt caacagcgtg ggcagctgga tgatctacga gggcgagggc 480
agcggcctga tccgcgagga ccccatcggc gccggcgccc tgtacgacta cggccgctgg 540
ctggtggtgg tgaccggctg gaccctgttc gtgggcgtgt acatcgtgat cgagatcgcc 600
cgcggcaact aagagcactg ggacgcccac cgcccctttc cctccgctgc caggcgagca 660
tgttgtggta attctggaac acaagaagag aaattgctgg gtttagaaca agattataaa 720
cgaattcggt gctcagtgat cacttgacag tttttttttt ttttaaatat tacccaaaat 780
gctccccaaa taagaaatgc atcagctcag tcagtgaata caaaaaagga attatttttc 840
cctttgaggg tcttttatac atctctcctc caaccccacc ctctattctg tttcttcctc 900
ctcacatggg ggtacacata cacagcttcc tcttttggtt ccatccttac caccacacca 960
cacgcacact ccacatgccc agcagagtgg cacttggtgg ccagaaagtg tgagcctcat 1020
gatctgctgt ctgtagttct gtgagctcag gtccctcaaa ggcctcggag cacccccttc 1080
cttgtgactg agccagggcc tgcatttttg gttttcccca ccccacacat tctcaaccat 1140
agtccttcta acaataccaa tagctaggac ccggctgctg tgcactggga ctggggattc 1200
cacatgtttg ccttgggagt ctcaagctgg actgcca 1237

<210> SEQ ID NO 67
<211> LENGTH: 2463
<212> TYPE: DNA
<213> ORGANISM: Artificial Sequence
<220> FEATURE:
<223> OTHER INFORMATION: COX8-ND1-3'UTR

<400> SEQUENCE: 67
atgtccgtcc tgacgcgcct gctgctgcgg ggcttgacac ggctcggctc ggcggctcca 60
gtgcggcgcg ccagaatcca ttcgttgatg gccaacctcc tactcctcat tgtacccatt 120
ctaatcgcaa tggcattcct aatgcttacc gaacgaaaaa ttctaggcta tatgcaacta 180
cgcaaaggcc ccaacgttgt aggcccctac gggctactac aacccttcgc tgacgccata 240
aaactcttca ccaaagagcc cctaaaaccc gccacatcta ccatcaccct ctacatcacc 300
gccccgacct tagctctcac catcgctctt ctactatgga ccccccctccc catgcccaac 360

-continued

```
cccctggtca acctcaacct aggcctccta tttattctag ccacctctag cctagccgtt    420

tactcaatcc tctggtcagg gtgggcatca aactcaaact acgccctgat cggcgcactg    480

cgagcagtag cccaaacaat ctcatatgaa gtcaccctag ccatcattct actatcaaca    540

ttactaatga gtggctcctt taacctctcc acccttatca caacacaaga acacctctgg    600

ttactcctgc catcatggcc cttggccatg atgtggttta tctccacact agcagagacc    660

aaccgaaccc ccttcgacct tgccgaaggg gagtccgaac tagtctcagg cttcaacatc    720

gaatacgccg caggcccctt cgccctattc ttcatggccg aatacacaaa cattattatg    780

atgaacaccc tcaccactac aatcttccta ggaacaacat atgacgcact ctcccctgaa    840

ctctacacaa catattttgt caccaagacc ctacttctaa cctccctgtt cttatggatt    900

cgaacagcat acccccgatt ccgctacgac caactcatgc acctcctatg gaaaaacttc    960

ctaccactca ccctagcatt acttatgtgg tatgtctcca tgcccattac aatctccagc   1020

attccccctc aaacctaaga gcactgggac gcccaccgcc cctttccctc cgctgccagg   1080

cgagcatgtt gtggtaattc tggaacacaa gaagagaaat tgctgggttt agaacaagat   1140

tataaacgaa ttcggtgctc agtgatcact tgacagtttt ttttttttt aaatattacc   1200

caaaatgctc cccaaataag aaatgcatca gctcagtcag tgaatacaaa aaaggaatta   1260

tttttccctt tgagggtctt ttatacatct ctcctccaac cccaccctct attctgtttc   1320

ttcctcctca catgggggta cacatacaca gcttcctctt ttggttccat ccttaccacc   1380

acaccacacg cacactccac atgcccagca gagtggcact tggtggccag aaagtgtgag   1440

cctcatgatc tgctgtctgt agttctgtga gctcaggtcc ctcaaaggcc tcggagcacc   1500

cccttccttg tgactgagcc agggcctgca tttttggttt tccccacccc acacattctc   1560

aaccatagtc cttctaacaa taccaatagc taggacccgg ctgctgtgca ctgggactgg   1620

ggattccaca tgtttgcctt gggagtctca agctggactg ccagcccctg tcctcccttc   1680

acccccattg cgtatgagca tttcagaact ccaaggagtc acaggcatct ttatagttca   1740

cgttaacata tagacactgt tggaagcagt tccttctaaa agggtagccc tggacttaat   1800

accagccgga tacctctggc ccccacccca ttactgtacc tctggagtca ctactgtggg   1860

tcgccactcc tctgctacac agcacggctt tttcaaggct gtattgagaa gggaagttag   1920

gaagaagggt gtgctgggct aaccagccca cagagctcac attcctgtcc cttgggtgaa   1980

aaatacatgt ccatcctgat atctcctgaa ttcagaaatt agcctccaca tgtgcaatgg   2040

ctttaagagc cagaagcagg gttctgggaa ttttgcaagt tacctgtggc caggtgtggt   2100

ctcggttacc aaatacggtt acctgcagct ttttagtcct ttgtgctccc acgggtctac   2160

agagtcccat ctgcccaaag gtcttgaagc ttgacaggat gttttcgatt actcagtctc   2220

ccagggcact actggtccgt aggattcgat tggtcggggt aggagagtta aacaacattt   2280

aaacagagtt ctctcaaaaa tgtctaaagg gattgtaggt agataacatc caatcactgt   2340

ttgcacttat ctgaaatctt ccctcttggc tgcccccagg tatttactgt ggagaacatt   2400

gcataggaat gtctggaaaa agcttctaca acttgttaca gccttcacat ttgtagaagc   2460

ttt                                                                 2463
```

<210> SEQ ID NO 68
<211> LENGTH: 1663
<212> TYPE: DNA
<213> ORGANISM: Artificial Sequence
<220> FEATURE:
<223> OTHER INFORMATION: COX8-ND1-3'UTR*

<400> SEQUENCE: 68
atgtccgtcc tgacgcgcct gctgctgcgg ggcttgacac ggctcggctc ggcggctcca 60
gtgcggcgcg ccagaatcca ttcgttgatg gccaacctcc tactcctcat tgtacccatt 120
ctaatcgcaa tggcattcct aatgcttacc gaacgaaaaa ttctaggcta tatgcaacta 180
cgcaaaggcc ccaacgttgt aggcccctac gggctactac aacccttcgc tgacgccata 240
aaactcttca ccaaagagcc cctaaaaccc gccacatcta ccatcaccct ctacatcacc 300
gccccgacct tagctctcac catcgctctt ctactatgga ccccccctccc catgcccaac 360 cccctggtca acctcaacct aggcctccta tttattctag ccacctctag cctagccgtt 420
tactcaatcc tctggtcagg gtgggcatca aactcaaact acgccctgat cggcgcactg 480
cgagcagtag cccaaacaat ctcatatgaa gtcaccctag ccatcattct actatcaaca 540
ttactaatga gtggctcctt taacctctcc acccttatca caacacaaga acacctctgg 600
ttactcctgc catcatggcc cttggccatg atgtggttta tctccacact agcagagacc 660
aaccgaaccc ccttcgacct tgccgaaggg gagtccgaac tagtctcagg cttcaacatc 720
gaatacgccg caggcccctt cgccctattc ttcatggccg aatacacaaa cattattatg 780
atgaacaccc tcaccactac aatcttccta ggaacaacat atgacgcact ctcccctgaa 840
ctctacacaa catattttgt caccaagacc ctacttctaa cctccctgtt cttatggatt 900
cgaacagcat acccccgatt ccgctacgac caactcatgc acctcctatg gaaaaacttc 960
ctaccactca ccctagcatt acttatgtgg tatgtctcca tgcccattac aatctccagc 1020 attcccccctc aaacctaaga gcactgggac gcccaccgcc cctttccctc cgctgccagg 1080
cgagcatgtt gtggtaattc tggaacacaa gaagagaaat tgctgggttt agaacaagat 1140
tataaacgaa ttcggtgctc agtgatcact tgacagtttt tttttttttt aaatattacc 1200
caaaatgctc cccaaataag aaatgcatca gctcagtcag tgaatacaaa aaaggaatta 1260
tttttccctt tgagggtctt ttatacatct ctcctccaac cccaccctct attctgtttc 1320
ttcctcctca catgggggta cacatacaca gcttcctctt ttggttccat ccttaccacc 1380
acaccacacg cacactccac atgcccagca gagtggcact tggtggccag aaagtgtgag 1440
cctcatgatc tgctgtctgt agttctgtga gctcaggtcc ctcaaaggcc tcggagcacc 1500
cccttccttg tgactgagcc agggcctgca tttttggttt tccccacccc acacattctc 1560
aaccatagtc cttctaacaa taccaatagc taggacccgg ctgctgtgca ctgggactgg 1620
ggattccaca tgtttgcctt gggagtctca agctggactg cca 1663

<210> SEQ ID NO 69
<211> LENGTH: 2463
<212> TYPE: DNA
<213> ORGANISM: Artificial Sequence
<220> FEATURE:
<223> OTHER INFORMATION: COX8-opt_ND1-3'UTR

<400> SEQUENCE: 69
atgtccgtcc tgacgcgcct gctgctgcgg ggcttgacac ggctcggctc ggcggctcca 60
gtgcggcgcg ccagaatcca ttcgttgatg gccaacctgc tgctgctgat cgtgcccatc 120
ctgatcgcca tggccttcct gatgctgacc gagcgcaaga tcctgggcta catgcagctg 180
cgcaagggcc ccaacgtggt gggcccctac ggcctgctgc agcccttcgc cgacgccatc 240
aagctgttca ccaaggagcc cctgaagccc gccaccagca ccatcaccct gtacatcacc 300

```
gcccccaccc tggccctgac catcgccctg ctgctgtgga ccccccctgcc catgcccaac    360
cccctggtga acctgaacct gggcctgctg ttcatcctgg ccaccagcag cctggccgtg    420
tacagcatcc tgtggagcgg ctgggccagc aacagcaact acgccctgat cggcgccctg    480
cgcgccgtgg cccagaccat cagctacgag gtgaccctgg ccatcatcct gctgagcacc    540
ctgctgatga gcggcagctt caacctgagc accctgatca ccacccagga gcacctgtgg    600
ctgctgctgc ccagctggcc cctggccatg atgtggttca tcagcaccct ggccgagacc    660
aaccgcaccc ccttcgacct ggccgagggc gagagcgagc tggtgagcgg cttcaacatc    720
gagtacgccg ccggcccctt cgccctgttc ttcatggccg agtacaccaa catcatcatg    780
atgaacaccc tgaccaccac catcttcctg ggcaccacct acgacgccct gagccccgag    840
ctgtacacca cctacttcgt gaccaagacc ctgctgctga ccagcctgtt cctgtggatc    900
cgcaccgcct acccccgctt ccgctacgac cagctgatgc acctgctgtg gaagaacttc    960
ctgcccctga ccctggccct gctgatgtgg tacgtgagca tgcccatcac catcagcagc   1020
atcccccccc agacctaaga gcactgggac gcccaccgcc cctttccctc cgctgccagg   1080
cgagcatgtt gtggtaattc tggaacacaa gaagagaaat tgctgggttt agaacaagat   1140
tataaacgaa ttcggtgctc agtgatcact tgacagtttt tttttttttt aaatattacc   1200
caaaatgctc cccaaataag aaatgcatca gctcagtcag tgaatacaaa aaaggaatta   1260
tttttccctt tgagggtctt ttatacatct ctcctccaac ccccaccctct attctgtttc   1320
ttcctcctca catgggggta cacatacaca gcttcctctt ttggttccat ccttaccacc   1380
acaccacacg cacactccac atgcccagca gagtggcact tggtggccag aaagtgtgag   1440
cctcatgatc tgctgtctgt agttctgtga gctcaggtcc ctcaaaggcc tcggagcacc   1500
cccttccttg tgactgagcc agggcctgca tttttggttt tccccacccc acacattctc   1560
aaccatagtc cttctaacaa taccaatagc taggacccgg ctgctgtgca ctgggactgg   1620
ggattccaca tgtttgcctt gggagtctca agctggactg ccagcccctg tcctcccttc   1680
acccccattg cgtatgagca tttcagaact ccaaggagtc acaggcatct ttatagttca   1740
cgttaacata tagacactgt tggaagcagt tccttctaaa agggtagccc tggacttaat   1800
accagccgga tacctctggc ccccacccca ttactgtacc tctggagtca ctactgtggg   1860
tcgccactcc tctgctacac agcacggctt tttcaaggct gtattgagaa gggaagttag   1920
gaagaagggt gtgctgggct aaccagccca cagagctcac attcctgtcc cttgggtgaa   1980
aaatacatgt ccatcctgat atctcctgaa ttcagaaatt agcctccaca tgtgcaatgg   2040
ctttaagagc cagaagcagg gttctgggaa ttttgcaagt tacctgtggc caggtgtggt   2100
ctcggttacc aaatacggtt acctgcagct ttttagtcct ttgtgctccc acgggtctac   2160
agagtcccat ctgcccaaag gtcttgaagc ttgacaggat gttttcgatt actcagtctc   2220
ccagggcact actggtccgt aggattcgat tggtcggggt aggagagtta aacaacattt   2280
aaacagagtt ctctcaaaaa tgtctaaagg gattgtaggt agataacatc caatcactgt   2340
ttgcacttat ctgaaatctt ccctcttggc tgcccccagg tatttactgt ggagaacatt   2400
gcataggaat gtctggaaaa agcttctaca acttgttaca gccttcacat ttgtagaagc   2460
ttt                                                                 2463
```

<210> SEQ ID NO 70
<211> LENGTH: 1663
<212> TYPE: DNA
<213> ORGANISM: Artificial Sequence
<220> FEATURE:
<223> OTHER INFORMATION: COX8-opt_ND1-3'UTR*

<400> SEQUENCE: 70
atgtccgtcc tgacgcgcct gctgctgcgg ggcttgacac ggctcggctc ggcggctcca 60
gtgcggcgcg ccagaatcca ttcgttgatg gccaacctgc tgctgctgat cgtgcccatc 120
ctgatcgcca tggccttcct gatgctgacc gagcgcaaga tcctgggcta catgcagctg 180
cgcaagggcc ccaacgtggt gggcccctac ggcctgctgc agcccttcgc cgacgccatc 240
aagctgttca ccaaggagcc cctgaagccc gccaccagca ccatcaccct gtacatcacc 300
gcccccaccc tggccctgac catcgccctg ctgctgtgga cccccctgcc catgcccaac 360
cccctggtga acctgaacct gggcctgctg ttcatcctgg ccaccagcag cctggccgtg 420
tacagcatcc tgtggagcgg ctgggccagc aacagcaact acgccctgat cggcgccctg 480
cgcgccgtgg cccagaccat cagctacgag gtgaccctgg ccatcatcct gctgagcacc 540
ctgctgatga gcggcagctt caacctgagc accctgatca ccacccagga gcacctgtgg 600
ctgctgctgc ccagctggcc cctggccatg atgtggttca tcagcaccct ggccgagacc 660
aaccgcaccc ccttcgacct ggccgagggc gagagcgagc tggtgagcgg cttcaacatc 720
gagtacgccg ccggcccctt cgccctgttc ttcatggccg agtacaccaa catcatcatg 780
atgaacaccc tgaccaccac catcttcctg ggcaccacct acgacgccct gagccccgag 840
ctgtacacca cctacttcgt gaccaagacc ctgctgctga ccagcctgtt cctgtggatc 900
cgcaccgcct acccccgctt ccgctacgac cagctgatgc acctgctgtg gaagaacttc 960
ctgcccctga ccctggccct gctgatgtgg tacgtgagca tgcccatcac catcagcagc 1020
atcccccccc agacctaaga gcactgggac gcccaccgcc cctttccctc cgctgccagg 1080
cgagcatgtt gtggtaattc tggaacacaa gaagagaaat tgctgggttt agaacaagat 1140
tataaacgaa ttcggtgctc agtgatcact tgacagtttt tttttttttt aaatattacc 1200
caaaatgctc cccaaataag aaatgcatca gctcagtcag tgaatacaaa aaaggaatta 1260
tttttccctt tgagggtctt ttatacatct ctcctccaac cccaccctct attctgtttc 1320
ttcctcctca catgggggta cacatacaca gcttcctctt ttggttccat ccttaccacc 1380
acaccacacg cacactccac atgcccagca gagtggcact tggtggccag aaagtgtgag 1440
cctcatgatc tgctgtctgt agttctgtga gctcaggtcc ctcaaaggcc tcggagcacc 1500
cccttccttg tgactgagcc agggcctgca tttttggttt tccccacccc acacattctc 1560
aaccatagtc cttctaacaa taccaatagc taggacccgg ctgctgtgca ctgggactgg 1620
ggattccaca tgtttgcctt gggagtctca agctggactg cca 1663

<210> SEQ ID NO 71
<211> LENGTH: 3071
<212> TYPE: DNA
<213> ORGANISM: Artificial Sequence
<220> FEATURE:
<223> OTHER INFORMATION: OPA1-ND4-3'UTR

<400> SEQUENCE: 71
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240

```
cgactacgtc gggccgctgt ggcctgatgc taaaactaat cgtcccaaca attatgttac    300
taccactgac atggctttcc aaaaaacaca tgatttggat caacacaacc acccacagcc    360
taattattag catcatccct ctactatttt ttaaccaaat caacaacaac ctatttagct    420
gttccccaac cttttcctcc gaccccctaa caaccccct cctaatgcta actacctggc    480
tcctacccct cacaatcatg gcaagccaac gccacttatc cagtgaacca ctatcacgaa    540
aaaaactcta cctctctatg ctaatctccc tacaaatctc cttaattatg acattcacag    600
ccacagaact aatcatgttt tatatcttct tcgaaaccac acttatcccc accttggcta    660
tcatcacccg atggggcaac cagccagaac gcctgaacgc aggcacatac ttcctattct    720
acaccctagt aggctccctt cccctactca tcgcactaat ttacactcac aacaccctag    780
gctcactaaa cattctacta ctcactctca ctgcccaaga actatcaaac tcctgggcca    840
acaacttaat gtggctagct tacacaatgg cttttatggt aaagatgcct ctttacggac    900
tccacttatg gctccctaaa gcccatgtcg aagcccccat cgctgggtca atggtacttg    960
ccgcagtact cttaaaacta ggcggctatg gtatgatgcg cctcacactc attctcaacc   1020
ccctgacaaa acacatggcc taccccttcc ttgtactatc cctatggggc atgattatga   1080
caagctccat ctgcctacga caaacagacc taaaatcgct cattgcatac tcttcaatca   1140
gccacatggc cctcgtagta acagccattc tcatccaaac cccctggagc ttcaccggcg   1200
cagtcattct catgatcgcc cacgggctta catcctcatt actattctgc ctagcaaact   1260
caaactacga acgcactcac agtcgcatca tgatcctctc tcaaggactt caaactctac   1320
tcccactaat ggctttttgg tggcttctag caagcctcgc taacctcgcc ttacccccca   1380
ctattaacct actgggagaa ctctctgtgc tagtaaccac gttctcctgg tcaaatatca   1440
ctctcctact tacaggactc aacatgctag tcacagccct atactccctc tacatgttta   1500
ccacaacaca atggggctca ctcacccacc acattaacaa catgaaaccc tcattcacac   1560
gagaaaacac cctcatgttc atgcacctat cccccattct cctcctatcc ctcaaccccg   1620
acatcattac cgggttttcc tcttaagagc actgggacgc ccaccgcccc tttccctccg   1680
ctgccaggcg agcatgttgt ggtaattctg gaacacaaga agagaaattg ctgggtttag   1740
aacaagatta taaacgaatt cggtgctcag tgatcacttg acagtttttt ttttttttaa   1800
atattaccca aaatgctccc caaataagaa atgcatcagc tcagtcagtg aatacaaaaa   1860
aggaattatt tttccctttg agggtctttt atacatctct cctccaaccc caccctctat   1920
tctgtttctt cctcctcaca tgggggtaca catacacagc ttcctctttt ggttccatcc   1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc cccaccccac   2160
acattctcaa ccatagtcct tctaacaata ccaatagcta ggacccggct gctgtgcact   2220
gggactgggg attccacatg tttgccttgg gagtctcaag ctggactgcc agcccctgtc   2280
ctcccttcac ccccattgcg tatgagcatt tcagaactcc aaggagtcac aggcatcttt   2340
atagttcacg ttaacatata gacactgttg gaagcagttc cttctaaaag ggtagccctg   2400
gacttaatac cagccggata cctctggccc ccaccccatt actgtacctc tggagtcact   2460
actgtgggtc gccactcctc tgctacacag cacggctttt tcaaggctgt attgagaagg   2520
gaagttagga agaagggtgt gctgggctaa ccagcccaca gagctcacat tcctgtccct   2580
tgggtgaaaa atacatgtcc atcctgatat ctcctgaatt cagaaattag cctccacatg   2640
```

-continued

```
tgcaatggct ttaagagcca gaagcagggt tctgggaatt ttgcaagtta cctgtggcca   2700

ggtgtggtct cggttaccaa atacggttac ctgcagcttt ttagtccttt gtgctcccac   2760

gggtctacag agtcccatct gcccaaaggt cttgaagctt gacaggatgt tttcgattac   2820

tcagtctccc agggcactac tggtccgtag gattcgattg gtcggggtag gagagttaaa   2880

caacatttaa acagagttct ctcaaaaatg tctaaaggga ttgtaggtag ataacatcca   2940

atcactgttt gcacttatct gaaatcttcc ctcttggctg cccccaggta tttactgtgg   3000

agaacattgc ataggaatgt ctggaaaaag cttctacaac ttgttacagc cttcacattt   3060

gtagaagctt t                                                        3071
```

<210> SEQ ID NO 72
<211> LENGTH: 2271
<212> TYPE: DNA
<213> ORGANISM: Artificial Sequence
<220> FEATURE:
<223> OTHER INFORMATION: OPA1-ND4-3'UTR*

<400> SEQUENCE: 72

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgatgc taaaactaat cgtcccaaca attatgttac    300

taccactgac atggctttcc aaaaaacaca tgatttggat caacacaacc acccacagcc    360

taattattag catcatccct ctactatttt ttaaccaaat caacaacaac ctatttagct    420

gttccccaac cttttcctcc gaccccctaa caaccccct cctaatgcta actacctggc    480

tcctacccct cacaatcatg gcaagccaac gccacttatc cagtgaacca ctatcacgaa    540

aaaaactcta cctctctatg ctaatctccc tacaaatctc cttaattatg acattcacag    600

ccacagaact aatcatgttt tatatcttct tcgaaaccac acttatcccc accttggcta    660

tcatcacccg atggggcaac cagccagaac gcctgaacgc aggcacatac ttcctattct    720

acaccctagt aggctccctt cccctactca tcgcactaat ttacactcac aacaccctag    780

gctcactaaa cattctacta ctcactctca ctgcccaaga actatcaaac tcctgggcca    840

acaacttaat gtggctagct tacacaatgg cttttatggt aaagatgcct ctttacggac    900

tccacttatg gctccctaaa gcccatgtcg aagcccccat cgctgggtca atggtacttg    960

ccgcagtact cttaaaacta ggcggctatg gtatgatgcg cctcacactc attctcaacc   1020

ccctgacaaa acacatggcc taccccttcc ttgtactatc cctatggggc atgattatga   1080

caagctccat ctgcctacga caaacagacc taaaatcgct cattgcatac tcttcaatca   1140

gccacatggc cctcgtagta acagccattc tcatccaaac cccctggagc ttcaccggcg   1200

cagtcattct catgatcgcc cacgggctta catcctcatt actattctgc ctagcaaact   1260

caaactacga acgcactcac agtcgcatca tgatcctctc tcaaggactt caaactctac   1320

tcccactaat ggctttttgg tggcttctag caagcctcgc taacctcgcc ttacccccca   1380

ctattaacct actgggagaa ctctctgtgc tagtaaccac gttctcctgg tcaaatatca   1440

ctctcctact tacaggactc aacatgctag tcacagccct atactccctc tacatgttta   1500

ccacaacaca atggggctca ctcacccacc acattaacaa catgaaaccc tcattcacac   1560
```

```
gagaaaacac cctcatgttc atgcacctat cccccattct cctcctatcc ctcaaccccg   1620

acatcattac cgggttttcc tcttaagagc actgggacgc ccaccgcccc tttccctccg   1680

ctgccaggcg agcatgttgt ggtaattctg gaacacaaga agagaaattg ctgggtttag   1740

aacaagatta taaacgaatt cggtgctcag tgatcacttg acagtttttt tttttttaa    1800

atattaccca aaatgctccc caaataagaa atgcatcagc tcagtcagtg aatacaaaaa   1860

aggaattatt tttccctttg agggtctttt atacatctct cctccaaccc caccctctat   1920

tctgtttctt cctcctcaca tgggggtaca catacacagc ttcctctttt ggttccatcc   1980

ttaccaccac accacacgca cactccacat gcccagcaga gtggcacttg gtggccagaa   2040

agtgtgagcc tcatgatctg ctgtctgtag ttctgtgagc tcaggtccct caaaggcctc   2100

ggagcacccc cttccttgtg actgagccag ggcctgcatt tttggttttc cccaccccac   2160

acattctcaa ccatagtcct tctaacaata ccaatagcta ggacccggct gctgtgcact   2220

gggactgggg attccacatg tttgccttgg gagtctcaag ctggactgcc a            2271
```

<210> SEQ ID NO 73
<211> LENGTH: 3071
<212> TYPE: DNA
<213> ORGANISM: Artificial Sequence
<220> FEATURE:
<223> OTHER INFORMATION: OPA1-opt_ND4-3'UTR

<400> SEQUENCE: 73

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgatgc tgaagctgat cgtgcccacc atcatgctgc    300

tgcctctgac ctggctgagc aagaaacaca tgatctggat caacaccacc acgcacagcc    360

tgatcatcag catcatccct ctgctgttct tcaaccagat caacaacaac ctgttcagct    420

gcagccccac cttcagcagc gaccctctga caacacctct gctgatgctg accacctggc    480

tgctgcccct cacaatcatg gcctctcaga gacacctgag cagcgagccc ctgagccgga    540

agaaactgta cctgagcatg ctgatctccc tgcagatctc tctgatcatg accttcaccg    600

ccaccgagct gatcatgttc tacatctttt tcgagacaac gctgatcccc acactggcca    660

tcatcaccag atggggcaac cagcctgaga gactgaacgc cggcacctac tttctgttct    720

acaccctcgt gggcagcctg ccactgctga ttgccctgat ctacacccac aacaccctgg    780

gctccctgaa catcctgctg ctgacactga cagcccaaga gctgagcaac agctgggcca    840

acaatctgat gtggctggcc tacacaatgg ccttcatggt caagatgccc ctgtacggcc    900

tgcacctgtg gctgcctaaa gctcatgtgg aagcccctat cgccggctct atggtgctgg    960

ctgcagtgct gctgaaactc ggcggctacg gcatgatgcg gctgaccctg attctgaatc   1020

ccctgaccaa gcacatggcc tatccatttc tggtgctgag cctgtggggc atgattatga   1080

ccagcagcat ctgcctgcgg cagaccgatc tgaagtccct gatcgcctac agctccatca   1140

gccacatggc cctggtggtc accgccatcc tgattcagac cccttggagc tttacaggcg   1200

ccgtgatcct gatgattgcc cacggcctga caagcagcct gctgttttgt ctggccaaca   1260

gcaactacga gcggacccac agcagaatca tgatcctgtc tcagggcctg cagaccctcc   1320

tgcctcttat ggctttttgg tggctgctgg cctctctggc caatctggca ctgcctccta   1380
```

ccatcaatct gctgggcgag ctgagcgtgc tggtcaccac attcagctgg tccaatatca 1440
ccctgctgct caccggcctg aacatgctgg ttacagccct gtactccctg tacatgttca 1500
ccaccacaca gtggggaagc ctgacacacc acatcaacaa tatgaagccc agcttcaccc 1560
gcgagaacac cctgatgttc atgcatctga gccccattct gctgctgtcc ctgaatcctg 1620
atatcatcac cggcttctcc agctgagagc actgggacgc ccaccgcccc tttccctccg 1680
ctgccaggcg agcatgttgt ggtaattctg gaacacaaga agagaaattg ctgggtttag 1740
aacaagatta taaacgaatt cggtgctcag tgatcacttg acagtttttt ttttttttaa 1800
atattaccca aaatgctccc caaataagaa atgcatcagc tcagtcagtg aatacaaaaa 1860
aggaattatt tttccctttg agggtctttt atacatctct cctccaaccc caccctctat 1920
tctgtttctt cctcctcaca tgggggtaca catacacagc ttcctctttt ggttccatcc 1980
ttaccaccac accacacgca cactccacat gcccagcaga gtggcacttg gtggccagaa 2040
agtgtgagcc tcatgatctg ctgtctgtag ttctgtgagc tcaggtccct caaaggcctc 2100
ggagcacccc cttccttgtg actgagccag ggcctgcatt tttggttttc cccaccccac 2160
acattctcaa ccatagtcct tctaacaata ccaatagcta ggacccggct gctgtgcact 2220
gggactgggg attccacatg tttgccttgg gagtctcaag ctggactgcc agcccctgtc 2280
ctcccttcac cccattgcg tatgagcatt tcagaactcc aaggagtcac aggcatcttt 2340
atagttcacg ttaacatata gacactgttg gaagcagttc cttctaaaag ggtagccctg 2400
gacttaatac cagccggata cctctggccc ccaccccatt actgtacctc tggagtcact 2460
actgtgggtc gccactcctc tgctacacag cacggctttt tcaaggctgt attgagaagg 2520
gaagttagga agaagggtgt gctgggctaa ccagcccaca gagctcacat tcctgtccct 2580
tgggtgaaaa atacatgtcc atcctgatat ctcctgaatt cagaaattag cctccacatg 2640
tgcaatggct ttaagagcca gaagcagggt tctgggaatt ttgcaagtta cctgtggcca 2700
ggtgtggtct cggttaccaa atacggttac ctgcagcttt ttagtccttt gtgctcccac 2760
gggtctacag agtcccatct gcccaaaggt cttgaagctt gacaggatgt tttcgattac 2820
tcagtctccc agggcactac tggtccgtag gattcgattg gtcggggtag gagagttaaa 2880
caacatttaa acagagttct ctcaaaaatg tctaaaggga ttgtaggtag ataacatcca 2940
atcactgttt gcacttatct gaaatcttcc ctcttggctg cccccaggta tttactgtgg 3000
agaacattgc ataggaatgt ctggaaaaag cttctacaac ttgttacagc cttcacattt 3060
gtagaagctt t 3071

<210> SEQ ID NO 74
<211> LENGTH: 2271
<212> TYPE: DNA
<213> ORGANISM: Artificial Sequence
<220> FEATURE:
<223> OTHER INFORMATION: OPA1-opt_ND4-3'UTR*

<400> SEQUENCE: 74
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatgc tgaagctgat cgtgcccacc atcatgctgc 300

```
tgcctctgac ctggctgagc aagaaacaca tgatctggat caacaccacc acgcacagcc    360
tgatcatcag catcatccct ctgctgttct tcaaccagat caacaacaac ctgttcagct    420
gcagccccac cttcagcagc gaccctctga caacacctct gctgatgctg accacctggc    480
tgctgcccct cacaatcatg gcctctcaga gacacctgag cagcgagccc ctgagccgga    540
agaaactgta cctgagcatg ctgatctccc tgcagatctc tctgatcatg accttcaccg    600
ccaccgagct gatcatgttc tacatctttt tcgagacaac gctgatcccc acactggcca    660
tcatcaccag atggggcaac cagcctgaga gactgaacgc cggcacctac tttctgttct    720
acaccctcgt gggcagcctg ccactgctga ttgccctgat ctacacccac aacaccctgg    780
gctccctgaa catcctgctg ctgacactga cagcccaaga gctgagcaac agctgggcca    840
acaatctgat gtggctggcc tacacaatgg ccttcatggt caagatgccc ctgtacggcc    900
tgcacctgtg gctgcctaaa gctcatgtgg aagcccctat cgccggctct atggtgctgg    960
ctgcagtgct gctgaaactc ggcggctacg gcatgatgcg gctgaccctg attctgaatc   1020
ccctgaccaa gcacatggcc tatccatttc tggtgctgag cctgtggggc atgattatga   1080
ccagcagcat ctgcctgcgg cagaccgatc tgaagtccct gatcgcctac agctccatca   1140
gccacatggc cctggtggtc accgccatcc tgattcagac cccttggagc tttacaggcg   1200
ccgtgatcct gatgattgcc cacggcctga caagcagcct gctgttttgt ctggccaaca   1260
gcaactacga gcggacccac agcagaatca tgatcctgtc tcagggcctg cagaccctcc   1320
tgcctcttat ggctttttgg tggctgctgg cctctctggc caatctggca ctgcctccta   1380
ccatcaatct gctgggcgag ctgagcgtgc tggtcaccac attcagctgg tccaatatca   1440
ccctgctgct caccggcctg aacatgctgg ttacagccct gtactccctg tacatgttca   1500
ccaccacaca gtggggaagc ctgacacacc acatcaacaa tatgaagccc agcttcaccc   1560
gcgagaacac cctgatgttc atgcatctga gccccattct gctgctgtcc ctgaatcctg   1620
atatcatcac cggcttctcc agctgagagc actgggacgc ccaccgcccc tttccctccg   1680
ctgccaggcg agcatgttgt ggtaattctg gaacacaaga agagaaattg ctgggtttag   1740
aacaagatta taaacgaatt cggtgctcag tgatcacttg acagtttttt tttttttaa   1800
atattaccca aaatgctccc caaataagaa atgcatcagc tcagtcagtg aatacaaaaa   1860
aggaattatt tttccctttg agggtctttt atacatctct cctccaaccc caccctctat   1920
tctgtttctt cctcctcaca tgggggtaca catacacagc ttcctctttt ggttccatcc   1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggtttc cccaccccac   2160
acattctcaa ccatagtcct tctaacaata ccaatagcta ggacccggct gctgtgcact   2220
gggactgggg attccacatg tttgccttgg gagtctcaag ctggactgcc a            2271
```

<210> SEQ ID NO 75
<211> LENGTH: 3071
<212> TYPE: DNA
<213> ORGANISM: Artificial Sequence
<220> FEATURE:
<223> OTHER INFORMATION: OPA1-opt_ND4*-3'UTR

<400> SEQUENCE: 75

```
gtgctgcccg cctagaaagg gtgaagtggt tgtttccgtg acggactgag tacgggtgcc     60
tgtcaggctc ttgcggaagt ccatgcgcca ttgggagggc ctcggccgcg gctctgtgcc    120
```

-continued

```
cttgctgctg agggccactt cctgggtcat tcctggaccg ggagccgggc tggggctcac    180
acgggggctc ccgcgtggcc gtctcggcgc ctgcgtgacc tccccgccgg cgggatgtgg    240
cgactacgtc gggccgctgt ggcctgatgc tgaagctgat cgtgcccacc atcatgctgc    300
tgcccctgac ctggctgagc aagaagcaca tgatctggat caacaccacc acccacagcc    360
tgatcatcag catcatcccc ctgctgttct tcaaccagat caacaacaac ctgttcagct    420
gcagccccac cttcagcagc gacccccctga ccaccccccct gctgatgctg accacctggc    480
tgctgcccct gaccatcatg gccagccagc gccacctgag cagcgagccc ctgagccgca    540
agaagctgta cctgagcatg ctgatcagcc tgcagatcag cctgatcatg accttcaccg    600
ccaccgagct gatcatgttc tacatcttct tcgagaccac cctgatcccc accctggcca    660
tcatcacccg ctggggcaac cagcccgagc gcctgaacgc cggcacctac ttcctgttct    720
acaccctggt gggcagcctg cccctgctga tcgccctgat ctacacccac aacaccctgg    780
gcagcctgaa catcctgctg ctgaccctga ccgcccagga gctgagcaac agctgggcca    840
acaacctgat gtggctggcc tacaccatgg ccttcatggt gaagatgccc ctgtacggcc    900
tgcacctgtg gctgcccaag gcccacgtgg aggcccccat cgccggcagc atggtgctgg    960
ccgccgtgct gctgaagctg ggcggctacg gcatgatgcg cctgaccctg atcctgaacc   1020
ccctgaccaa gcacatggcc taccccttcc tggtgctgag cctgtggggc atgatcatga   1080
ccagcagcat ctgcctgcgc cagaccgacc tgaagagcct gatcgcctac agcagcatca   1140
gccacatggc cctggtggtg accgccatcc tgatccagac cccctggagc ttcaccggcg   1200
ccgtgatcct gatgatcgcc cacggcctga ccagcagcct gctgttctgc ctggccaaca   1260
gcaactacga gcgcacccac agccgcatca tgatcctgag ccagggcctg cagaccctgc   1320
tgcccctgat ggccttctgg tggctgctgg ccagcctggc caacctggcc ctgcccccca   1380
ccatcaacct gctgggcgag ctgagcgtgc tggtgaccac cttcagctgg agcaacatca   1440
ccctgctgct gaccggcctg aacatgctgg tgaccgccct gtacagcctg tacatgttca   1500
ccaccaccca gtggggcagc ctgacccacc acatcaacaa catgaagccc agcttcaccc   1560
gcgagaacac cctgatgttc atgcacctga gccccatcct gctgctgagc ctgaaccccg   1620
acatcatcac cggcttcagc agctaagagc actgggacgc ccaccgcccc tttccctccg   1680
ctgccaggcg agcatgttgt ggtaattctg gaacacaaga agagaaattg ctgggtttag   1740
aacaagatta taaacgaatt cggtgctcag tgatcacttg acagtttttt ttttttttaa   1800
atattaccca aaatgctccc caaataagaa atgcatcagc tcagtcagtg aatacaaaaa   1860
aggaattatt tttccctttg agggtctttt atacatctct cctccaaccc caccctctat   1920
tctgtttctt cctcctcaca tgggggtaca catacacagc ttcctctttt ggttccatcc   1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc cccaccccac   2160
acattctcaa ccatagtcct tctaacaata ccaatagcta ggacccggct gctgtgcact   2220
gggactgggg attccacatg tttgccttgg gagtctcaag ctggactgcc agcccctgtc   2280
ctcccttcac ccccattgcg tatgagcatt tcagaactcc aaggagtcac aggcatcttt   2340
atagttcacg ttaacatata gacactgttg gaagcagttc cttctaaaag ggtagccctg   2400
gacttaatac cagccggata cctctggccc ccaccccatt actgtacctc tggagtcact   2460
```

-continued actgtgggtc gccactcctc tgctacacag cacggctttt tcaaggctgt attgagaagg 2520
gaagttagga agaagggtgt gctgggctaa ccagcccaca gagctcacat tcctgtccct 2580
tgggtgaaaa atacatgtcc atcctgatat ctcctgaatt cagaaattag cctccacatg 2640
tgcaatggct ttaagagcca gaagcagggt tctgggaatt ttgcaagtta cctgtggcca 2700
ggtgtggtct cggttaccaa atacggttac ctgcagcttt ttagtccttt gtgctcccac 2760
gggtctacag agtcccatct gcccaaaggt cttgaagctt gacaggatgt tttcgattac 2820
tcagtctccc agggcactac tggtccgtag gattcgattg gtcggggtag gagagttaaa 2880
caacatttaa acagagttct ctcaaaaatg tctaaaggga ttgtaggtag ataacatcca 2940
atcactgttt gcacttatct gaaatcttcc ctcttggctg cccccaggta tttactgtgg 3000
agaacattgc ataggaatgt ctggaaaaag cttctacaac ttgttacagc cttcacattt 3060
gtagaagctt t 3071

<210> SEQ ID NO 76
<211> LENGTH: 2271
<212> TYPE: DNA
<213> ORGANISM: Artificial Sequence
<220> FEATURE:
<223> OTHER INFORMATION: OPA1-opt_ND4*-3'UTR*

<400> SEQUENCE: 76
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatgc tgaagctgat cgtgcccacc atcatgctgc 300
tgcccctgac ctggctgagc aagaagcaca tgatctggat caacaccacc acccacagcc 360
tgatcatcag catcatcccc ctgctgttct tcaaccagat caacaacaac ctgttcagct 420
gcagccccac cttcagcagc gacccccctga ccaccccccct gctgatgctg accacctggc 480
tgctgcccct gaccatcatg gccagccagc gccacctgag cagcgagccc ctgagccgca 540
agaagctgta cctgagcatg ctgatcagcc tgcagatcag cctgatcatg accttcaccg 600
ccaccgagct gatcatgttc tacatcttct tcgagaccac cctgatcccc accctggcca 660
tcatcacccg ctggggcaac cagcccgagc gcctgaacgc cggcacctac ttcctgttct 720
acaccctggt gggcagcctg cccctgctga tcgccctgat ctacacccac aacaccctgg 780
gcagcctgaa catcctgctg ctgaccctga ccgcccagga gctgagcaac agctgggcca 840
acaacctgat gtggctggcc tacaccatgg ccttcatggt gaagatgccc ctgtacggcc 900
tgcacctgtg gctgcccaag gcccacgtgg aggcccccat cgccggcagc atggtgctgg 960
ccgccgtgct gctgaagctg ggcggctacg gcatgatgcg cctgaccctg atcctgaacc 1020
ccctgaccaa gcacatggcc taccccttcc tggtgctgag cctgtggggc atgatcatga 1080
ccagcagcat ctgcctgcgc cagaccgacc tgaagagcct gatcgcctac agcagcatca 1140
gccacatggc cctggtggtg accgccatcc tgatccagac cccctggagc ttcaccggcg 1200
ccgtgatcct gatgatcgcc cacggcctga ccagcagcct gctgttctgc ctggccaaca 1260
gcaactacga gcgcacccac agccgcatca tgatcctgag ccagggcctg cagaccctgc 1320
tgcccctgat ggccttctgg tggctgctgg ccagcctggc caacctggcc ctgcccccca 1380
ccatcaacct gctgggcgag ctgagcgtgc tggtgaccac cttcagctgg agcaacatca 1440

```
ccctgctgct gaccggcctg aacatgctgg tgaccgccct gtacagcctg tacatgttca   1500

ccaccaccca gtggggcagc ctgacccacc acatcaacaa catgaagccc agcttcaccc   1560

gcgagaacac cctgatgttc atgcacctga gccccatcct gctgctgagc ctgaaccccg   1620

acatcatcac cggcttcagc agctaagagc actgggacgc ccaccgcccc tttccctccg   1680

ctgccaggcg agcatgttgt ggtaattctg gaacacaaga agagaaattg ctgggtttag   1740

aacaagatta taaacgaatt cggtgctcag tgatcacttg acagtttttt tttttttaa   1800

atattaccca aaatgctccc caaataagaa atgcatcagc tcagtcagtg aatacaaaaa   1860

aggaattatt tttccctttg agggtctttt atacatctct cctccaaccc caccctctat   1920

tctgtttctt cctcctcaca tgggggtaca catacacagc ttcctctttt ggttccatcc   1980

ttaccaccac accacacgca cactccacat gcccagcaga gtggcacttg gtggccagaa   2040

agtgtgagcc tcatgatctg ctgtctgtag ttctgtgagc tcaggtccct caaaggcctc   2100

ggagcacccc cttccttgtg actgagccag ggcctgcatt tttggttttc cccaccccac   2160

acattctcaa ccatagtcct tctaacaata ccaatagcta ggacccggct gctgtgcact   2220

gggactgggg attccacatg tttgccttgg gagtctcaag ctggactgcc a            2271
```

<210> SEQ ID NO 77
<211> LENGTH: 2216
<212> TYPE: DNA
<213> ORGANISM: Artificial Sequence
<220> FEATURE:
<223> OTHER INFORMATION: OPA1-ND6-3'UTR

<400> SEQUENCE: 77

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgatga tgtatgcttt gtttctgttg agtgtgggtt    300

tagtaatggg gtttgtgggg ttttcttcta agccttctcc tatttatggg ggtttagtat    360

tgattgttag cggtgtggtc gggtgtgtta ttattctgaa ttttggggga ggttatatgg    420

gtttaatggt ttttttaatt tatttagggg gaatgatggt tgtctttgga tatactacag    480

cgatggctat tgaggagtat cctgaggcat gggggtcagg ggttgaggtc ttggtgagtg    540

ttttagtggg gttagcgatg gaggtaggat tggtgctgtg ggtgaaagag tatgatgggg    600

tggtggttgt ggtaaacttt aatagtgtag gaagctggat gatttatgaa ggagaggggt    660

cagggttgat tcgggaggat cctattggtg cgggggcttt gtatgattat gggcgttggt    720

tagtagtagt tactggttgg acattgtttg ttggtgtata tattgtaatt gagattgctc    780

gggggaatta ggagcactgg gacgcccacc gcccctttcc ctccgctgcc aggcgagcat    840

gttgtggtaa ttctggaaca caagaagaga aattgctggg tttagaacaa gattataaac    900

gaattcggtg ctcagtgatc acttgacagt tttttttttt tttaaatatt acccaaaatg    960

ctccccaaat aagaaatgca tcagctcagt cagtgaatac aaaaaaggaa ttatttttcc   1020

ctttgagggt cttttataca tctctcctcc aaccccaccc tctattctgt ttcttcctcc   1080

tcacatgggg gtacacatac acagcttcct cttttggttc catccttacc accacaccac   1140

acgcacactc cacatgccca gcagagtggc acttggtggc cagaaagtgt gagcctcatg   1200
```

atctgctgtc tgtagttctg tgagctcagg tccctcaaag gcctcggagc accccccttcc 1260 ttgtgactga gccagggcct gcatttttgg ttttccccac cccacacatt ctcaaccata 1320
gtccttctaa caataccaat agctaggacc cggctgctgt gcactgggac tggggattcc 1380
acatgtttgc cttgggagtc tcaagctgga ctgccagccc ctgtcctccc ttcaccccca 1440
ttgcgtatga gcatttcaga actccaagga gtcacaggca tctttatagt tcacgttaac 1500
atatagacac tgttggaagc agttccttct aaaagggtag ccctggactt aataccagcc 1560
ggatacctct ggcccccacc ccattactgt acctctggag tcactactgt gggtcgccac 1620
tcctctgcta cacagcacgg ctttttcaag gctgtattga gaagggaagt taggaagaag 1680
ggtgtgctgg gctaaccagc ccacagagct cacattcctg tcccttgggt gaaaaataca 1740
tgtccatcct gatatctcct gaattcagaa attagcctcc acatgtgcaa tggctttaag 1800
agccagaagc agggttctgg gaattttgca agttacctgt ggccaggtgt ggtctcggtt 1860
accaaatacg gttacctgca gctttttagt cctttgtgct cccacgggtc tacagagtcc 1920
catctgccca aaggtcttga agcttgacag gatgttttcg attactcagt ctcccagggc 1980
actactggtc cgtaggattc gattggtcgg ggtaggagag ttaaacaaca tttaaacaga 2040
gttctctcaa aaatgtctaa agggattgta ggtagataac atccaatcac tgtttgcact 2100
tatctgaaat cttccctctt ggctgccccc aggtatttac tgtggagaac attgcatagg 2160
aatgtctgga aaaagcttct acaacttgtt acagccttca catttgtaga agcttt 2216

<210> SEQ ID NO 78
<211> LENGTH: 1416
<212> TYPE: DNA
<213> ORGANISM: Artificial Sequence
<220> FEATURE:
<223> OTHER INFORMATION: OPA1-ND6-3'UTR*

<400> SEQUENCE: 78
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatga tgtatgcttt gtttctgttg agtgtgggtt 300
tagtaatggg gtttgtgggg ttttcttcta agccttctcc tatttatggg ggtttagtat 360
tgattgttag cggtgtggtc gggtgtgtta ttattctgaa ttttggggga ggttatatgg 420
gtttaatggt ttttttaatt tatttagggg gaatgatggt tgtctttgga tatactacag 480
cgatggctat tgaggagtat cctgaggcat gggggtcagg ggttgaggtc ttggtgagtg 540
ttttagtggg gttagcgatg gaggtaggat tggtgctgtg ggtgaaagag tatgatgggg 600
tggtggttgt ggtaaacttt aatagtgtag gaagctggat gatttatgaa ggagaggggt 660
cagggttgat tcgggaggat cctattggtg cgggggcttt gtatgattat gggcgttggt 720
tagtagtagt tactggttgg acattgtttg ttggtgtata tattgtaatt gagattgctc 780
gggggaatta ggagcactgg gacgcccacc gcccctttcc ctccgctgcc aggcgagcat 840
gttgtggtaa ttctggaaca caagaagaga aattgctggg tttagaacaa gattataaac 900
gaattcggtg ctcagtgatc acttgacagt tttttttttt tttaaatatt acccaaaatg 960
ctccccaaat aagaaatgca tcagctcagt cagtgaatac aaaaaaggaa ttattttttcc 1020 ctttgagggt cttttataca tctctcctcc aaccccaccc tctattctgt ttcttcctcc 1080
tcacatgggg gtacacatac acagcttcct cttttggttc catccttacc accacaccac 1140
acgcacactc cacatgccca gcagagtggc acttggtggc cagaaagtgt gagcctcatg 1200
atctgctgtc tgtagttctg tgagctcagg tccctcaaag gcctcggagc accccccttcc 1260 ttgtgactga gccagggcct gcatttttgg ttttccccac cccacacatt ctcaaccata 1320
gtccttctaa caataccaat agctaggacc cggctgctgt gcactgggac tggggattcc 1380
acatgtttgc cttgggagtc tcaagctgga ctgcca 1416

<210> SEQ ID NO 79
<211> LENGTH: 2216
<212> TYPE: DNA
<213> ORGANISM: Artificial Sequence
<220> FEATURE:
<223> OTHER INFORMATION: OPA1-opt_ND6-3'UTR

<400> SEQUENCE: 79
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatga tgtacgccct gttcctgctg agcgtgggcc 300
tggtgatggg cttcgtgggc ttcagcagca agcccagccc catctacggc ggcctggtgc 360
tgatcgtgag cggcgtggtg ggctgcgtga tcatcctgaa cttcggcggc ggctacatgg 420
gcctgatggt gttcctgatc tacctgggcg gcatgatggt ggtgttcggc tacaccaccg 480
ccatggccat cgaggagtac cccgaggcct ggggcagcgg cgtggaggtg ctggtgagcg 540
tgctggtggg cctggccatg gaggtgggcc tggtgctgtg ggtgaaggag tacgacggcg 600
tggtggtggt ggtgaacttc aacagcgtgg gcagctggat gatctacgag ggcgagggca 660
gcggcctgat ccgcgaggac cccatcggcg ccggcgccct gtacgactac ggccgctggc 720
tggtggtggt gaccggctgg accctgttcg tgggcgtgta catcgtgatc gagatcgccc 780
gcggcaacta agagcactgg gacgcccacc gcccctttcc ctccgctgcc aggcgagcat 840
gttgtggtaa ttctggaaca caagaagaga aattgctggg tttagaacaa gattataaac 900
gaattcggtg ctcagtgatc acttgacagt tttttttttt tttaaatatt acccaaaatg 960
ctccccaaat aagaaatgca tcagctcagt cagtgaatac aaaaaaggaa ttatttttcc 1020
ctttgagggt cttttataca tctctcctcc aaccccaccc tctattctgt ttcttcctcc 1080
tcacatgggg gtacacatac acagcttcct cttttggttc catccttacc accacaccac 1140
acgcacactc cacatgccca gcagagtggc acttggtggc cagaaagtgt gagcctcatg 1200
atctgctgtc tgtagttctg tgagctcagg tccctcaaag gcctcggagc accccccttcc 1260 ttgtgactga gccagggcct gcatttttgg ttttccccac cccacacatt ctcaaccata 1320
gtccttctaa caataccaat agctaggacc cggctgctgt gcactgggac tggggattcc 1380
acatgtttgc cttgggagtc tcaagctgga ctgccagccc ctgtcctccc ttcaccccca 1440
ttgcgtatga gcatttcaga actccaagga gtcacaggca tctttatagt tcacgttaac 1500
atatagacac tgttggaagc agttccttct aaaagggtag ccctggactt aataccagcc 1560
ggatacctct ggcccccacc ccattactgt acctctggag tcactactgt gggtcgccac 1620
tcctctgcta cacagcacgg ctttttcaag gctgtattga gaagggaagt taggaagaag 1680
ggtgtgctgg gctaaccagc ccacagagct cacattcctg tcccttgggt gaaaaataca 1740
tgtccatcct gatatctcct gaattcagaa attagcctcc acatgtgcaa tggctttaag 1800
agccagaagc agggttctgg gaattttgca agttacctgt ggccaggtgt ggtctcggtt 1860
accaaatacg gttacctgca gctttttagt cctttgtgct cccacgggtc tacagagtcc 1920
catctgccca aaggtcttga agcttgacag gatgttttcg attactcagt ctcccagggc 1980
actactggtc cgtaggattc gattggtcgg ggtaggagag ttaaacaaca tttaaacaga 2040
gttctctcaa aaatgtctaa agggattgta ggtagataac atccaatcac tgtttgcact 2100
tatctgaaat cttccctctt ggctgccccc aggtatttac tgtggagaac attgcatagg 2160
aatgtctgga aaaagcttct acaacttgtt acagccttca catttgtaga agcttt 2216

<210> SEQ ID NO 80
<211> LENGTH: 1416
<212> TYPE: DNA
<213> ORGANISM: Artificial Sequence
<220> FEATURE:
<223> OTHER INFORMATION: OPA1-opt_ND6-3'UTR*

<400> SEQUENCE: 80
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatga tgtacgccct gttcctgctg agcgtgggcc 300
tggtgatggg cttcgtgggc ttcagcagca agcccagccc catctacggc ggcctggtgc 360
tgatcgtgag cggcgtggtg ggctgcgtga tcatcctgaa cttcggcggc ggctacatgg 420
gcctgatggt gttcctgatc tacctgggcg gcatgatggt ggtgttcggc tacaccaccg 480
ccatggccat cgaggagtac cccgaggcct ggggcagcgg cgtggaggtg ctggtgagcg 540
tgctggtggg cctggccatg gaggtgggcc tggtgctgtg ggtgaaggag tacgacggcg 600
tggtggtggt ggtgaacttc aacagcgtgg gcagctggat gatctacgag ggcgagggca 660
gcggcctgat ccgcgaggac cccatcggcg ccggcgccct gtacgactac ggccgctggc 720
tggtggtggt gaccggctgg accctgttcg tgggcgtgta catcgtgatc gagatcgccc 780
gcggcaacta agagcactgg gacgcccacc gcccctttcc ctccgctgcc aggcgagcat 840
gttgtggtaa ttctggaaca caagaagaga aattgctggg tttagaacaa gattataaac 900
gaattcggtg ctcagtgatc acttgacagt tttttttttt tttaaatatt acccaaaatg 960
ctccccaaat aagaaatgca tcagctcagt cagtgaatac aaaaaaggaa ttatttttcc 1020
ctttgagggt cttttataca tctctcctcc aaccccaccc tctattctgt ttcttcctcc 1080
tcacatgggg gtacacatac acagcttcct cttttggttc catccttacc accacaccac 1140
acgcacactc cacatgccca gcagagtggc acttggtggc cagaaagtgt gagcctcatg 1200
atctgctgtc tgtagttctg tgagctcagg tccctcaaag gcctcggagc accccttcc 1260 ttgtgactga gccagggcct gcatttttgg ttttccccac cccacacatt ctcaaccata 1320
gtccttctaa caataccaat agctaggacc cggctgctgt gcactgggac tggggattcc 1380
acatgtttgc cttgggagtc tcaagctgga ctgcca 1416

<210> SEQ ID NO 81
<211> LENGTH: 2642

<212> TYPE: DNA
<213> ORGANISM: Artificial Sequence
<220> FEATURE:
<223> OTHER INFORMATION: OPA1-ND1-3'UTR

<400> SEQUENCE: 81
gtgctgcccg cctagaaagg gtgaagtggt tgtttccgtg acggactgag tacgggtgcc 60
tgtcaggctc ttgcggaagt ccatgcgcca ttgggagggc ctcggccgcg gctctgtgcc 120
cttgctgctg agggccactt cctgggtcat tcctggaccg ggagccgggc tggggctcac 180
acgggggctc ccgcgtggcc gtctcggcgc ctgcgtgacc tccccgccgg cgggatgtgg 240
cgactacgtc gggccgctgt ggcctgatgg ccaacctcct actcctcatt gtacccattc 300
taatcgcaat ggcattccta atgcttaccg aacgaaaaat tctaggctat atgcaactac 360
gcaaaggccc caacgttgta ggcccctacg ggctactaca acccttcgct gacgccataa 420
aactcttcac caaagagccc ctaaaacccg ccacatctac catcaccctc tacatcaccg 480
ccccgacctt agctctcacc atcgctcttc tactatggac ccccctcccc atgcccaacc 540
ccctggtcaa cctcaaccta ggcctcctat ttattctagc cacctctagc ctagccgttt 600
actcaatcct ctggtcaggg tgggcatcaa actcaaacta cgccctgatc ggcgcactgc 660
gagcagtagc ccaaacaatc tcatatgaag tcaccctagc catcattcta ctatcaacat 720
tactaatgag tggctccttt aacctctcca cccttatcac aacacaagaa cacctctggt 780
tactcctgcc atcatggccc ttggccatga tgtggtttat ctccacacta gcagagacca 840
accgaacccc cttcgacctt gccgaagggg agtccgaact agtctcaggc ttcaacatcg 900
aatacgccgc aggcccctta gccctattct tcatggccga atacacaaac attattatga 960
tgaacaccct caccactaca atcttcctag gaacaacata tgacgcactc tcccctgaac 1020
tctacacaac atattttgtc accaagaccc tacttctaac ctccctgttc ttatggattc 1080
gaacagcata cccccgattc cgctacgacc aactcatgca cctcctatgg aaaaacttcc 1140
taccactcac cctagcatta cttatgtggt atgtctccat gcccattaca atctccagca 1200
ttccccctca aacctaagag cactgggacg cccaccgccc ctttccctcc gctgccaggc 1260
gagcatgttg tggtaattct ggaacacaag aagagaaatt gctgggttta gaacaagatt 1320
ataaacgaat tcggtgctca gtgatcactt gacagttttt tttttttta aatattaccc 1380 aaaatgctcc ccaaataaga aatgcatcag ctcagtcagt gaatacaaaa aaggaattat 1440
ttttcccttt gagggtcttt tatacatctc tcctccaacc ccaccctcta ttctgtttct 1500
tcctcctcac atgggggtac acatacacag cttcctcttt tggttccatc cttaccacca 1560
caccacacgc acactccaca tgcccagcag agtggcactt ggtggccaga aagtgtgagc 1620
ctcatgatct gctgtctgta gttctgtgag ctcaggtccc tcaaaggcct cggagcaccc 1680
ccttccttgt gactgagcca gggcctgcat ttttggtttt ccccaccccca cacattctca 1740 accatagtcc ttctaacaat accaatagct aggacccggc tgctgtgcac tgggactggg 1800
gattccacat gtttgccttg ggagtctcaa gctggactgc cagcccctgt cctcccttca 1860
cccccattgc gtatgagcat ttcagaactc caaggagtca caggcatctt tatagttcac 1920
gttaacatat agacactgtt ggaagcagtt ccttctaaaa gggtagccct ggacttaata 1980
ccagccggat acctctggcc cccaccccat tactgtacct ctggagtcac tactgtgggt 2040
cgccactcct ctgctacaca gcacggcttt ttcaaggctg tattgagaag ggaagttagg 2100
aagaagggtg tgctgggcta accagcccac agagctcaca ttcctgtccc ttgggtgaaa 2160

```
aatacatgtc catcctgata tctcctgaat tcagaaatta gcctccacat gtgcaatggc   2220

tttaagagcc agaagcaggg ttctgggaat tttgcaagtt acctgtggcc aggtgtggtc   2280

tcggttacca aatacggtta cctgcagctt tttagtcctt tgtgctccca cgggtctaca   2340

gagtcccatc tgcccaaagg tcttgaagct tgacaggatg ttttcgatta ctcagtctcc   2400

cagggcacta ctggtccgta ggattcgatt ggtcggggta ggagagttaa acaacattta   2460

aacagagttc tctcaaaaat gtctaaaggg attgtaggta gataacatcc aatcactgtt   2520

tgcacttatc tgaaatcttc cctcttggct gcccccaggt atttactgtg gagaacattg   2580

cataggaatg tctggaaaaa gcttctacaa cttgttacag ccttcacatt tgtagaagct   2640

tt                                                                  2642
```

<210> SEQ ID NO 82
<211> LENGTH: 1842
<212> TYPE: DNA
<213> ORGANISM: Artificial Sequence
<220> FEATURE:
<223> OTHER INFORMATION: OPA1-ND1-3'UTR*

<400> SEQUENCE: 82

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgatgg ccaacctcct actcctcatt gtacccattc    300

taatcgcaat ggcattccta atgcttaccg aacgaaaaat tctaggctat atgcaactac    360

gcaaaggccc caacgttgta ggcccctacg ggctactaca acccttcgct gacgccataa    420

aactcttcac caaagagccc ctaaaacccg ccacatctac catcaccctc tacatcaccg    480

ccccgacctt agctctcacc atcgctcttc tactatggac ccccctcccc atgcccaacc    540

ccctggtcaa cctcaaccta ggcctcctat ttattctagc cacctctagc ctagccgttt    600

actcaatcct ctggtcaggg tgggcatcaa actcaaacta cgccctgatc ggcgcactgc    660

gagcagtagc ccaaacaatc tcatatgaag tcaccctagc catcattcta ctatcaacat    720

tactaatgag tggctccttt aacctctcca cccttatcac aacacaagaa cacctctggt    780

tactcctgcc atcatggccc ttggccatga tgtggtttat ctccacacta gcagagacca    840

accgaacccc cttcgacctt gccgaagggg agtccgaact agtctcaggc ttcaacatcg    900

aatacgccgc aggccccttc gccctattct tcatggccga atacacaaac attattatga    960

tgaacaccct caccactaca atcttcctag gaacaacata tgacgcactc tcccctgaac   1020

tctacacaac atattttgtc accaagaccc tacttctaac ctccctgttc ttatggattc   1080

gaacagcata cccccgattc cgctacgacc aactcatgca cctcctatgg aaaaacttcc   1140

taccactcac cctagcatta cttatgtggt atgtctccat gcccattaca atctccagca   1200

ttccccctca aacctaagag cactgggacg cccaccgccc ctttccctcc gctgccaggc   1260

gagcatgttg tggtaattct ggaacacaag aagagaaatt gctgggttta gaacaagatt   1320

ataaacgaat tcggtgctca gtgatcactt gacagttttt ttttttttta aatattaccc   1380

aaaatgctcc ccaaataaga aatgcatcag ctcagtcagt gaatacaaaa aaggaattat   1440

ttttcccttt gagggtcttt tatacatctc tcctccaacc ccaccctcta ttctgtttct   1500

tcctcctcac atgggggtac acatacacag cttcctcttt tggttccatc cttaccacca   1560
```

```
caccacacgc acactccaca tgcccagcag agtggcactt ggtggccaga aagtgtgagc   1620

ctcatgatct gctgtctgta gttctgtgag ctcaggtccc tcaaaggcct cggagcaccc   1680

ccttccttgt gactgagcca gggcctgcat tttggtttt ccccacccca cacattctca    1740

accatagtcc ttctaacaat accaatagct aggacccggc tgctgtgcac tgggactggg   1800

gattccacat gtttgccttg ggagtctcaa gctggactgc ca                      1842
```

<210> SEQ ID NO 83
<211> LENGTH: 2642
<212> TYPE: DNA
<213> ORGANISM: Artificial Sequence
<220> FEATURE:
<223> OTHER INFORMATION: OPA1-opt_ND1-3'UTR

<400> SEQUENCE: 83

```
gtgctgcccg cctagaaagg gtgaagtggt tgtttccgtg acggactgag tacgggtgcc     60

tgtcaggctc ttgcggaagt ccatgcgcca ttgggagggc ctcggccgcg gctctgtgcc    120

cttgctgctg agggccactt cctgggtcat tcctggaccg ggagccgggc tggggctcac    180

acgggggctc ccgcgtggcc gtctcggcgc ctgcgtgacc tccccgccgg cgggatgtgg    240

cgactacgtc gggccgctgt ggcctgatgg ccaacctgct gctgctgatc gtgcccatcc    300

tgatcgccat ggccttcctg atgctgaccg agcgcaagat cctgggctac atgcagctgc    360

gcaagggccc caacgtggtg ggcccctacg gcctgctgca gcccttcgcc gacgccatca    420

agctgttcac caaggagccc ctgaagcccg ccaccagcac catcaccctg tacatcaccg    480

cccccaccct ggccctgacc atcgccctgc tgctgtggac cccccctgccc atgcccaacc    540

ccctggtgaa cctgaacctg ggcctgctgt tcatcctggc caccagcagc ctggccgtgt    600

acagcatcct gtggagcggc tgggccagca acagcaacta cgccctgatc ggcgccctgc    660

gcgccgtggc ccagaccatc agctacgagg tgaccctggc catcatcctg ctgagcaccc    720

tgctgatgag cggcagcttc aacctgagca ccctgatcac cacccaggag cacctgtggc    780

tgctgctgcc cagctggccc ctggccatga tgtggttcat cagcaccctg gccgagacca    840

accgcacccc cttcgacctg gccgagggcg agagcgagct ggtgagcggc ttcaacatcg    900

agtacgccgc cggccccttc gccctgttct tcatggccga gtacaccaac atcatcatga    960

tgaacaccct gaccaccacc atcttcctgg gcaccaccta cgacgccctg agccccgagc   1020

tgtacaccac ctacttcgtg accaagaccc tgctgctgac cagcctgttc ctgtggatcc   1080

gcaccgccta cccccgcttc cgctacgacc agctgatgca cctgctgtgg aagaacttcc   1140

tgcccctgac cctggccctg ctgatgtggt acgtgagcat gcccatcacc atcagcagca   1200

tcccccccca gacctaagag cactgggacg cccaccgccc ctttccctcc gctgccaggc   1260

gagcatgttg tggtaattct ggaacacaag aagagaaatt gctgggttta gaacaagatt   1320

ataaacgaat tcggtgctca gtgatcactt gacagttttt tttttttta aatattaccc    1380

aaaatgctcc ccaaataaga aatgcatcag ctcagtcagt gaatacaaaa aaggaattat   1440

ttttcccttt gagggtcttt tatacatctc tcctccaacc ccaccctcta ttctgtttct   1500

tcctcctcac atgggggtac acatacacag cttcctcttt tggttccatc cttaccacca   1560

caccacacgc acactccaca tgcccagcag agtggcactt ggtggccaga aagtgtgagc   1620

ctcatgatct gctgtctgta gttctgtgag ctcaggtccc tcaaaggcct cggagcaccc   1680

ccttccttgt gactgagcca gggcctgcat tttggtttt ccccacccca cacattctca    1740
```

```
accatagtcc ttctaacaat accaatagct aggacccggc tgctgtgcac tgggactggg   1800
gattccacat gtttgccttg ggagtctcaa gctggactgc cagcccctgt cctcccttca   1860
cccccattgc gtatgagcat ttcagaactc caaggagtca caggcatctt tatagttcac   1920
gttaacatat agacactgtt ggaagcagtt ccttctaaaa gggtagccct ggacttaata   1980
ccagccggat acctctggcc cccaccccat tactgtacct ctggagtcac tactgtgggt   2040
cgccactcct ctgctacaca gcacggcttt ttcaaggctg tattgagaag ggaagttagg   2100
aagaagggtg tgctgggcta accagcccac agagctcaca ttcctgtccc ttgggtgaaa   2160
aatacatgtc catcctgata tctcctgaat tcagaaatta gcctccacat gtgcaatggc   2220
tttaagagcc agaagcaggg ttctgggaat tttgcaagtt acctgtggcc aggtgtggtc   2280
tcggttacca aatacggtta cctgcagctt tttagtcctt tgtgctccca cgggtctaca   2340
gagtcccatc tgcccaaagg tcttgaagct tgacaggatg ttttcgatta ctcagtctcc   2400
cagggcacta ctggtccgta ggattcgatt ggtcggggta ggagagttaa acaacattta   2460
aacagagttc tctcaaaaat gtctaaaggg attgtaggta gataacatcc aatcactgtt   2520
tgcacttatc tgaaatcttc cctcttggct gcccccaggt atttactgtg gagaacattg   2580
cataggaatg tctggaaaaa gcttctacaa cttgttacag ccttcacatt tgtagaagct   2640
tt                                                                  2642
```

<210> SEQ ID NO 84
<211> LENGTH: 1842
<212> TYPE: DNA
<213> ORGANISM: Artificial Sequence
<220> FEATURE:
<223> OTHER INFORMATION: OPA1-opt_ND1-3'UTR*

<400> SEQUENCE: 84

```
gtgctgcccg cctagaaagg gtgaagtggt tgtttccgtg acggactgag tacgggtgcc     60
tgtcaggctc ttgcggaagt ccatgcgcca ttgggagggc ctcggccgcg gctctgtgcc    120
cttgctgctg agggccactt cctgggtcat tcctggaccg ggagccgggc tggggctcac    180
acgggggctc ccgcgtggcc gtctcggcgc ctgcgtgacc tccccgccgg cgggatgtgg    240
cgactacgtc gggccgctgt ggcctgatgg ccaacctgct gctgctgatc gtgcccatcc    300
tgatcgccat ggccttcctg atgctgaccg agcgcaagat cctgggctac atgcagctgc    360
gcaagggccc caacgtggtg ggcccctacg gcctgctgca gcccttcgcc gacgccatca    420
agctgttcac caaggagccc ctgaagcccg ccaccagcac catcaccctg tacatcaccg    480
cccccaccct ggccctgacc atcgccctgc tgctgtggac ccccctgccc atgcccaacc    540
ccctggtgaa cctgaacctg ggcctgctgt tcatcctggc caccagcagc ctggccgtgt    600
acagcatcct gtggagcggc tgggccagca acagcaacta cgccctgatc ggcgccctgc    660
gcgccgtggc ccagaccatc agctacgagg tgaccctggc catcatcctg ctgagcaccc    720
tgctgatgag cggcagcttc aacctgagca ccctgatcac cacccaggag cacctgtggc    780
tgctgctgcc cagctggccc ctggccatga tgtggttcat cagcaccctg gccgagacca    840
accgcacccc cttcgacctg gccgagggcg agagcgagct ggtgagcggc ttcaacatcg    900
agtacgccgc cggccccttc gccctgttct tcatggccga gtacaccaac atcatcatga    960
tgaacaccct gaccaccacc atcttcctgg gcaccaccta cgacgccctg agccccgagc   1020
tgtacaccac ctacttcgtg accaagaccc tgctgctgac cagcctgttc ctgtggatcc   1080
gcaccgccta cccccgcttc cgctacgacc agctgatgca cctgctgtgg aagaacttcc   1140
```

-continued

```
tgcccctgac cctggccctg ctgatgtggt acgtgagcat gcccatcacc atcagcagca    1200

tcccccccca gacctaagag cactgggacg cccaccgccc ctttccctcc gctgccaggc    1260

gagcatgttg tggtaattct ggaacacaag aagagaaatt gctgggttta gaacaagatt    1320

ataaacgaat tcggtgctca gtgatcactt gacagttttt tttttttta aatattaccc    1380

aaaatgctcc ccaaataaga aatgcatcag ctcagtcagt gaatacaaaa aaggaattat    1440

ttttcccttt gagggtcttt tatacatctc tcctccaacc ccaccctcta ttctgtttct    1500

tcctcctcac atgggggtac acatacacag cttcctcttt tggttccatc cttaccacca    1560

caccacacgc acactccaca tgcccagcag agtggcactt ggtggccaga aagtgtgagc    1620

ctcatgatct gctgtctgta gttctgtgag ctcaggtccc tcaaaggcct cggagcaccc    1680

ccttccttgt gactgagcca gggcctgcat ttttggtttt ccccacccca cacattctca    1740

accatagtcc ttctaacaat accaatagct aggacccggc tgctgtgcac tgggactggg    1800

gattccacat gtttgccttg ggagtctcaa gctggactgc ca                      1842
```

<210> SEQ ID NO 85
<211> LENGTH: 18
<212> TYPE: DNA
<213> ORGANISM: Artificial Sequence
<220> FEATURE:
<223> OTHER INFORMATION: beta-actin-S primer

<400> SEQUENCE: 85

```
cgagatcgtg cgggacat                                                   18
```

<210> SEQ ID NO 86
<211> LENGTH: 19
<212> TYPE: DNA
<213> ORGANISM: Artificial Sequence
<220> FEATURE:
<223> OTHER INFORMATION: beta-actin-A primer

<400> SEQUENCE: 86

```
caggaaggag ggctggaac                                                  19
```

<210> SEQ ID NO 87
<211> LENGTH: 19
<212> TYPE: DNA
<213> ORGANISM: Artificial Sequence
<220> FEATURE:
<223> OTHER INFORMATION: ND4-S primer

<400> SEQUENCE: 87

```
ctgcctacga caaacagac                                                  19
```

<210> SEQ ID NO 88
<211> LENGTH: 19
<212> TYPE: DNA
<213> ORGANISM: Artificial Sequence
<220> FEATURE:
<223> OTHER INFORMATION: ND4-A primer

<400> SEQUENCE: 88

```
agtgcgttcg tagtttgag                                                  19
```

<210> SEQ ID NO 89
<211> LENGTH: 21
<212> TYPE: DNA
<213> ORGANISM: Artificial Sequence
<220> FEATURE:

-continued

<223> OTHER INFORMATION: ND6-F primer

<400> SEQUENCE: 89
atgatgtatg ctttgtttct g 21

<210> SEQ ID NO 90
<211> LENGTH: 21
<212> TYPE: DNA
<213> ORGANISM: Artificial Sequence
<220> FEATURE:
<223> OTHER INFORMATION: ND6-R primer

<400> SEQUENCE: 90
ctaattcccc cgagcaatct c 21

<210> SEQ ID NO 91
<211> LENGTH: 18
<212> TYPE: DNA
<213> ORGANISM: Artificial Sequence
<220> FEATURE:
<223> OTHER INFORMATION: ND6-S primer

<400> SEQUENCE: 91
agtgtgggtt tagtaatg 18

<210> SEQ ID NO 92
<211> LENGTH: 18
<212> TYPE: DNA
<213> ORGANISM: Artificial Sequence
<220> FEATURE:
<223> OTHER INFORMATION: ND6-A primer

<400> SEQUENCE: 92
tgcctcagga tactcctc 18

<210> SEQ ID NO 93
<211> LENGTH: 20
<212> TYPE: DNA
<213> ORGANISM: Artificial Sequence
<220> FEATURE:
<223> OTHER INFORMATION: beta-actin-F primer

<400> SEQUENCE: 93
ctccatcctg gcctcgctgt 20

<210> SEQ ID NO 94
<211> LENGTH: 20
<212> TYPE: DNA
<213> ORGANISM: Artificial Sequence
<220> FEATURE:
<223> OTHER INFORMATION: beta-actin-R primer

<400> SEQUENCE: 94
gctgtcacct tcaccgttcc 20

<210> SEQ ID NO 95
<211> LENGTH: 23
<212> TYPE: DNA
<213> ORGANISM: Artificial Sequence
<220> FEATURE:
<223> OTHER INFORMATION: ND6-F primer

<400> SEQUENCE: 95
gggttttctt ctaagccttc tcc 23

-continued

<210> SEQ ID NO 96
<211> LENGTH: 23
<212> TYPE: DNA
<213> ORGANISM: Artificial Sequence
<220> FEATURE:
<223> OTHER INFORMATION: ND6-R primer

<400> SEQUENCE: 96
ccatcatact ctttcaccca cag 23

<210> SEQ ID NO 97
<211> LENGTH: 20
<212> TYPE: DNA
<213> ORGANISM: Artificial Sequence
<220> FEATURE:
<223> OTHER INFORMATION: opt_ND6-F primer

<400> SEQUENCE: 97
cgcctgctga ccggctgcgt 20

<210> SEQ ID NO 98
<211> LENGTH: 20
<212> TYPE: DNA
<213> ORGANISM: Artificial Sequence
<220> FEATURE:
<223> OTHER INFORMATION: opt_ND6-R

<400> SEQUENCE: 98
ccaggcctcg gggtactcct 20

<210> SEQ ID NO 99
<211> LENGTH: 21
<212> TYPE: DNA
<213> ORGANISM: Artificial Sequence
<220> FEATURE:
<223> OTHER INFORMATION: ND1-F primer

<400> SEQUENCE: 99
atggccgcat ctccgcacac t 21

<210> SEQ ID NO 100
<211> LENGTH: 21
<212> TYPE: DNA
<213> ORGANISM: Artificial Sequence
<220> FEATURE:
<223> OTHER INFORMATION: ND1-R primer

<400> SEQUENCE: 100
ttaggtttga gggggaatgc t 21

<210> SEQ ID NO 101
<211> LENGTH: 21
<212> TYPE: DNA
<213> ORGANISM: Artificial Sequence
<220> FEATURE:
<223> OTHER INFORMATION: ND1-F primer

<400> SEQUENCE: 101
aacctcaacc taggcctcct a 21

<210> SEQ ID NO 102
<211> LENGTH: 21
<212> TYPE: DNA
<213> ORGANISM: Artificial Sequence
<220> FEATURE:
<223> OTHER INFORMATION: ND1-R primer

<400> SEQUENCE: 102
tggcaggagt aaccagaggt g 21

<210> SEQ ID NO 103
<211> LENGTH: 23
<212> TYPE: DNA
<213> ORGANISM: Artificial Sequence
<220> FEATURE:
<223> OTHER INFORMATION: ND1-F primer

<400> SEQUENCE: 103
aggaggctct gtctggtatc ttg 23

<210> SEQ ID NO 104
<211> LENGTH: 21
<212> TYPE: DNA
<213> ORGANISM: Artificial Sequence
<220> FEATURE:
<223> OTHER INFORMATION: ND1-R primer

<400> SEQUENCE: 104
ttttaggggc tctttggtga a 21

<210> SEQ ID NO 105
<211> LENGTH: 22
<212> TYPE: DNA
<213> ORGANISM: Artificial Sequence
<220> FEATURE:
<223> OTHER INFORMATION: opt-ND1-F primer

<400> SEQUENCE: 105
gccgcctgct gaccggctgc gt 22

<210> SEQ ID NO 106
<211> LENGTH: 24
<212> TYPE: DNA
<213> ORGANISM: Artificial Sequence
<220> FEATURE:
<223> OTHER INFORMATION: opt-ND1-R primer

<400> SEQUENCE: 106
tgatgtacag ggtgatggtg ctgg 24

<210> SEQ ID NO 107
<211> LENGTH: 19
<212> TYPE: DNA
<213> ORGANISM: Artificial Sequence
<220> FEATURE:
<223> OTHER INFORMATION: ND4-S primer

<400> SEQUENCE: 107
gccaacagca actacgagc 19

<210> SEQ ID NO 108
<211> LENGTH: 20
<212> TYPE: DNA
<213> ORGANISM: Artificial Sequence
<220> FEATURE:
<223> OTHER INFORMATION: ND4-A primer

<400> SEQUENCE: 108
tgatgttgct ccagctgaag 20

<210> SEQ ID NO 109
<211> LENGTH: 20

-continued

<212> TYPE: DNA
<213> ORGANISM: Artificial Sequence
<220> FEATURE:
<223> OTHER INFORMATION: opt-ND4-S primer

<400> SEQUENCE: 109
gcctgaccct gatcctgaac 20

<210> SEQ ID NO 110
<211> LENGTH: 20
<212> TYPE: DNA
<213> ORGANISM: Artificial Sequence
<220> FEATURE:
<223> OTHER INFORMATION: opt-ND4-A primer

<400> SEQUENCE: 110
gtgcgctcgt agttgctgtt 20

<210> SEQ ID NO 111
<211> LENGTH: 376
<212> TYPE: DNA
<213> ORGANISM: Homo sapiens

<400> SEQUENCE: 111
gggcagtgcc tccccgcccc gccgctggcg tcaagttcag ctccacgtgt gccatcagtg 60
gatccgatcc gtccagccat ggcttcctat tccaagatgg tgtgaccaga catgcttcct 120
gctccccgct tagcccacgg agtgactgtg gttgtggtgg gggggttctt aaaataactt 180
tttagccccc gtcttcctat tttgagtttg gttcagatct taagcagctc catgcaactg 240
tatttatttt tgatgacaag actcccatct aaagtttttc tcctgcctga tcatttcatt 300
ggtggctgaa ggattctaga gaaccttttg ttcttgcaag gaaaacaaga atccaaaacc 360
agtgactgtt ctgtga 376

<210> SEQ ID NO 112
<211> LENGTH: 146
<212> TYPE: DNA
<213> ORGANISM: Homo sapiens

<400> SEQUENCE: 112
ggggtctttg tcctctgtac tgtctctctc cttgccccta acccaaaaag cttcattttt 60
ctgtgtaggc tgcacaagag ccttgattga agatatattc tttctgaaca gtatttaagg 120
tttccaataa aatgtacacc cctcag 146

<210> SEQ ID NO 113
<211> LENGTH: 1956
<212> TYPE: DNA
<213> ORGANISM: Homo sapiens

<400> SEQUENCE: 113
tgttgggtcc aagaaggaat ttctttccat ccctgtgagg caatgggtgg gaatgatagg 60
acaggcaaag agaagcttcc tcaggctagc aaaaatatca tttgatgtat tgattaaaaa 120
agcacttgct tgatgtatct ttggcgtgtg tgctactctc atctgtgtgt atgtgtgttg 180
tgtgtgtgtg tgtgtgcatg cacatatgtg ttcactctgc tactttgtaa gttttaggct 240
aggttgcttt accagctgtt tacttctttt ttgttgttgt tttgagacaa ggtttcgctc 300
tgccaccctg gctggagtgc agtggcgtga tcttggctca cggcaacctc tgcctcctgg 360
ggctcaagca attatcccac ctcagcctcc tgagcagctg ggactacagg tgcatgccac 420

```
aacacctggc tgatatttgt attttttgta gagacaggat tttgccaagt tgcccaggct    480
ggtcttgaac tcctaggctt aagcaatcca cccaccttgg cctcctgaag tgccaggatc    540
acagacgtga gccactacac ccagcccagc tgtttacttc tttaaccata cttttgattt    600
tatttttga ccaaaatgaa ctaacccagg taatcttcca gggaccgcaa ttccagaacc    660
tcatagtatt tcttccattt ccagcagctg attagaagtc caggatcatg tgaagtcagg    720
cagggtcaca gttcctgatg gcacattatg gacagagaat tccattttgt tttctaaccc    780
atgatgaaaa cccacgtgag tcagtgtgtg aacagggatc attaattttt tccccctagg    840
tggaaggaaa aaggcactta ctttgcaggt tacagaaatt actgggagag gatatcgtca    900
taaaaagagc caggccaaat tggaatattt ttgtgatctg catcatgatg ctgaaaatag    960
caattatttg ggaattgggt ttgaaaactg aattgttgcc agagaattaa accaggtgaa   1020
aggtcctttt gaattcagat tgtcttctga acatccaggc tgatcatctg agagcagtca   1080
aatctacttc cccaaaaaga gaccagggta ggtttatttg cttttatttt taatgtttgc   1140
ctgtgtttcc aagtgtgaac aaaacagtgt gtgatctatt cttggattca ttttgatcag   1200
tatttattca aacccagtct ctctccagga cataaaactg aaatcagata tgttcttttt   1260
aagcccaaac cctctccttt ctagatccaa cccttcaccc ctaattttat gatggctata   1320
gccatggact tccccaagaa aagatcaccc agaaataaga ccacctgtga cagttaccag   1380
cttttattca taaccttagc ttcccaacta ttgagcattt tctaaggtcc ctgctgtctt   1440
ttggtctctg gtttgatttg tggcaaacag atgaagtaac agactgctat gaaggaccac   1500
aaaaacggca gcctctggaa aaaccattag aaagtcagtg gcagatccag taaataatat   1560
cgccagcctc agcataatct gctgctgact cgattcagtg gactctaaag tgcccagcct   1620
cctgacctga gctctcctgc catctgtgag actaccagag gtcttatctg ctgtccacat   1680
ggcaactggg catgagtacc tggccacctt gcttccctct ttgcctggtc caagtgagtg   1740
tctgctgcct ctgtcctgcc ttgttttcct ggctctaaac caactccacc cactcttaat   1800
ggaaactcag tctggctttg tgtgtttctg ggaagcacat gacttctggg aatgggcaag   1860
gaagaggagt gaaacaaaaa ctgtcagcta tgtgtgcctg gtctgggatc cttctctggg   1920
tgacagtggc atcatgaatc ttagaatcag ctcccc                              1956
```

<210> SEQ ID NO 114
<211> LENGTH: 411
<212> TYPE: DNA
<213> ORGANISM: Homo sapiens

<400> SEQUENCE: 114

```
gaatcatgca agcttcctcc ctcagccatt gatggaaagt tcagcaagat cagcaacaaa     60
accaagaaaa atgatccttg cgtgctgaat atctgaaaag agaaattttt cctacaaaat    120
ctcttgggtc aagaaagttc tagaatttga attgataaac atggtgggtt ggctgagggt    180
aagagtatat gaggaacctt ttaaacgaca acaatactgc tagctttcag gatgattttt    240
aaaaaataga ttcaaatgtg ttatcctctc tctgaaacgc ttcctataac tcgagtttat    300
aggggaagaa aaagctattg tttacaatta tatcaccatt aaggcaactg ctacaccctg    360
ctttgtattc tgggctaaga ttcattaaaa actagctgct cttaacttac a             411
```

<210> SEQ ID NO 115
<211> LENGTH: 1465
<212> TYPE: DNA
<213> ORGANISM: Homo sapiens

<400> SEQUENCE: 115
gagcactggg acgcccaccg ccccttccc tccgctgcca ggcgagcatg ttgtggtaat 60
tctggaacac aagaagagaa attgctgggt ttagaacaag attataaacg aattcggtgc 120
tcagtgatca cttgacagtt tttttttttt ttaaatatta cccaaaatgc tccccaaata 180
agaaatgcat cagctcagtc agtgaataca aaaaaggaat tatttttccc tttgagggtc 240
tttatacatc tctcctccaa ccccaccctc tattctgttt cttcctcctc acatgggggt 300
acacatacac agcttcctct tttggttcca tccttaccac cacaccacac gcacactcca 360
catgcccagc agagtggcac ttggtggcca gaaagtgtga gcctcatgat ctgctgtctg 420
tagttctgtg agctcaggtc cctcaaaggc ctcggagcac ccccttcctg gtgactgagc 480
cagggcctgc atttttggtt ttccccaccc cacacattct caaccatagt ccttctaaca 540
ataccaatag ctaggacccg gctgctgtgc actgggactg gggattccac atgtttgcct 600
tgggagtctc aagctggact gccagcccct gtcctccctt cacccccatt gcgtatgagc 660
atttcagaac tccaaggagt cacaggcatc tttatagttc acgttaacat atagacactg 720
ttggaagcag ttccttctaa aagggtagcc ctggacttaa taccagccgg atacctctgg 780
cccccacccc attactgtac ctctggagtc actactgtgg gtcgccactc ctctgctaca 840
cagcacggct ttttcaaggc tgtattgaga agggaagtta ggaagaaggg tgtgctgggc 900
taaccagccc acagagctca cattcctgtc ccttgggtga aaaatacatg tccatcctga 960
tatctcctga attcagaaat tagcctccac atgtgcaatg gctttaagag ccagaagcag 1020
ggttctggga attttgcaag ttatcctgtg gccaggtgtg gtctcggtta ccaaatacgg 1080
ttacctgcag ctttttagtc ctttgtgctc ccacgggtct gcagagtccc atctgcccaa 1140
aggtcttgaa gcttgacagg atgttttcat tactcagtct cccagggcac tgctggtccg 1200
tagggattca ttggtcgggg tgggagagtt aaacaacatt taaacagagt tctctcaaaa 1260
atgtctaaag ggattgtagg tagataacat ccaatcactg tttgcactta tctgaaatct 1320
tccctcttgg ctgcccccag gtatttactg tggagaacat tgcataggaa tgtctggaaa 1380
aagcctctac aacttgttac agccttcaca tttgtacaat tcattgattc tcttttcctt 1440
ccacaataaa atggtataca agaac 1465

<210> SEQ ID NO 116
<211> LENGTH: 288
<212> TYPE: DNA
<213> ORGANISM: Homo sapiens

<400> SEQUENCE: 116
gagacttgga ctcaagtcat aggcttcttt cagtctttat gtcacctcag gagacttatt 60
tgagaggaag ccttctgtac ttgaagttga tttgaaatat gtaagaattg atgatgtatt 120
tgcaaacatt aatgtgaaat aaattgaatt taatgttgaa tactttcagg cattcactta 180
ataaagacac tgttaagcac tgttatgctc agtcatacac gcgaaaggta caatgtcttt 240
tagctaattc taattaaaaa ttacagactg gtgtacaaga tacttgtg 288

<210> SEQ ID NO 117
<211> LENGTH: 83
<212> TYPE: DNA
<213> ORGANISM: Homo sapiens

<400> SEQUENCE: 117

-continued cccaccaccc tggcctgctg tcctgcgtct atccatgtgg aatgctggac aataaagcga 60
gtgctgccca ccctccagct gcc 83

<210> SEQ ID NO 118
<211> LENGTH: 66
<212> TYPE: DNA
<213> ORGANISM: Homo sapiens

<400> SEQUENCE: 118
tttatattga actgtaaata tgtcactaga gaaataaaat atggacttcc aatctacgta 60
aactta 66

<210> SEQ ID NO 119
<211> LENGTH: 214
<212> TYPE: DNA
<213> ORGANISM: Homo sapiens

<400> SEQUENCE: 119
accacgatcg ttatgctgag tatgttaagc tctttatgac tgtttttgta gtggtataga 60
gtactgcaga atacagtaag ctgctctatt gtagcatttc ttgatgttgc ttagtcactt 120
atttcataaa caacttaatg ttctgaataa tttcttacta aacattttgt tattgggcaa 180
gtgattgaaa atagtaaatg ctttgtgtga ttga 214

<210> SEQ ID NO 120
<211> LENGTH: 286
<212> TYPE: DNA
<213> ORGANISM: Homo sapiens

<400> SEQUENCE: 120
tcttggaata taaagaattt cttcaggttg aattacctag aagtttgtca ctgacttgtg 60
ttcctgaact atgacacatg aatatgtggg ctaagaaata gttcctcttg ataaataaac 120
aattaacaaa tactttggac agtaagtctt tctcagttct taatgataat gcagggcact 180
tactagcata agaattggtt tgggatttaa ctgtttatga agctaacttg atttccgtgt 240
tttgttaaaa tttcattgtt ctagcacatc tttaactgtg atagtt 286

<210> SEQ ID NO 121
<211> LENGTH: 721
<212> TYPE: DNA
<213> ORGANISM: Homo sapiens

<400> SEQUENCE: 121
gagacgtgca cttggtcgtg cgcccaggga ggaagccgca ccaccagcca gcgcaggccc 60
tggtggagag gcctccctgg ctgcctctgg gaggggtgct gccttgtaga tggagcaagt 120
gagcactgag ggtctggtgc caatcctgta ggcacaaaac cagaagtttc tacattctct 180
atttttgtta atcatcttct ctttttccag aatttggaag ctagaatggt gggaatgtca 240
gtagtgccag aaagagagaa ccaagcttgt ctttaaagtt actgatcaca ggacgttgct 300
ttttcactgt ttcctattaa tcttcagctg aacacaagca aaccttctca ggaggtgtct 360
cctaccctct tattgttcct cttacgctct gctcaatgaa accttcctct tgagggtcat 420
tttcctttct gtattaatta taccagtgtt aagtgacata gataagaact ttgcacactt 480
caaatcagag cagtgattct ctcttctctc cccttttcct tcagagtgaa tcatccagac 540
tcctcatgga taggtcgggt gttaaagttg ttttgattat gtaccttttg atagatccac 600
ataaaaagaa atgtgaagtt ttcttttact atcttttcat ttatcaagca gagacctttg 660

-continued ttgggaggcg gtttgggaga acacatttct aatttgaatg aaatgaaatc tattttcagt 720
g 721

<210> SEQ ID NO 122
<211> LENGTH: 163
<212> TYPE: DNA
<213> ORGANISM: Homo sapiens

<400> SEQUENCE: 122
cagaagaagt gacggctggg ggcacagtgg gctgggcgcc cctgcagaac atgaaccttc 60
cgctcctggc tgccacaggg tcctccgatg ctggcctttg cgcctctaga ggcagccact 120
catggattca agtcctggct ccgcctcttc catcaggacc act 163

<210> SEQ ID NO 123
<211> LENGTH: 60
<212> TYPE: DNA
<213> ORGANISM: Homo sapiens

<400> SEQUENCE: 123
agaggacaca ctctgcaccc ccccaccccca cgaccttggc ccgagcccct ccgtgaggaa 60

<210> SEQ ID NO 124
<211> LENGTH: 65
<212> TYPE: DNA
<213> ORGANISM: Rattus norvegicus

<400> SEQUENCE: 124
agcccttccg ccaggctgtg tgtcaggccc gtggtgggtg ttttgtagta gtgtagagca 60
ttgca 65

<210> SEQ ID NO 125
<211> LENGTH: 231
<212> TYPE: DNA
<213> ORGANISM: Homo sapiens

<400> SEQUENCE: 125
cttatgttct gtgcgcattc tggcaggaat tctgtctctt cagagactca tcctcaaaac 60
aagacttgac actgtgtcct tgccccagtc ctaggaactg tggcacacag agatgttcat 120
tttaaaaacg gatttcatga aacactcttg tacttatgtt tataagagag cactgggtag 180
ccaagtgatc ttcccattca cagagttagt aaacctctgt actacatgct g 231

<210> SEQ ID NO 126
<211> LENGTH: 28
<212> TYPE: PRT
<213> ORGANISM: Homo sapiens

<400> SEQUENCE: 126

Met Ala Ala Ser Pro His Thr Leu Ser Ser Arg Leu Leu Thr Gly Cys
1 5 10 15

Val Gly Gly Ser Val Trp Tyr Leu Glu Arg Arg Thr
20 25

<210> SEQ ID NO 127
<211> LENGTH: 29
<212> TYPE: PRT
<213> ORGANISM: Homo sapiens

<400> SEQUENCE: 127

```
Met Ser Val Leu Thr Arg Leu Leu Leu Arg Gly Leu Thr Arg Leu Gly
1               5                   10                  15

Ser Ala Ala Pro Val Arg Arg Ala Arg Ile His Ser Leu
            20                  25


<210> SEQ ID NO 128
<211> LENGTH: 10
<212> TYPE: PRT
<213> ORGANISM: Homo sapiens

<400> SEQUENCE: 128

Met Trp Arg Leu Arg Arg Ala Ala Val Ala
1               5                   10


<210> SEQ ID NO 129
<211> LENGTH: 28
<212> TYPE: PRT
<213> ORGANISM: Homo sapiens

<400> SEQUENCE: 129

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25


<210> SEQ ID NO 130
<211> LENGTH: 122
<212> TYPE: PRT
<213> ORGANISM: Saccharomyces cerevisiae

<400> SEQUENCE: 130

Met Ala Phe Lys Ser Phe Ile Tyr Ser Lys Gly Tyr His Arg Ser Ala
1               5                   10                  15

Ala Gln Lys Lys Thr Ala Thr Ser Phe Phe Asp Ser Ser Tyr Gln Tyr
            20                  25                  30

Leu Arg Gln Asn Gln Gly Leu Val Asn Ser Asp Pro Val Leu His Ala
        35                  40                  45

Ser His Leu His Pro His Pro Val Val Val Ala Asn Val Asn Tyr Asn
    50                  55                  60

Asn Val Asp Asp Ile Leu His Pro His Asp Leu Asp Ser Ser Ile Asn
65                  70                  75                  80

Asn Thr Asn Asn Pro Leu Thr His Glu Glu Leu Leu Tyr Asn Gln Asn
                85                  90                  95

Val Ser Leu Arg Ser Leu Lys Gln Gln Gln Ser Thr Asn Tyr Val Asn
            100                 105                 110

Asn Asn Asn Asn Asn Gln His Arg Tyr Tyr
        115                 120


<210> SEQ ID NO 131
<211> LENGTH: 174
<212> TYPE: PRT
<213> ORGANISM: Larimichthys crocea

<400> SEQUENCE: 131

Met Arg Lys Arg Ser Leu Arg Cys His Leu Trp Ser Ala Asn Ala Ser
1               5                   10                  15

Leu Ser Pro Arg Lys Asp Glu Val Thr Ser Arg Lys Glu Ser Glu Asn
            20                  25                  30

Leu Val Lys Gly Lys Lys Asn Lys Lys Ser His Leu His Leu Leu Leu
        35                  40                  45
```

Phe Thr Ala Ser Lys Ile Gly Thr Asp Ser Val Phe Asp Val Gln Lys
    50                  55                  60

Ser Lys Glu Cys Cys Lys Glu Leu Gly Leu Leu Phe Thr Ser Leu Ile
65                  70                  75                  80

His Ser Ile Gly Ser Phe Pro Phe Asp Glu Glu Pro Lys Ala Ala Ala
                85                  90                  95

Val Phe Leu Pro Gly Ser Leu Pro Gln Leu Thr Val Leu Val Leu Ala
            100                 105                 110

Pro Gly Ser Gly Ser Cys Pro Thr Gly Lys Ser Thr Pro His Leu Ala
        115                 120                 125

Ala Ser Gly Arg Asn Ala Glu Leu Leu Arg Pro Gln Asn Ser Met Ile
    130                 135                 140

Val Arg Gln Phe Thr Cys Arg Gly Thr Ile Ser Ser His Leu Cys Ala
145                 150                 155                 160

His Leu Arg Lys Pro His Asp Ser Arg Asn Met Ala Arg Pro
                165                 170

<210> SEQ ID NO 132
<211> LENGTH: 56
<212> TYPE: PRT
<213> ORGANISM: Trypanosoma brucei

<400> SEQUENCE: 132

Met Leu Arg Arg Thr Ser Phe Asn Phe Thr Gly Arg Ala Met Ile Ser
1               5                   10                  15

Arg Gly Ser Pro Glu Trp Ser His Arg Leu Asp Leu Lys Lys Gly Lys
            20                  25                  30

Lys Thr Thr Met Met His Lys Leu Gly Thr Ser Lys Pro Asn Asn Ala
        35                  40                  45

Leu Gln Tyr Ala Gln Met Thr Leu
    50                  55

<210> SEQ ID NO 133
<211> LENGTH: 46
<212> TYPE: PRT
<213> ORGANISM: Neurospora crassa

<400> SEQUENCE: 133

Met Ile Ser Arg Ser Ala Leu Ser Arg Gly Ser Gln Leu Ala Leu Arg
1               5                   10                  15

Arg Pro Ala Ala Ala Lys Thr Ala Gln Arg Gly Phe Ala Ala Ala Ala
            20                  25                  30

Ala Ser Pro Ala Ala Ser Tyr Glu Pro Thr Thr Ile Ala Gly
        35                  40                  45

<210> SEQ ID NO 134
<211> LENGTH: 128
<212> TYPE: PRT
<213> ORGANISM: Homo sapiens

<400> SEQUENCE: 134

Met Pro Glu Leu Ile Leu Tyr Val Ala Ile Thr Leu Ser Val Ala Glu
1               5                   10                  15

Arg Leu Val Gly Pro Gly His Ala Cys Ala Glu Pro Ser Phe Arg Ser
            20                  25                  30

Ser Arg Cys Ser Ala Pro Leu Cys Leu Leu Cys Ser Gly Ser Ser Ser
        35                  40                  45

```
Pro Ala Thr Ala Pro His Pro Leu Lys Met Phe Ala Cys Ser Lys Phe
    50                  55                  60

Val Ser Thr Pro Ser Leu Val Lys Ser Thr Ser Gln Leu Leu Ser Arg
65                  70                  75                  80

Pro Leu Ser Ala Val Val Leu Lys Arg Pro Glu Ile Leu Thr Asp Glu
                85                  90                  95

Ser Leu Ser Ser Leu Ala Val Ser Cys Pro Leu Thr Ser Leu Val Ser
            100                 105                 110

Ser Arg Ser Phe Gln Thr Ser Ala Ile Ser Arg Asp Ile Asp Thr Ala
        115                 120                 125


<210> SEQ ID NO 135
<211> LENGTH: 115
<212> TYPE: PRT
<213> ORGANISM: Homo sapiens

<400> SEQUENCE: 135

Met Tyr Arg Leu Met Ser Ala Val Thr Ala Arg Ala Ala Ala Pro Gly
1               5                   10                  15

Gly Leu Ala Ser Ser Cys Gly Arg Arg Gly Val His Gln Arg Ala Gly
            20                  25                  30

Leu Pro Pro Leu Gly His Gly Trp Val Gly Gly Leu Gly Leu Gly Leu
        35                  40                  45

Gly Leu Ala Leu Gly Val Lys Leu Ala Gly Gly Leu Arg Gly Ala Ala
    50                  55                  60

Pro Ala Gln Ser Pro Ala Ala Pro Asp Pro Glu Ala Ser Pro Leu Ala
65                  70                  75                  80

Glu Pro Pro Gln Glu Gln Ser Leu Ala Pro Trp Ser Pro Gln Thr Pro
                85                  90                  95

Ala Pro Pro Cys Ser Arg Cys Phe Ala Arg Ala Ile Glu Ser Ser Arg
            100                 105                 110

Asp Leu Leu
        115


<210> SEQ ID NO 136
<211> LENGTH: 140
<212> TYPE: PRT
<213> ORGANISM: Schizosaccharomyces pombe

<400> SEQUENCE: 136

Met Thr Val Leu Ala Pro Leu Arg Arg Leu His Thr Arg Ala Ala Phe
1               5                   10                  15

Ser Ser Tyr Gly Arg Glu Ile Ala Leu Gln Lys Arg Phe Leu Asn Leu
            20                  25                  30

Asn Ser Cys Ser Ala Val Arg Arg Tyr Gly Thr Gly Phe Ser Asn Asn
        35                  40                  45

Leu Arg Ile Lys Lys Leu Lys Asn Ala Phe Gly Val Val Arg Ala Asn
    50                  55                  60

Ser Thr Lys Ser Thr Ser Thr Val Thr Thr Ala Ser Pro Ile Lys Tyr
65                  70                  75                  80

Asp Ser Ser Phe Val Gly Lys Thr Gly Gly Glu Ile Phe His Asp Met
                85                  90                  95

Met Leu Lys His Asn Val Lys His Val Phe Gly Tyr Pro Gly Gly Ala
            100                 105                 110

Ile Leu Pro Val Phe Asp Ala Ile Tyr Arg Ser Pro His Phe Glu Phe
        115                 120                 125
```

```
Ile Leu Pro Arg His Glu Gln Ala Ala Gly His Ala
    130                 135                 140


<210> SEQ ID NO 137
<211> LENGTH: 125
<212> TYPE: PRT
<213> ORGANISM: Glycine max

<400> SEQUENCE: 137

Met Ile Leu Cys Pro Leu Glu Ala Phe Ile Val Gln His Ile Leu Thr
1               5                   10                  15

Ile Ser Val Met Gly Leu Leu Ser Cys Phe Arg Ser Thr Val Leu Arg
            20                  25                  30

Lys Cys Ser Lys Gly Ser Ser Gly Met Ser Arg Phe Leu Tyr Thr Asn
        35                  40                  45

Asn Phe Gln Arg Asn Leu Ile Ser Ser Gly Gly Asn Glu Ser Tyr Tyr
    50                  55                  60

Gly Tyr Phe Asn Arg Arg Ser Tyr Thr Ser Leu Tyr Met Gly Thr Gly
65                  70                  75                  80

Thr Val Gly Gly Ile Thr Ser Ala Arg Ile Arg Val Pro Asn Val Gly
                85                  90                  95

Cys Glu Gly Phe Met Cys Ser Ser His Leu Ser Ile Thr Gln Arg Asn
            100                 105                 110

Ser Arg Leu Ile His Ser Thr Ser Lys Ile Val Pro Asn
        115                 120                 125


<210> SEQ ID NO 138
<211> LENGTH: 107
<212> TYPE: PRT
<213> ORGANISM: Chlamydomonas reinhardtii

<400> SEQUENCE: 138

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met
            100                 105


<210> SEQ ID NO 139
<211> LENGTH: 87
<212> TYPE: PRT
<213> ORGANISM: Homo sapiens

<400> SEQUENCE: 139

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
```

```
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn
                85


<210> SEQ ID NO 140
<211> LENGTH: 56
<212> TYPE: PRT
<213> ORGANISM: Homo sapiens

<400> SEQUENCE: 140

Met Ala Val Leu Trp Arg Leu Ser Ala Val Cys Gly Ala Leu Gly Gly
1               5                   10                  15

Arg Ala Leu Leu Leu Arg Thr Pro Val Val Arg Pro Ala His Ile Ser
            20                  25                  30

Ala Phe Leu Gln Asp Arg Pro Ile Pro Glu Trp Cys Gly Val Gln His
        35                  40                  45

Ile His Leu Ser Pro Ser His His
    50                  55


<210> SEQ ID NO 141
<211> LENGTH: 162
<212> TYPE: PRT
<213> ORGANISM: Homo sapiens

<400> SEQUENCE: 141

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe


<210> SEQ ID NO 142
<211> LENGTH: 117
<212> TYPE: PRT
<213> ORGANISM: Oryza sativa

<400> SEQUENCE: 142
```

```
Met Ala Leu Leu Leu Arg His Ser Pro Lys Leu Arg Arg Ala His Ala
1               5                   10                  15

Ile Leu Gly Cys Glu Arg Gly Thr Val Val Arg His Phe Ser Ser Ser
            20                  25                  30

Thr Cys Ser Ser Leu Val Lys Glu Asp Thr Val Ser Ser Ser Asn Leu
        35                  40                  45

His Pro Glu Tyr Ala Lys Lys Ile Gly Gly Ser Asp Phe Ser His Asp
    50                  55                  60

Arg Gln Ser Gly Lys Glu Leu Gln Asn Phe Lys Val Ser Pro Gln Glu
65                  70                  75                  80

Ala Ser Arg Ala Ser Asn Phe Met Arg Ala Ser Lys Tyr Gly Met Pro
                85                  90                  95

Ile Thr Ala Asn Gly Val His Ser Leu Phe Ser Cys Gly Gln Val Val
            100                 105                 110

Pro Ser Arg Cys Phe
        115
```

<210> SEQ ID NO 143
<211> LENGTH: 66
<212> TYPE: PRT
<213> ORGANISM: Neurospora crassa

<400> SEQUENCE: 143

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala
65
```

<210> SEQ ID NO 144
<211> LENGTH: 44
<212> TYPE: PRT
<213> ORGANISM: Homo sapiens

<400> SEQUENCE: 144

```
Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
            20                  25                  30

Thr Lys Asn Gln Trp Leu Leu Thr Pro Ser Arg Glu
        35                  40
```

<210> SEQ ID NO 145
<211> LENGTH: 68
<212> TYPE: PRT
<213> ORGANISM: Homo sapiens

<400> SEQUENCE: 145

```
Met Ala Ser Arg Val Leu Ser Ala Tyr Val Ser Arg Leu Pro Ala Ala
1               5                   10                  15

Phe Ala Pro Leu Pro Arg Val Arg Met Leu Ala Val Ala Arg Pro Leu
            20                  25                  30

Ser Thr Ala Leu Cys Ser Ala Gly Thr Gln Thr Arg Leu Gly Thr Leu
```

```
        35                  40                  45

Gln Pro Ala Leu Val Leu Ala Gln Val Pro Gly Arg Val Thr Gln Leu
    50                  55                  60

Cys Arg Gln Tyr
65


<210> SEQ ID NO 146
<211> LENGTH: 67
<212> TYPE: PRT
<213> ORGANISM: Homo sapiens

<400> SEQUENCE: 146

Met Phe Ala Cys Ala Lys Leu Ala Cys Thr Pro Ser Leu Ile Arg Ala
1               5                   10                  15

Gly Ser Arg Val Ala Tyr Arg Pro Ile Ser Ala Ser Val Leu Ser Arg
            20                  25                  30

Pro Glu Ala Ser Arg Thr Gly Glu Gly Ser Thr Val Phe Asn Gly Ala
        35                  40                  45

Gln Asn Gly Val Ser Gln Leu Ile Gln Arg Glu Phe Gln Thr Ser Ala
    50                  55                  60

Ile Ser Arg
65


<210> SEQ ID NO 147
<211> LENGTH: 273
<212> TYPE: PRT
<213> ORGANISM: Artificial Sequence
<220> FEATURE:
<223> OTHER INFORMATION: crATP6_hsADCK3

<400> SEQUENCE: 147

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met Gly Gly Met Ala Ala
            100                 105                 110

Ile Leu Gly Asp Thr Ile Met Val Ala Lys Gly Leu Val Lys Leu Thr
        115                 120                 125

Gln Ala Ala Val Glu Thr His Leu Gln His Leu Gly Ile Gly Gly Glu
    130                 135                 140

Leu Ile Met Ala Ala Arg Ala Leu Gln Ser Thr Ala Val Glu Gln Ile
145                 150                 155                 160

Gly Met Phe Leu Gly Lys Val Gln Gly Gln Asp Lys His Glu Glu Tyr
                165                 170                 175

Phe Ala Glu Asn Phe Gly Gly Pro Glu Gly Glu Phe His Phe Ser Val
            180                 185                 190

Pro His Ala Ala Gly Ala Ser Thr Asp Phe Ser Ser Ala Ser Ala Pro
        195                 200                 205
```

```
Asp Gln Ser Ala Pro Pro Ser Leu Gly His Ala His Ser Glu Gly Pro
    210                 215                 220

Ala Pro Ala Tyr Val Ala Ser Gly Pro Phe Arg Glu Ala Gly Phe Pro
225                 230                 235                 240

Gly Gln Ala Ser Ser Pro Leu Gly Arg Ala Asn Gly Arg Leu Phe Ala
                245                 250                 255

Asn Pro Arg Asp Ser Phe Ser Ala Met Gly Phe Gln Arg Arg Phe Gly
            260                 265                 270

Gly


<210> SEQ ID NO 148
<211> LENGTH: 132
<212> TYPE: PRT
<213> ORGANISM: Artificial Sequence
<220> FEATURE:
<223> OTHER INFORMATION: ncATP9_ncATP9

<400> SEQUENCE: 148

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Ser Thr Arg Val Leu Ala Ser Arg Leu Ala Ser Gln
65                  70                  75                  80

Met Ala Ala Ser Ala Lys Val Ala Arg Pro Ala Val Arg Val Ala Gln
                85                  90                  95

Val Ser Lys Arg Thr Ile Gln Thr Gly Ser Pro Leu Gln Thr Leu Lys
            100                 105                 110

Arg Thr Gln Met Thr Ser Ile Val Asn Ala Thr Thr Arg Gln Ala Phe
        115                 120                 125

Gln Lys Arg Ala
    130


<210> SEQ ID NO 149
<211> LENGTH: 119
<212> TYPE: PRT
<213> ORGANISM: Zea mays

<400> SEQUENCE: 149

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
```

```
            100                 105                 110

Pro Glu Ala Ala Arg Pro Tyr
        115


<210> SEQ ID NO 150
<211> LENGTH: 391
<212> TYPE: PRT
<213> ORGANISM: Artificial Sequence
<220> FEATURE:
<223> OTHER INFORMATION: ncATP9_zmLOC100282174_spilv1_ncATP9

<400> SEQUENCE: 150

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Ala Ser Thr Arg Val Leu Ala Ser Arg Leu
                325                 330                 335

Ala Ser Gln Met Ala Ala Ser Ala Lys Val Ala Arg Pro Ala Val Arg
```

```
            340                 345                 350

Val Ala Gln Val Ser Lys Arg Thr Ile Gln Thr Gly Ser Pro Leu Gln
        355                 360                 365

Thr Leu Lys Arg Thr Gln Met Thr Ser Ile Val Asn Ala Thr Thr Arg
    370                 375                 380

Gln Ala Phe Gln Lys Arg Ala
385                 390


<210> SEQ ID NO 151
<211> LENGTH: 455
<212> TYPE: PRT
<213> ORGANISM: Artificial Sequence
<220> FEATURE:
<223> OTHER INFORMATION: zmLOC100282174_hsADCK3_crATP6 _hsATP5G3

<400> SEQUENCE: 151

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
    130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                165                 170                 175

Val Gln Gly Gln Asp Lys His Glu Glu Tyr Phe Ala Glu Asn Phe Gly
            180                 185                 190

Gly Pro Glu Gly Glu Phe His Phe Ser Val Pro His Ala Ala Gly Ala
        195                 200                 205

Ser Thr Asp Phe Ser Ser Ala Ser Ala Pro Asp Gln Ser Ala Pro Pro
    210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                245                 250                 255

Leu Gly Arg Ala Asn Gly Arg Leu Phe Ala Asn Pro Arg Asp Ser Phe
            260                 265                 270

Ser Ala Met Gly Phe Gln Arg Arg Phe Met Ala Leu Gln Gln Ala Ala
        275                 280                 285

Pro Arg Val Phe Gly Leu Leu Gly Arg Ala Pro Val Ala Leu Gly Gln
    290                 295                 300

Ser Gly Ile Leu Thr Gly Ser Ser Gly Phe Lys Asn Gln Gly Phe Asn
```

```
305                 310                 315                 320

Gly Ser Leu Gln Ser Val Glu Asn His Val Tyr Ala Gln Ala Phe Ser
                325                 330                 335

Thr Ser Ser Gln Glu Glu Gln Ala Ala Pro Ser Ile Gln Gly Ala Ser
            340                 345                 350

Gly Met Lys Leu Pro Gly Met Ala Gly Ser Met Leu Leu Gly Lys Ser
        355                 360                 365

Arg Ser Gly Leu Arg Thr Gly Ser Met Val Pro Phe Ala Ala Gln Gln
    370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455


<210> SEQ ID NO 152
<211> LENGTH: 348
<212> TYPE: PRT
<213> ORGANISM: Artificial Sequence
<220> FEATURE:
<223> OTHER INFORMATION: zmLOC100282174_hsADCK3_hsATP5G3

<400> SEQUENCE: 152

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
    130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                165                 170                 175

Val Gln Gly Gln Asp Lys His Glu Glu Tyr Phe Ala Glu Asn Phe Gly
            180                 185                 190

Gly Pro Glu Gly Glu Phe His Phe Ser Val Pro His Ala Ala Gly Ala
        195                 200                 205

Ser Thr Asp Phe Ser Ser Ala Ser Ala Pro Asp Gln Ser Ala Pro Pro
```

```
    210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                245                 250                 255

Leu Gly Arg Ala Asn Gly Arg Leu Phe Ala Asn Pro Arg Asp Ser Phe
            260                 265                 270

Ser Ala Met Gly Phe Gln Arg Arg Phe Met Phe Ala Cys Ala Lys Leu
        275                 280                 285

Ala Cys Thr Pro Ser Leu Ile Arg Ala Gly Ser Arg Val Ala Tyr Arg
    290                 295                 300

Pro Ile Ser Ala Ser Val Leu Ser Arg Pro Glu Ala Ser Arg Thr Gly
305                 310                 315                 320

Glu Gly Ser Thr Val Phe Asn Gly Ala Gln Asn Gly Val Ser Gln Leu
                325                 330                 335

Ile Gln Arg Glu Phe Gln Thr Ser Ala Ile Ser Arg
            340                 345
```

<210> SEQ ID NO 153
<211> LENGTH: 185
<212> TYPE: PRT
<213> ORGANISM: Artificial Sequence
<220> FEATURE:
<223> OTHER INFORMATION: ncATP9_zmLOC100282174

<400> SEQUENCE: 153

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr
            180                 185
```

<210> SEQ ID NO 154
<211> LENGTH: 455
<212> TYPE: PRT
<213> ORGANISM: Artificial Sequence
<220> FEATURE:
<223> OTHER INFORMATION: hsADCK3_zmLOC100282174_crATP6 _hsATP5G3

<400> SEQUENCE: 154

```
Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Met Ala Leu Leu Arg Ala Ala Val Ser Glu Leu Arg Arg Arg
                165                 170                 175

Gly Arg Gly Ala Leu Thr Pro Leu Pro Ala Leu Ser Ser Leu Leu Ser
            180                 185                 190

Ser Leu Ser Pro Arg Ser Pro Ala Ser Thr Arg Pro Glu Pro Asn Asn
        195                 200                 205

Pro His Ala Asp Arg Arg His Val Ile Ala Leu Arg Arg Cys Pro Pro
    210                 215                 220

Leu Pro Ala Ser Ala Val Leu Ala Pro Glu Leu Leu His Ala Arg Gly
225                 230                 235                 240

Leu Leu Pro Arg His Trp Ser His Ala Ser Pro Leu Ser Thr Ser Ser
                245                 250                 255

Ser Ser Ser Arg Pro Ala Asp Lys Ala Gln Leu Thr Trp Val Asp Lys
            260                 265                 270

Trp Ile Pro Glu Ala Ala Arg Pro Tyr Met Ala Leu Gln Gln Ala Ala
        275                 280                 285

Pro Arg Val Phe Gly Leu Leu Gly Arg Ala Pro Val Ala Leu Gly Gln
    290                 295                 300

Ser Gly Ile Leu Thr Gly Ser Ser Gly Phe Lys Asn Gln Gly Phe Asn
305                 310                 315                 320

Gly Ser Leu Gln Ser Val Glu Asn His Val Tyr Ala Gln Ala Phe Ser
                325                 330                 335

Thr Ser Ser Gln Glu Glu Gln Ala Ala Pro Ser Ile Gln Gly Ala Ser
            340                 345                 350

Gly Met Lys Leu Pro Gly Met Ala Gly Ser Met Leu Leu Gly Lys Ser
        355                 360                 365

Arg Ser Gly Leu Arg Thr Gly Ser Met Val Pro Phe Ala Ala Gln Gln
    370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
```

-continued

```
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455


<210> SEQ ID NO 155
<211> LENGTH: 455
<212> TYPE: PRT
<213> ORGANISM: Artificial Sequence
<220> FEATURE:
<223> OTHER INFORMATION: crATP6 _hsADCK3_zmLOC100282174_hsATP5G3

<400> SEQUENCE: 155

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met Met Ala Ala Ile Leu
            100                 105                 110

Gly Asp Thr Ile Met Val Ala Lys Gly Leu Val Lys Leu Thr Gln Ala
        115                 120                 125

Ala Val Glu Thr His Leu Gln His Leu Gly Ile Gly Gly Glu Leu Ile
    130                 135                 140

Met Ala Ala Arg Ala Leu Gln Ser Thr Ala Val Glu Gln Ile Gly Met
145                 150                 155                 160

Phe Leu Gly Lys Val Gln Gly Gln Asp Lys His Glu Glu Tyr Phe Ala
                165                 170                 175

Glu Asn Phe Gly Gly Pro Glu Gly Glu Phe His Phe Ser Val Pro His
            180                 185                 190

Ala Ala Gly Ala Ser Thr Asp Phe Ser Ser Ala Ser Ala Pro Asp Gln
        195                 200                 205

Ser Ala Pro Pro Ser Leu Gly His Ala His Ser Glu Gly Pro Ala Pro
    210                 215                 220

Ala Tyr Val Ala Ser Gly Pro Phe Arg Glu Ala Gly Phe Pro Gly Gln
225                 230                 235                 240

Ala Ser Ser Pro Leu Gly Arg Ala Asn Gly Arg Leu Phe Ala Asn Pro
                245                 250                 255

Arg Asp Ser Phe Ser Ala Met Gly Phe Gln Arg Arg Phe Met Ala Leu
            260                 265                 270

Leu Arg Ala Ala Val Ser Glu Leu Arg Arg Arg Gly Arg Gly Ala Leu
        275                 280                 285

Thr Pro Leu Pro Ala Leu Ser Ser Leu Leu Ser Ser Leu Ser Pro Arg
    290                 295                 300

Ser Pro Ala Ser Thr Arg Pro Glu Pro Asn Asn Pro His Ala Asp Arg
```

```
305                 310                 315                 320

Arg His Val Ile Ala Leu Arg Arg Cys Pro Pro Leu Pro Ala Ser Ala
                325                 330                 335

Val Leu Ala Pro Glu Leu Leu His Ala Arg Gly Leu Leu Pro Arg His
            340                 345                 350

Trp Ser His Ala Ser Pro Leu Ser Thr Ser Ser Ser Ser Ser Arg Pro
        355                 360                 365

Ala Asp Lys Ala Gln Leu Thr Trp Val Asp Lys Trp Ile Pro Glu Ala
    370                 375                 380

Ala Arg Pro Tyr Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455


<210> SEQ ID NO 156
<211> LENGTH: 285
<212> TYPE: PRT
<213> ORGANISM: Artificial Sequence
<220> FEATURE:
<223> OTHER INFORMATION: hsADCK3_zmLOC100282174

<400> SEQUENCE: 156

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
```

```
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly
        275                 280                 285


<210> SEQ ID NO 157
<211> LENGTH: 394
<212> TYPE: PRT
<213> ORGANISM: Artificial Sequence
<220> FEATURE:
<223> OTHER INFORMATION: hsADCK3_zmLOC100282174_crATP6

<400> SEQUENCE: 157

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly Met Ala Leu
        275                 280                 285

Gln Gln Ala Ala Pro Arg Val Phe Gly Leu Leu Gly Arg Ala Pro Val
```

```
    290                 295                 300

Ala Leu Gly Gln Ser Gly Ile Leu Thr Gly Ser Ser Gly Phe Lys Asn
305                 310                 315                 320

Gln Gly Phe Asn Gly Ser Leu Gln Ser Val Glu Asn His Val Tyr Ala
                325                 330                 335

Gln Ala Phe Ser Thr Ser Ser Gln Glu Glu Gln Ala Ala Pro Ser Ile
            340                 345                 350

Gln Gly Ala Ser Gly Met Lys Leu Pro Gly Met Ala Gly Ser Met Leu
        355                 360                 365

Leu Gly Lys Ser Arg Ser Gly Leu Arg Thr Gly Ser Met Val Pro Phe
    370                 375                 380

Ala Ala Gln Gln Ala Met Asn Met Gly Gly
385                 390


<210> SEQ ID NO 158
<211> LENGTH: 574
<212> TYPE: PRT
<213> ORGANISM: Artificial Sequence
<220> FEATURE:
<223> OTHER INFORMATION: ncATP9_zmLOC100282174_spilv1_GNFP_ncATP9

<400> SEQUENCE: 158

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
```

```
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Val Ser Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
        355                 360                 365

Tyr Pro Asp His Met Lys Gln His Asp Phe Phe Lys Ser Ala Met Pro
    370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
                405                 410                 415

Arg Ile Glu Leu Lys Gly Ile Asp Phe Lys Glu Asp Gly Asn Ile Leu
            420                 425                 430

Gly His Lys Leu Glu Tyr Asn Tyr Asn Ser His Asn Val Tyr Ile Met
        435                 440                 445

Ala Asp Lys Gln Lys Asn Gly Ile Lys Val Asn Phe Lys Ile Arg His
    450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495

Ser Thr Gln Ser Ala Leu Ser Lys Asp Pro Asn Glu Met Ala Ser Thr
            500                 505                 510

Arg Val Leu Ala Ser Arg Leu Ala Ser Gln Met Ala Ala Ser Ala Lys
        515                 520                 525

Val Ala Arg Pro Ala Val Arg Val Ala Gln Val Ser Lys Arg Thr Ile
    530                 535                 540

Gln Thr Gly Ser Pro Leu Gln Thr Leu Lys Arg Thr Gln Met Thr Ser
545                 550                 555                 560

Ile Val Asn Ala Thr Thr Arg Gln Ala Phe Gln Lys Arg Ala
                565                 570
```

<210> SEQ ID NO 159
<211> LENGTH: 810
<212> TYPE: PRT
<213> ORGANISM: Artificial Sequence
<220> FEATURE:
<223> OTHER INFORMATION: ncATP9_zmLOC100282174_spilv1_lcSirt5_
osP0644B06.24-2_hsATP5G2_ncATP9

<400> SEQUENCE: 159

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45
```

-continued

```
Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Arg Lys Arg Ser Leu Arg Cys His Leu Trp
                325                 330                 335

Ser Ala Asn Ala Ser Leu Ser Pro Arg Lys Asp Glu Val Thr Ser Arg
            340                 345                 350

Lys Glu Ser Glu Asn Leu Val Lys Gly Lys Lys Asn Lys Lys Ser His
        355                 360                 365

Leu His Leu Leu Leu Phe Thr Ala Ser Lys Ile Gly Thr Asp Ser Val
    370                 375                 380

Phe Asp Val Gln Lys Ser Lys Glu Cys Cys Lys Glu Leu Gly Leu Leu
385                 390                 395                 400

Phe Thr Ser Leu Ile His Ser Ile Gly Ser Phe Pro Phe Asp Glu Glu
                405                 410                 415

Pro Lys Ala Ala Ala Val Phe Leu Pro Gly Ser Leu Pro Gln Leu Thr
            420                 425                 430

Val Leu Val Leu Ala Pro Gly Ser Gly Ser Cys Pro Thr Gly Lys Ser
        435                 440                 445

Thr Pro His Leu Ala Ala Ser Gly Arg Asn Ala Glu Leu Leu Arg Pro
    450                 455                 460

Gln Asn Ser Met Ile Val Arg Gln Phe Thr Cys Arg Gly Thr Ile Ser
```

465 470 475 480

Ser His Leu Cys Ala His Leu Arg Lys Pro His Asp Ser Arg Asn Met
485 490 495

Ala Arg Pro Met Ala Leu Leu Leu Arg His Ser Pro Lys Leu Arg Arg
500 505 510

Ala His Ala Ile Leu Gly Cys Glu Arg Gly Thr Val Val Arg His Phe
515 520 525

Ser Ser Ser Thr Cys Ser Ser Leu Val Lys Glu Asp Thr Val Ser Ser
530 535 540

Ser Asn Leu His Pro Glu Tyr Ala Lys Lys Ile Gly Gly Ser Asp Phe
545 550 555 560

Ser His Asp Arg Gln Ser Gly Lys Glu Leu Gln Asn Phe Lys Val Ser
565 570 575

Pro Gln Glu Ala Ser Arg Ala Ser Asn Phe Met Arg Ala Ser Lys Tyr
580 585 590

Gly Met Pro Ile Thr Ala Asn Gly Val His Ser Leu Phe Ser Cys Gly
595 600 605

Gln Val Val Pro Ser Arg Cys Phe Met Pro Glu Leu Ile Leu Tyr Val
610 615 620

Ala Ile Thr Leu Ser Val Ala Glu Arg Leu Val Gly Pro Gly His Ala
625 630 635 640

Cys Ala Glu Pro Ser Phe Arg Ser Ser Arg Cys Ser Ala Pro Leu Cys
645 650 655

Leu Leu Cys Ser Gly Ser Ser Ser Pro Ala Thr Ala Pro His Pro Leu
660 665 670

Lys Met Phe Ala Cys Ser Lys Phe Val Ser Thr Pro Ser Leu Val Lys
675 680 685

Ser Thr Ser Gln Leu Leu Ser Arg Pro Leu Ser Ala Val Val Leu Lys
690 695 700

Arg Pro Glu Ile Leu Thr Asp Glu Ser Leu Ser Ser Leu Ala Val Ser
705 710 715 720

Cys Pro Leu Thr Ser Leu Val Ser Ser Arg Ser Phe Gln Thr Ser Ala
725 730 735

Ile Ser Arg Asp Ile Asp Thr Ala Met Ala Ser Thr Arg Val Leu Ala
740 745 750

Ser Arg Leu Ala Ser Gln Met Ala Ala Ser Ala Lys Val Ala Arg Pro
755 760 765

Ala Val Arg Val Ala Gln Val Ser Lys Arg Thr Ile Gln Thr Gly Ser
770 775 780

Pro Leu Gln Thr Leu Lys Arg Thr Gln Met Thr Ser Ile Val Asn Ala
785 790 795 800

Thr Thr Arg Gln Ala Phe Gln Lys Arg Ala
805 810

<210> SEQ ID NO 160
<211> LENGTH: 459
<212> TYPE: PRT
<213> ORGANISM: Homo sapiens

<400> SEQUENCE: 160

Met Leu Lys Leu Ile Val Pro Thr Ile Met Leu Leu Pro Leu Thr Trp
1 5 10 15

Leu Ser Lys Lys His Met Ile Trp Ile Asn Thr Thr Thr His Ser Leu
20 25 30

```
Ile Ile Ser Ile Ile Pro Leu Leu Phe Phe Asn Gln Ile Asn Asn Asn
        35                  40                  45

Leu Phe Ser Cys Ser Pro Thr Phe Ser Ser Asp Pro Leu Thr Thr Pro
    50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
            100                 105                 110

Thr Glu Leu Ile Met Phe Tyr Ile Phe Phe Glu Thr Thr Leu Ile Pro
        115                 120                 125

Thr Leu Ala Ile Ile Thr Arg Trp Gly Asn Gln Pro Glu Arg Leu Asn
    130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175

Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
        195                 200                 205

Leu Tyr Gly Leu His Leu Trp Leu Pro Lys Ala His Val Glu Ala Pro
    210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
        275                 280                 285

Ser Ser Ile Ser His Met Ala Leu Val Val Thr Ala Ile Leu Ile Gln
    290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
        355                 360                 365

Leu Pro Pro Thr Ile Asn Leu Leu Gly Glu Leu Ser Val Leu Val Thr
    370                 375                 380

Thr Phe Ser Trp Ser Asn Ile Thr Leu Leu Leu Thr Gly Leu Asn Met
385                 390                 395                 400

Leu Val Thr Ala Leu Tyr Ser Leu Tyr Met Phe Thr Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
        435                 440                 445

Leu Asn Pro Asp Ile Ile Thr Gly Phe Ser Ser
```

```
    450                 455


<210> SEQ ID NO 161
<211> LENGTH: 174
<212> TYPE: PRT
<213> ORGANISM: Homo sapiens

<400> SEQUENCE: 161

Met Met Tyr Ala Leu Phe Leu Leu Ser Val Gly Leu Val Met Gly Phe
1               5                   10                  15

Val Gly Phe Ser Ser Lys Pro Ser Pro Ile Tyr Gly Gly Leu Val Leu
            20                  25                  30

Ile Val Ser Gly Val Val Gly Cys Val Ile Ile Leu Asn Phe Gly Gly
        35                  40                  45

Gly Tyr Met Gly Leu Met Val Phe Leu Ile Tyr Leu Gly Gly Met Met
    50                  55                  60

Val Val Phe Gly Tyr Thr Thr Ala Met Ala Ile Glu Glu Tyr Pro Glu
65                  70                  75                  80

Ala Trp Gly Ser Gly Val Glu Val Leu Val Ser Val Leu Val Gly Leu
                85                  90                  95

Ala Met Glu Val Gly Leu Val Leu Trp Val Lys Glu Tyr Asp Gly Val
            100                 105                 110

Val Val Val Val Asn Phe Asn Ser Val Gly Ser Trp Met Ile Tyr Glu
        115                 120                 125

Gly Glu Gly Ser Gly Leu Ile Arg Glu Asp Pro Ile Gly Ala Gly Ala
    130                 135                 140

Leu Tyr Asp Tyr Gly Arg Trp Leu Val Val Val Thr Gly Trp Thr Leu
145                 150                 155                 160

Phe Val Gly Val Tyr Ile Val Ile Glu Ile Ala Arg Gly Asn
                165                 170


<210> SEQ ID NO 162
<211> LENGTH: 316
<212> TYPE: PRT
<213> ORGANISM: Homo sapiens

<400> SEQUENCE: 162

Met Ala Asn Leu Leu Leu Leu Ile Val Pro Ile Leu Ile Ala Met Ala
1               5                   10                  15

Phe Leu Met Leu Thr Glu Arg Lys Ile Leu Gly Tyr Met Gln Leu Arg
            20                  25                  30

Lys Gly Pro Asn Val Val Gly Pro Tyr Gly Leu Leu Gln Pro Phe Ala
        35                  40                  45

Asp Ala Ile Lys Leu Phe Thr Lys Glu Pro Leu Lys Pro Ala Thr Ser
    50                  55                  60

Thr Ile Thr Leu Tyr Ile Thr Ala Pro Thr Leu Ala Leu Thr Ile Ala
65                  70                  75                  80

Leu Leu Leu Trp Thr Pro Leu Pro Met Pro Asn Pro Leu Val Asn Leu
                85                  90                  95

Asn Leu Gly Leu Leu Phe Ile Leu Ala Thr Ser Ser Leu Ala Val Tyr
            100                 105                 110

Ser Ile Leu Trp Ser Gly Trp Ala Ser Asn Ser Asn Tyr Ala Leu Ile
        115                 120                 125

Gly Ala Leu Arg Ala Val Ala Gln Thr Ile Ser Tyr Glu Val Thr Leu
    130                 135                 140

Ala Ile Ile Leu Leu Ser Thr Leu Leu Met Ser Gly Ser Phe Asn Leu
```

-continued

```
145                 150                 155                 160

Ser Thr Leu Ile Thr Thr Gln Glu His Leu Trp Leu Leu Leu Pro Ser
                165                 170                 175

Trp Pro Leu Ala Met Met Trp Phe Ile Ser Thr Leu Ala Glu Thr Asn
            180                 185                 190

Arg Thr Pro Phe Asp Leu Ala Glu Gly Glu Ser Glu Leu Val Ser Gly
        195                 200                 205

Phe Asn Ile Glu Tyr Ala Ala Gly Pro Phe Ala Leu Phe Phe Met Ala
    210                 215                 220

Glu Tyr Thr Asn Ile Ile Met Met Asn Thr Leu Thr Thr Thr Ile Phe
225                 230                 235                 240

Leu Gly Thr Thr Tyr Asp Ala Leu Ser Pro Glu Leu Tyr Thr Thr Tyr
                245                 250                 255

Phe Val Thr Lys Thr Leu Leu Leu Thr Ser Leu Phe Leu Trp Ile Arg
            260                 265                 270

Thr Ala Tyr Pro Arg Phe Arg Tyr Asp Gln Leu Met His Leu Leu Trp
        275                 280                 285

Lys Asn Phe Leu Pro Leu Thr Leu Ala Leu Leu Met Trp Tyr Val Ser
    290                 295                 300

Met Pro Ile Thr Ile Ser Ser Ile Pro Pro Gln Thr
305                 310                 315
```